United States Patent
Kaspar et al.

(10) Patent No.: US 12,168,777 B2
(45) Date of Patent: Dec. 17, 2024

(54) MEANS AND METHOD FOR PRODUCING AND PURIFYING VIRAL VECTORS

(71) Applicant: Novartis AG, Basel (CH)

(72) Inventors: Brian K. Kaspar, New Albany, OH (US); James Michael Hatfield, Gurnee, IL (US); Joseph Balleydier, Holly Springs, NC (US); Allan Arman Kaspar, Carlsbad, CA (US); Robert Emil Hodge, Libertyville, IL (US)

(73) Assignee: Novartis AG, Basel (CH)

( * ) Notice: Subject to any disclaimer, the term of this patent is extended or adjusted under 35 U.S.C. 154(b) by 266 days.

(21) Appl. No.: 16/761,869

(22) PCT Filed: Nov. 1, 2018

(86) PCT No.: PCT/US2018/058744
§ 371 (c)(1),
(2) Date: May 6, 2020

(87) PCT Pub. No.: WO2019/094253
PCT Pub. Date: May 16, 2019

(65) Prior Publication Data
US 2021/0317474 A1 Oct. 14, 2021

Related U.S. Application Data

(60) Provisional application No. 62/583,035, filed on Nov. 8, 2017.

(51) Int. Cl.
| | | |
|---|---|---|
| C12N 15/86 | (2006.01) | |
| A61K 9/00 | (2006.01) | |
| A61P 25/28 | (2006.01) | |
| C07K 14/47 | (2006.01) | |
| C12N 15/113 | (2010.01) | |
| C12N 15/64 | (2006.01) | |

(52) U.S. Cl.
CPC ............ *C12N 15/86* (2013.01); *A61K 9/0019* (2013.01); *A61P 25/28* (2018.01); *C07K 14/47* (2013.01); *C12N 15/1137* (2013.01); *C12N 15/64* (2013.01); *C12Y 115/01001* (2013.01)

(58) Field of Classification Search
None
See application file for complete search history.

(56) References Cited

U.S. PATENT DOCUMENTS

| | | |
|---|---|---|
| 5,139,941 A | 8/1992 | Muzyczka et al. |
| 5,173,414 A | 12/1992 | Lebkowski et al. |
| 5,173,418 A | 12/1992 | Molin et al. |
| 5,786,211 A | 7/1998 | Johnson |
| 5,871,982 A | 2/1999 | Wilson et al. |
| 6,258,595 B1 | 7/2001 | Gao et al. |
| 6,376,237 B1 | 4/2002 | Colosi |
| 6,756,207 B1 | 6/2004 | Giuliano et al. |
| 7,198,951 B2 | 4/2007 | Gao et al. |
| 7,704,721 B2 | 4/2010 | Wright et al. |
| 8,361,977 B2 | 1/2013 | Baker et al. |
| 8,980,853 B2 | 3/2015 | Bennett et al. |
| 9,415,121 B2 | 8/2016 | Kaspar et al. |
| 10,793,861 B2 | 10/2020 | Kaspar et al. |
| 2005/0053922 A1 | 3/2005 | Schaffer et al. |
| 2009/0202490 A1 | 8/2009 | Schaffer et al. |
| 2012/0177605 A1 | 7/2012 | Kaspar et al. |
| 2013/0072548 A1 | 3/2013 | Wright et al. |
| 2015/0252384 A1 | 9/2015 | Kaspar et al. |
| 2016/0038613 A1 | 2/2016 | Kaspar et al. |
| 2016/0152955 A1 | 6/2016 | Sakamoto et al. |
| 2016/0272976 A1 | 9/2016 | Kaspar et al. |
| 2017/0216458 A1 | 8/2017 | Kaspar et al. |
| 2018/0036431 A1 | 2/2018 | Kaspar et al. |
| 2019/0336618 A1 | 11/2019 | Kaspar |
| 2020/0179467 A1 | 6/2020 | Kaspar et al. |
| 2021/0255185 A1 | 8/2021 | Kaspar et al. |

FOREIGN PATENT DOCUMENTS

| | | |
|---|---|---|
| CN | 105087650 A | 11/2015 |
| EP | 2933335 A1 | 10/2015 |
| EP | 3054006 A1 | 8/2016 |
| WO | WO 95/13365 A1 | 5/1995 |
| WO | WO 95/13392 A1 | 5/1995 |
| WO | WO 96/17947 A1 | 6/1996 |
| WO | WO 97/06243 A1 | 2/1997 |
| WO | WO 97/08298 A1 | 3/1997 |
| WO | WO 97/09441 A2 | 3/1997 |
| WO | WO 97/21825 A1 | 6/1997 |
| WO | WO-9809657 A2 | 3/1998 |
| WO | WO 99/11764 A2 | 3/1999 |
| WO | WO 01/83692 A2 | 11/2001 |
| WO | WO-2004113494 A2 | 12/2004 |
| WO | WO-2005046598 A2 | 5/2005 |
| WO | WO-2010002846 A1 | 1/2010 |

(Continued)

OTHER PUBLICATIONS

Qu et al., Journal of Chromatography B, 990, pp. 15-22 (Year: 2015).*
Amir et al., "Rett syndrome is caused by mutations in X-linked MECP2, encoding methyl-CpG-binding protein 2," Nature Genetics, Oct. 1999, 23:185-188.
Baker, M., "Digital PCR hits its stride," Nature Methods, Jun. 2012, 9(6):541-544.
Boutin et al., "Prevalence of Serum IgG and Neutralizing Factors Against Adeno-Associated Virus (AAV) Types 1, 2, 5, 6, 8, and 9 in the Healthy Population: Implications for Gene Therapy Using AAV Vectors," Human Gene Therapy, 2010, vol. 21, No. 6, 704-712.
Carter, B.J., "Adeno-associated virus vectors," Current Opinion in Biotechnology, 1992, 3(5): 533-539.

(Continued)

*Primary Examiner* — Shanon A. Foley
*Assistant Examiner* — Myron G Hill
(74) *Attorney, Agent, or Firm* — Joshua J. Buchman

(57) ABSTRACT

Methods for preparing and purifying viral particles, and compositions and uses comprising the same, are provided.

54 Claims, 36 Drawing Sheets

Specification includes a Sequence Listing.

(56) References Cited

FOREIGN PATENT DOCUMENTS

| WO | WO 2010/129021 A1 | 11/2010 | |
|---|---|---|---|
| WO | WO-2011079018 A2 | 6/2011 | |
| WO | WO-2011094198 A1 * | 8/2011 | ........... A61K 38/465 |
| WO | WO-2013190059 A1 | 12/2013 | |
| WO | WO-2013192005 A2 | 12/2013 | |
| WO | WO 2014/022582 A1 | 2/2014 | |
| WO | WO 2014/178863 A1 | 11/2014 | |
| WO | WO-2015013148 A2 | 1/2015 | |
| WO | WO 2015/031392 A9 | 3/2015 | |
| WO | WO-2016004319 A1 * | 1/2016 | ............. A61K 35/76 |
| WO | WO-2016100575 A1 | 6/2016 | |
| WO | WO-2016128407 A1 | 8/2016 | |
| WO | WO-2016128408 A1 | 8/2016 | |
| WO | WO 2017/160360 A2 | 9/2017 | |
| WO | WO 2017/173283 A1 | 10/2017 | |
| WO | WO 2017/181113 A1 | 10/2017 | |
| WO | WO-2018055206 A1 | 3/2018 | |
| WO | WO 2019/011817 A1 | 1/2019 | |
| WO | WO 2019/094253 A1 | 5/2019 | |
| WO | WO 2019/236949 A1 | 12/2019 | |

OTHER PUBLICATIONS

Chu et al., "SV40 DNA transfection of cells in suspension: analysis of efficiency of transcription and translation of T-antigen," Gene (1981) 13:197-202.
Clark et al., "A stable cell line carrying adenovirus-inducible rep and cap genes allows for infectivity titration of adeno-associated virus vectors," Gene Therapy (1996) 3:1124-1132.
Crowther et al., "An Adeno-Associated Virus-Based Toolkit for Preferential Targeting and Manipulating Quiescent Neural Stem Cells in the Adult Hippocampus," Stem Cell Reports, Mar. 13, 2018, vol. 10, pp. 1146-1159.
De et al., "High Levels of Persistent Expression of α1-Antitrypsin Mediated by the Nonhuman Primate Serotype rh. 10 Adeno-associated Virus Despite Preexisting Immunity to Common Human Adeno-associated Viruses," Mol. Ther, Jan. 2006, 13(1): 67-76.
Duque et al., "A Large Animal Model of Spinal Muscular Atrophy and Correction of Phenotype," Ann Neurol 2015, 77:399-414.
Eaves et al., "Isolation and Properties of an Exocellular Nuclease of Serratia Marcescens," J. Bact. 1963, 85, 273-278.
Encinas et al., "Gene regulation in adult neural stem cells. Current challenges and possible applications," Advanced Drug Delivery Reviews, 2017, 120: 118-132.
Ebinger et al., "Headache and Backache After Lumbar Puncture in Children and Adolescents: A Prospective Study," Pediatrics, Jun. 2004, 113(6):1588-1592.
Farkas et al., "Multimode light microscopy and the dynamics of molecules, cells, and tissues," Ann. Rev. Physiol. (1993) 55:785-817.
Farrar et al., "Emerging Therapies and Challenges in Spinal Muscular Atrophy," Ann Neurol., 2017, 81: 355-368.
Foust et al., "Rescue of the spinal muscular atrophy phenotype in a mouse model by early postnatal delivery of SMN," Nature Biotechnol., Mar. 2010, 28(3): 271-274, 11 pages provided.
Foust et al., "Therapeutic AAV9-mediated Suppression of Mutant SOD1 Slows Disease Progression and Extends Survival in Models of Inherited ALS," Molecular Therapy, Dec. 2013, vol. 21, No. 12, 2148-2159.
Gao et al., "Clades of Adeno-associated viruses are widely disseminated in human tissues," J. Virol (2004) 78(12): 6381-6388.
GenBank NCBI Reference Sequence AF085716.1, Adeno-associated virus 5 DNA binding trs helicase (Rep22) and capsid protein (VP1) genes, complete cds, Feb. 9, 1999, 3 pages.
GenBank NCBI Reference Sequence AX753246.1, Sequence 1 from Patent EP1310571, Jun. 23, 2003, 2 pages.
GenBank NCBI Reference Sequence AX753249.1, Sequence 4 from Patent EP1310571, Jun. 23, 2003, 2 pages.
GenBank NCBI Reference Sequence NC_001401.2, Adeno-associated virus-2, complete genome, Aug. 13, 2018, 6 pages.
GenBank NCBI Reference Sequence NC_001829.1, Adeno-associated virus-4, complete genome, Aug. 13, 2018, 3 pages.
GenBank NCBI Reference Sequence NC_001862.1, Adeno-associated virus 6, complete genome, Jan. 12, 2004, 3 pages.
GenBank NCBI Reference Sequence NC_002077.1, Adeno-associated virus-1, complete genome, Aug. 13, 2018, 3 pages.
GenBank NCBI Reference Sequence: NM_000344.2, *Homo sapiens* survival of motor neuron 1, telomeric (SMN1), transcript variant d, mRNA, Aug. 10, 2008, 4 pages.
GenBank NCBI Reference Sequence NM_017411.4, *Homo sapiens* survival of motor neuron 2, centromeric (SMN2), transcript variant d, mRNA, Apr. 20, 2021, 5 pages.
Giuliano and Taylor, "Measurement and manipulation of cytoskeletal dynamics in living cells," Curr. Op. Cell Biol., 1995, 7:4-12.
Giuliano et al., "Fluorescent protein biosensors: measurement of molecular dynamics in living cells," Annu. Rev. Biophys. Biomol. Struct. (1995) 24:405-434.
Glanzman et al., "The Children's Hospital of Philadelphia Infant Test of Neuromuscular Disorders (Chop Intend): test development and reliability." Neuromuscular Disorders, Mar. 2010, 20(3):155-161, 11 pages provided.
Graham et al., "A new technique for the assay of infectivity of human adenovirus 5 DNA," Virology, (1973) 52:456-467.
Gurney et al., "Motor neuron degeneration in mice that express a human Cu, Zn superoxide dismutase mutation," Science, Jun. 1994, vol. 264, pp. 1772-1775.
Guy et al., "Reversal of Neurological Defects in a Mouse Model of Rett Syndrome," Science, Feb. 2007, 315(5815): 1143-1147.
Hahn et al., "Patterns of elevated free calcium and calmodulin activation in living cells," Nature (1992) 359:736-738.
Hermens et al., "Purification of Recombinant Adeno-Associated Virus by Iodixanol Gradient Ultracentrifugation Allows Rapid and Reproducible Preparation of Vector Stocks for Gene Transfer in the Nervous System," Human Gene Therapy, Jul. 1999, 10:1885-1891.
Hermonat et al., "Use of adeno-associated virus as a mammalian DNA cloning vector: Transduction of neomycin resistance into mammalian tissue culture cells," PNAS USA, Oct. 1984, 81:6466-6470.
Hildebrandt et al., "Targeting of neural stem cells in the hippocampus of adult rats by custom-made Ad vectors," Brain Struct Funct (2010) 215:105-113.
Jeune et al., "Pre-existing Anti-Adeno-Associated Virus Antibodies as a Challenge in AAV Gene Therapy," Human Gene Therapy Methods, Apr. 2013, 24(2):59-67.
Kaplitt et al., "Safety and tolerability of gene therapy with an adeno-associated virus (AAV) borne GAD gene for Parkinson's disease: an open label, phase I trial" Lancet (2007) 369:2097-2105.
Kiechl-Kohlendorfer et al., "Cerebrospinal Fluid Leakage After Lumbar Puncture in Neonates: Incidence and Sonographic Appearance," American Journal of Roentgenology, 2003, 181: 231-234.
Kotterman et al., "Enhanced selective gene delivery to neural stem cells in vivo by an adeno-associated viral variant," Development (2015) 142: 1885-1892.
Laughlin et al., "Cloning of infectious adeno-associated virus genomes in bacterial plasmids," Gene, 1983, 23:65-73.
Lebkowski et al., "Adeno-Associated Virus: a Vector System for Efficient Introduction and Integration of DNA into a Variety of Mammalian Cell Types," Mol Cell Biol, Oct. 1988, 8(10): 3988-3996.
Lefebvre et al., "Correlation between severity and SMN protein level in spinal muscular atrophy," Nature Genetics, (1997) 16:265-269.
Lefebvre et al., "Identification and Characterization of a Spinal Muscular Atrophy-Determining Gene," Cell, Jan. 1995, 80:155-65.
Levitt et al., "Definition of an efficient synthetic poly(A) site," Genes & Development, 1989, 3:1019-1025.
Lock et al., "Absolute Determination of Single-Stranded and Self-Complementary Adeno-Associated Viral Vector Genome Titers by Droplet Digital PCR," Human Gene Therapy Methods (Apr. 2014) 25(2):115-125.

(56) References Cited

OTHER PUBLICATIONS

Lorson et al., "A single nucleotide in the SMN gene regulates splicing and is responsible for spinal muscular atrophy," PNAS, May 1999, 96: 6307-6311.

Lowes et al., "Impact of Age and Motor Function in a Phase 1/2A Study of Infants With SMA Type 1 Receiving Single-Dose Gene Replacement Therapy," Pediatric Neurology (2019) 98: 39-45.

Marks, Jr., W.J. et al., "Gene delivery of AAV2-neurturin for Parkinson's disease: a double-blind, randomised, controlled trial," Lancet Neurol. (2010) 9:1164-1172.

Matagne et al., "A codon-optimized Mecp2 transgene corrects breathing deficits and improves survival in a mouse model of Rett syndrome," Neurobiology of Disease, 2017, vol. 99, pp. 1-11.

McCarty et al., "Sequences Required for Coordinate Induction of Adeno-Associated Virus p19 and p40 Promoters by Rep Protein," J Virol., Jun. 1991, 65(6):2936-2945.

McLaughlin et al., "Adeno-Associated Virus General Transduction Vectors: Analysis of Proviral Structures," J Virol, Jun. 1988, 62(6):1963-1973.

Mendell et al., "Phase I Gene Transfer Clinical Trial for Spinal Muscular Atrophy Type 1 Delivering avxs-101," Protocol No. AVXS-101-CL-101 (formerly AVXS-101), IND No. 15699, Version 14.0, Apr. 21, 2016, 63 pages.

Mendell et al., "Phase I Gene Transfer clinical trial for spinal muscular atrophy type 1 delivering the survival motor neuron gene by self-complementary AAV9," The Research Institute at Nationwide Children's Hospital Center for Gene Therapy, Protocol Version 1.0, Oct. 5, 2012, 33 pages.

Mendell, J.R., "Phase I Gene Transfer clinical trial for spinal muscular atrophy type 1 delivering the survival motor neuron gene by self-complementary AAV9," The Research Institute at Nationwide Children's Hospital Center for Gene Therapy, IND# 15699, Version 6.2, Apr. 4, 2014, 34 pages.

Mendell et al., "Single-Dose Gene-Replacement Therapy for Spinal Muscular Atrophy," N Engl J Med 2017, 337(18): 1713-1722.

Mendell et al., Supplementary Appendix to Single-Dose Gene-Replacement Therapy for Spinal Muscular Atrophy, N Engl J Med 2017, 337(18): 1713-1722, 4 pages.

Mingozzi et al., "Pharmacological Modulation of Humoral Immunity in a Nonhuman Primate Model of AAV Gene Transfer for Hemophilia B," Mol Ther, Jul. 2012, 20(7):1410-1416.

Monani et al., "A Single Nucleotide Difference That Alters Splicing Patterns Distinguishes the SMA Gene SMN1 From the Copy Gene SMN2," Human Molecular Genetics, 1999, vol. 8, No. 7, 1177-1183.

Monani, U.R., "Spinal Muscular Atrophy: A Deficiency in a Ubiquitous Protein; a Motor Neuron-Specific Disease," Neuron, Dec. 2005, 48: 885-896.

Monteilhet et al., "A 10 Patient Case Report on the Impact of Plasmapheresis Upon Neutralizing Factors Against Adeno-associated Virus (AAV) Types 1, 2, 6, and 8," Mol. Therapy, Nov. 2011, 19(11): 2084-2091.

Mori et al., "Two novel adeno-associated viruses from cynomolgus monkey: pseudotyping characterization of capsid protein," Virology, (2004) 330: 375-383.

Muzyczka, N., "Use of adeno-associated virus as a general transduction vector for mammalian cells," Curr. Top. Microbiol. Immunol (1992) 158:97-129.

Myslinski et al., "An unusually compact external promoter for RNA polymerase III transcription of the human H1RNA gene," Nucleic Acids Research, 2001, 29(12): 2502-2509.

Nestle et al., "An extracellular nuclease from Serratia marcescens. II. Specificity of the enzyme," J. Biol. Chem., Oct. 1969, 244(19), 5219-5225.

Oertle et al., "Nogo-A Inhibits Neurite Outgrowth and Cell Spreading with Three Discrete Regions," The Journal of Neuroscience, Jul. 2003, 23(13): 5393-5406.

Oprea et al., "Plastin 3 is a Protective Modifier of Autosomal Recessive Spinal Muscular Atrophy," Science, Apr. 2008, 320(5875): 524-527, 11 pages provided.

Pacak et al., "Recombinant Adeno-Associated Virus Serotype 9 Leads to Preferential Cardiac Transduction In Vivo," Circ. Res, (2006) 99(4): e3-e9.

Park et al., "Spinal Muscular Atrophy: New and Emerging Insights from Model Mice," Curr Neurol Neurosci Rep., Mar. 2010, 10(2): 108-117, 14 pages provided.

Paul et al., "Increased Viral Titer Through Concentration of Viral Harvests from Retroviral Packaging Lines," Human Gene Therapy, 1993, vol. 4, No. 5, pp. 609-615.

Perrin et al., "An experimental rabies vaccine produced with a new BHK-21 suspension cell culture process: use of serum-free medium and perfusion-reactor system," Vaccine (1995) 13:1244-1250.

Potter et al., "A simplified purification protocol for recombinant adeno-associated virus vectors," Molecular Therapy—Methods & Clinical Development, vol. 1, Jan. 2014, pp. 14034, 8 pages.

Prior et al., "A Positive Modifier of Spinal Muscular Atrophy in the SMN2 Gene," The American Journal of Human Genetics, Sep. 2009, 85, 408-413.

Proll et al., "Potential of label-free detection in high-content-screening applications," Journal of Chromatography, Aug. 2007, 1161(1-2): 2-8.

Qu et al., "Scalable Downstream Strategies for Purification of Recombinant Adeno-Associated Virus Vectors in Light of the Properties," Current Pharmaceutical Biotechnology, 2015, 16(8), 684-695.

Rao et al., "Gene Therapy for Spinal Muscular Atrophy: An Emerging Treatment Option for a Devastating Disease", J Manag Care Spec Pharm, Dec. 2018, 24(12-a Suppl): S3-S16.

Rashnonejad et al., "Large-Scale Production of Adeno-Associated Viral Vector Serotype-9 Carrying the Human Survival Motor Neuron Gene," Mol Biotechnol (2016) 58: 30-36.

Ruffing et al., "Mutations in the carboxy terminus of adeno-associated virus 2 capsid proteins affect viral infectivity: lack of an RGD integrin-binding motif," Journal of General Virology (1994), 75, 3385-3392.

Samulski et al., "Helper-free stocks of recombinant adeno-associated viruses: normal integration does not require viral gene expression," J. Virol, Sep. 1989, 63(9): 3822-3828.

Samulski et al., "Cloning of adeno-associated virus into pBR322: rescue of intact virus from the recombinant plasmid in human cells," Proc. Natl. Acad. Sci. USA (1982), 79(6): 2077-281.

Schmidt et al., "Selective Targeting of Adenoviral Vectors to Neural Precursor Cells in the Hippocampus of Adult Mice: New Prospects for In Situ Gene Therapy," Stem Cells, 2007, 25: 2910-2918.

Senapathy and Carter, "Molecular Cloning of Adeno-associated Virus Variant Genomes and Generation of Infectious Virus by Recombination in Mammalian Cells," J. Biol. Chem., Apr. 1984, 259(7):4661-4666.

Singh et al., "A Multi-Exon-Skipping Detection Assay Reveals Surprising Diversity of Splice Isoforms of Spinal Muscular Atrophy Genes," PLoS ONE, 7(11): e49595, 17 pages.

Srivastava et al., "Nucleotide Sequence and Organization of the Adeno-Associated Virus 2 Genome," J Virol., Feb. 1983, 45(2): 555-564.

Strobel et al., "Comparative Analysis of Cesium Chloride- and Iodixanol-Based Purification of Recombinant Adeno-Associated Viral Vectors for Preclinical Applications," Human Gene Therapy Methods, 26(4):147-157.

Sun et al., "Engineered viral vectors for functional interrogation, deconvolution, and manipulation of neural circuits," Curr. Opin. Neurobiol. 2018, 50: 163-170.

Sykes et al., "Quantitation of targets for PCR by use of limiting dilution," Biotechniques, 1992, 13(3):444-449.

Tomono et al., "Ultracentrifugation-free chromatography-mediated large-scale purification of recombinant adeno-associated virus serotype 1 (rAAV1)," Molecular Therapy—Methods & Clinical Development, (2016) 3:15058, 8 pages.

Tratschin et al., "A Human Parvovirus, Adeno-Associated Virus, as a Eucaryotic Vector: Transient Expression and Encapsidation of the Procaryotic Gene for Chloramphenicol Acetyltransferase," Mol Cell Biol., 1984, 4(10): 2072-2081.

(56) References Cited

OTHER PUBLICATIONS

Tratschin et al., "Adeno-Associated Virus Vector for High-Frequency Integration, Expression, and Rescue of Genes in Mammalian Cells," Mol Cell Biol., Nov. 1985, 5(11): 3251-3260.
UniProt Accession No. Q16637 (SMN_HUMAN), Nov. 1, 1996, 23 pages.
United States Pharmacopeia <787>, Subvisible Particulate Matter in Therapeutic Protein Injections, May 2021, 3 pages.
United States Pharmacopeia <785>, Osmolality and Osmolarity, USP32-NF27 p. 305, Pharmacopeial Forum: vol. No. 34(5) p. 1251, http://www.uspbpep.com/usp32/pub/data/v32270/usp32nf27s0_c785.html, 4 pages.
United States Pharmacopeia <791>, pH, USP29-NF24 p. 2730, Pharmacopeial Forum: vol. No. 29(6) p. 2037, http://www.uspbpep.com/usp29/v29240/usp29nf24s0_c791.html.
Waggoner et al., "Multiparameter fluorescence imaging microscopy: reagents and instruments," Hum. Pathol. (1996) 27:494-502.
Wang et al., "Adeno-associated virus serotype 8 efficiently delivers genes to muscle and heart," Nature Biotech (2005) 23(3): 321-328.
Worgall et al., "Treatment of Late Infantile Neuronal Ceroid Lipofuscinosis by CNS Administration of a Serotype 2 Adeno-Associated Virus Expressing CLN2 cDNA," Human Gene Therapy, May 2008, 19(5):463-474.
Wright et al., "Manufacturing and Regulatory Strategies for Clinical AAV2-hRPE65," Current Gene Therapy, 2010, 10: 341-349.
Wright et al., "Product-Related Impurities in Clinical-Grade Recombinant AAV Vectors: Characterization and Risk Assessment," Biomedicines 2014, 2, 80-97.
AveXis, Inc., AveXis, Inc.'s Initial Response to the Form FDA 483 Issued on Aug. 2, 2019 to the San Diego, CA Quality Control Laboratory, FEI: 3014617030, Investigators: Scott T. Ballard and Mibaly S. Ligmond, dated Aug. 23, 2019, 59 pages.
Department of Health and Human Services, Food and Drug Administration, Form FDA 483, dated Aug. 2, 2019, to the San Diego, CA Quality Control Laboratory, FEI No. 3014617030, 5 pages.
Keown, A., "Kaspar Brothers Impeded Internal Investigation into Data Manipulation, Novartis Claims," BioSpace, Sep. 25, 2019, 6 pages, retrieved from https://www.biospace.com/article/novartis-continues-to-point-its-finger-at-the-kaspar-brothers-over-avexis-data-manipulation/.
Novartis, "Novartis data again demonstrate age-appropriate development when Zolgensma is used presymptomatically, and post-hoc data reveal SMA Type 1 patients could speak, swallow, and maintain airway protection," Mar. 14, 2022, 5 pages.
U.S. Department of Health and Human Services et al., "Q4B Evaluation and Recommendation of Pharmacopoeial Texts for Use in the ICH Regions. Annex 3(R1) Test for Particulate Contamination: Subvisible Particles General Chapter Guidance for Industry," Sep. 2017, 10 pages, retrieved from https://www.fda.gov/media/71231/download.
Clark, K.R. et al., "Highly Purified Recombinant Adeno-Associated Virus Vectors are Biologically Active and Free of Detectable Helper and Wild-Type Viruses," Hum Gene Ther., Apr. 1999, 10(6): 1031-1039.
Embury, C.M., et al., "Cathepsin B Improves β-Amyloidosis and Learning and Memory in Models of Alzheimer's Disease" Journal of Neuroimmune Pharmacology, 2017, vol. 12, pp. 340-352.
Kiyota, T., et al., "AAV2/1 CD74 Gene Transfer Reduces β-amyloidosis and Improves Learning and Memory in a Mouse Model of Alzheimer's Disease," Molecular Therapy, 2015, vol. 23(11), pp. 1712-1721 (10 pages provided).
Robert, M-A., et al., "Manufacturing of recombinant adeno-associated viruses using mammalian expression platforms," Biotechnology Journal, 2017, vol. 12, 1600193, 16 pages.
Schnepp, B. and Clark, K.R., "Highly Purified Recombinant Adeno-Associated Virus Vectors. Preparation and Quantitation," Methods Mol Med., 2002, 69: 427-443.
Miyake and Shimada, "3. Delivery and Expression Series Viral Vector Mediated Gene Delivery and Expression (4)", Nihon Ika Daigaku Igakkai Zasshi, 2012, vol. 8, pp. 150-156 (with English abstract).
Mizutani, Ken'ichi, "Neural Progenitor Cells", Brain Science Dictionary, [Online] Apr. 17, 2017, Internet, retrieved from: https://bsd.neuroinf.jp/w/index.php?title=%E7%A5%9E%E7%B5%8C%E5%89%8D%E9%A7%86%E7%B4%B0%E8%83%9E&oldid=37640 (with English machine translation), 15 pages.
Day, et al., Onasemnogene abeparvovec gene therapy for symptomatic infantile-onset spinal muscular atrophy in patients with two copies of SMN2 (STR1VE): an open-label, single-arm, multicentre, phase 3 trial, Lancet Neurology, 20, 284-293, Apr. 2021.
Novartis Gene Therapies: gMAP Program Updates after Jan. 9, 2023, downloaded from https://www.sma-europe.eu/news/novartis-gene-therapies-g-map-programme-updates-after-9-january-2023.

* cited by examiner pSMN map pAAV2/9 map

| Step / Notebook Page | Date | Details | | | | Notes |
|---|---|---|---|---|---|---|
| Thaw Page 3 | 7/22/2015 | Flasks seeded | 25 | Old Passage | 0 | Cells were not counted, but full vial from ATCC ($1\times10^6$ cells) were plated. Four media changes between this step and the next. |
| | | Seeding Density | $1\times10^6$ cells | New Passage | 1* | |
| Passage Page 5 | 7/27/2015 | Flasks seeded | 75 | Old Passage | 1 | Cells before splitting were 95% confluent. Adherence selection step after seeding lead to significant portion of non-adherent cells lost; ~35% cell loss by visual inspection. |
| | | Seeding Density | 1:1 | New Passage | 2 | |
| Passage Page 7 | 7/29/2015 | Flasks seeded | 75 | Old Passage | 2 | Adherence selection step included after seeding. |
| | | Seeding Density | 1:1 | New Passage | 3 | |
| Passage Page 8 | 7/31/2015 | Flasks seeded | 2 x 175 | Old Passage | 3 | Adherence selection step included after seeding, with much less pronounced loss of cells by visual inspection. |
| | | Seeding Density | 1:4.7 | New Passage | 4 | |
| Passage Page 9 | 8/3/2015 | Flasks seeded | 8 x 175 | Old Passage | 4 | One media change between this step and the next. |
| | | Seeding Density | 1:4 | New Passage | 5 | |
| Passage Page 10 | 8/6/2015 | Flasks seeded | 20 x 175 | Old Passage | 5 | One media change between this step and the next. |
| | | Seeding Density | 1:3 or 1:2 | New Passage | 6 | |
| Harvest/ Cryo-preservation Pages 11-15 | 8/9/2015 | Cell Concentration | $1\times10^7$ cells/mL | Vials Filled | 22 | Pooled 2 cell suspensions to yield $1\times10^8$ cells and $1.2\times10^8$ cells. |

Note: All Total Cells reported above have the unit of "cells" and indicate total cells recovered.
All Seeding Densities reported above have the unit of "cells/cm$^2$"
All flask sizes reported above have the unit of "cm$^2$".
All Cell Concentrations reported above have the unit of "cells/mL".
* Thawing was considered a passage, thus thawed cells were labeled as "passage 1".

8,000 cells/cm² , D5 Trans, D9 Harvest

| | Volume | Titer | Total vg | Step Recovery | Total Recovery |
|---|---|---|---|---|---|
| Lysate Pool | 3200 | 4.06E+10 | 1.30E+14 | | |
| post C0HC + 0.45 | 4000 | 3.68E+10 | 1.47E+14 | 113% | 113% |
| TFF1 UF Retentate | 400 | 2.96E+11 | 1.18E+14 | 80% | 91% |
| TFF1 DF Retentate | 580 | 2.14E+11 | 1.24E+14 | 105% | 96% |
| TFF1 UF Permeate | 3600 | <4E8 | 1.44E+12 | 1% | |

12,000 cells/cm², D4 Trans, D8 Harvest

| | Volume | Titer | Total vg | Step Recovery | Total Recovery |
|---|---|---|---|---|---|
| | 3200 | 6.25E+10 | 2.00E+14 | | |
| | 4000 | 4.73E+10 | 1.89E+14 | 95% | 95% |
| | 400 | 4.30E+11 | 1.72E+14 | 91% | 86% |
| | 502 | 3.64E+11 | 1.83E+14 | 106% | 91% |
| | 3600 | <4.0E8 | 1.44E+12 | 1% | |

Figure 12B

8,000 cells/cm², D5 Transfect, D9 Harvest

| | Volume | ug/mL | Total HCP ug | HCP Step Clearance | Total HCP Clearance |
|---|---|---|---|---|---|
| Lysate Pool | 3200 | 67.52 | 216065 | | |
| post C0HC + 0.45 | 4000 | 49.47 | 197862 | 8.4% | 8.42% |
| TFF1 UF Retentate | 400 | 170.90 | 68358 | 65.5% | 68.36% |
| TFF1 DF Retentate | 580 | 52.17 | 30261 | 55.7% | 86% |
| TFF1 UF Permeate | 3600 | 29.50 | 106186 | 54% | |

12,000 cells/cm², D4 Transfect, D8 Harvest

| | Volume | ug/mL | Total HCP ug | HCP Step Clearance | Total HCP Clearance |
|---|---|---|---|---|---|
| | 3200 | 58.38 | 186813 | | |
| | 4000 | 35.25 | 140988 | 24.5% | 24.53% |
| | 400 | 120.09 | 48036 | 65.9% | 74.29% |
| | 502 | 17.48 | 8775 | 81.7% | 95% |
| | 3600 | 26.69 | 96080.4 | 68% | |

| Test Description | Test Method | Proposed Test Limit | NCH Phase 1 Lot NCHAAV9SMN0613 Date Manufactured: 18-Dec-2013 Test Date: 13-Feb-2017 to 08-Aug-2017 [1] | AVXS-101 Lot 600156 Date Manufactured: 07-Nov-2017 Test Date: 08-Nov-2017 to 26-Dec-2017 | AVXS-101 Lot 600307 Date Manufactured: 04-Dec-2017 Test Date: 05-Dec-2017 to 30-Jan-2017 |
|---|---|---|---|---|---|
| Genomic Titer by ddPCR | SOP-137 | $2.0 \times 10^{13} - 6.0 \times 10^{13}$ vg/mL | $1.1 \times 10^{13}$ vg/mL (n=9) [1] | $3.7 \times 10^{13}$ vg/mL (n=9) [2] | $4.0 \times 10^{13}$ vg/mL (n=14) [2] |
| Infectious Titer | SOP-192 | Report Results | $5.9 \times 10^{9}$ IU/mL [3] | $1.3 \times 10^{10}$ IU/mL [3] | $6.7 \times 10^{9}$ IU/mL [3] |
| Subvisible Particles | SOP-262 | ≤6000 particles/cont ≥ 10 μm; ≤600 particles/cont ≥ 25 μm | 22 particles/cont ≥ 10 μm; 4 particles/cont ≥ 25 μm | 119 particles/cont ≥ 10 μm; 4 particles/cont ≥ 25 μm | 9 particles/cont ≥ 10 μm; 2 particles/cont ≥ 25 μm |
| pH | SOP-057 | 7.5 – 8.5 | 7.9 | 7.9 | 8.0 |
| Osmolality | SOP-128 | 384 – 448 mOsm/kg | 410 mOsm/kg | 415 mOsm/kg | 410 mOsm/kg |
| Appearance by Visual Inspection | SOP-164 | Clear to slightly opaque, colorless to faint white solution, free of visible particulates | Clear and colorless solution, free of visible particles | Faint white, slightly opaque, free of visible particles [4] | Colorless, slightly opaque, free of visible particles |
| Total Protein by BCA | SOP-184 | $128 – 320$ μg/mL per $1.0 \times 10^{13}$ vg/mL | 167 μg/mL [3] (177 μg/mL) [5] | 179 μg/mL [3] (661 μg/mL) [5] | 176 μg/mL [3] (702 μg/mL) [5] |
| Residual hcDNA by qPCR | SOP-190 | $\leq 1.2 \times 10^{6}$ pg/mL per $1.0 \times 10^{13}$ vg/mL | $3.7 \times 10^{5}$ pg/mL [3] ($3.9 \times 10^{5}$ pg/mL) [5] | $0.76 \times 10^{5}$ pg/mL [3] ($2.8 \times 10^{5}$ pg/mL) [5] | $0.68 \times 10^{5}$ pg/mL [3] ($2.72 \times 10^{5}$ pg/mL) [5] |
| % Empty Capsid by AUC | SOP-263 | ≤ 7% | 7% | 2% | 4% |
| Vector ID by SDSPAGE | SOP-180 | Main Bands of VP1, VP2, VP3 co-migrate with AVXS-101 control | Main Bands of VP1, VP2, VP3 co-migrate with AVXS-101 control. Main Band MWs: VP1: 84.9–89.5 kDa; VP2: 65.9–69.1 kDa; VP3: 57.1–59.0 kDa | Main Bands of VP1, VP2, VP3 co-migrate with AVXS-101 control. Main Band MWs: VP1: 83.6–84.4; VP2: 64.6–65.5; VP3: 56.2–57.2 | Main Bands of VP1, VP2, VP3 co-migrate with AVXS-101 control. Main Band MWs: VP1: 82.9–84.9; VP2: 64.3–65.2; VP3: 56.0–56.7 |
| Purity by SDS-PAGE | SOP-180 | % Total Purity (VP1, VP2, VP3): ≥ 95% | % Total Purity: 98% (Avg n=4 gels) | % Total Purity: 99% (Avg, n=4 gels) | % Total Purity: 99% (Avg, n=4 gels) |

Figure 17A

| Test Description | Test Method | Proposed Test Limit | NCH Phase 1 Lot NCHAAV9SMN0613 Date Manufactured: 18-Dec-2013 Test Date: 13-Feb-2017 to 08-Aug-2017 [1] | AVXS-101 Lot 600156 Date Manufactured: 07-Nov-2017 Test Date: 08-Nov-2017 to 26-Dec-2017 | AVXS-101 Lot 600307 Date Manufactured: 04-Dec-2017 Test Date: 05-Dec-2017 to 30-Jan-2017 |
|---|---|---|---|---|---|
| Total Impurities by SDS-PAGE | SOP-180 | % Total Impurities ≤5%<br><br>No single un-named impurity >2%<br><br>Named Impurities:<br>Report value<br><br>– Imp 1A (~71-73 kDa)<br>– Imp 1 (~61-67 kDa)<br>– Imp 2 (~56-64 kDa)<br>– Imp 3 (~48-58 kDa)<br>– Imp 4 (~33-38 kDa)<br>– Imp 5 (~30-34 kDa) | % Total Impurities: 2% (Avg n=4 gels)<br><br>Individual Impurities (Avg n=4 gels)<br>– Imp 1: 1.5%<br>– Imp 3: <LOQ (1.0%) | % Total Impurities: 1% (Avg n=4 gels)<br><br>Individual Impurities (Avg n=4 gels)<br>– Imp 1: <LOQ (1.0%)<br>– Imp 3: <LOQ (1.0%)<br>– Imp 4: <LOQ (1.0%) | % Total Impurities: 1% (Avg n=4 gels)<br><br>Individual Impurities (Avg n=4 gels)<br>– Imp 1: 1.0%<br>– Imp 4: <LOQ (1.0%) |
| Vector Identity by Western | SOP-179 | Positive for AAV Capsid Protein | Positive for AAV Capsid Protein<br><br>Main Band MW<br>VP1: 79.7 kDa<br>VP2: 64.1 kDa<br>VP3: 55.7 kDa | Positive for AAV Capsid Protein<br><br>Main Band MW<br>VP1: 80.2 kDa<br>VP2: 66.2 kDa<br>VP3: 58.2 kDa | Positive for AAV Capsid Protein<br><br>Main Band MW<br>VP1: 79.1 kDa<br>VP2: 64.8 kDa<br>VP3: 57.5 kDa |
| Residual HCP by ELISA | SOP-183 | ≤40 ng/mL per $1.0 \times 10^{13}$ vg/mL | <LOQ (8 ng/mL) [5] | <LOQ (8 ng/mL) [5] | <LOQ (8 ng/mL) [5] |
| Vector Genome Identity by ddPCR | SOP-137 | Confirms | Confirms | Confirms | Confirms |
| Residual BSA by ELISA | SOP-181 | ≤3.0 ng/mL per $1.0 \times 10^{13}$ vg/mL | <LOQ (0.50 ng/mL) [5] | <LOQ (0.50 ng/mL) [5] | <LOQ (0.50 ng/mL) [5] |
| Residual Benzonase by ELISA | SOP-182 | ≤1.0 ng/mL per $1.0 \times 10^{13}$ vg/mL | <LOQ (0.20 ng/mL) [5] | <LOQ (0.20 ng/mL) [5] | <LOQ (0.20 ng/mL) [5] |
| In-vivo Relative Potency | SOP-285 | 80 – 120% | 100% [6] | | |

Figure 17B

[1] NCH Phase 1 Lot AAV9SMN0613 was manufactured prior to the current "Proposed Test Limit" for genomic titer by ddPCR. Genomic titer value for this lot was re-established in August 2017 using improved SOP-137 (v3).

[2] Differences in Genomic Titer results between Process A and Process B lots are due to different manufacturing target concentrations. Lot NCH AAV9SMN0613 was originally formulated a lower target titer concentration now determined to be $1.1 \times 10^{13}$ vg/mL by the currently used ddPCR assay (SOP-137), while AVXS-101 Lots 600156 and 600307 were formulated with a target titer concentration of $4.0 \times 10^{13}$ vg/mL when measured by the same method (SOP-137).

[3] Adjusted result per $1.0 \times 10^{13}$ vg/mL to enable appropriate specifications across range of acceptable concentrations from $2.0 \times 10^{13}$ vg/mL to $6.0 \times 10^{13}$ vg/mL. Actual values have been multiplied by the following factors to provide values per $1.0 \times 10^{13}$ vg/mL: 1/1.06 (Lot NCH AAV9SMN0613), 1/3.7 (Lot 600156) and 1/4.0 (Lot 600307).

[4] Differences in appearance results between Process A and Process B are due to different vector concentrations (genomic titer). Lot NCH AAV9SMN0613 has a significantly lower vector concentration than the Process B lots. As a result, Lot NCH AAV9SMN0613 is more dilute leading to a more clear and colorless solution while the colorless to white and slightly opaque observations for Process B lots results from a close to 4 times concentration of viral particles in solution per mL.

[5] Actual result not adjusted to $1.0 \times 10^{13}$ vg/mL because results are below LOQ of the respective methods.

[6] Lot NCHAAV9SMN0613 is designated as the initial potency Reference Standard for SOP-285 with an assigned potency value of 100%. All results generated using SOP-285 v5.

Figure 17B (cont.)

| Test Description | Proposed Test Limits | Pair Wise Comparison | | |
|---|---|---|---|---|
| | | Process A (Phase 1) | Process B (Phase 3) | Relative %Difference |
| Genomic Titer by ddPCR | $2.0 \times 10^{13} - 6.0 \times 10^{13}$ vg/mL | $1.1 \times 10^{13}$ vg/mL | $3.7 \times 10^{13}$ vg/mL | NA [1] |
| Infectious Titer | Report Results | $0.59 \times 10^{10}$ IU/mL | $1.3 \times 10^{10}$ IU/mL | 120% [2] |
| Subvisible Particles ≥ 10 μm | ≤ 6000 particles/cont ≥ 10 μm | 22 | 119 | 441% [3] |
| Subvisible Particles ≥ 25 μm | ≤ 600 particles/cont ≥ 25 μm | 4 | 4 | 0% |
| pH | 7.5 – 8.5 | 7.9 | 7.9 | 0% |
| Osmolality | 384 – 448 mOsm/kg | 410 mOsm/kg | 415 mOsm/kg | 1% |
| Appearance | Clear to slightly opaque, colorless to faint white solution, free of visible particulates | Clear and colorless solution, free of visible particles | Faint white, slightly opaque, free of visible particles | NA |
| Total Protein by BCA | 128 – 320 μg/mL per $1.0 \times 10^{13}$ vg/mL | 167 μg/mL | 179 μg/mL | 7% |
| Residual hcDNA by qPCR | ≤ $1.2 \times 10^{6}$ pg/mL per $1.0 \times 10^{13}$ vg/mL | $3.7 \times 10^{5}$ pg/mL | $0.76 \times 10^{5}$ pg/mL | 80% |
| % Empty Capsid by AUC | ≤ 7% | 7% | 2% | 71% [4] |
| Purity by SDS-PAGE | ≥ 95% | 98% | 99% | 1% |
| Total Impurities by SDS-PAGE | ≤ 5% | 2% | 1% | 50% |
| Residual HCP by ELISA | ≤ 40 ng/mL per $1.0 \times 10^{13}$ vg/mL | < LOQ (8 ng/mL) | < LOQ (8 ng/mL) | 0% |
| Residual BSA by ELISA | ≤ 3.0 ng/mL per $1.0 \times 10^{13}$ vg/mL | < LOQ (0.50 ng/mL) | < LOQ (0.50 ng/mL) | 0% |
| Residual Benzonase by ELISA | ≤ 1.0 ng/mL per $1.0 \times 10^{13}$ vg/mL | < LOQ (0.20 ng/mL) | < LOQ (0.20 ng/mL) | 0% |
| In-vivo Relative Potency | 80 – 120% | 100% | | |

[1] Relative % difference not applicable as the manufacturing target for genomic titer was changed between Process A and Process B.

[2] This value should be viewed in the context of expected variability for a biological assay which can often vary between 50% to 200% of the true value. That being said, AveXis recognized the need for improvement and has recently performed additional development and qualification work to improve this assay (SOP-328 and RPT-471). It should also be noted that infectivity efficiency of the HeLa RC32 cell line by AAV9-based viral vectors remains challenging.

[3] Considerable relative % difference for subvisible particles between Process A and Process B is noted; however, the absolute value for Process B is well below the proposed testing limits.

[4] Process B using CsCl gradient is more effective in removing empty capsids when compared to Process A which used iodixanol.

Figure 18

| Test Description | Proposed Test Limits | Pair Wise Comparison | | |
|---|---|---|---|---|
| | | Process B (600156) | Process B (600307) | Relative %Difference |
| Genomic Titer by ddPCR | $2.0 \times 10^{13} - 6.0 \times 10^{13}$ vg/mL | $3.7 \times 10^{13}$ vg/mL | $4.0 \times 10^{13}$ vg/mL | 8% |
| Infectious Titer | Report Results | $1.3 \times 10^{10}$ IU/mL | $0.67 \times 10^{10}$ IU/mL | 48% |
| Subvisible Particles $\geq 10$ μm | $\leq 6000$ particles/cont $\geq 10$ μm | 119 | 9 | 92% [1] |
| Subvisible Particles $\geq 25$ μm | $\leq 600$ particles/cont $\geq 25$ μm | 4 | 2 | 50% |
| pH | 7.5 – 8.5 | 7.9 | 8.0 | 1% |
| Osmolality | 384 – 448 mOsm/kg | 415 mOsm/kg | 410 mOsm/kg | 1% |
| Appearance | Clear to slightly opaque, colorless to faint white solution, free of visible particulates | Faint white, slightly opaque, free of visible particles | Colorless, slightly opaque, free of visible particles | NA |
| Total Protein by BCA | 128 – 320 μg/mL per $1.0 \times 10^{13}$ vg/mL | 179 μg/mL | 176 μg/mL | 2% |
| Residual hcDNA by qPCR | $\leq 1.2 \times 10^{6}$ pg/mL per $1.0 \times 10^{13}$ vg/mL | $0.76 \times 10^{5}$ pg/mL | $0.68 \times 10^{5}$ pg/mL | 11% |
| % Empty Capsid by AUC | $\leq 7\%$ | 2% | 4% | 100% [1] |
| Purity by SDS-PAGE | $\geq 95\%$ | 99% | 99% | 0% |
| Total Impurities by SDS-PAGE | $\leq 5\%$ | 1% | 1% | 0% |
| Residual HCP by ELISA | $\leq 40$ ng/mL per $1.0 \times 10^{13}$ vg/mL | < LOQ (8 ng/mL) | < LOQ (8 ng/mL) | 0% |
| Residual BSA by ELISA | $\leq 3.0$ ng/mL per $1.0 \times 10^{13}$ vg/mL | < LOQ (0.50 ng/mL) | < LOQ (0.50 ng/mL) | 0% |
| Residual Benzonase by ELISA | $\leq 1.0$ ng/mL per $1.0 \times 10^{13}$ vg/mL | < LOQ (0.20 ng/mL) | < LOQ (0.20 ng/mL) | 0% |
| In-vivo Relative Potency | 80 – 120% | | | |

[1] Relative % difference for subvisible particles and % Empty Capsid is ~100% between the two Process B lots; however, all values are well below the proposed testing limits and the Process B lots are considered to be consistent with regards to these test results.

Figure 19

| Attribute | Method | Stability Time-point (mos) | | | | |
|---|---|---|---|---|---|---|
| | | 0 | 3 | 6 | 9 | 12 |
| | | February 2017 | May 2017 | August 2017 | November 2017 | February 2018 |
| Genomic Titer by ddPCR | SOP-137 v1.0 | $6.6 \times 10^{12}$ vg/mL | $6.1 \times 10^{12}$ vg/mL | $6.5 \times 10^{12}$ vg/mL | NA | NA |
| | SOP-137 v3.0 | N/A | N/A | $1.1 \times 10^{13}$ vg/mL [1] | $8.7 \times 10^{12}$ vg/mL | Target 26Feb18 |
| In vivo Relative Potency [2] | SOP-285 | 100% | | | | Pending |
| Infectious Titer | SOP-192 | $6.3 \times 10^{9}$ IU/mL | $8.4 \times 10^{9}$ IU/mL [3] | $1.1 \times 10^{10}$ IU/mL | $6.3 \times 10^{9}$ IU/mL | Pending |
| Purity by SDS-PAGE | SOP-180 | %Total Purity: 98% (n=4 gels)<br><br>%Total Impurities: 2% (n=4 gels)<br><br>Individual Impurities:<br>Imp 1: 1.7%<br>Imp 3: <LOQ (1.0%) | % Total Purity: 98% (n=4 gels)<br><br>%Total Impurities: 2% (n=4 gels)<br><br>Individual Impurities:<br>Imp 1: 1.7% | % Total Purity: 99% (n=4 gels)<br><br>%Total Impurities: 1% (n=4 gels)<br><br>Individual Impurities:<br>Imp 1: 1.2% | % Total Purity: 99% (Avg n=4 gels)<br><br>%Total Impurities: 1% (Avg n=4 gels)<br><br>Individual Impurities:<br>Imp 1: 1.3% | Pending |

[1] Lot was re-tested using an improved method, SOP-137 v3.0, per CAPA-19 around the 6-mo timepoint. As a result, a new titer value of $1.1 \times 10^{13}$ vg/mL was re-assigned for NCH Lot NCHAAV9SMN0613. All subsequent stability time-points were analyzed using SOP-137 v3.0.

[2] Lot NCHAAV9SMN0613 was manufactured in December 2013 and was tested on February 2017 as T0. A 100% potency was assigned at T0 and the potencies for all subsequent time points were calculated relative to the T0 value.

[3] Infectious Titer testing was performed approximately 4 months from $T_0$ as it was added to the respective stability protocol on June 2017.

Figure 20

| NCHAAV SMN0613 | Empty Peak | | | Full Peak 1 | | | Full Peak 2 | | |
|---|---|---|---|---|---|---|---|---|---|
| | s-value | %area | MW (MDa) | s-value | %area | MW (MDa) | s-value | %area | MW (MDa) |
| Rep 1 (red) | 62.58 | 8.53 | 1.97 | 85.23 | 47.76 | 3.11 | 101.76 | 37.20 | 4.01 |
| Rep 2 (blue) | 62.50 | 8.39 | 2.36 | 85.33 | 49.14 | 3.77 | 101.94 | 39.36 | 4.85 |
| Avg | 62.54 | 8.46 | 2.17 | 85.28 | 48.45 | 3.44 | 101.85 | 38.28 | 4.43 |

| 600156 | Empty Peak | | | Full Peak 1 | | | Full Peak 2 | | |
|---|---|---|---|---|---|---|---|---|---|
| | s-value | %area | MW (MDa) | s-value | %area | MW (MDa) | s-value | %area | MW (MDa) |
| Rep 1 (red) | 61.80 | 1.29 | 2.77 | 86.74 | 54.23 | 4.62 | 104.12 | 43.72 | 6.06 |
| Rep 2 (blue) | 55.52 | 1.83 | 2.97 | 85.89 | 54.95 | 5.55 | 102.86 | 41.80 | 7.31 |
| Avg | 58.66 | 1.56 | 2.87 | 86.32 | 54.59 | 5.09 | 103.49 | 42.76 | 6.69 |

SEQUENCE LISTING

<160> NUMBER OF SEQ ID NOS: 4

<210> SEQ ID NO 1
<211> LENGTH: 2359
<212> TYPE: DNA
<213> ORGANISM: Artificial
<220> FEATURE:
<223> OTHER INFORMATION: vector construct

<400> SEQUENCE: 1

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggaatt cacgcgtgga     120
tctgaattca attcacgcgt ggtacctctg gtcgttacat aacttacggt aaatggcccg     180
cctggctgac cgcccaacga ccccgccca ttgacgtcaa taatgacgta tgttcccata      240
gtaacgccaa tagggacttt ccattgacgt caatgggtgg agtatttacg gtaaactgcc     300
cacttggcag tacatcaagt gtatcatatg ccaagtacgc cccctattga cgtcaatgac     360
ggtaaatggc ccgcctggca ttatgcccag tacatgacct tatgggactt tcctacttgg     420
cagtacatct actcgaggcc acgttctgct tcactctccc catctccccc cctccccac      480 ccccaatttt gtatttattt atttttaat tattttgtgc agcgatgggg gcggggggg      540 ggggggggcg cgcgccaggc ggggcggggc ggggcgaggg gcggggcggg gcgaggcgga     600
gaggtgcggc ggcagccaat cagagcggcg cgctccgaaa gtttcctttt atggcgaggc    660
ggcggcggcg gcggccctat aaaaagcgaa gcgcgcggcg ggcgggagcg ggatcagcca     720
ccgcggtggc ggcctagagt cgacgaggaa ctgaaaaacc agaaagttaa ctggtaagtt     780
tagtcttttt gtcttttatt tcaggtcccg gatccggtgg tggtgcaaat caaagaactg     840
ctcctcagtg gatgttgcct ttacttctag gcctgtacgg aagtgttact tctgctctaa     900
aagctgcgga attgtacccg cggccgatcc accggtccgg aattcccggg atatcgtcga     960
cccacgcgtc cgggccccac gctgcgcacc cgcgggtttg ctatggcgat gagcagcggc    1020
ggcagtggtg gcggcgtccc ggagcaggag gattccgtgc tgttccggcg cggcacaggc    1080
cagagcgatg attctgacat ttgggatgat acagcactga taaaagcata tgataaagct    1140
gtggcttcat ttaagcatgc tctaaagaat ggtgacattt gtgaacttc gggtaaacca     1200 aaaccacac ctaaaagaaa acctgctaag aagaataaaa gccaaaagaa gaatactgca     1260
gcttccttac aacagtggaa agttggggac aaatgttctg ccatttggtc agaagacggt     1320
tgcatttacc cagctaccat tgcttcaatt gattttaaga gagaaacctg tgttgtggtt     1380
tacactggat atggaaatag agaggagcaa aatctgtccg atctactttc cccaatctgt     1440
gaagtagcta ataatataga acagaatgct caagagaatg aaaatgaaag ccaagtttca     1500
```

```
acagatgaaa gtgagaactc caggtctcct ggaaataaat cagataacat caagcccaaa    1560
tctgctccat ggaactcttt tctccctcca ccacccccca tgccagggcc aagactggga    1620
ccaggaaagc caggtctaaa attcaatggc ccaccaccgc caccgccacc accaccaccc    1680
cacttactat catgctggct gcctccattt ccttctggac caccaataat tcccccacca    1740
cctcccatat gtccagattc tcttgatgat gctgatgctt tgggaagtat gttaatttca    1800
tggtacatga gtggctatca tactggctat tatatgggtt ttagacaaaa tcaaaaagaa    1860
ggaaggtgct cacattcctt aaattaagga gaaatgctgg catagagcag cactaaatga    1920
caccactaaa gaaacgatca gacagatcta gaaagcttat cgataccgtc gactagagct    1980
cgctgatcag cctcgactgt gccttctagt tgccagccat ctgttgtttg ccctccccc     2040 gtgccttcct tgaccctgga aggtgccact cccactgtcc tttcctaata aaatgaggaa    2100
attgcatcgc attgtctgag taggtgtcat tctattctgg ggggtggggt ggggcaggac    2160 agcaagggg aggattggga agacaatagc aggcatgctg gggagagatc gatctgagga    2220
acccctagtg atggagttgg ccactccctc tctgcgcgct cgctcgctca ctgaggccgg    2280
gcgaccaaag gtcgcccgac gcccgggctt tgcccgggcg gcctcagtga gcgagcgagc    2340
gcgcagagag ggagtggcc                                                 2359
```

<210> SEQ ID NO 2
<211> LENGTH: 294
<212> TYPE: PRT
<213> ORGANISM: Homo sapiens

<400> SEQUENCE: 2

```
Met Ala Met Ser Ser Gly Gly Ser Gly Gly Gly Val Pro Glu Gln Glu
1               5                   10                  15

Asp Ser Val Leu Phe Arg Arg Gly Thr Gly Gln Ser Asp Asp Ser Asp
            20                  25                  30

Ile Trp Asp Asp Thr Ala Leu Ile Lys Ala Tyr Asp Lys Ala Val Ala
        35                  40                  45

Ser Phe Lys His Ala Leu Lys Asn Gly Asp Ile Cys Glu Thr Ser Gly
    50                  55                  60

Lys Pro Lys Thr Thr Pro Lys Arg Lys Pro Ala Lys Lys Asn Lys Ser
65                  70                  75                  80

Gln Lys Lys Asn Thr Ala Ala Ser Leu Gln Gln Trp Lys Val Gly Asp
                85                  90                  95

Lys Cys Ser Ala Ile Trp Ser Glu Asp Gly Cys Ile Tyr Pro Ala Thr
            100                 105                 110

Ile Ala Ser Ile Asp Phe Lys Arg Glu Thr Cys Val Val Val Tyr Thr
        115                 120                 125

Gly Tyr Gly Asn Arg Glu Glu Gln Asn Leu Ser Asp Leu Leu Ser Pro
    130                 135                 140

Ile Cys Glu Val Ala Asn Asn Ile Glu Gln Asn Ala Gln Glu Asn Glu
145                 150                 155                 160

Asn Glu Ser Gln Val Ser Thr Asp Glu Ser Glu Asn Ser Arg Ser Pro
                165                 170                 175

Gly Asn Lys Ser Asp Asn Ile Lys Pro Lys Ser Ala Pro Trp Asn Ser
            180                 185                 190

Phe Leu Pro Pro Pro Pro Met Pro Gly Pro Arg Leu Gly Pro Gly
        195                 200                 205

Lys Pro Gly Leu Lys Phe Asn Gly Pro Pro Pro Pro Pro Pro
    210                 215                 220
```

```
Pro Pro His Leu Leu Ser Cys Trp Leu Pro Pro Phe Pro Ser Gly Pro
225                 230                 235                 240

Pro Ile Ile Pro Pro Pro Pro Ile Cys Pro Asp Ser Leu Asp Asp
            245                 250                 255

Ala Asp Ala Leu Gly Ser Met Leu Ile Ser Trp Tyr Met Ser Gly Tyr
            260                 265                 270

His Thr Gly Tyr Tyr Met Gly Phe Arg Gln Asn Gln Lys Glu Gly Arg
            275                 280                 285

Cys Ser His Ser Leu Asn
        290

<210> SEQ ID NO 3
<211> LENGTH: 736
<212> TYPE: PRT
<213> ORGANISM: Adeno-associated virus 9

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
            85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
            165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
```

-continued

```
            290                 295                 300
Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                    325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
                355                 360                 365

Ala Asp Val Phe Met Ile Pro Gln Tyr Gly Tyr Leu Thr Leu Asn Asp
        370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                    405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                    645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720
```

Tyr Ser Glu Pro Arg Pro Ile Gly Thr Arg Tyr Leu Thr Arg Asn Leu
            725                 730                 735

<210> SEQ ID NO 4
<211> LENGTH: 1621
<212> TYPE: DNA
<213> ORGANISM: Homo sapiens

<400> SEQUENCE: 4

```
ccacaaatgt gggagggcga taaccactcg tagaaagcgt gagaagttac tacaagcggt      60
cctcccggcc accgtactgt tccgctccca gaagccccgg gcggcggaag tcgtcactct     120
taagaaggga cggggcccca cgctgcgcac ccgcgggttt gctatggcga tgagcagcgg     180
cggcagtggt ggcggcgtcc cggagcagga ggattccgtg ctgttccggc gcggcacagg     240
ccagagcgat gattctgaca tttgggatga tacagcactg ataaaagcat atgataaagc     300
tgtggcttca tttaagcatg ctctaaagaa tggtgacatt tgtgaaactt cgggtaaacc     360
aaaaaccaca cctaaaagaa aacctgctaa gaagaataaa agccaaaaga agaatactgc     420
agcttcctta caacagtgga aagttgggga caaatgttct gccatttggt cagaagacgg     480
ttgcatttac ccagctacca ttgcttcaat tgattttaag agagaaacct gtgttgtggt     540
ttacactgga tatggaaata gagaggagca aaatctgtcc gatctacttt ccccaatctg     600
tgaagtagct aataatatag aacagaatgc tcaagagaat gaaaatgaaa gccaagtttc     660
aacagatgaa agtgagaact ccaggtctcc tggaaataaa tcagataaca tcaagcccaa     720
atctgctcca tggaactctt ttctccctcc accaccccc atgccagggc caagactggg     780
accaggaaag ccaggtctaa aattcaatgg cccaccaccg ccaccgccac caccaccacc     840
ccacttacta tcatgctggc tgcctccatt tccttctgga ccaccaataa ttcccccacc     900
acctcccata tgtccagatt ctcttgatga tgctgatgct ttgggaagta tgttaatttc     960
atggtacatg agtggctatc atactggcta ttatatgggt ttcagacaaa atcaaaaaga    1020
aggaaggtgc tcacattcct taaattaagg agaaatgctg gcatagagca gcactaaatg    1080
acaccactaa agaaacgatc agacagatct ggaatgtgaa gcgttataga agataactgg    1140
cctcatttct tcaaaatatc aagtgttggg aaagaaaaaa ggaagtggaa tgggtaactc    1200
ttcttgatta aaagttatgt aataaccaaa tgcaatgtga atatttttac tggactcttt    1260
tgaaaaacca tctgtaaaag actggggtgg gggtgggagg ccagcacggt ggtgaggcag    1320
ttgagaaaat ttgaatgtgg attagatttt gaatgatatt ggataattat tggtaatttt    1380
atggcctgtg agaagggtgt tgtagtttat aaaagactgt cttaatttgc atacttaagc    1440
atttaggaat gaagtgttag agtgtcttaa aatgtttcaa atggtttaac aaaatgtatg    1500
tgaggcgtat gtggcaaaat gttacagaat ctaactggtg gacatggctg ttcattgtac    1560
tgttttttc tatcttctat atgtttaaaa gtatataata aaaatattta atttttttt     1620
a                                                                   1621
```

MEANS AND METHOD FOR PRODUCING AND PURIFYING VIRAL VECTORS

RELATED APPLICATIONS

This application is a U.S. National Phase Application, filed under 35 USC § 371, of International Application No. PCT/US2018/058744, filed Nov. 1, 2018 which claims priority to U.S. provisional patent application No. 62/583,035, filed Nov. 8, 2017, the contents of each of which are incorporated by reference herein in their entirety.

SEQUENCE LISTING

The instant application contains a Sequence Listing which has been submitted in ASCII format via EFS-WEB and is hereby incorporated by reference in its entirety. Said ASCII copy, created on May 3, 2020 is named AVEX-003N01US_SeqList.txt and is 14,698 bytes in size.

FIELD OF THE DISCLOSURE

This disclosure relates to methods for preparing and purifying viral particles and compositions and uses comprising the same.

BACKGROUND

Adeno-associated virus (AAV) is a member of the parvoviridae family. The AAV genome is composed of a linear single-stranded DNA molecule which contains approximately 4.7 kilobases (kb) and consists of two major open reading frames encoding the non-structural Rep (replication) and structural Cap (capsid) proteins. Flanking the AAV coding regions are two cis-acting inverted terminal repeat (ITR) sequences, approximately 145 nucleotides in length, with interrupted palindromic sequences that can fold into hairpin structures that function as primers during initiation of DNA replication. In addition to their role in DNA replication, the ITR sequences have been shown to be necessary for viral integration, rescue from the host genome, and encapsidation of viral nucleic acid into mature virions (Muzyczka, (1992) Curr. Top. Micro. Immunol. 158:97-129).

Multiple serotypes of AAV exist and offer varied tissue tropism. Known serotypes include, for example, AAV1, AAV2, AAV3, AAV4, AAV5, AAV6, AAV7, AAV8, AAV9, AAV10 and AAV11. AAV9 is described in U.S. Pat. No. 7,198,951 and in Gao et al., J. Virol., 78: 6381-6388 (2004), which are hereby incorporated by reference in their entirety. Advances in the delivery of AAV6 and AAV8 have made possible the transduction by these serotypes of skeletal and cardiac muscle following simple systemic intravenous or intraperitoneal injections. See Pacak et al., Circ. Res., 99(4): 3-9 (2006) and Wang et al., Nature Biotech. 23(3): 321-8 (2005). The use of AAV to target cell types within the central nervous system, though, has required surgical intraparenchymal injection. See Kaplitt et al., "Safety and tolerability of gene therapy with an adeno-associated virus (AAV) borne GAD gene for Parkinson's disease: an open label, phase I trial." *Lancet*, 369:2097-2105; Marks et al., "Gene delivery of AAV2-neurturin for Parkinson's disease: a double-blind, randomized, controlled trial." Lancet Neurol 9:11164-1172; and Worgall et al., "Treatment of late infantile neuronal ceroid lipofuscinosis by CNS administration of a serotype 2 adeno-associated virus expressing CLN2 cDNA." Hum Gene Ther, 19(5):463-74.

The nucleotide sequence of the AAV serotype 2 (AAV2) genome is presented in Srivastava et al., J Virol, 45: 555-564 (1983) as corrected by Ruffing et al., J Gen Virol, 75: 3385-3392 (1994). Cis-acting sequences directing viral DNA replication (rep), encapsidation/packaging and host cell chromosome integration are contained within the ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, Current Topics in Microbiology and Immunology, 158: 97-129 (1992).

Vectors derived from AAV are particularly attractive for delivering genetic material because (i) they are able to infect (transduce) a wide variety of non-dividing and dividing cell types including muscle fibers and neurons; (ii) they are devoid of the virus structural genes, thereby eliminating the natural host cell responses to virus infection, e.g., interferon-mediated responses; (iii) wild-type viruses have never been associated with any pathology in humans; (iv) in contrast to wild type AAVs, which are capable of integrating into the host cell genome, replication-deficient AAV vectors generally persist as episomes, thus limiting the risk of insertional mutagenesis or activation of oncogenes; and (v) in contrast to other vector systems, AAV vectors do not trigger a significant immune response (see ii), thus granting long-term expression of the therapeutic transgenes (provided their gene products are not rejected).

Self-complementary adeno-associated vectors (scAAV) are viral vectors engineered from the naturally occurring adeno-associated virus (AAV) for use in gene therapy. ScAAV is termed "self-complementary" because the coding region has been designed to form an intramolecular double-stranded DNA template. A rate-limiting step for the standard AAV genome life cycle involves the second-strand synthesis since the typical AAV genome is a single-stranded DNA template. However, this is not the case for scAAV genomes. Upon infection, rather than waiting for cell mediated synthesis of the second strand, the two complementary halves of scAAV will associate to form one double stranded DNA (dsDNA) unit that is ready for immediate replication and transcription.

There remains a need to develop a scalable method to manufacture and purify an AAV pharmaceutical product with, for example, low empty capsids, low host cell protein, and/or low contaminating DNA, while retaining high potency.

SUMMARY

The present disclosure provides a method to prepare purified viral particle preparations, including AAV particle preparations.

In some embodiments, the present disclosure provides a pharmaceutical composition comprising (a) between $1-8 \times 10^{13}$ AAV9 viral vector genomes/mL (vg/mL), (b) less than about 7% empty viral capsids, (c) less than about 100 ng/mL host cell protein per $1\times10^{13}$ vg/mL, and (d) less than about $5\times10^6$ pg/mL residual host cell DNA per $1\times10^{13}$ vg/mL, and wherein at least about 80% of the $1-8\times10^{13}$ AAV9 viral vector genomes/mL are functional. In one embodiment, the AAV9 viral vector comprises a polynucleotide encoding a survival motor neuron (SMN) protein. In one embodiment, the AAV9 viral vector comprises a polynucleotide encoding a methyl-CpG-binding protein 2 (MECP2) protein. In one embodiment, the AAV9 viral vector comprises a polynucleotide encoding a short hairpin RNA (shRNA) targeting superoxide dismutase 1 (SOD1). In one embodiment, the AAV9 viral vector comprises a modified AAV2 ITR, a chicken beta-actin (CB) promoter, a cytomegalovirus (CMV) immediate/early enhancer, a modified SV40 late 16 s intron, a bovine growth hormone (BGH) polyadenylation signal, and an unmodified AAV2 ITR.

The present disclosure provides a pharmaceutical formulation. In some embodiments, the aqueous pharmaceutical formulation comprises (a) an AAV9 viral vector comprising a polynucleotide encoding a survival motor neuron (SMN) protein, (b) a Tris buffer, (c) magnesium chloride, (d) sodium chloride, and (e) a poloxamer (e.g., poloxamer 188), wherein the pharmaceutical composition does not comprise a preservative. In one embodiment of the formulation, the AAV9 viral vector further comprises a modified AAV2 ITR, a chicken beta-actin (CB) promoter, a cytomegalovirus (CMV) immediate/early enhancer, a modified SV40 late 16 s intron, a Bovine growth hormone (BGH) polyadenylation signal, and an unmodified AAV2 ITR. In one embodiment of the formulation, the Tris buffer concentration is about 10-30 nM, e.g., about 20 mM. In one embodiment, the pH of the formulation is about 7.7 to about 8.3, e.g., about pH 8.0 (e.g., as measured by USP <791> (incorporated by reference in its entirety)). In one embodiment of the formulation, the magnesium chloride concentration is about 0.5-1.5 mM, e,g, about 1 mM. In one embodiment of the formulation, the sodium chloride concentration is about 100-300 mM, e.g., about 200 mM. In one embodiment, the formulation comprises about 0.005% w/v poloxamer 188.

Another aspect of the disclosure is directed to a method of treating type I spinal muscular atrophy (SMA) in a patient in need thereof, comprising administering an AAV9 viral vector comprising a polynucleotide encoding a SMN protein (e.g., a composition or formulation as disclosed herein) to the patient by an intrathecal or intravenous route, wherein the patient is (a) nine months old or younger, (b) has a body weight of at least about 2.6 kg, (c) has bi-allelic SMN1 null mutations or deletions, and (d) has at least one functional copy of SMN2. In one embodiment, the AAV9 viral vector comprises a modified AAV2 ITR, a chicken beta-actin (CB) promoter, a cytomegalovirus (CMV) immediate/early enhancer, a modified SV40 late 16 s intron, a Bovine growth hormone (BGH) polyadenylation signal, and an unmodified AAV2 ITR. In an embodiment, the patient has a body weight of no more than about 8.5 kg. In one embodiment, the patient does not have a c.859G>C substitution in exon 7 of at least one copy of the SMN2 gene. In an embodiment, the treatment is administered to the patient before the age of 6 months. In an embodiment, the treatment is administered to the patient before the onset of one or more SMA symptoms selected from hypotonia, delay in motor skills, poor head control, round shoulder posture and hypermobility of joints. In one embodiment, the patient has anti-AAV9 antibody titers at or below 1:100 as determined by an ELISA binding immunoassay prior to administration.

Also disclosed herein is a method of treating a pediatric patient with spinal muscular atrophy (SMA) Type I, with or without disease onset, comprising administering to the patient a composition or formulation comprising an adeno-associated virus (AAV) vector as disclosed herein.

The present disclosure is also directed to a method of treating Rett Syndrome in a patient in need thereof, comprising administering an AAV9 viral vector comprising a polynucleotide encoding a methyl-CpG-binding protein 2 (MECP2) protein to the patient by an intrathecal or intravenous route.

The present disclosure is also directed to a method of treating amyotrophic lateral sclerosis (ALS) in a patient in need thereof, comprising administering an AAV9 viral vector comprising a polynucleotide encoding a short hairpin RNA (shRNA) targeting superoxide dismutase 1 (SOD1) to the patient by an intrathecal or intravenous route.

Another aspect of the disclosure is directed to a method of treating a patient suffering from type I SMA, comprising the steps of (a) determining the weight of the patient, (b) obtaining a kit containing vials of an AAV9 viral vector pharmaceutical composition, and (c) administering the AAV9 viral vector from the vials to the patient, wherein the viral vector concentration in each vial is about $2.0\times10^{13}$ vg/mL, wherein the AAV9 viral vector comprises a polynucleotide encoding a SMN protein; and wherein the kit comprises the following number of vials:

| Patient Weight (kg) | 5.5 ± 0.4 mL vial | 8.3 ± 0.4 mL vial | Total Vials Per Kit |
|---|---|---|---|
| 2.6-3.0 | 0 | 2 | 2 |
| 3.1-3.5 | 2 | 1 | 3 |
| 3.6-4.0 | 1 | 2 | 3 |
| 4.1-4.5 | 0 | 3 | 3 |
| 4.6-5.0 | 2 | 2 | 4 |
| 5.1-5.5 | 1 | 3 | 4 |
| 5.6-6.0 | 0 | 4 | 4 |
| 6.1-6.5 | 2 | 3 | 5 |
| 6.6-7.0 | 1 | 4 | 5 |
| 7.1-7.5 | 0 | 5 | 5 |
| 7.6-8.0 | 2 | 4 | 6 |
| 8.1-8.5 | 1 | 5 | 6 |

In one embodiment, the kit comprises an AAV9 viral vector comprising a mutated AAV2 ITR, a chicken beta-actin (CB) promoter, a cytomegalovirus (CMV) immediate/early enhancer, a modified SV40 late 16 s intron, a Bovine growth hormone (BGH) polyadenylation signal, and an AAV2 ITR. In one embodiment, the AAV viral vector is administered by infusion at a dose of about $1.0\times10^{14}$-$2.5\times10^{14}$ vg/kg.

Another aspect of this disclosure is directed to a kit for treating a patient suffering from type I spinal muscular atrophy (SMA) comprising vials containing the composition AAV9 viral vector comprises a polynucleotide encoding a survival motor neuron (SMN) protein or the formulation comprising (a) an AAV9 viral vector comprising a polynucleotide encoding a survival motor neuron (SMN) protein, (b) a Tris buffer, (c) magnesium chloride, (d) sodium chloride, and (e) a poloxamer (e.g., poloxamer 188).

Another aspect of this disclosure is directed to a kit comprising vials containing about 5.5 mL or about 8.3 mL of an AAV9 viral vector comprising a polynucleotide encoding a survival motor neuron (SMN) protein, and formulated at a concentration of about $2.0\times10^{13}$ vg/mL in 20 mM Tris, 1 mM $MgCl_2$, 200 mM NaCl, 0.005% w/v Poloxamer 188 at pH 7.7-8.3, e.g., about 8.0.

Another aspect of this disclosure is directed to a method of treating type I SMA, comprising administering a volume of the composition the composition AAV9 viral vector comprises a polynucleotide encoding a survival motor neuron (SMN) protein or the formulation comprising (a) an AAV9 viral vector comprising a polynucleotide encoding a survival motor neuron (SMN) protein, (b) a Tris buffer, (c) magnesium chloride, (d) sodium chloride, and (e) a poloxamer (e.g., poloxamer 188) by intravenous infusion to a patient in need thereof.

Another aspect of this disclosure is directed to methods of manufacturing of an AAV viral vector. In one embodiment, a method of manufacturing an AAV viral vector comprises the steps of (a) culturing adherent cells, (b) transfecting the adherent cells with plasmid(s) to enable production of the AAV viral vector, (c) lysing the adherent cells to isolate the AAV viral vector, (d) acidifying and clarifying the cell lysate of (c), (e) purifying the product of (d) using cation exchange chromatography (CEX), (f) filtering the product of (e) using tangential flow filtration (TFF), (g) ultracentrifuging the product of (f) in a cesium chloride (CsCl) buffer; and (h) collecting the AAV viral vectors from the product of (g).

Another aspect of this disclosure is directed to a method of purifying an AAV viral vector from a cell culture lysate, comprising the steps of (a) acidifying and clarifying the cell lysate, (b) purifying the product of (a) using cation exchange chromatography (CEX), (c) filtering the product of (b) through a tangential flow filtration, (d) ultracentrifuging the product of (c) using a 2-4 M cesium chloride (CsCl) buffer, (e) collecting the AAV viral vectors from the product of (d), (f) filtering the product of (e) through a tangential flow filtration. In an embodiment, the method is performed at industrial scale. In an embodiment, the method produces a yield of more than $5 \times 10^{15}$ vg, or more than $8 \times 10^{15}$ vg or more than $1 \times 10^{16}$ vg per manufacturing batch.

Another aspect of this disclosure is directed to a method of treating a patient having SMA Type 1 by administering an AAV9 viral vector comprising a polynucleotide encoding a SMN protein as prepared according to any of the methods disclosed herein.

Another aspect of this disclosure is directed to a method of treating a patient having Rett Syndrome by administering an AAV9 viral vector comprising a polynucleotide encoding an MECP2 protein as prepared according to any of the methods herein.

Another aspect of this disclosure is directed to a method of treating a patient having ALS by administering an AAV9 viral vector comprising a polynucleotide encoding an shRNA targeting SOD1 as prepared according to according to any of the methods herein.

Another aspect of this disclosure is directed to an AAV9 viral vector comprising a polynucleotide encoding a SMN protein, manufactured according to any of the methods herein. Another aspect of this disclosure is directed to a pharmaceutical composition comprising an AAV9 viral vector comprising a polynucleotide encoding a SMN protein, manufactured according to any of the methods herein.

Another aspect of this disclosure is directed to an aqueous pharmaceutical composition comprising an AAV9 viral vector comprising a polynucleotide encoding a SMN protein, a Tris buffer, a magnesium chloride solution, and a sodium chloride solution, wherein the pharmaceutical composition does not comprise a preservative, and wherein the composition is manufactured according to any of the methods herein.

Another aspect of this disclosure is directed to an AAV9 viral vector comprising a polynucleotide encoding an MECP2 protein, manufactured according to any of the methods herein.

Another aspect of this disclosure is directed to a pharmaceutical composition comprising an AAV9 viral vector comprising a polynucleotide encoding an MECP2 protein, manufactured according to any of the methods herein.

Another aspect of this disclosure is directed to an AAV9 viral vector comprising a polynucleotide encoding an shRNA targeting SOD1, manufactured according to any of the methods herein.

Another aspect of this disclosure is directed to method of treating Type I SMA in a patient in need thereof by intravenously administering a pharmaceutical composition comprising (a) a self-complementary AAV9 viral vector comprising a modified AAV2 ITR, a chicken beta-actin (CB) promoter, a cytomegalovirus (CMV) immediate/early enhancer, a modified SV40 late 16 s intron, a bovine growth hormone (BGH) polyadenylation signal, and an unmodified AAV2 ITR, (b) 20 mM Tris at pH 8.0, (c) 1 mM $MgCl_2$, (d) 200 mM NaCl, and (e) 0.005% Poloxamer 188, wherein the patient has a body weight of 2.6 kg to 8.5 kg. In one embodiment, the composition does not comprise a preservative.

In one embodiment, the patient is (a) is nine months old or younger, (b) has a body weight of at least about 2.6 kg, (c) has bi-allelic SMN1 null mutations or deletions, and (d) has at least one functional copy of SMN2.

Another aspect of this disclosure is directed to a composition suitable or manufactured for intravenously administering a pharmaceutical composition comprising (a) a self-complementary AAV9 viral vector comprising a modified AAV2 ITR, a chicken beta-actin (CB) promoter, a cytomegalovirus (CMV) immediate/early enhancer, a modified SV40 late 16 s intron, a bovine growth hormone (BGH) polyadenylation signal, and an unmodified AAV2 ITR, (b) 20 mM Tris at pH 8.0, (c) 1 mM $MgCl_2$, (d) 200 mM NaCl, and (e) 0.005% Poloxamer 188.

In some embodiments, disclosed herein is a composition or formulation, wherein the composition or formulation comprises at least one of the following: (a) less than about 0.09 ng of benzonase per $1.0 \times 10^{13}$ vg, (b) less than about 30 μg/g (ppm) of cesium, (c) about 20-80 ppm of Poloxamer 188, (d) less than about 0.22 ng of BSA per $1.0 \times 10^{13}$ vg, (e) less than about $6.8 \times 10^5$ pg of residual plasmid DNA per $1.0 \times 10^{13}$ vg, (f) less than about $1.1 \times 10^5$ pg of residual hcDNA per $1.0 \times 10^{13}$ vg, and (g) less than about 4 ng of rHCP per $1.0 \times 10^{13}$ vg, In some embodiments, the present disclosure provides an upstream process to produce an intermediate (e.g., frozen intermediate) derived from a working cell bank, wherein the upstream process comprises the steps of (a) culturing cells, (b) transfecting the cultured cells with plasmids (e.g., three plasmids), (c) harvesting the expanded viral particles from the cells after a culture period, (d) purifying the viral particles via filtration to remove any intact cells or cellular debris, (e) subjecting the eluent from step (d) to tangential flow filtration, and (g) optionally freezing the resultant intermediate preparation of purified viral particles. In some embodiments, the upstream process is combined with further processing steps, particular. g., further purification and formulations steps to produce a final pharmaceutical product.

In one embodiment, the working cell bank comprises HEK293 cells. In other embodiments, another cell type or derivative that is available in the art and is suitable for use in the methods disclosure herein is used.

In one embodiment, the transfecting step utilizes polyethyleneimine. In one embodiment, the transfecting step comprises a triple vector transfection using a transgene plasmid, e.g., pSMN, a pAAV plasmid and a pHELP plasmid.

In one embodiment, the process further comprises lysing the transfected cells with lysis buffer and surfactant.

In one embodiment, the harvesting step includes treating the product with an endonuclease, such as benzonase, for example, at a concentration between 50-200 U/ml, e.g., at a concentration between 75-150 U/ml, to reduce residual host cell DNA.

In one embodiment, the purifying step includes depth filtration and subsequent filtration through a filter that removes large molecule contaminants and cell debris, for example a 0.45 micron filter, but that permits vector genomes to pass therethrough. Any suitable depth filter may be used.

In one embodiment, the tangential flow filtration ("TFF") achieves between 5-15×, e.g., 6-10× concentration of the eluent of step (d) and at least 4 diavolumes, e.g., 6 diavolumes diafiltration or 10 diavolumes, or 12 diavolumes, or 15 diavolumes diafiltration. Any suitable TFF filter may be used. In an embodiment, the TFF membrane is a cellulose membrane. In an embodiment the TFF membrane has a 300 kDa cutoff.

Second, the present disclosure provides a downstream process to process the intermediate (e.g., the frozen intermediate) to a filtered drug substance. The downstream process steps include an acidification and clarification step (using filtration), followed by cation exchange chromatography, tangential flow filtration, CsCl ultracentrifugation and a further tangential flow filtration step to produce a filtered drug substance where the purified AAV particles are suspended in a pharmaceutically acceptable carrier.

In one embodiment, the acidification and clarification step includes depth filtration and subsequent filtration through a filter that removes large molecule contaminants and cell debris, for example a 0.45 micron filter. In some embodiments, the pH adjustment is controlled. As part of this step, in one embodiment, a detergent, for example Tween, is added. In some embodiments, the rate of Tween addition and the concentration range of Tween is controlled.

In one embodiment, the cation exchange chromatography comprises a membrane-based chromatography resin using a composite sulfonyl resin with a 0.2 micron pore size.

In one embodiment, the Cesium Chloride (CsCl) ultracentrifugation step uses between 2-4 M CsCl, e.g., about 3 M CsCl.

In another embodiment, the CsCl ultracentrifugation step is performed at about 40-50 kRPM for about 20-25 hrs. In another embodiment, the CsCl ultracentrifugation step is performed at about 45 kRPM for about 22 hrs.

In one embodiment, the tangential flow filtration ("TFF") achieves between 5-15×, e.g., 6-10× concentration of the eluent of step (d) and at least 4 diavolumes, e.g., 6 diavolumes diafiltration or 10 diavolumes, or 12 diavolumes, or 15 diavolumes diafiltration. In an embodiment, the TFF membrane has a 300 kDa cutoff.

In one embodiment, the eluent is below the level of detection of Cesium (Cs). In another embodiment, the level of detection of Cs is below 50 per million (ppm). In another embodiment, the level of detection of Cs is about 50-70 ppm. In another embodiment, the level of detection of Cs is about 70-90 parts per million (ppm). In another embodiment, the level of detection of Cs is about 90-110 parts per million (ppm). In another embodiment, the level of detection of Cs is about 110-130 parts per million (ppm). In another embodiment, the level of detection of Cs is about 130-150 parts per million (ppm). In another embodiment, the level of detection of Cs is less than 150 parts per million (ppm).

These purification methods can be used to prepare high yield viral preparations, including AAV preparations (e.g., AAV9-SMN), that comprise less than $5 \times 10^6$ pg/ml residual host cell DNA (hcDNA) per $1 \times 10^{13}$ vector genomes ("vg")/ml, e.g., less than $1.2 \times 10^6$ pg/mL hcDNA per $1 \times 10^{13}$ vg/mL. Thus, a 5 kg patient receiving $7.5 \times 10^{15}$ vg would get no more than up to $1.2 \times 10^6$ pg/mL*$7.5 \times 10^{15}$ vg/($1 \times 10^{13}$ vg/mL)=$8.4 \times 10^7$ pg hcDNA=84,000 ng hcDNA per 5 kg dose. In one embodiment, a preparation comprises less than $5.0 \times 10^5$ pg residual host cell DNA per $1.0 \times 10^{13}$ vg, less than $2.0 \times 10^5$ pg residual host cell DNA per $1.0 \times 10^{13}$ vg, less than $1.1 \times 10^5$ pg residual host cell DNA per $1.0 \times 10^{13}$ vg, less than $1.0 \times 10^5$ pg residual host cell DNA per $1.0 \times 10^{13}$ vg, less than $0.9 \times 10^5$ pg residual host cell DNA per $1.0 \times 10^{13}$ vg, less than $0.8 \times 10^5$ pg residual host cell DNA per $1.0 \times 10^{13}$ vg, or any concentration in between.

In one embodiment, the AAV is a replication defective AAV9, e.g., scAAV9, with AAV2-derived ITRs. In another embodiment, the AAV vector carries an SMN transgene. In an embodiment, the SMN-coding DNA is set out in GenBank Accession Number NM_000344.2. Conservative nucleotide substitutions of SMN DNA are also contemplated (e.g., a guanine to adenine change at position 625, as set forth in GenBank Accession Number NM_000344.2).

Another aspect of the disclosure is directed to a pharmaceutical composition comprising AAV particles in a formulation suitable for either (a) intravenous ("IV") injection or (b) intrathecal ("IT") administration.

In another embodiment, the pharmaceutical composition has less than 10% empty capsids, less than 8% empty capsids, less than 7% empty capsids, less than 5% empty capsids, less than 3% empty capsids, or less than 1% empty capsids. In some embodiments, the pharmaceutical composition has less than about 5% empty capsids. In one embodiment, the number of empty capsids is below the limit of detection. In some embodiments, it is advantageous for the pharmaceutical composition to have low amounts of empty capsids, because those empty capsids may generate an adverse response (e.g., immune response, inflammatory response, liver response, and/or cardiac response) with no therapeutic benefit.

In another embodiment, the residual host cell protein ("rHCP") in said pharmaceutical composition is less than or equal to 100 ng/ml rHCP per $1 \times 10^{13}$ vg/ml, e.g., less than or equal to 40 ng/ml rHCP per $1 \times 10^{13}$ vg/ml or 1-50 ng/ml rHCP per $1 \times 10^{13}$ vg/ml. In one embodiment, a pharmaceutical composition disclosed herein comprises less than 10 ng rHCP per $1.0 \times 10^{13}$ vg, or less than 5 ng rHCP per $1.0 \times 10^{13}$ vg, less than 4 ng rHCP per $1.0 \times 10^{13}$ vg, or less than 3 ng rHCP per $1.0 \times 10^{13}$ vg, or any concentration in between.

In another embodiment, the residual host cell DNA ("hcDNA") in said pharmaceutical composition is less than or equal to $5 \times 10^6$ pg/ml hcDNA per $1 \times 10^{13}$ vg/ml, less than or equal to $1.2 \times 10^6$ pg/ml rHDNA per $1 \times 10^{13}$ vg/ml, or $1 \times 10^5$ pg/ml rHDNA per $1 \times 10^{13}$ vg/ml to $1.2 \times 10^6$ pg/ml per $1 \times 10^{13}$ vg/ml. In one embodiment, the residual host cell DNA in said pharmaceutical composition is less than $5.0 \times 10^5$ pg per $1.0 \times 10^{13}$ vg, less than $2.0 \times 10^5$ pg per $1.0 \times 10^{13}$ vg, less than $1.1 \times 10^5$ pg per $1.0 \times 10^{13}$ vg, less than $1.0 \times 10^5$ pg hcDNA per $1.0 \times 10^{13}$ vg, less than $0.9 \times 10^5$ pg hcDNA per $1.0 \times 10^{13}$ vg, less than $0.8 \times 10^5$ pg hcDNA per $1.0 \times 10^{13}$ vg, or any concentration in between.

In an embodiment, the residual plasmid DNA in said pharmaceutical composition is less than or equal to $1.7 \times 10^6$ pg/ml per $1 \times 10^{13}$ vg/ml, or $1 \times 10^5$ pg/ml per $1 \times 10^{13}$ vg/ml to $1.7 \times 10^6$ pg/ml per $1 \times 10^{13}$ vg/ml. In one embodiment, the residual plasmid DNA in said pharmaceutical composition is less than $10.0 \times 10^5$ pg per $1.0 \times 10^{13}$ vg, less than $8.0 \times 10^5$ pg per $1.0 \times 10^{13}$ vg, or less than $6.8 \times 10^5$ pg per $1.0 \times 10^{13}$ vg.

In an embodiment, a pharmaceutical composition disclosed herein comprises less than 0.5 ng per $1.0 \times 10^{13}$ vg, less than 0.3 ng per $1.0 \times 10^{13}$ vg, less than 0.22 ng per $1.0 \times 10^{13}$ vg, or less than 0.2 ng per $1.0 \times 10^{13}$ vg, or any concentration in between of bovine serum albumin (BSA). In one embodiment, the benzonase in said pharmaceutical composition is less than 0.2 ng per $1.0 \times 10^{13}$ vg, less than 0.1 ng per $1.0 \times 10^{13}$ vg, less than 0.09 ng per $1.0 \times 10^{13}$ vg, less than 0.08 ng per $1.0 \times 10^{13}$ vg or any concentration in between. In one embodiment, the Poloxamer 188 in said pharmaceutical composition is about 10-150 ppm, about 15-100 ppm, or about 20-80 ppm. In one embodiment, the cesium in said pharmaceutical composition is less than 50 µg/g (ppm), less than 30 µg/g (ppm) or less than 20 µg/g (ppm), or any concentration in between.

In an embodiment, a pharmaceutical composition disclosed herein comprises total impurities, e.g., as determined by SDS-PAGE, of less than 10%, less than 8%, less than 7%, less than 6%, less than 5%, less than 4%, less than 3%, less than 2%, or any percentage in between. In one embodiment, the total purity, e.g., as determined by SDS-PAGE, is greater than 90%, greater than 92%, greater than 93%, greater than 94%, greater than 95%, greater than 96%, greater than 97%, greater than 98%, or any percentage in between. In one embodiment of the pharmaceutical composition, no single unnamed related impurity, e.g., as measured by SDS-PAGE, is greater than 5%, greater than 4%, greater than 3% or greater than 2%, or any percentage in between. In one embodiment, the pharmaceutical composition comprises a percentage of filled capsids relative to total capsids (e.g., peak 1+peak 2 as measured by analytical ultracentrifugation) of greater than 85%, greater than 86%, greater than 87%, greater than 88%, greater than 89%, greater than 90%, greater than 91%, greater than 91.9%, greater than 92%, greater than 93%, or any percentage in between. In one embodiment of the pharmaceutical composition, the percentage of filled capsids measured in peak 1 by analytical ultracentrifugation is 20-80%, 25-75%, 30-75%, 35-75%, or 37.4-70.3%. In one embodiment of the pharmaceutical composition, the percentage of filled capsids measured in peak 2 by analytical ultracentrifugation is 20-80%, 20-70%, 22-65%, 24-62%, or 24.9-60.1%.

In one embodiment, a pharmaceutical composition disclosed herein comprises a genomic titer of $1.0-5.0 \times 10^{13}$ vg/mL, $1.2-3.0 \times 10^{13}$ vg/mL or $1.7-2.3 \times 10^{13}$ vg/mL.

In one embodiment, a pharmaceutical composition disclosed herein exhibits a bioburden of less than 5 CFU/mL, less than 4 CFU/mL less than 3 CFU/mL, less than 2 CFU/mL, or less than 1 CFU/mL, or any concentration in between. In one embodiment, the amount of endotoxin in accordance with USP, e.g. USP <85> (incorporated by reference in its entirety) is less than 1.0 EU/mL, less than 0.8 EU/mL or less than 0.75 EU/mL.

In one embodiment, the osmolality of a pharmaceutical composition disclosed herein in accordance with USP, e.g. USP <785> (incorporated by reference in its entirety) is 350-450 mOsm/kg, 370-440 mOsm/kg or 390-430 mOsm/kg. In one embodiment, the pharmaceutical composition contains fewer than 1200 particles that are greater than 25 µm per container, fewer than 1000 particles that are greater than 25 µm per container, fewer than 600 particles that are greater than 25 µm per container, fewer than 500 particles that are greater than 25 µm per container, or any value in between. In one embodiment, the pharmaceutical composition contains fewer than 10000 particles that are greater than 10 µm per container, fewer than 8000 particles that are greater than 10 µm per container, or fewer than 6000 particles that are greater than 10 µm per container.

In one embodiment, the pharmaceutical composition has a genomic titer of $0.5-5.0 \times 10^{13}$ vg/mL, $1.0-4.0 \times 10^{13}$ vg/mL, $1.5-3.0 \times 10^{13}$ vg/mL or $1.7-2.3 \times 10^{13}$ vg/mL.

In one embodiment, a pharmaceutical composition disclosed herein comprises one or more of the following: less than about 0.09 ng of benzonase per $1.0 \times 10^{13}$ vg, less than about 30 µg/g (ppm) of cesium, about 20-80 ppm of Poloxamer 188, less than about 0.22 ng of BSA per $1.0 \times 10^{13}$ vg, less than about $6.8 \times 10^5$ pg of residual plasmid DNA per $1.0 \times 10^{13}$ vg, less than about $1.1 \times 10^5$ pg of residual hcDNA per $1.0 \times 10^{13}$ vg, less than about 4 ng of rHCP per $1.0 \times 10^{13}$ vg, pH 7.7-8.3, about 390-430 mOsm/kg, less than about 600 particles that are ≥25 µm in size per container, less than about 6000 particles that are ≥10 µm in size per container, about $1.7 \times 10^{13}$-$2.3 \times 10^{13}$ vg/mL genomic titer, infectious titer of about $3.9 \times 10^8$-$8.4 \times 10^{10}$ IU per $1.0 \times 10^{13}$ vg, total protein of about 100-300 µs per $1.0 \times 10^{13}$ vg, median survival of ≥24 days of Δ7SMA mice with about $7.5 \times 10^{13}$ vg/kg dose of viral vector, about 70-130% relative potency based on a in vitro cell-based assay, and/or less than about 5% empty capsid. In various embodiments, the pharmaceutical compositions disclosed herein comprising any of the viral particles discussed herein (e.g., AAV SMN, AAV MECP2, or AAV SOD1 viral particles), retain a potency of between ±20%, between ±15%, between ±10%, or between ±5%, of a reference standard. In some embodiments, potency is measured using a suitable in vitro cellular assay or in vivo animal model. For example, the potency or % functional AAV SMN viral particles may be determined using an animal model of SMA, e.g., the SMAΔ7 mouse, or a quantitative cell-based assay using a suitable cell line, e.g., primary neural progenitor cells (NPCs) isolated from the cortex of SMAΔ7 mice. In one embodiment, the potency is assessed as against a reference standard using the methods in Foust et al., Nat. Biotechnol., 28(3), pp. 271-274 (2010). Any suitable reference standard may be used. The potency or % functional AAV MeCP2 may be assayed using a suitable in vitro cellular assay or in vivo animal model, e.g., an Mecp2 knockout mouse as in Guy et al., "Reversal of neurological defects in a mouse model of Rett syndrome." Science, 315(5815):1143-7. The potency or % functional AAV SOD1 may be assayed using a suitable in vitro cellular assay or in vivo animal model, e.g., a SOD1 mutant mouse as in Gurney et al., "Motor neuron degeneration in mice that express a human Cu,Zn superoxide dismutase mutation." Science, 264(5166):1772-5. In one embodiment, the pharmaceutical composition has an in vivo potency as determined by median survival in an SMAΔ7 mouse given a $7.5 \times 10^{13}$ vg/kg dose of greater than 15 days, greater than 20 days, greater than 22 days or greater than 24 days. In an embodiment, the pharmaceutical composition has an in vivo relative potency as tested by a cell-based assay of 50-150%, 60-140% or 70-130% relative to a reference standard and/or suitable control.

In one embodiment, an intravenous ("IV") formulation has a pH between 7.5 and 8.5, a genomic titer of between about $1-8 \times 10^{13}$ viral vector genomes/mL (vg/mL), or between $2\times10^{13}$ vg/ml-$6\times10^{13}$ vg/ml, and optionally an osmolality of 384-448 mOsm/kg. In one embodiment, an IV formulation comprises $MgCl_2$, NaCl, pluronic F68, in Tris buffer at pH 8.0.

In one embodiment, for IV administration, the AAV-9 vector carrying the SMN transgene is administered under sterile conditions in an appropriate setting (e.g., interventional suite, operating room, dedicated procedure room) one-time through a venous catheter inserted into a peripheral limb vein (arm or leg) at the indicated dose, and is slowly infused over approximately 30-60 minutes, In another embodiment, the disclosure herein provides compositions and methods of delivering a polynucleotide to the central nervous system of a patient in need thereof comprising intrathecal ("IT") delivery of rAAV9 and a non-ionic, low-osmolar contrast agent to the patient, wherein the rAAV9 comprises a self-complementary genome including the polynucleotide. The polynucleotide is delivered to, for example, the brain, the spinal cord, a glial cell, an astrocyte and/or a lower motor neuron. The non-ionic, low-osmolar contrast agent is, for example, iobitridol, iohexol, iomeprol, iopamidol, iopentol, iopromide, ioversol or ioxilan. In some embodiments, the polynucleotide is a survival motor neuron (SMN) polynucleotide. In one embodiment, the contrast agent is iohexol, e.g., iohexol 180 (sold as Omnipaque 180, containing 388 mg iohexol equivalent to 180 mg of organic iodine per mL).

In one embodiment, for IT administration, the scAAV9 vector carrying the SMN transgene is diluted with normal saline and pre-mixed with an appropriate, hyperbaric contrast medium approved and labeled for pediatric use for radiographic monitoring of the injection via lumbar intrathecal injection (such as Omnipaque 180). The total volume of aqueous composition comprising AAV-9 vector carrying the SMN transgene plus contrast medium and/or saline will not exceed 5 mL. The contrast agent and scAAV-9 vector carrying the SMN transgene may be co-formulated, co-packaged or packaged and delivered to patient center separately.

Patients receive scAAV-9 vector carrying the SMN transgene via intrathecal injection under sterile conditions in a PICU patient room or other appropriate setting (e.g., interventional suite, operating room, dedicated procedure room) with immediate access to acute critical care management. Sites may use an atraumatic needle inserted with the bevel parallel to the dura fibers; this has been shown to considerably reduce damage to the dura and consequently decrease the risk for cerebrospinal fluid leak after lumbar puncture (Ebinger et al., "Headache and Backache After Lumbar Puncture in Children and Adolescents: A Prospective Study." Pediatrics, 113(6):1588-1592; Kiechl-Kohlendorfer et al., "Cerebrospinal Fluid Leakage After Lumbar Puncture in Neonates: Incidence and Sonographic Appearance." American Journal of Roentgenology, 181(1):231-234) including in children.

Sedation/anesthesia is recommended for all patients receiving IT injections. Method and medications will be at the discretion of the local anesthesiologist, but should incorporate a sufficient degree of sedation or anxiolysis to ensure analgesia and lack of movement for the procedure and post-procedure Trendelenburg positioning placement. Patients will be placed in the Trendelenburg position, tilted head-down at 30° for 15 minutes following administration of IT therapy to enhance distribution to cervical and brain regions.

Patients are placed in the lateral decubitus position and a catheter with stylet is inserted by a lumbar puncture into the L3-L4 or L4-L5 interspinous space into the subarachnoid space. Subarachnoid cannulation is confirmed with the flow of clear cerebrospinal fluid (CSF) from the catheter. CSF will be removed and disposed of as per institutional guidelines. ScAAV-9 vector carrying the SMN transgene in the pre-mixed contrast solution is injected directly into the subarachnoid space.

In one embodiment, the present disclosure provides a method of treating a neurological disease in a patient in need thereof comprising intravenous or intrathecal delivery of the pharmaceutical composition disclosed herein, wherein the parvovirus comprises a self-complementary rAAV9 genome, wherein the engineered transgene comprises an SMN polynucleotide and wherein the disease is SMA.

In another embodiment, the present disclosure provides a method of treating a neurological disease in a patient in need thereof comprising intrathecal delivery of a pharmaceutical composition disclosed herein with a contrast agent, wherein the parvovirus comprises a self-complementary rAAV9 genome, wherein the engineered transgene comprises an SMN polynucleotide, wherein the disease is SMA, and wherein the contrast agent is omnipaque 180.

In another embodiment, the present disclosure provides method of treating a type II, III, or IV SMA in a patient in need thereof comprising intrathecal delivery of the pharmaceutical composition disclosed herein with a contrast agent, wherein the parvovirus comprises a self-complementary rAAV9 genome, wherein the engineered transgene comprises an SMN polynucleotide, and wherein the contrast agent is omnipaque 180.

In another embodiment, the present disclosure provides a method of treating type I SMA in a patient in need thereof comprising intravenous delivery of the pharmaceutical composition disclosed herein, wherein the parvovirus comprises a self-complementary rAAV9 genome, and wherein the engineered transgene comprises an SMN polynucleotide. In some embodiments, the patient is 0-9 months old. In some embodiments, the patient is 0-6 months old. In other embodiments, the pediatric patient is up to about 8 kg in weight. In some embodiments, the pediatric patient is about 8.5 kg or less. In some embodiments, the pediatric patient is about 2.6 kg or more.

In another embodiment, the present disclosure provides a kit for treating type I SMA in a patient in need thereof, comprising intravenous administration of the pharmaceutical composition disclosed here contained in vials. In some embodiments, the weight of the patient is measured and the dose is calculated based on the weight of the patient.

Unless otherwise defined, all technical and scientific terms used herein have the same meaning as commonly understood by one of ordinary skill in the art to which this disclosure belongs.

As used herein, the singular forms of a word also include the plural form of the word, unless the context clearly dictates otherwise; as examples, the terms "a," "an," and "the" are understood to be singular or plural and the term "or" is understood to be inclusive. By way of example, "an element" means one or more element.

Throughout the specification the word "comprising," or variations such as "comprises," will be understood to imply the inclusion of a stated element, integer or step, or group of elements, integers or steps, but not the exclusion of any other element, integer or step, or group of elements, integers or steps. Throughout the specification the word "consisting of" or variations such as "consists of" will be understood to imply the inclusion of a stated element, integer or step, or group of elements, integers or steps, and the exclusion of any other element, integer or step, or group of elements, integers or steps. Throughout the specification the word "consisting essentially of," or variations such as "consists essentially of" will be understood to imply the inclusion of a stated element, integer or step, or group of elements, integers or steps, and any other element, integer or step, or group of elements, integers or steps that do not materially affect the basic and novel characteristics of the disclosure and/or claim.

About can be understood as within 10%, 9%, 8%, 7%, 6%, 5%, 4%, 3%, 2%, 1%, 0.5%, 0.1%, 0.05%, or 0.01% of the stated value. When used in reference to a percentage value, "about" can be understood as within ±1% (e.g., "about 5%" can be understood as within 4%-6%) or ±0.5% (e.g., "about 5%" can be understood as within 4.5%-5.5%). Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed disclosure. In the case of conflict, the present Specification, including definitions, will control. In addition, the materials, methods, and examples are illustrative only and are not intended to be limiting. Other features and advantages of the disclosure will be apparent from the following detailed description and claims.

BRIEF DESCRIPTION OF THE FIGURES

Various objects and advantages and a more complete understanding of the present disclosure are apparent and more readily appreciated by reference to the following Detailed Description and to the appended claims when taken in conjunction with the accompanying Drawing wherein:

FIG. 1A shows the plasmid map of pSMN. pSMN is a plasmid that encodes the information for a recombinant self-complementary AAV DNA genome that expresses the human survival motor neuron (SMN) cDNA under the control of a chicken-beta-actin hybrid promoter with an immediate/early cytomegalo virus (CMV) enhancer element. The SMN cDNA encodes a full length, functional protein. The expression cassette contains a modified intron sequence derived from simian virus 40 (SV40) and a bovine growth hormone (BGH) polyadenylation signal. The expression cassette (CMV-CB-SV40-SMN-BGHpA) is flanked by AAV2 derived inverted terminal repeats (ITRs). The left ITR is modified to preferentially package self-complementary AAV genomes. Together, the regions between and including the ITRs are packaged into recombinant AAV9 capsids during the manufacture of the find drugs product. Key pSMN components that are not intended for packaging into recombinant AAV genomes include an open reading frame encoding resistance to kanamycin (KanR) and an origin of replication (ori) derived from pUC. The ori and KanR regions are useful for plasmid manufacture.

FIG. 1B shows the plasmid map of the pHELP plasmid. The pHELP plasmid contains the Trans-acting Adenoviral components necessary for recombinant adeno-associated virus production. The pHELP plasmid contains the regions of the adenovirus genome that provide factors that are important for AAV replication, namely E2A, E4, and VA RNA. The adenovirus E1 functions involved in rAVV replication are provided by the transfection host 293 cells. The pHELP plasmid does not, however, contain other adenovirus replication or structural genes. The adenovirus sequences present in this plasmid represent only ~28% (9,280/35,938) of the adenovirus genome and does not contain the cis elements critical for replication, such as the inverted terminal repeats. Therefore, no infectious adenovirus is expected to be generated from such a production system.

FIG. 1C shows the plasmid map of the AAV plasmid. The wild type AAV genome contains two non-coding structural elements called inverted terminal repeats that flank the rep and cap open reading frames. Rep and cap encode viral replication and capsid proteins respectively. In the production of recombinant adeno-associated viral vectors; the viral ITRs are the only elements used in cis while the viral open reading frames are supplied in trans. Using the transient transfection of adherent HEK293 cells method to make AAV addresses the cis/trans roles for the different genetic elements by dividing them to separate plasmids. The pAAV2/9 plasmid contains open reading frames for the AAV2 rep gene and the AAV9 cap gene.

FIG. 3 shows a summary of cell processing details for the selection of HEK293 cells for exceptional adherence and pre-master cell bank (MCB) banking.

FIGS. 12 A-B show recovery of viral vector and host cell protein (HCP) clearance at the TFF1 step.

FIGS. 17A-B provide a table that illustrates the comparability and manufacturing consistency results—Process A (Phase 1) and Process B (Phase 3) Products. Process B products are shown to have additional benefits as compared to Process A.

FIG. 18 shows the comparability between Process A and Process B using pair-wise comparison of Process A (Phase 1 Lot NCHAAV9SMN0613) and Process B (Phase 3 Lot 600156). Process B products are shown to have additional benefits as compared to Process A.

FIG. 19 shows the manufacturing consistency assessment by pair-wise comparison of Process B (Phase 3) lots 600156 and 600307.

FIG. 20 shows the stability profile for NCH Lot NCHAAV9SMN0613 stored at real-time storage condition ≤−60° C. over 12 months.

DETAILED DESCRIPTION

Figure 1A:
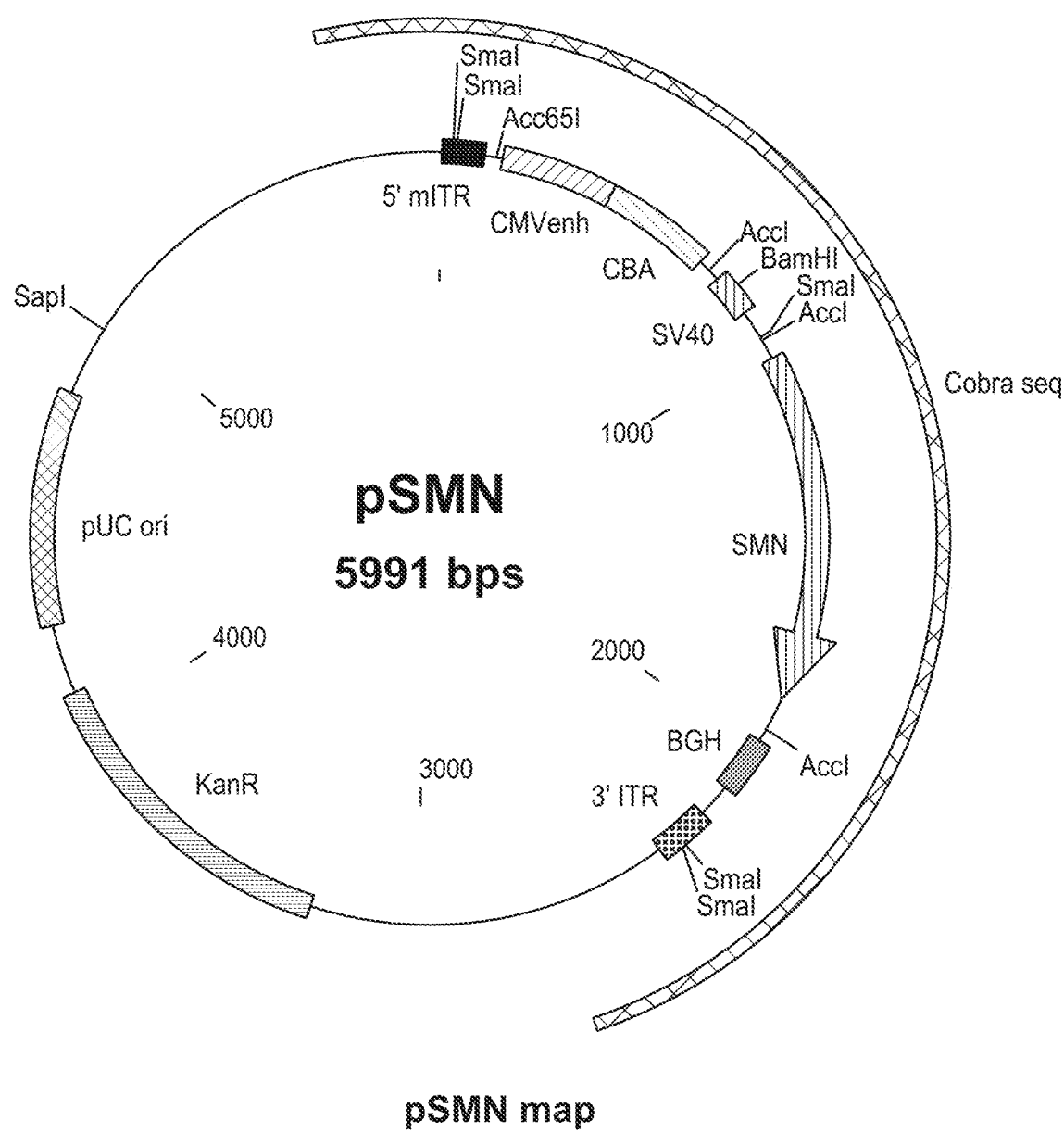
FIGS. 1A-1C. Plasmid maps of pSMN, pHELP and pAAV.

In order to advance development of AAV gene therapy beyond animal models and into clinical studies and/or for therapeutic uses, a scalable process capable of producing viral material suitable for human use was developed.

In some embodiments, by "vector" is meant any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

In some embodiments, by an "AAV vector" is meant a vector derived from an adeno-associated virus serotype, including without limitation, AAV-1, AAV-2, AAV-3, AAV-4, AAV-5, AAV-6, AAV-7, AAV-8 and AAV-9. AAV vectors can have one or more of the AAV wild-type genes deleted in whole or part, e.g., the rep and/or cap genes, but retain functional flanking ITR sequences. Functional ITR sequences are necessary for the rescue, replication and packaging of the AAV virion. Thus, an AAV vector is defined herein to include at least those sequences that in cis provide for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging. In one embodiment, the vector is an AAV-9 vector, with AAV-2 derived ITRs. Also by an "AAV vector" is meant the protein shell or capsid, which provides an efficient vehicle for delivery of vector nucleic acid to the nucleus of target cells.

In some embodiments, by "scAAV" is meant a self-complementary adeno-associated virus (scAAV), which is a viral vector engineered from the naturally occurring adeno-associated virus (AAV) for use in gene therapy. scAAV is termed "self-complementary" because the coding region has been designed to form an intra-molecular double-stranded DNA template.

In some embodiments, the term "vector-related impurities" refers to all types of AAV particles other than bona fide recombinant AAV particles. Vector-related impurities include empty AAV capsids (also referred to as "empties", or "empty particles"), and AAV particles containing polynucleotide sequences other than the intended vector genome (also referred to "AAV-encapsidated nucleic acid impurities" or "AAV-encapsidated DNA impurities").

In some embodiments, "recombinant virus" is meant a virus that has been genetically altered, e.g., by the addition or insertion of a heterologous nucleic acid construct into the particle. "Recombinant" may abbreviated "r", e.g., rAAV may refer to recombinant AAV. The term "AAV" as used herein is intended to encompass "recombinant AAV" or "rAAV."

In some embodiments, by "AAV virion" is meant a complete virus particle, such as a wild-type (wt) AAV virus particle (comprising a linear, single-stranded AAV nucleic acid genome associated with an AAV capsid protein coat). In this regard, single-stranded AAV nucleic acid molecules of either complementary sense, e.g., "sense" or "antisense" strands, can be packaged into any one AAV virion and both strands are equally infectious.

In some embodiments, the terms "recombinant AAV virion," "rAAV virion," "AAV vector particle," "full capsids," and "full particles" are defined herein as an infectious, replication-defective virus including an AAV protein shell, encapsidating a heterologous nucleotide sequence of interest which is flanked on both sides by AAV ITRs. A rAAV virion is produced in a suitable host cell which has had sequences specifying an AAV vector, AAV helper functions and accessory functions introduced therein. In this manner, the host cell is rendered capable of encoding AAV polypeptides that provide for packaging the AAV vector (containing a recombinant nucleotide sequence of interest) into infectious recombinant virion particles for subsequent gene delivery.

In some embodiments, the terms "empty capsid," and "empty particle," refer to an AAV virion that includes an AAV protein shell but that lacks in whole or part the polynucleotide construct comprising the heterologous nucleotide sequence of interest flanked on both sides by AAV ITRs.

The term "host cell" denotes, for example, microorganisms, yeast cells, insect cells, and mammalian cells, that can be, or have been, used as recipients of an AAV helper construct, an AAV vector plasmid, an accessory function vector, or other transfer DNA. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

In another embodiment, the term "AAV helper functions" refer to AAV-derived coding sequences which can be expressed to provide AAV gene products that, in turn, function in trans for productive AAV replication. Thus: AAV helper functions include both of the major AAV open reading frames (ORFs), rep and cap. The Rep expression products have been shown to possess many functions, including, among others: recognition, binding and nicking of the AAV origin of DNA replication; DNA helicase activity; and modulation of transcription from AAV (or other heterologous) promoters. The Cap expression products supply necessary packaging functions. AAV helper functions are used herein to complement AAV functions in trans that are missing from AAV vectors.

In one embodiment, the term "AAV helper construct" refers generally to a nucleic acid molecule that includes nucleotide sequences providing AAV functions deleted from an AAV vector which is to be used to produce a transducing vector for delivery of a nucleotide sequence of interest. AAV helper constructs are commonly used to provide transient expression of AAV rep and/or cap genes to complement missing AAV functions that are necessary for AAV replication; however, helper constructs lack AAV ITRs and can neither replicate nor package themselves. AAV helper constructs can be in the form of a plasmid, phage, transposon, cosmid, virus, or virion. A number of AAV helper constructs have been described, such as the commonly used plasmids pAAV/Ad and p1M29+45 which encode both Rep and Cap expression products. See, e.g., Samulski et al. (1989) J. Virol. 63:3822-3828; and McCarty et al. (1991) J. Virol. 65:2936-2945. A number of other vectors have been described which encode Rep and/or Cap expression products. See, e.g., U.S. Pat. Nos. 5,139,941 and 6,376,237.

In another embodiment, the term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous DNA moieties into suitable host cells.

As used herein, the term "cell line" refers to a population of cells capable of continuous or prolonged growth and division in vitro. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. In some embodiments, the terms "HEK293 cells", "293 cells" or their grammatical equivalents are used interchangeably here and refer to the host/packing cell line used in the methods disclosed herein.

In some embodiments, the term "eluent" may be understood, in context, to refer to the buffer used to elute a substance. In some embodiments, the term "eluent" may be understood, in context, to refer to the eluted substance, e.g., the desired product or substance from a prior purification step, e.g., for assaying or further purification.

In some embodiments, the methods described here are performed using good manufacturing practice (GMP) and at industrial scale. GMPs are regulatory practices, e.g., those enforced by the Federal Drug Agency (FDA), for ensuring pharmaceutical quality. GMP regulations establish controls for manufacturing processes. Examples of current GMP regulations are published by FDA. In some embodiments, the methods described herein employ GMP procedures for producing AAV viral vectors at industrial scale. To date, industrial scale production of AAV viral vectors for gene therapy has been challenging because of scalability issues. Thus, in some embodiments, the methods described herein provided an advantage by producing AAV viral vectors, e.g., in adherent cells, at industrial scale and at purity levels sufficient to administer to a human. The term "industrial scale" refers to methods of producing viral vector in cells at larger than bench scale, e.g., commercial scale, e.g., where the yield is more than $5 \times 10^{15}$ vg, or more than $8 \times 10^{15}$ vg or more than $1 \times 10^{16}$ vg per manufacturing batch.

Upstream Process

In some embodiments, an upstream process is used to produce an intermediate derived from a working cell bank, wherein the upstream process comprises the steps of (a) culturing cells, e.g., adherent cells, (b) transfecting the cultured cells, e.g., adherent cells, with three plasmids, (c) harvesting the expanded viral particles from the cells after a culture period, e.g., by total cell lysis, (d) purifying the viral particles via filtration to remove any intact cells or cellular debris, (e) subjecting the eluent from step (d) to tangential flow filtration, and (f) optionally freezing the resultant intermediate preparation of purified viral particles. In some embodiments, the intermediate preparation may be frozen. In other embodiments, the intermediate preparation need not be frozen prior to downstream processing. In some embodiments, the AAV prepared with the upstream process disclosed herein is an AAV encoding an shRNA targeting SOD1, an AAV comprising a polynucleotide encoding MECP2, or an AAV comprising a polynucleotide encoding SMN, as described herein. In some embodiments, the upstream process is conducted under GMP and at industrial scale.

1. Cell Line Transfection and Culturing

In one aspect, disclosed herein are rAAV genomes. The rAAV genomes comprise one or more AAV ITRs flanking a polynucleotide encoding a polypeptide (including, but not limited to, an SMN polypeptide) or encoding siRNA, shRNA, antisense, and/or miRNA directed at mutated proteins or control sequences of their genes. The polynucleotide is operatively linked to transcriptional control DNAs, specifically promoter DNA, enhancer DNA and polyadenylation signal sequence DNA that are functional in target cells to form a gene cassette. The gene cassette may also include intron sequences to facilitate processing of an RNA transcript when expressed in mammalian cells.

In some embodiments, the rAAV (e.g., rAAV9) genome encodes a trophic or protective factor for treatment of neurodegenerative disorders, including but not limited to Alzheimer's disease, Parkinson's disease, Huntington's disease along with nervous system injury including spinal cord and brain trauma/injury, stroke, and brain cancers. Non-limiting examples of known nervous system growth factors include nerve growth factor (NGF), brain-derived neurotrophic factor (BDNF), neurotrophin-3 (NT-3), neurotrophin-4/5 (NT-4/5), neurotrophin-6 (NT-6), ciliary neurotrophic factor (CNTF), glial cell line-derived neurotrophic factor (GDNF), the fibroblast growth factor family (e.g., FGF's 1-15), leukemia inhibitory factor (LIF), certain members of the insulin-like growth factor family (e.g., IGF-1), the neurturins, persephin, the bone morphogenic proteins (BMPs), the immunophilins, the transforming growth factor (TGF) family of growth factors, the neuregulins, epidermal growth factor (EGF), platelet-derived growth factor (PDGF), vascular endothelial growth factor family (e.g. VEGF 165), follistatin, Hif1, and others. Also generally contemplated are zinc finger transcription factors that regulate each of the trophic or protective factors contemplated herein. In further embodiments, methods to modulate neuro-immune function are contemplated, including but not limited to, inhibition of microglial and astroglial activation through, for example, NFkB inhibition, or NFkB for neuroprotection (dual action of NFkB and associated pathways in different cell types) by siRNA, shRNA, antisense, or miRNA. In still further embodiments, the rAAV (e.g., rAAV9) genome encodes an apoptotic inhibitor (e.g., bcl2, bclxL). Use of a rAAV (e.g., rAAV9) encoding a trophic factor or spinal cord injury modulating protein or a suppressor of an inhibitor of axonal growth (e.g., a suppressor of Nogo [Oertle et al., The Journal of Neuroscience, 23(13): 5393-5406 (2003)] is also contemplated for treating spinal cord injury.

For treatment of neurodegenerative disorders such as Parkinson's disease, the rAAV (e.g. rAAV9) genome encodes in various embodiments Aromatic acid dopa decarboxylase (AADC), Tyrosine hydroxylase, GTP-cyclohydrolase 1 (gtpch1), apoptotic inhibitors (e.g., bcl2, bclxL), glial cell line-derived neurotrophic factor (GDNF), the inhibitory neurotransmitter-amino butyric acid (GABA), or enzymes involved in dopamine biosynthesis. In further embodiments, the rAAV (e.g. rAAV9) genome may encode, for example, modifiers of Parkin and/or synuclein.

For treatment of neurodegenerative disorders such as Alzheimer's disease, in some embodiments, methods to increase acetylcholine production are contemplated. In some embodiments, methods of increasing the level of a choline acetyltransferase (ChAT) or inhibiting the activity of an acetylcholine esterase (AchE) are contemplated.

The rAAV (e.g. rAAV9) genome encodes in some embodiments, siRNA, shRNA, antisense, and/or miRNA for use in methods to decrease mutant Huntington protein (htt) expression for treating a neurodegenerative disorder such as Huntington's disease.

The rAAV (e.g. rAAV9) genome encodes in various embodiments siRNA, shRNA, antisense, and/or miRNA for use in for treatment of neurodegenerative disorders such as ALS. Treatment results in a decrease in the expression of molecular markers of disease, such as TNF-α nitric oxide, peroxynitrite, and/or nitric oxide synthase (NOS).

In some embodiments, the vectors encode short hairpin RNAs (shRNAs) directed at mutated proteins such as superoxide dismutase (SOD, e.g., SOD-1) for ALS, or neurotrophic factors such as GDNF or IGF1 for ALS or Parkinson's disease.

In one embodiment, the methods and materials described herein may be used for the treatment of ALS. ALS is a neurodegenerative disease resulting in progressive loss of motor neurons in the brain and spinal cord, with symptoms including the loss of ability to speak, eat, move and eventually breathe. The disease typically results in death within 3-5 years of diagnosis. While the cause of 90-95% of ALS causes is unknown, a subset of ALS is caused by genetic mutations in the superoxide dismutase 1 (SOD1) gene, where a mutation causes a toxic dominant gain-of-function. Mouse studies show that SOD1 knockout does not result in disease and hence therapies that knock down levels of mutant SOD1 are thought to alleviate disease symptoms.

In some embodiments, the AAV vector encodes an shRNA targeting SOD1 for ALS. An exemplary AAV, e.g., scAAV9, construct encoding shRNA for SOD1 is provided in WO2015031392 and US2016272976, the contents of which are hereby incorporated in their entirety. In some embodiments, an AAV construct encoding shRNA for SOD1 may be prepared using the methods disclosed herein. In some embodiments, these AAV constructs may be used to treat ALS. In some embodiments, the SOD1 AAV exhibits less than 10%, e.g., less than 7%, 5%, 4%, 3%, 2%, or 1% empty capsids. In some embodiments, the SOD1 AAV exhibits low amounts of residual host cell protein, host cell DNA, plasmid DNA, and/or endotoxin, e.g., levels discussed herein for the preparation and purification of AAV vectors. As used herein, "AVXS-301" is a non-limiting example of an scAAV9 vector, i.e., comprising a polynucleotide (e.g. pSOD1sh) encoding anti-human SOD1 shRNA, a modified AAV2 ITR, a human H1 promoter, and an unmodified AAV2 ITR. The modified and unmodified ITRs may come in either orientation (i.e., 5' or 3') relative to the anti-human SOD1 shRNA expression cassette.

As used herein, the "pSOD1sh" vector plasmid comprises a polynucleotide encoding a short hairpin RNA (shRNA) targeting the expression of the superoxide dismutase 1 (SOD1) gene, i.e., an anti-SOD1 shRNA cassette, wherein the cassette is flanked by adeno-associated virus inverted terminal repeat (ITR) sequences, e.g., "left" and "right" of the polynucleotide encoding the pSOD1sh. In some embodiments, the polynucleotide encoding pSOD1sh is transcribed into a short hairpin RNA that specifically targets the human SOD1 mRNA. In some embodiments, the ITR sequences surrounding the polynucleotide encoding pSOD1sh are native, variant, or modified AAV ITR sequences. In some embodiments, at least one ITR sequence is a native, variant or modified AAV2 ITR sequence. In some embodiments, ITRs flank the polynucleotide encoding pSOD1sh. In some embodiments, the two ITR sequences are both native, variant or modified AAV2 ITR sequences. In some embodiments, the "left" ITR is a modified AAV2 ITR sequence that allows for production of self-complementary genomes, and the "right" ITR is a native AAV2 ITR sequence. In some embodiments, the "right" ITR is a modified AAV2 ITR sequence that allows for the production of self-complementary genomes, and the "left" ITR is a native AAV2 ITR sequence. In some embodiments, the pSOD1sh vector further comprises a segment of the human H1 RNA promoter, e.g., as described by Myslinksi. Myslinkski et al. "An unusually compact external promoter for RNA polymerase III transcription of the human H1RNA gene." Nucleic Acids Research, 29(12):2502-2509. In some embodiments, the pSOD1sh vector further comprises a unique stuffer sequence made from segments of random plasmid backbones to increase the size of the expression cassette. In some embodiments, the pSOD1sh vector comprises a polynucleotide encoding anti-human SOD1 shRNA, a modified AAV2 ITR, a human H1 promoter, and an unmodified AAV2 ITR In one embodiment, the methods and materials described herein may be used for the treatment of neurodevelopmental disorders such as Rett Syndrome. Rett Syndrome is a rare neurological disorder first recognized in infancy, resulting from mutations in the MECP2 gene on the X chromosome in 90-95% of cases. Ruthie et al., "Rett syndrome is caused by mutations in X-linked MECP2, encoding methyl-CpG-binding protein 2." *Nature Genetics*, 23:185-188. Boys who have only one copy of the X chromosome typically die shortly after birth, while girls who have two copies of the X chromosome usually have one functional copy of the gene. They begin to develop symptoms between 6-18 months, with hallmark symptoms like hand wringing or squeezing, clapping, rubbing, washing, or hand to mouth movements. The disease is progressive with significant disability that can include autistic-like behaviors, breathing irregularities, feeding and swallowing difficulties, growth retardation and seizures. There are 200 known mutations of the MECP2 gene, and depending on the level of X inactivation and dosage compensation, the severity of disease varies widely from patient to patient. Mouse studies show that MECP2 mutation does not cause neurons to die, suggesting that it is not a neurodegenerative disorder. Guy et al, "Reversal of Neurological Defects in a Mouse Model of Rett Syndrome." *Science,* 315(5815)"1143-1147.

For embodiments relating to Rett Syndrome, the rAAV (e.g. rAAV9) genome may encode, for example, methyl cytosine binding protein 2 (MeCP2). An exemplary AAV, e.g., scAAV9, construct comprising a polynucleotide encoding MeCP2 is provided in U.S. Pat. No. 9,415,121, the contents of which are hereby incorporated in their entirety. In some embodiments, an AAV construct comprising a polynucleotide encoding MeCP2 may be prepared using the methods disclosed herein. In some embodiments, these AAV constructs may be used to treat Rett Syndrome. In some embodiments, the MeCP2 AAV exhibits less than 10%, e.g., less than 7%, 5%, 4%, 3%, 2%, or 1% empty capsids. In some embodiments, the MeCP2 AAV exhibits low amounts of residual host cell protein, host cell DNA, plasmid DNA, and/or endotoxin, e.g., levels discussed herein for the preparation and purification of AAV vectors.

As used herein, "AVXS-201" is a non-limiting example of an scAAV9 vector, i.e., comprising a polynucleotide (e.g. pMECP2) comprising a MECP2 cDNA expression cassette, a modified AAV2 ITR, a murine Mecp2 promoter, a modified SV40 intro, a minimal polyadenylation signal, and an unmodified AAV2 ITR. The modified and unmodified ITRs may come in either orientation (i.e., 5' or 3') relative to the MECP2 cDNA expression cassette.

As used herein, the "pMECP2" vector plasmid comprises a polynucleotide encoding an MECP2 protein, a modified AAV2 ITR, a murine Mecp2 promoter, a modified SV40 intro, a minimal polyadenylation signal, and an unmodified AAV2 ITR. In some embodiments, pMECP2 is a vector construct comprising a polynucleotide encoding an MECP2 protein, i.e. a MECP2 cDNA expression cassette, wherein the cassette is flanked by adeno-associated virus inverted terminal repeat (ITR) sequences, e.g., "left" and "right" of the polynucleotide encoding the MECP2 gene. In some embodiments, the polynucleotide encoding MECP2 is a human MECP2 sequence, e.g., a naturally occurring human MECP2 sequence or isoforms, variants, or mutants thereof. In some embodiments, the ITR sequences are native, variant, or modified AAV ITR sequences. In some embodiments, at least one ITR sequence is a native, variant or modified AAV2 ITR sequence. In some embodiments, the two ITR sequences are both native, variant or modified AAV2 ITR sequences. In some embodiments, the "left" ITR is a modified AAV2 ITR sequence that allows for production of self-complementary genomes, and the "right" ITR is a native AAV2 ITR sequence. In some embodiments, the "right" ITR is a modified AAV2 ITR sequence that allows for the production of self-complementary genomes, and the "left" ITR is a native AAV2 ITR sequence. In some embodiments, the pMECP2 vector further comprises a segment but not all of the mouse Mecp2 promoter. In some embodiments, the pMECP2 vector further comprises a Simian Virus 40 (SV40) intron. In some embodiments, the pMECP2 vector further comprises a minimal polyadenylation signal, e.g., as defined by Levitt et al., "Definition of an efficient synthetic poly(A) site." Genes & Development, 3:1019-1025.

In some embodiments, the rAAV genomes disclosed herein lack AAV rep and cap DNA. AAV DNA in the rAAV genomes (e.g., ITRs) may be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10 and AAV-11. The nucleotide sequences of the genomes of the AAV serotypes are known in the art. For example, the complete genome of AAV-1 is provided in GenBank Accession No. NC_002077; the complete genome of AAV-2 is provided in GenBank Accession No. NC_001401 and Srivastava et al., Virol., 45: 555-564 {1983): the complete genome of AAV-3 is provided in GenBank Accession No. NC_1829; the complete genome of AAV-4 is provided in GenBank Accession No. NC 001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al., J. Virol., 78: 6381-6388 (2004); the AAV-10 genome is provided in Mol. Ther., 13(1): 67-76 (2006); and the AAV-11 genome is provided in Virology, 330(2): 375-383 (2004).

As used herein, the "pSMN" vector plasmid comprises a polynucleotide encoding an SMN protein, i.e, a SMN cDNA expression cassette, wherein the cassette is flanked by adeno-associated virus inverted terminal repeat (ITR) sequences, e.g., "left" and "right" of the polynucleotide encoding the SMN gene. In some embodiments, the polynucleotide encoding SMN is a human SMN sequence, e.g., a naturally occurring human SMN sequence or isoforms, variants, or mutants thereof. In some embodiments, the ITR sequences are native, variant, or modified AAV ITR sequences. In some embodiments, at least one ITR sequence is a native, variant, or modified AAV2 ITR sequence. In some embodiments, the two ITR sequences are both native, variant, or modified AAV2 ITR sequences. In some embodiments, the "left" ITR is a modified AAV2 ITR sequence that allows for the production of self-complementary genomes, and the "right" ITR is a native AAV2 ITR sequence. In some embodiments, the "right" ITR is a modified AAV2 ITR sequence that allows for the production of self-complementary genomes, and the "left" ITR is a native AAV2 ITR sequence. In some embodiments, the pSMN plasmid further comprises a CMV enhancer/chicken beta-actin ("CB") promoter. In some embodiments, the pSMN plasmid further comprises a Simian Virus 40 (SV40) intron. In some embodiments, the pSMN plasmid further comprises a bovine growth hormone (BGH) polyadenylation (polyA) termination signal. Exemplary sequences that may be used for one or more of the components discussed above are showing in Table 1 below. In some embodiments, all of the sequences shown in Table 1 below are used. In some embodiments, "AVXS-101," is a non-limiting example of a vector construct using all the sequences in Table 1 and falling within the scope of the term pSMN.

In some embodiments, a pSMN vector may comprise a SMN cDNA expression cassette, a modified AAV2 ITR, a chicken beta-actin (CB) promoter, a cytomegalovirus (CMV) immediate/early enhancer, a modified SV40 late 16 s intron, a bovine growth hormone (BGH) polyadenylation signal, and an unmodified AAV2 ITR. The modified and unmodified ITRs may come in either orientation (i.e., 5' or 3') relative to the SMN cDNA expression cassette.

In some embodiments, e.g., during the manufacturing processes described herein the vector construct sequence is encapsidated, e.g., into AAV9 virions. In these embodiments, encapsidation is in a non-replicating, recombinant AAV9 capsid capable of delivering a stable, function transgene, e.g. a fully functional human SMN transgene, MECP2 transgene, or anti-SOD1 shRNA. In some embodiments, the capsid is comprised of 60 viral proteins (VP1, VP2, VP3), e.g., in a ratio of 1:1:10 produced by alternate splicing such that VP2 and VP3 are two truncated forms of VP1, all with common C-terminal sequences. In some embodiments, the product of the manufacturing process, e.g., a drug product, may comprise a non-replicating, recombinant AAV9 capsid to deliver a stable, fully functional human SMN transgene, a MECP2 transgene, or a anti-SOD1 shRNA. In some embodiments, the capsid is comprised of 60 viral proteins (VP1, VP2, VP3) in a ratio of 1:1:10 produced by alternate splicing such that VP2 and VP3 are two truncated forms of VP1, all with common C-terminal sequences.

In some embodiments, the amount of functional viral vectors is determined by the % of functional vg/mL as measured using a suitable in vitro cellular assay or in vivo animal model. For example, the % of functional AAV SMN may be assayed by relative potency using an animal model of SMA, e.g., the SMAΔ7 mouse, or a quantitative cell-based assay using a suitable cell line, e.g., primary neural progenitor cells (NPCs) isolated from the cortex of SMAΔ7 mice. The % of functional AAV MeCP2 may be assayed using a suitable in vitro cellular assay or in vivo animal model, e.g., an Mecp2 knockout mouse. The % of functional AAV SOD1 may be assayed using a suitable in vitro cellular assay or in vivo animal model, e.g., a SOD1 mutant mouse.

The DNA sequence of an exemplary vector construct, e.g., AVXS-101 is described in Table 1.

TABLE 1

AVXS-101 Vector Construct DNA Sequence Summary Component (all nucleotide start and stop positions are in relation to SEQ ID NO: 1)

| | Start Position | Stop Position | Size (nt) | Description | Non-limiting description of potential benefits |
|---|---|---|---|---|---|
| "Left" Mutated AAV2 ITR | 1 | 106 | 106 | Modification to the "left" ITR by deleting the terminal resolution site to allow hairpin formation of genome | Without being limited by theory, this mutated ITR may allow for a second-generation self-complementary vector to maximize vector potency, allowing lower systemic doses |
| CMV Enhancer/CB Promoter | 153 | 432 | 280 | Portion of the CMV immediate/early enhancer | Without being limited by theory, this may allow for constitutive high-level SMN expression |
| | 439 | 704 | 266 | CB core promoter | |
| SV40 Intron | 774 | 870 | 97 | Intron from the SV40 (to enhance accumulation of steady level of mRNA for translation) | Without being limited by theory, this may allow for increased gene expression |
| Human SMN cDNA | 1003 | 1887 | 885 | Modified from Genbank Accession #NM_017411 | Without being limited by theory, this may allow the for expression of a full-length SMN protein |
| BGH Poly A Termination Signal | 1973 | 2204 | 232 | BGH Poly A signal | Without being limited by theory, this may provide a Poly A of the SMN mRNA (transcription termination signal) for high-level, efficient gene expression |
| "Right" AAV2 ITR | 2217 | 2359 | 143 | Unmodified AAV2 ITR | Without being limited by theory, this AAV2 ITR in cis may provide for both viral DNA replication and packaging of the AAV vector genome |

In another aspect, the DNA sequence of the AVXS-101 vector construct is provided in SEQ ID NO: 1:

```
                                                  (SEQ ID NO: 1)
ctgcgcgctc gctcgctcac tgaggccgcc cgggcaaagc ccgggcgtcg    50
ggcgaccttt ggtcgcccgg cctcagtgag cgagcgagcg cgcagagagg   100
gagtggaatt cacgcgtgga tctgaattca attcacgcgt ggtacctctg   150
gtcgttacat aacttacggt aaatggcccg cctggctgac cgcccaacga   200
cccccgccca ttgacgtcaa taatgacgta tgttcccata gtaacgccaa   250
tagggacttt ccattgacgt caatgggtgg agtatttacg gtaaactgcc   300
cacttggcag tacatcaagt gtatcatatg ccaagtacgc ccctattga    350 cgtcaatgac ggtaaatggc ccgcctggca ttatgcccag tacatgacct   400
tatgggactt tcctacttgg cagtacatct actcgaggcc acgttctgct   450
tcactctccc catctccccc ccctccccac ccccaatttt gtatttattt   500
attttttaat tattttgtgc agcgatgggg gcggggggg ggggggggcg    550 cgcgccaggc gggcggggc ggggcgaggg gcggggcggg gcgaggcgga    600
gaggtgcggc ggcagccaat cagagcggcg cgctccgaaa gtttcctttt   650
atggcgaggc ggcggcggcg gcggccctat aaaaagcgaa gcgcgcggcg   700
ggcgggagcg ggatcagcca ccgcggtggc ggcctagagt cgacgaggaa   750
ctgaaaaacc agaaagttaa ctggtaagtt tagtctttt gtcttttatt    800 tcaggtcccg gatccggtgg tggtgcaaat caaagaactg ctcctcagtg   850
gatgttgcct ttacttctag gcctgtacgg aagtgttact tctgctctaa   900
aagctgcgga attgtacccg cggccgatcc accggtccgg aattcccggg   950
atatcgtcga cccacgcgtc cgggcccac gctgcgcacc cgcgggtttg   1000
ctatggcgat gagcagcggc ggcagtggtg gcggcgtccc ggagcaggag  1050
gattccgtgc tgttccggcg cggcacaggc cagagcgatg attctgacat  1100
ttgggatgat acagcactga taaaagcata tgataaagct gtggcttcat  1150
ttaagcatgc tctaaagaat ggtgacattt gtgaaacttc gggtaaacca  1200
aaaaccacac ctaaagaaa acctgctaag aagaataaaa gccaaagaa   1250 gaatactgca gcttccttac aacagtggaa agttgggac aaatgttctg    1300 ccatttggtc agaagacggt tgcatttacc cagctaccat tgcttcaatt  1350
gattttaaga gagaaacctg tgttgtggtt tacactggat atggaaatag  1400
agaggagcaa aatctgtccg atctactttc cccaatctgt gaagtagcta  1450
ataatataga acagaatgct caagagaatg aaaatgaaag ccaagtttca  1500
acagatgaaa gtgagaactc caggtctcct ggaaataaat cagataacat  1550
caagcccaaa tctgctccat ggaactcttt tctccctcca ccaccccca   1600 tgccagggcc aagactggga ccaggaaagc caggtctaaa attcaatggc  1650
ccaccaccgc caccgccacc accaccaccc cacttactat catgctggct  1700
gcctccattt ccttctggac caccaataat tcccccacca cctcccatat  1750
gtccagattc tcttgatgat gctgatgctt tgggaagtat gttaatttca  1800
tggtacatga gtggctatca tactggctat tatatggggtt ttagacaaaa  1850 tcaaaaagaa ggaaggtgct cacattcctt aaattaagga gaaatgctgg  1900
catagagcag cactaaatga caccactaaa gaaacgatca gacagatcta  1950
```

```
gaaagcttat cgataccgtc gactagagct cgctgatcag cctcgactgt    2000
gccttctagt tgccagccat ctgttgtttg cccctccccc gtgccttcct    2050
tgaccctgga aggtgccact cccactgtcc tttcctaata aaatgaggaa    2100
attgcatcgc attgtctgag taggtgtcat tctattctgg ggggtggggt    2150
ggggcaggac agcaaggggg aggattggga agacaatagc aggcatgctg    2200
gggagagatc gatctgagga acccctagtg atggagttgg ccactccctc    2250
tctgcgcgct cgctcgctca ctgaggccgg gcgaccaaag gtcgcccgac    2300
gcccgggctt tgcccgggcg gcctcagtga gcgagcgagc gcgcagagag    2350 ggagtggcc                                                 2359.
```

In some embodiments, the amino acid sequence of the SMN protein encoded by the pSMN plasmid comprises:

(SEQ ID NO: 2)
MAMSSGGSGGGVPEQEDSVLFRRGTGQSDDSDIWDDTALIKAYDKAVASF

KHALKNGDICETSGKPKTTPKRKPAKKNKSQKKNTAASLQQWKVGDKCSA

IWSEDGCIYPATIASIDFKRETCVVVYTGYGNREEQNLSDLLSPICEVAN

NIEQNAQENENESQVSTDESENSRSPGNKSDNIKPKSAPWNSFLPPPPPM

PGPRLGPGKPGLKFNGPPPPPPPPPHLLSCWLPPFPSGPPIIPPPPIC

PDSLDDADALGSMLISWYMSGYHTGYYMGFRQNQKEGRCSHSLN.

In some embodiments, AAV capsid proteins VP1, VP2, VP3 are derived from the same transcript. These have alternative start sites but share a carboxy terminus. Below, VP1 specific amino acid sequences are shown in black and are bolded. Amino acid sequences common to VP1 and VP2 are underlined and in italics. Amino acids common to all three capsid proteins are bolded and in italics.

ferred to cells permissible for infection with a helper virus of AAV (e.g., adenovirus, E1-deleted adenovirus or herpesvirus) for assembly of the rAAV genome into infectious viral particles with AAV9 capsid proteins. Techniques to produce rAAV particles, in which an AAV genome to be packaged, rep and cap genes, and helper virus functions are provided to a cell are standard in the art. In some embodiments, production of rAAV involves the following components present within a single cell (denoted herein as a packaging cell): a rAAV genome, AAV rep and cap genes separate from (i.e., not in) the rAAV genome, and helper virus functions. Production of pseudotyped rAAV is disclosed in, for example, WO 01/83692 which is incorporated by reference herein in its entirety. In various embodiments, AAV capsid proteins may be modified to enhance delivery of the recombinant vector. Modifications to capsid proteins are generally known in the art. See, for example, US 2005/0053922 and US 2009/0202490, the disclosures of which are incorporated by reference herein in their entirety.

General principles of rAAV production are reviewed in, for example, Carter, 1992, Current Opinions in Biotechnol- (SEQ ID NO: 3)
```
  1 MAADGYLPDW LEDNLSEGIR EWWALKPGAP QPKANQQHQD NARGLVLPGY KYLGPGNGLD

61 KGEPVNAADA AALEHDKAYD QQLKAGDNPY LKYNHADAEF QERLKEDTSF GGNLGRAVFQ

121 AKKRLLEPLG LVEEAAKTAP GKKRPVEQSP QEPDSSAGIG KSGAQPAKKR LNFGQTGDTE

181 SVPDPQPIGE PPAAPSGVGS LTMASGGGAP VADNNEGADG VGSSSGNWHC DSQWLGDRVI

241 TTSTRTWALP TYNNHLYKQI SNSTSGGSSN DNAYFGYSTP WGYFDFNRFH CHFSPRDWQR

301 LINNNWGFRP KRLNFKLFNI QVKEVTDNNG VKTIANNLTS TVQVFTDSDY QLPYVLGSAH

361 EGCLPPFPAD VFMIPQYGYL TLNDGSQAVG RSSFYCLEYF PSQMLRTGNN FQFSYEFENV

421 PFHSSYAHSQ SLDRLMNPLI DQYLYYLSKT INGSGQNQQT LKFSVAGPSN MAVQGRNYIP

481 GPSYRQQRVS TTVTQNNNSE FAWPGASSWA LNGRNSLMNP GPAMASHKEG EDRFFPLSGS

541 LIFGKQGTGR DNVDADKVMI TNEEEIKTTN PVATESYGQV ATNHQSAQAQ AQTGWVQNQG

601 ILPGMVWQDR DVYLQGPIWA PFHSSYAHSQ SLDRLMNPLI KHPPPQILIK NTPVPADPPT

661 AFNKDKLNSF ITQYSTGQVS VEIEWELQKE NSKRWNPEIQ YTSNYYKSNN VEFAVNTEGV

721 YSEPRPIGTR YLTRNL.
```

In one embodiment, the AAV capsid proteins are derived from a transcript encoding the amino acid sequence set forth in SEQ ID NO: 3.

In another aspect, disclosed herein are DNA plasmids comprising rAAV genomes. The DNA plasmids are transogy, 1533-539; and Muzyczka, 1992, CUM Topics in Microbial. and Immunol., 158:97-129). Various approaches are described in Ratschin et al., Mol. Cell. Biol. 4:2072 (1984); Hennonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595. The foregoing documents are hereby incorporated by reference in their entirety herein, with particular emphasis on those sections of the documents relating to rAAV production.

An exemplary method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

The disclosure herein thus provides, in various embodiments, packaging cells that produce infectious rAAV. Packaging cells may be non-adherent cells cultured in suspension or adherent cells. In one embodiment any suitable packaging cell line may be used, such as HeLa cells, HEK 293 cells and PerC.6 cells (a cognate 293 line). In one embodiment, the cell line is HEK 293 cells.

To increase the viral vector production yield, adherent cells may be cultured and selected for improved adherence to culture flasks. In some embodiments, improves transfection efficiency and cell count during subsequent bioreactor seeding steps. During subculture, cells may be detached from the cell culture surface by methods known in the art. For example, cells may be lifted by scraping or by incubating in a solution comprising proteases. In an exemplary embodiment, HEK293 cells may be washed with PBS and dissociated with trypsin for ~2 minutes at room temperature. Dissociation may be stopped by adding growth media containing serum, and cell clumps may be dissociated by repeated pipetting of the suspension. Cell suspension may then be pelleted, and the isolated pellet may be resuspended in a suitable complete growth media. Cells may then be seeded in new cell culture chambers, and allowed to adhere. Cells that do not adhere to the surface after a period of time may be removed by gentle aspiration with cell culture media, before the cell culture media was completely replaced with growth media. In some embodiments, the period of time that cells are allowed to adhere may be about 2 hours, about 3 hours, about 4 hours, about 5 hours, about 6 hours or about 7 hours. When the cells have been expanded, the process may be repeated to increase the fraction of cells that adhere strongly to the culture flasks. In some embodiments, the process is repeated at least 2 times, at least 3 times, at least 4 times, at least 5 times, or any suitable number of times. In an exemplary embodiment, HEK293 cells are seeded in 75 $cm^2$ flask, allowed to adhere for 4 hours in the 37° C. incubator before weakly adherent cells are removed by aspirating and replace cell culture media. In an exemplary embodiment, the process of selecting for strongly adherent cells is repeated for three cell culture passages.

In other embodiments, rAAV9 (i.e., infectious encapsidated rAAV9 particles) comprises a rAAV genome disclosed herein. In one aspect, the rAAV genome is a self-complementary genome.

In another aspect, rAAV are provided such as a rAAV9 named "rAAV SMN." In some embodiments, the rAAV SMN genome has in sequence a first AAV2 ITR, the chicken-β actin promoter with a cytomegalovirus enhancer, an SV40 intron, a polynucleotide encoding SMN, a polyadenylation signal sequence from bovine growth hormone, and a second AAV2 ITR. In some embodiments, polynucleotide encoding SMN is a human SMN gene, e.g., set forth in or derived from GenBank Accession Number MN_000344.2, Genbank Accession #NM_017411, or any other suitable human SMN isoform. An exemplary SMN sequence comprises a sequence of:

```
                                                            (SEQ ID NO: 4)
  1 CCACAAATGT GGGAGGGCGA TAACCACTCG TAGAAAGCGT GAGAAGTTAC TACAAGCGGT

61 CCTCCCGGCC ACCGTACTGT TCCGCTCCCA GAAGCCCCGG GCGGCGGAAG TCGTCACTCT

121 TAAGAAGGGA CGGGGCCCCA CGCTGCGCAC CCGCGGGTTT GCTATGGCGA TGAGCAGCGG

181 CGGCAGTGGT GGCGGCGTCC CGGAGCAGGA GGATTCCGTG CTGTTCCGGC GCGGCACAGG

241 CCAGAGCGAT GATTCTGACA TTTGGGATGA TACAGCACTG ATAAAAGCAT ATGATAAAGC

301 TGTGGCTTCA TTTAAGCATG CTCTAAAGAA TGGTGACATT TGTGAAACTT CGGGTAAACC

361 AAAAACCACA CCTAAAAGAA AACCTGCTAA GAAGAATAAA AGCCAAAAGA AGAATACTGC

421 AGCTTCCTTA CAACAGTGGA AAGTTGGGGA CAAATGTTCT GCCATTTGGT CAGAAGACGG

481 TTGCATTTAC CCAGCTACCA TTGCTTCAAT TGATTTTAAG AGAGAAACCT GTGTTGTGGT

541 TTACACTGGA TATGGAAATA GAGAGGAGCA AAATCTGTCC GATCTACTTT CCCCAATCTG

601 TGAAGTAGCT AATAATATAG AACAGAATGC TCAAGAGAAT GAAAATGAAA GCCAAGTTTC
```

```
-continued
 661 AACAGATGAA AGTGAGAACT CCAGGTCTCC TGGAAATAAA TCAGATAACA TCAAGCCCAA

721 ATCTGCTCCA TGGAACTCTT TTCTCCCTCC ACCACCCCCC ATGCCAGGGC CAAGACTGGG

781 ACCAGGAAAG CCAGGTCTAA AATTCAATGG CCCACCACCG CCACCGCCAC CACCACCACC

841 CCACTTACTA TCATGCTGGC TGCCTCCATT TCCTTCTGGA CCACCAATAA TTCCCCCACC

901 ACCTCCCATA TGTCCAGATT CTCTTGATGA TGCTGATGCT TTGGGAAGTA TGTTAATTTC

961 ATGGTACATG AGTGGCTATC ATACTGGCTA TTATATGGGT TTCAGACAAA ATCAAAAAGA

1021 AGGAAGGTGC TCACATTCCT TAAATTAAGG AGAAATGCTG GCATAGAGCA GCACTAAATG

1081 ACACCACTAA AGAAACGATC AGACAGATCT GGAATGTGAA GCGTTATAGA AGATAACTGG

1141 CCTCATTTCT TCAAAATATC AAGTGTTGGG AAAGAAAAAA GGAAGTGGAA TGGGTAACTC

1201 TTCTTGATTA AAAGTTATGT AATAACCAAA TGCAATGTGA AATATTTTAC TGGACTCTTT

1261 TGAAAAACCA TCTGTAAAAG ACTGGGGTGG GGGTGGGAGG CCAGCACGGT GGTGAGGCAG

1321 TTGAGAAAAT TTGAATGTGG ATTAGATTTT GAATGATATT GGATAATTAT TGGTAATTTT

1381 ATGGCCTGTG AGAAGGGTGT TGTAGTTTAT AAAAGACTGT CTTAATTTGC ATACTTAAGC

1441 ATTTAGGAAT GAAGTGTTAG AGTGTCTTAA AATGTTTCAA ATGGTTTAAC AAAATGTATG

1501 TGAGGCGTAT GTGGCAAAAT GTTACAGAAT CTAACTGGTG GACATGGCTG TTCATTGTAC

1561 TGTTTTTTTC TATCTTCTAT ATGTTTAAAA GTATATAATA AAAATATTTA ATTTTTTTTT

1621 A.
```

Conservative nucleotide substitutions of SMN DNA are also contemplated (e.g., a guanine to adenine change at position 625 of GenBank Accession Number NM_000344.2). In some embodiments, the genome lacks AAV rep and cap DNA, that is, there is no AAV rep or cap DNA between the ITRs of the genome. SMN polypeptides contemplated include, but are not limited to, the human SMN1 polypeptide set out in NCBI protein database number NP 000335.1. In embodiments the SMN DNA comprises a polynucleotide which encodes a human SMN polypeptide (for example the human SMN protein identified by Uniprot accession number Q16637, isoform 1 (Q16637-1)). Also contemplated is the SMN1-modifier polypeptide plastin-3 (PLS3) [Oprea et al., Science 320(5875): 524-527 (2008)]. Sequences encoding other polypeptides may be substituted for the SMN DNA.

Pre-transfection, cells are expanded in suitable culture media, in flasks or a suitable bioreactor, or both. In some embodiments, cells may be expanded in bioreactors that provide continuous circulation of cell culture media. In one embodiment, cells are expanded in 200 m$^2$, 333 m$^2$, or 500 m$^2$ iCELL is bioreactors. One culture media is DMEM with 5-10% FBS, 4.5 g/L glucose, 4 mM L-glutamine. In some embodiments, adherent cells are added to media in a recirculation media bag and circulated through the bioreactor. In some embodiments, cell culture media or any other media is continuously recirculated through the bioreactor using a peristaltic pump. Cells may be seeded at a suitable density in the flasks or bioreactors for culturing and transfection. The seeding density may depend on the cell type and the amount of time till transfection. In some embodiments, cells are seeded at about 8000-16000 cells/cm$^2$. In an embodiment, HEK293 cells are seeded at 8000-12,000 cell/cm$^2$.

Suitable methods for the transduction and reintroduction of transduced cells into a subject are known in the art. In one embodiment, cells can be transduced in vitro by combining rAAV with the cells, e.g., in appropriate media, and screening for those cells harboring the DNA of interest using conventional techniques such as Southern blots and/or PCR, or by using selectable markers.

In some embodiments, a packaging cell line is transfected with three plasmids: a plasmid encoding or comprising the vector sequence to be packaged within the AAV vector (e.g., pSMN, pMECP2 transgene, or pSOD1sh), pHELP and pAAV2/9. Transfection can be performed using any of the techniques known in the art, including but not limited to electroporation, lipofection, e.g. with a lipofectamine, cationic polymers and cationic lipids. Any suitable transfection media may be used. In one embodiment of the transfection process, adherent human embryonic kidney (HEK293) cells are transfected with a triple DNA plasmid polyethylenimine (PEI) co-precipitation. In one embodiment, a scAAV9.CB.SMN vector (a self-complementary AAV9 vector comprising a CB promoter and a polynucleotide encoding SMN) is produced using triple DNA plasmid transfection into adherent HEK293 cells using a PEI co-precipitation in a large-scale adherent cell bioreactor. In one embodiment, the DMEM growth medium used for cell expansion is replaced with a modified DMEM transfection media. This media is formulated without calcium and L-glutamine. In one embodiment, the transfection media is DMEM with no FBS, no calcium, no L-glutamine and 4.5 g/L glucose. In some embodiments, transfection media without serum (e.g., without FBS) improves transfection efficacy. In an embodiment, the transfection media is OptiMEM (Invitrogen/Thermo Fisher). In one embodiment, the three plasmids (pSMN, pHELP and pAAV2/9) are mixed together with PEI in transfection media and allowed to react. In some embodiments, the three plasmids are mixed together in about 1:1:1 molar ratio. In some embodiments, the plasmids and PEI are mixed in a ratio of 1:1 by weight of DNA:PEI. In some embodiments, the plasmids and PEI are mixed in a ratio of less than 1:1 by weight of DNA:PEI. In an embodiment, pSMN, pHELP and pAAV2/9 are mixed in 1:1:1 molar ratio in OptiMEM media. In such an embodiment, PEI is added such that DNA:PEI is 1:1 by weight. In some embodiments, the reaction is allowed to occur for 0-60 minutes, or 10-45 minutes, or 20-30 minutes. In an embodiment, the reaction is allowed to occur for 15-30 minutes.

In an embodiment, the present disclosure provides a method for manufacturing a AAV based viral vector comprising the steps of (i) culturing adherent HEK293 cells in an industrial scale bioreactor, (2) transfecting the adherent cells with plasmids for less than 60 minutes to enable production of the AAV vector, and optionally applying further processing, purification, formulation and filling steps to produce a pharmaceutical product. In one embodiment of this process, the scAAV9.CB.SMN vector is produced using triple DNA plasmid transfection using a polyethylenimine ("PEI") coprecipitation. In an embodiment, the 3 plasmids utilized for this transfection are pSMN, pAAV2/9, and pHELP Transfection may be performed by contacting the packaging cell line with the DNA-PEI coprecipitate. In some embodiments, the DNA-PEI coprecipitate in transfection media is filled into a media recirculation bag. In some embodiments, the DNA-PEI coprecipitate in transfection media is circulated into the bioreactor and completely displaces the growth media. In some embodiments, the DNA-PEI coprecipitate in transfection media is allowed to contact the adherent cells in the bioreactor. In some embodiments, DNA-PEI coprecipitate in transfection media is allowed to contact the adherent cells in the bioreactor for up to two hours. In some embodiments, the transfection occurs for one to two hours. In some embodiments, the transfection occurs for less than one hour, for example, 10 minutes, 20 minutes, 30 minutes, 40 minutes or 50 minutes. In some embodiments, the transfection occurs for one to two hours. In some embodiments, the transfection is stopped by recirculating complete growth media through the bioreactor and completely displacing the transfection media.

2. Harvesting the Expanded Viral Particles

After a suitable cell expansion period post-transfection, in some embodiments the cells are lysed and the viral particles harvested. In some embodiments, the cells are dissociated from the reactor before the cell lysis process is initiated. In some embodiments, the cells are lysed in situ. Optionally, the viral particles are harvested without lysing. In some embodiments, an endonuclease is added, e.g., circulated into the bioreactor to a final target concentration. The endonuclease may be one that degrades both DNA and RNA. In one embodiment, the endonuclease is a genetically engineered endonuclease from Serratia marcescens (Eaves, G. N. et al. J. Bact. 1963, 85, 273-278; Nestle, M. et al. J. Biol. Chem. 1969, 244, 5219-5225) that is sold under the name Benzonase® (EMD Millipore). The enzyme is produced and purified from E. coli strain W3110, a mutant of strain K12, containing the pNUC1 production plasmid (U.S. Pat. No. 5,173,418, which is hereby incorporated by reference in its entirety). Structurally, the protein is a dimer of identical 245 amino acid, about 30 kDa subunits with two important disulfide bonds. Benzonase® degrades all forms of DNA and RNA (single stranded, double stranded, linear and circular) and is effective over a wide range of operating conditions, digesting nucleic acids to 5'-monophosphate terminated oligonucleotides 2-5 bases in length. Benzonase® is produced under current good manufacturing practices (cGMP) and, thus, can be used in industrial scale processes for the purification of proteins and/or viral particles. Other endonucleases that are produced under cGMP conditions can likewise be used in the purification methods disclosed in this application. In one embodiment, benzonase is added to the bioreactor to a final concentration of between 50-200 U/ml, e.g., 75-150 U/ml, e.g., about 100 U/mL. In some embodiments the addition of Benzonase significantly reduces host cell DNA while allowing for high vg production in a bioreactor.

In some embodiments, the endonuclease is allowed to mix before the lysis buffer is added to the reactor. In some embodiments, the cell lysis solution is allowed to mix with the adherent cells for up to 1 hour, up to 2 hours, up to 3 hours, up to 4 hours or up to 5 hours. In some embodiments, the lysis buffer may comprise magnesium chloride and/or Tween-20 in a suitable buffer. In an exemplary embodiment, the lysis buffer is 500 mM HEPES, 10% Tween 20, 20 mM $MgCl_2$, pH 8.0. A Salt Sucrose Solution (SSS) which quenches the Benzonase reaction may be added to stop the lysis reaction. In some embodiments, the SSS is added to a harvest bag comprising rinse buffer and mixed for 15 minutes. In some embodiments, the bioreactor is rinsed with a Bioreactor Rinse Buffer, and the rinse is then collected in the harvest collection bag, along with the quenched cell lysis solution and the lysed cell contents, all of which together comprises the bulk harvest. In some embodiments, the Bioreactor Rinse Buffer may comprise Tris, MgCl2, NaCl, Tween-20 and sucrose. In an exemplary embodiment, the Bioreactor Rinse Buffer comprises 20 mM Tris, 1 mM $MgCl_2$, 500 mM NaCl, 1% Tween-20 w/v and 1% sucrose w/v at pH 8.1.

3. Purifying the Viral Particles

After harvest, the bulk harvest viral particles may be concentrated and purified, typically via filtration. In one embodiment, the viral particles are filtered by depth filtration followed by filtration through a filter that removes large molecule contaminants and cell debris, for example a 0.45 μm filter, but that permits vector genomes to pass therethrough. Any suitable depth filter may be used.

As understood in the art, depth filtration refers to the use of a porous filter medium to clarify solutions containing significant quantities of large particles (e.g., intact cells or cellular debris) in comparison to membrane filtration which would rapidly become clogged under such conditions. A variety of depth filtration media of varying pore sizes are commercially available from a variety of manufacturers such as Millipore, Pall, General Electric, and Sartorious.

The target flow rate for depth filtration may be reduced to keep the filter inlet pressure within specification. Once all bulk harvest has been filtered, the depth filter may, in certain embodiments, be chased with the diafiltration buffer used for a subsequent first tangential flow filtration step ("TFF1"). The depth filter pool is mixed. The depth filter pool may then be filtered through a 0.45 μm filter to further clarify the bulk harvest material. The 0.45 μm filter is then chased with TFF1 buffer.

4. Tangential Flow Filtration

In various embodiments, tangential flow filtration is used to concentrate the bulk harvest, and remove salts and proteins, e.g., using Tangential Flow Filtration. Tangential Flow Filtration (TFF) (also referred to as Cross Flow Filtration CFF) is well known to those of skill in the art and equipment and protocols for its implementation in a wide range of situations are commercially available from a variety of manufacturers including but not limited to the Pall Corporation, Port Washington, NY and Spectrum Labs, Rancho Dominguez, CA Generally, TFF may involve the recirculation of the retentate across the surface of the membrane. This gentle cross flow feed can, in certain embodiments, minimize membrane fouling, maintain a high filtration rate, and provide high product recovery. In one embodiment, the TFF step may be implemented with a flat sheet system, as exemplified herein. Flat sheet systems may be used in large scale production where such systems are provided with a means (e.g., an open flow channel) to prevent excessive shear forces on the viral particles. Alternatively, the TFF step may be implemented with a hollow fiber system, as exemplified herein. In one embodiment, the Molecular Weight Cut Off (MWCO) of the TFF system is between 200-400 kDa, e.g., about 300 kDa.

In one embodiment, the TFF1 step is performed using a 300 kDa MW cut-off regenerated cellulose membrane cassette. The cassette is flushed and sanitized with NaOH solution and equilibrated with TFF1 buffer. In one embodiment, the TFF1 buffer comprises 20 mM Tris, 1 mM $MgCl_2$, 500 mM NaCl, 1% Sucrose, pH 8.1.

In some embodiments, the concentration phase of the TFF1 step is selected to reduce the volume of the clarified harvest approximately 10×. Once the target retentate volume is reached, diafiltration operations may be started. The retentate can, in some embodiments, be diafiltered with about 6 diavolumes of TFF1 buffer. In some embodiments, the retentate is diafiltered with about 5-20, or 10-15, or 12 diavolumes of TFF1 buffer. Once 6 diavolumes of permeate total flow have been achieved, the retentate may be concentrated again and harvested. Rinses, e.g., two successive rinses of the membrane, may be executed to increase the product recovery of the intermediate drug substance.

5. Intermediate Product

In some embodiments, the intermediate drug substance may then be frozen on dry ice or in a freezer and then transferred to ≤−60° C. storage. In other embodiments, the intermediate product need not be frozen prior to the downstream process.

In some embodiments, multiple intermediate product substance lots are pooled together for further processing (e.g., for purification by a downstream process, e.g., as described herein). The multiple intermediate product substance lots may be pooled prior to freezing and storage. In other embodiments, the multiple intermediate product substance lots may be pooled after thawing the frozen and stored lots.

Downstream Process

In some embodiments, a downstream process is used to process the intermediate product (e.g. the pooled intermediate product) to a filtered drug substance. In some embodiments, the downstream process steps include: (a) acidification and clarification (e.g., using filtration), (b) cation exchange chromatography, (c) tangential flow filtration ("TFF2"), (d) CsCl ultracentrifugation, (e) collection of viral vector and (f) further tangential flow filtration ("TFF3") to produce a filtered drug substance where the purified AAV particles are suspended in a pharmaceutically acceptable carrier. In some embodiments, the downstream process contains the following manufacturing steps subsequent to production of the TFF1 intermediate: thaw and pool TFF1 intermediate, acidification and clarification, cation exchange chromatography (CEX), tangential flow filtration (TFF2), CsCl ultracentrifugation for Full/Empty Capsid Separation, tangential flow filtration (TFF3) for Concentration/Buffer Exchange, TFF 3 pool material filtration to generate drug substance, dilution and filtration of drug substance to produce drug product, storage of the drug product and filling of drug product into vials.

In some embodiments, the downstream process disclosed herein may be used to process an intermediate comprising an AAV SMN, an AAV MECP2, or an AAV encoding shRNA targeting SOD1 as described herein.

1. Acidification and Clarification of Intermediate

In embodiments where the intermediate is frozen, the downstream process begins by thawing the TFF1 intermediate material. A detergent, e.g., Tween 20, may be used to promote flocculation of the bulk of host cell proteins and DNA under acidic pH. The pH of the TFF 1 intermediate containing detergent may then be lowered. The flocculant and precipitate formed when the pH is lowered may then be removed by filtering the solution through a depth filter and a filter that removes large molecule contaminants and cell debris, for example a 0.45 filter, but that permits vector genomes to pass therethrough. Any suitable depth filter may be used.

In one embodiment, Tween 20 is slowly added to the TFF1 Intermediate solution to achieve final concentration of between 10-20% Tween 20. In some embodiments, the target composition after addition of Tween 20 is 36% Tween 20 solution in 20 mM Tris, 1 mM $MgCl_2$, 500 mM NaCl, 1% Sucrose m/v, pH 8.1. In some embodiments, Tween 20 is added slowly over a span of about 1-6 hours. In some embodiments, Tween 20 is added slowly over 3-6 hours. In some embodiments, Tween 20 is added slowly over 4 hours. In some embodiments, the Tween 20/TFF1 Intermediate solution is allowed to incubate overnight at room temperature. In some embodiment, the Tween 20/TFF1 Intermediate solution is allowed to incubate for 8-20 hours at room temperature. In an exemplary embodiment, the Tween 20/TFF1 Intermediate solution is allowed to incubate for 12-20 hours at room temperature.

After incubation the pH of the Tween 20 containing TFF1 Intermediate may be lowered by adding any suitable acid. In some embodiments, 1M glycine pH 2.5 is added to achieve a target pH of 3.5±0.1. In some embodiments, the target pH is pH 3.0-4.0, about pH 3.3-3.7, about pH 3.4-3.6, or about pH 3.5. Once the pH is within the acceptable range, the solution may be passed through any size filter. In an exemplary embodiment, a depth filter (e.g., Clarisolve POD) in line with a 0.45 μm filter (e.g., Opticap XL10 Durapore filter) or 0.8/0.45 μm PES filter is used.

2. Cation Exchange Chromatography

In various embodiments, a cation exchange (CEX) capture chromatography step is used, e.g., to separate the viral capsids from host cell proteins, host cell DNA, host cell lipids, Tween 20 and other process-related impurities. The principles of cation exchange chromatography are well known in the art, but, briefly, this method relies on the charge-charge interactions between the positively-charged particles to be isolated and the negatively-charged resin used. In general, the column is first equilibrated by running a few diavolumes of buffer through until pH and conductivity is stabilized. The sample is then loaded and the column is washed with a loading buffer. Finally, an elution buffer is used to elute the sample of interest off the column, and fractions containing the sample are collected. The presence of the sample of interest can be detected by optical absorbance measurements of the eluant.

In one embodiment, the CEX step utilizes a CIMmultus S03-8000 Advanced Composite Column (Sulfonyl) (2 μm pores) chromatography column. In one embodiment, the elution peak is collected starting at a sharp rise in OD280. The OD280 will begin to rise when the conductivity is between 80-85 mS/cm. The CEX eluate may be collected according to routine procedures and may be collected in two fractions. In one embodiment, the first fraction starts at the sharp rise in OD280 and is collected for 1.5 collection volumes (CVs). In another embodiment, the second fraction starts immediately after the first fraction and is collected for 1.0 CV. The two fractions are pooled and then neutralized to pH 8.0±0.30. In one embodiment, a Neutralization Buffer comprises 1.0 M Tris pH 9.1±0.1 at 20° C.

3. Tangential Flow Filtration 2

In some embodiments, a tangential flow filtration step (TFF2) is used to concentrate, remove protein impurities, and exchange the buffer to an appropriate buffer for the subsequent CsCl ultracentrifugation step. Any suitable TFF membrane may be used. In an embodiment, the TFF2 step utilizes 300 kD MWCO regenerated cellulose membranes.

In some embodiments, the concentration phase of this step is designed to reduce the volume of the CEX eluate. In one embodiment, the retentate is diluted 2-fold with a diafiltration buffer and the retentate is concentrated to its initial volume. In one embodiment, the diafiltration buffer is the TFF2 NaCl diafiltration buffer that contains 20 mM Tris, 2 mM MgCl2, 150 mM NaCl, 0.2% Poloxamer 188, 1% Sucrose, pH 8.1±0.1 at 20° C. In such embodiments, this process may be repeated until diafiltration with the new buffer is complete. In one embodiment, the retentate is diluted 2-fold with a CsCl-containing diafiltration buffer and the retentate is concentrated to its initial volume. In an embodiment, the CsCl-containing diafiltration buffer is the TFF2 CsCl diafiltration buffer that contains 20 mM Tris, 2 mM MgCl$_2$, 3 M CsCl, 0.2% Poloxamer 188, pH 8.1±0.1 at 20° C. In such embodiments, this process may be repeated until diafiltration with the new buffer is complete. Once CsCl diafiltration is complete, the retentate may then be concentrated to a prescribed volume that is dependent on the system hold-up volume. In some embodiments, rinsing, e.g., two successive rinses of the membrane, are executed to maximize the product recovery from the TFF2 system.

4. CsCl Ultracentrifugation

In some embodiments where an AAV is used for in vivo gene transduction, the final product of rAAV may contain minimum impurities and empty particles. Two methods for purifying AAV vector are ultracentrifugation using either an iodixanol gradient or a CsCl gradient. One study comparing the two methods demonstrated that iodixanol yielded AAV vectors with higher vector purity, but had more empty viral capsids compared to CsCl. Strobel et al. "Comparative Analysis of Cesium Chloride- and Iodixanol-Based Purification of Recombinant Adeno-Associated Viral Vectors for Preclinical Applications." Human Gene Therapy Methods, 26(4):147-157. Even though the use of CsCl leads to lower amounts of empty viral capsids, CsCl may be toxic to cells and multiple purification steps may be needed to remove residual CsCl, leading to a long process time (~3.5 days) compared to shorter methods like iodixanol (~1 day). A different study has shown that the many steps to remove residual CsCl frequently results in the dramatic loss of rAAV, leading to low yields and recovery rate, often negating the other benefits of the method. Hermens et al. "Purification of Recombinant Adeno-Associated Virus by Iodixanol Gradient Ultracentrifugation Allows Rapid and Reproducible Preparation of Vector Stocks for Gene Transfer in the Nervous System." Human Gene Therapy, 10:1885-1891. Furthermore, while these two methods work well in a laboratory for producing preclinical samples, they are not scalable and thus not suitable for large-scale production of commercial products. See, e.g., Tomono et al., "Ultracentrifugation-free chromatography-mediated large-scale purification of recombinant adeno-associated virus serotype 1 (rAAV1)." Molecular Therapy—Methods & Clinical Development, 3:15058 ("purification methods using cesium chloride (CsCl) or iodixanol density ultracentrifugation are not suitable for large-scale production").

In some embodiments, an ultracentrifugation step is used, e.g., to separate empty capsids from full capsids. Unexpectedly, the CsCl ultracentrifugation method disclosed herein was scalable and suitable for large-scale production of purified AAV vectors. Ultracentrifugation may be performed by analytical ultracentrifugation, and may involve the use of gradient buffers. Examples of gradient buffers include but are not limited to CsCl, sucrose, iodixanol and others known in the art. Centrifugation can be performed in any centrifuge capable of reaching the desired g-forces, e.g., an automated Optima XPN 100 Ultra Centrifuge system or equivalent system equipped with Type 50.2 Ti rotor or equivalent rotor. After ultracentrifugation, empty capsids and full capsids separate into different bands within the tube, and may be extracted by drawing material from a specific band. In some embodiments, TFF2-purified filtered material is centrifuged at 241,600-302,000 g (~40,000-50,000 rpm in 50.2 Ti rotor). In some embodiments, TFF2-purified filtered material is centrifuged overnight. In some embodiments, TFF2-purified filtered material is centrifuged for 16-24 hours. In some embodiments, TFF2-purified filtered material is centrifuged for 20-24 hours. In some embodiments, TFF2-purified filtered material is centrifuged at 15-25° C. In an embodiment, TFF2-purified filtered material is centrifuged at 302,000 g (50,000 rpm in 50.2 Ti rotor) for 17 hours at 20° C. In some embodiments, the buffer for CsCl centrifugation can have one or more of the following ingredients, comprising (a) CsCl, further comprising one or more of (b) MgCl$_2$, (c) Poloxamer 188 and (d) Tris. In some embodiments, the buffer for CsCl can include all of (a), (b), (c) and (d). In some embodiments, the buffer for CsCl has a pH 7.5-8.5, or pH 7.9-8.2. In an embodiment, a suitable buffer for CsCl centrifugation is 20 mM Tris, 2 mM MgCl$_2$, 3 M CsCl, 0.2% Poloxamer 188, pH 8.1±0.10. After completion of the centrifugation step, tubes may be removed from the ultracentrifuge. In some embodiment, the highest band, Band A, contains the empty capsids. In some embodiments, the next highest bands, Bands B, C and D, contain the full capsid doublet bands. In some embodiments, the AAV viral vectors are collected using a syringe. In an embodiment, Bands B, C and D are removed by an 18 G needle attached to 30 mL syringe inserted just below band D to middle of tube. In other embodiments, the bands may be assayed for the presence of full or empty capsid using techniques known in the art and/or as described herein, and the bands containing full capsid collected.

The ratio of empty to non-empty viral capsids can be measured by standard laboratory techniques. In some embodiments, the measurement is done by optical absorbance measurements. In some embodiments, the measurement is done by UV absorbance measurements. In some embodiments, the total amount of capsid proteins and total amount of DNA can be determined from UV absorbance measurements. In some embodiments, the measurement is done by optical refractive index measurements. In some other embodiments, the measurement is done by analytical ultracentrifugation.

In one embodiment, the AAV viral vector collected after ultracentrifugation has less than 8% empty capsids, less than 7% empty capsids, less than 5%, less than 3%, or less than 1%. In one embodiment, the AAV viral vector collected after ultracentrifugation has 1-10% empty capsids. In one embodiment, the AAV viral vector collected after ultracentrifugation has 2-8% empty capsids. In one embodiment, the number of empty capsids is below the limit of detection. In another embodiment, the percentage of empty capsids is determined as a percentage of total capsids.

5. Tangential Flow Filtration 3 to Generate Filtered Drug Substance

In some embodiments, a tangential flow filtration step (TFF3) is used to remove CsCl and concentrate the full vector capsids. Tangential flow filtration may be performed using suitable membranes. In one embodiment, 300 kDa MWCO regenerated cellulose membranes are used. The vector capsids may be retained by the membranes. The concentration phase of TFF3 operation may be designed to reduce the concentration of residual CsCl and volume of the ultracentrifugation pool. In some embodiments, once the target retentate volume is reached, diafiltration is started. The retentate is diafiltered with up to 10 diavolumes of a suitable TFF3 buffer. In one embodiment a suitable TFF3 buffer can include one or more of the following components, comprising (a) Tris, (b) $MgCl_2$, (c) NaCl, or (d) Poloxamer 188. In one embodiment, a suitable TFF3 buffer can include all of (a), (b), (c) and (d). In one embodiment, the TFF3 buffer has pH 7.5-8.5, pH 7.7-8.3, or pH 8.0. In an embodiment a suitable TFF3 buffer comprises 20 mM Tris, 1 mM $MgCl_2$, 200 mM NaCl, 0.001% Poloxamer 188, pH 8.0±0.1 at 20° C. In another embodiment, a suitable TFF3 buffer comprises 20 mM Tris, 1 mM $MgCl_2$, 200 mM NaCl, 0.005% Poloxamer 188, pH 8.0±0.1 at 20° C. In one embodiment, the concentrated retentate is filtered using a 0.2 μm Pall Supor® EKV Sterilizing-Grade Filter (Mini Kleenpak) Filter to produce a filtered drug substance. In some embodiments, the methods described herein yield more than $5\times10^{15}$ vg, or more than $8\times10^{15}$ vg or more than $1\times10^{16}$ vg of rAAV per manufacturing batch.

Pharmaceutical Compositions

The viral (e.g., AAV) particles purified according to the methods disclosed herein may be produced in high yield with sufficient purity that they can be administered to a human subject. In some embodiments, the viral vector is formulated at a concentration of between about $1-8\times10^{13}$ viral vector genomes/mL (vg/mL), or about $1.7-2.3\times10^{13}$ vg/mL. In some embodiments, the viral vector is formulated at a concentration of about $1.9-2.1\times10^{13}$ vg/mL. In some embodiments, the viral vector is formulated at a concentration of about $2.0\times10^{13}$ vg/mL.

In some embodiments, during the production process of the viral vector, empty viral capsids that do not contain nucleic acid material may be generated. Pharmaceutical compositions comprising low amounts of empty viral capsids may be advantageous, because they avoid exposing patients, e.g., infants, with immature immune systems to antigenic material (empty capsids, host cell protein, host cell DNA) unnecessarily without therapeutic benefit. In some embodiments, such pharmaceutical compositions may reduce potential infusion reactions or broader immune responses and may improve therapeutic efficacy. Compared to full viral capsids with genome material, empty capsids have different densities, allowing the two species to be separated by gradient centrifugation, or other methods known in the art. In some embodiments, the empty capsids are separated by ultracentrifugation. In some embodiments, the empty capsids are separated by CsCl gradient ultracentrifugation. In other embodiments, the empty capsids are separated by iodixanol gradient ultracentrifugation. In some embodiments, the empty capsids are separated by sucrose gradient ultracentrifugation.

The ratio of empty to non-empty viral capsids can be measured by standard laboratory techniques. In some embodiments, the ratio is measured by optical absorbance measurements. In some embodiments, the ratio is measured by UV absorbance measurements. In some embodiments, the total amount of capsid proteins and total amount of DNA can be determined by UV absorbance measurements. In some embodiments, the measurement is determined by optical refractive index measurements. In some other embodiments, the measurement is determined by analytical ultracentrifugation.

High levels of empty capsids may pose challenges for the efficacy of viral vector treatments. In one embodiment, the pharmaceutical composition has less than 10% empty capsids, less than 8% empty capsids, less than 7%, less than about 5%, less than 3%, less than 1% empty capsids. In another embodiment, the pharmaceutical composition has 1-10% empty capsids. In another embodiment, the pharmaceutical composition has 2-8% empty capsids. In another embodiment, the pharmaceutical composition has less than or equal to 6% empty capsids, 5% empty capsids, 4% empty capsids, 3% empty capsids, 2% empty capsids, or fewer. In an embodiment, the number of empty capsids is below the limit of detection. In another embodiment, the percentage of empty capsids is determined as a percentage of total capsids, e.g., using AUC. In some embodiments, these low percentage empty capsids improve efficacy of treatment and/or reduce adverse events (e.g., inflammatory responses, liver injury) after administration to a patient, e.g., as compared to compositions having higher percentage empty capsids. In some embodiments, the methods of preparing viral vectors disclosed herein provide these improved percentages of empty capsids, as compared to the levels in prior methods, e.g., those not using adherent cells and/or the purification methods described herein.

During the production process of the viral vector, residual protein from the adherent cells (e.g. HEK293 cells) used to generate the viral vectors may not be completely separated out. Residual host cell proteins pose a potential to elicit an immune response. The amount of residual host cell can be measured by any standard laboratory techniques that can distinguish between the viral capsid proteins and the residual host cell proteins. In some embodiments, the amount of residual host cell proteins can be measured by size exclusion or ion exchange chromatography. In some embodiments, the measurement can be done by a western blot with parental cell-specific antibodies. In one embodiment, the amount of residual host cell protein can be measured by enzyme-linked immunosorbent assay (ELISA). In some embodiments, the amount of residual host cell protein can be measured by a commercial ELISA kit. In some embodiments, the amount of residual host cell protein can be measured by a Cygnus Technologies HEK293 HCP ELISA Kit.

In another embodiment, the residual host cell protein in said pharmaceutical composition is less than or equal to $5\times10^6$ pg/ml per $1\times10^{13}$ vg/ml, less than or equal to $1.2\times10^6$ pg/ml per $1\times10^{13}$ vg/mL or $1\times10^5$ pg/ml per $1\times10^{13}$ vg/ml to $1.2\times10^6$ pg/ml per $1\times10^{13}$ vg/ml or less than or equal to 40 ng/ml per $1\times10^{13}$ vg/ml. In an embodiment, the pharmaceutical composition comprises less than or equal to 5, 4, 3, 2, 1 or fewer ng residual host cell protein per $1.0\times10^{13}$ vg. In one embodiment, the pharmaceutical composition comprises less than or equal to 4 ng residual host cell protein per $1.0\times10^{13}$ vg.

During the production process of the viral vector, residual host cell DNA from the adherent cells (e.g. HEK293 cells) or residual plasmid DNA transfected to generate the viral vectors may not be completely removed. The purification process (e.g. acidification, clarification, tangential flow filtration etc.) removes the bulk of residual host cell or plasmid DNA. In one embodiment, measurement of the amount of residual host cell or plasmid DNA is performed by PCR. In another embodiment, measurement of the amount of residual host cell or plasmid DNA is performed by quantitative PCR (qPCR) with primers specific for host cell or plasmid sequences. In another embodiment, measurement of the amount of residual host cell or plasmid DNA is performed by digital droplet PCR (ddPCR). In one embodiment, the amount of plasmid DNA is determined using a qPCR assay with primers specific to the Kanamycin resistance gene region of the plasmid. In another embodiment, the amount of residual host cell DNA is determined by commercial qPCR assay kits, for example the resDNASEQ© Human Residual DNA Quantitation Kit by ThermoFisher, Residual DNA Quantification Supermix by Biorad, or any equivalent product. Reducing the amount of residual host cell or plasmid DNA may improve therapeutic outcomes and such compositions may be purified and/or selected for use in treatments disclosed herein.

In an embodiment, the residual host cell DNA in said pharmaceutical composition is less than or equal to $1.7 \times 10^6$ pg/ml per $1 \times 10^{13}$ vg/ml, $1 \times 10^5$ pg/ml per $1 \times 10^{13}$ vg/ml to $1.2 \times 10^6$ pg/ml per $1 \times 10^{13}$ vg/ml. In an embodiment, the residual host cell DNA in said pharmaceutical composition is less than or equal to $3 \times 10^5$, $2 \times 10^5$, $1.1 \times 10^5$, $1 \times 10^5$ pg or fewer per $1.0 \times 10^{13}$ vg. In embodiments, the residual host cell DNA in said pharmaceutical composition is less than or equal to $1.1 \times 10^5$ pg per $1.0 \times 10^{13}$ vg.

In another embodiment, the residual plasmid DNA in said pharmaceutical composition is less than or equal to $1.7 \times 10^6$ pg/ml per $1 \times 10^{13}$ vg/ml, $1 \times 10^5$ pg/ml per $1 \times 10^{13}$ vg/ml to $1.7 \times 10^6$ pg/ml per $1 \times 10^{13}$ vg/ml. In another embodiment, the residual plasmid DNA in said pharmaceutical composition is less than or equal to $6.8 \times 10^5$ pg per $1.0 \times 10^{13}$ vg.

In an embodiment, the residual host cell DNA in a pharmaceutical composition is less than or equal to $1.1 \times 10^5$ pg per $1.0 \times 10^{13}$ vg and the residual plasmid DNA in said pharmaceutical composition is less than or equal to $6.8 \times 10^5$ pg per $1.0 \times 10^{13}$ vg.

In an embodiment, the residual host cell DNA in a pharmaceutical composition is less than or equal to $1.1 \times 10^5$ pg per $1.0 \times 10^{13}$ vg, and the residual plasmid DNA in said pharmaceutical composition is less than or equal to $6.8 \times 10^5$ pg per $1.0 \times 10^{13}$ vg, and the residual host cell protein in said pharmaceutical composition is less than or equal to 4 ng per $1.0 \times 10^{13}$ vg.

In some embodiments, the amount of endotoxin in the pharmaceutical composition is less than about 1 EU/mL per $1.0 \times 10^{13}$ vg/mL, less than about 0.75 EU/mL per $1.0 \times 10^{13}$ vg/mL, less than about 0.5 EU/mL per $1.0 \times 10^{13}$ vg/mL, less than about 0.4 EU/mL per $1.0 \times 10^{13}$ vg/mL, less than about 0.35 EU/mL per $1.0 \times 10^{13}$ vg/mL, less than about 0.3 EU/mL per $1.0 \times 10^{13}$ vg/mL, less than about 0.25 EU/mL per $1.0 \times 10^{13}$ vg/mL, less than about 0.2 EU/mL per $1.0 \times 10^{13}$ vg/mL, less than about 0.15 EU/mL per $1.0 \times 10^{13}$ vg/mL, less than about 0.1 EU/mL per $1.0 \times 10^{13}$ vg/mL, less than about 0.05 EU/mL per $1.0 \times 10^{13}$ vg/mL, or, less than about 0.02 EU/mL per $1.0 \times 10^{13}$ vg/mL. Methods for determining the amount of endotoxin are known in the art, e.g., a limulus amoebocyte lysate (LAL) test. In embodiments, the endotoxin is assayed per U.S. Pharmacopiea ("USP") <85> (incorporated herein by reference in its entirety).

In one embodiment, the bovine serum albumin (BSA) in a pharmaceutical composition is less than 0.5 ng per $1.0 \times 10^{13}$ vg, less than 0.3 ng per $1.0 \times 10^{13}$ vg, or less than 0.22 ng per $1.0 \times 10^{13}$ vg. In one embodiment, the benzonase in said pharmaceutical composition is less than 0.2 ng per $1.0 \times 10^{13}$ vg, less than 0.1 ng per $1.0 \times 10^{13}$ vg, or less than 0.09 ng per $1.0 \times 10^{13}$ vg.

In one embodiment, a pharmaceutical composition disclosed herein comprises one or more of the following: less than about 0.09 ng of benzonase per $1.0 \times 10^{13}$ vg, less than about 30 µg/g (ppm) of cesium, about 20-80 ppm of Poloxamer 188, less than about 0.22 ng of BSA per $1.0 \times 10^{13}$ vg, less than about $6.8 \times 10^5$ pg of residual plasmid DNA per $1.0 \times 10^{13}$ vg, less than about $1.1 \times 10^5$ pg of residual hcDNA per $1.0 \times 10^{13}$ vg, less than about 4 ng of rHCP per $1.0 \times 10^{13}$ vg, pH 7.7-8.3, about 390-430 mOsm/kg, less than about 600 particles that are ≥25 µm in size per container, less than about 6000 particles that are ≥10 µm in size per container, about $1.7 \times 10^{13}$-$2.3 \times 10^{13}$ vg/mL genomic titer, infectious titer of about $3.9 \times 10^8$-$8.4 \times 10^{10}$ IU per $1.0 \times 10^{13}$ vg, total protein of about 100-300 µs per $1.0 \times 10^{13}$ vg, median survival of ≥24 days of Δ7SMA mice with about $7.5 \times 10^{13}$ vg/kg dose of viral vector, about 70-130% relative potency based on a in vitro cell-based assay, and/or less than about 5% empty capsid.

In one embodiment a pharmaceutical composition disclosed herein comprises one or more, e.g., all, of the following: pH 7.7-8.3 (e.g., as measured by USP <791>), about 390-430 mOsm/kg (e.g., as measured by USP <785>), less than about 600 particles that are ≥25 µm in size per container (e.g., as measured by USP <787>), less than about 6000 particles that are ≥10 µm in size per container (e.g., as measured by USP <787>), about $1.7 \times 10^{13}$-$2.3 \times 10^{13}$ vg/mL genomic titer, infectious titer of about $3.9 \times 10^8$-$8.4 \times 10^{10}$ IU per $1.0 \times 10^{13}$ vg, total protein of about 100-300 µg per $1.0 \times 10^{13}$ vg, median survival of ≥24 days of Δ7SMA mice with about $7.5 \times 10^{13}$ vg/kg dose of viral vector, e.g., in an in vivo functionality test, e.g., as described herein, about 70-130% relative potency based on a in vitro cell-based assay, and/or less than about 5% empty capsid. In embodiments, a pharmaceutical composition disclosed herein comprises a total purity greater than or equal to 95% (e.g., as determined by SDS-PAGE). In embodiments, a pharmaceutical composition disclosed herein comprises no single unnamed related impurity at a level greater than 2% (e.g., as determined by SDS-PAGE). In embodiments, a pharmaceutical composition disclosed herein comprises Endotoxin levels of less than or equal to 0.75 EU/mL (e.g., as measured by USP <85>). In embodiments, a pharmaceutical composition disclosed herein tests for no growth in a sterility test, e.g., as measured by USP <71>.

High levels of residual host cell protein, host cell DNA, plasmid DNA, and/or endotoxin may pose challenges for the efficacy of viral vector treatments. In some embodiments, these low amounts of residual host cell protein, host cell DNA, plasmid DNA, and/or endotoxin improve efficacy of treatment and/or reduce adverse events (e.g., inflammatory responses, liver injury) after administration to a patient, e.g., as compared to compositions having higher amounts. In some embodiments, the methods of preparing viral vectors disclosed herein provide these improved levels, as compared to the levels in prior methods, e.g., those not using adherent cells and/or the purification methods described herein. In some embodiments, the methods herein also allow for preparation of viral vectors with reduced percentages of empty capsids in addition to low amounts of residual host cell protein, host cell DNA, plasmid DNA, and/or endotoxin.

In some embodiments, the amount of residual cesium after TFF, e.g., the second TFF, is below about 50 µg/g. In some embodiments, the amount of residual cesium after the TFF, e.g., the second TFF, is below about 30 µg/g. In some embodiments, the amount of residual cesium after the TFF, e.g., the second TFF, is below about 20 ug/g. In some embodiments, the residual cesium in the pharmaceutical composition is less than or equal to 30 ug/g (ppm). In some embodiments, the amount of residual CsCl may be measured by mass spectrometry, inductively coupled plasma mass spectrometry (ICP-MS), and/or another suitable method. In some embodiments, the amount of residual cesium after the second TFF is below the limit of quantitation, e.g., using ICP-MS.

In some embodiments, the concentration of AAV viral vectors collected after the second TFF is greater than or equal to about $5 \times 10^{12}$ vg/ml, greater than or equal to about $1 \times 10^{13}$ vg/ml, or greater than or equal to about $3 \times 10^{13}$ vg/ml.

In one embodiment, a pharmaceutical composition has one or more of the following: less than 0.09 ng of benzonase per $1.0 \times 10^{13}$ vg, less than 30 µg/g (ppm) of cesium, about 20-80 ppm of Poloxamer 188, less than 0.22 ng of BSA per $1.0 \times 10^{13}$ vg, less than $6.8 \times 10^5$ pg of residual plasmid DNA per $1.0 \times 10^{13}$ vg, less than $1.1 \times 10^5$ pg of residual hcDNA per $1.0 \times 10^{13}$ vg, and less than 4 ng of rHCP per $1.0 \times 10^{13}$ vg.

In another embodiment, the pharmaceutical composition retains a potency of between ±20%, between ±15%, between ±10%, or between ±5%, of a reference standard. In one embodiment, the potency is assessed as against a reference standard using the methods in Foust et al., Nat. Biotechnol., 28(3), pp. 271-274 (2010). Any suitable reference standard may be used. In one embodiment, the pharmaceutical composition has an in vivo potency, as tested by SMAΔ7 mice. In an embodiment, a tested mouse given a $7.5 \times 10^{13}$ vg/kg dose has a median survival of greater than 15 days, greater than 20 days, greater than 22 days or greater than 24 days. In one embodiment, the pharmaceutical composition has an in vitro relative potency as tested by a cell-based assay to be 50-150%, 60-140% or 70-130% relative to a reference standard and/or suitable control.

The virus particles purified according to the present disclosure (e.g., viral particles) can be formulated according to known methods to prepare pharmaceutically useful compositions. The compositions of the disclosure can be formulated for administration to a mammalian subject, e.g., a human, using techniques known in the art. In particular delivery systems may be formulated for intramuscular, intradermal, mucosal, subcutaneous, intravenous, intrathecal, injectable depot type devices or topical administration.

When the delivery system is formulated as a solution or suspension, the delivery system is in an acceptable carrier, e.g., an aqueous carrier. A variety of aqueous carriers may be used, e.g., water, buffered water, 0.8% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration.

The compositions, e.g., pharmaceutical compositions, may contain pharmaceutically acceptable auxiliary substances to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. In some embodiments, the pharmaceutical composition comprises a preservative. In some other embodiments, the pharmaceutical composition does not comprise a preservative.

The genomic titer of viral vectors, e.g., those in the compositions and formulations disclosed herein, can be determined in a number of standard ways. PCR with primers specific to the viral vector can provide relative measurements, but quantitative PCR (qPCR) may be used for smaller samples and absolute measurements. Droplet Digital PCR (ddPCR) is a method for performing digital PCR that is based on water-oil emulsion droplet technology. A sample is fractionated into tens of thousands of droplets, and PCR amplification of the template molecules occurs in each individual droplet. One does not need to make a standard curve or have primers with high amplification efficiency, hence ddPCR does not typically use as much sample as traditional PCR-based techniques. In one embodiment, the genomic titer of the viral vector is determined using PCR. In another embodiment, the genomic titer of the viral vector is determined using qPCR. In another embodiment, the genomic titer of the viral vector is determined using ddPC. The method of determining viral genomic titer using ddPCR is described, for instance, in Lock et al., "Absolute Determination of Single-Stranded and Self-Complementary Adeno-Associated Viral Vector Genome Titers by Droplet Digital PCR,"*Human Gene Therapy Methods*, 25(2): 115-125.

In some embodiments, the PCR-based methods detect and quantify encapsidated AAV9 viral genome using specifically designed primers and probes targeting the SMN gene. In other embodiments, the PCR-based methods detect and quantify encapsidated AAV9 viral genome using specifically designed primers and probes targeting the chicken beta-actin promoter. In other embodiments, the PCR-based methods detect and quantify encapsidated AAV9 viral genome using specifically designed primers and probes targeting the CMV enhancer. In other embodiments, the PCR-based methods detect and quantify encapsidated AAV9 viral genome using specifically designed primers and probes targeting the ITR sequences. In other embodiments, the PCR-based methods detect and quantify encapsidated AAV9 viral genome using specifically designed primers and probes targeting the bovine growth hormone polyadenylation signal.

In some embodiments, the pharmaceutical composition is about pH 7.7-8.3 and has an osmolality of 390-430 mOsm/kg. In some embodiments, the pH is measured using a pH meter. In some embodiments, the pH is measured potentiometrically using a micro-electrode with temperature compensation in accordance with standards set by the United States Pharmacopeia (USP), e.g., <791> (incorporated by reference in its entirety). In some embodiments, the osmolality is measured using freezing point depression in accordance with USP, e.g., USP <785> (incorporated by reference in its entirety). In some embodiments, the osmolality is measured using a vapor pressure depression osmometer. In other embodiments, the osmolality is measured using a membrane osmometer.

In one embodiment, an intravenous formulation has a pH between 7.5 and 8.5, a genomic titer of $2 \times 10^{13}$ vg/ml-$6 \times 10^{13}$ vg/ml, and an osmolality of 384-448 mOsm/kg. In another embodiment, an intravenous formulation has a pH between 7.5 and 8.5, a genomic titer of $1.5 \times 10^{13}$ vg/ml-$3.5 \times 10^{13}$ vg/ml, and an osmolality of 384-448 mOsm/kg. In another embodiment, an intravenous formulation has a pH between 7.5 and 8.5, a genomic titer of $1.8 \times 10^{13}$ vg/ml-$2.2 \times 10^{13}$ vg/ml, and an osmolality of 384-448 mOsm/kg. In an embodiment, an IV formulation comprises about 0.1-2.0 mM $MgCl_2$. In an embodiment, an IV formulation comprises about 100-300 mM NaCl. In an embodiment, an IV formulation comprises about 0.001%-0.01% w/v Poloxamer 188. In an embodiment, an IV formulation is an aqueous formulation in 10-30 mM Tris buffer, e.g., at a pH of 7.5-8.5.

In an embodiment, an IV formulation comprises 1 mM MgCl$_2$, 200 mM NaCl, 0.005% w/v Poloxamer 188, in 20 mM Tris buffer at pH 8.0. In embodiments, the IV formulation comprises a genomic titer of about $1\times10^{13}$ to $3\times10^{13}$ vg/mL or $1.7\times10^{13}$ to $2.3\times10^{13}$ vg/mL.

Uses of Pharmaceutical Compositions

In other embodiments, disclosed herein are methods for delivery of a polynucleotide to the central nervous system of a patient comprising administering a rAAV9 with a genome including the polynucleotide. In some embodiments, the delivery is intrathecal delivery of a polynucleotide to the central nervous system of a patient comprising administering a rAAV9 with a genome including the polynucleotide. In some embodiments, a non-ionic, low-osmolar contrast agent is also administered to the patient. The non-ionic, low-osmolar contrast agent increases transduction of target cells in the central nervous system of the patient. In some embodiments, the rAAV9 genome is a self-complementary genome. In other embodiments, the rAAV9 genome is a single-stranded genome.

In some embodiments, the polynucleotide is delivered to a brain region. Areas of the brain contemplated for delivery include, but are not limited to, the motor cortex and the brain stem.

In some embodiments, the polynucleotide is delivered to the spinal cord. In some embodiments, the polynucleotide is delivered to a lower motor neuron. Embodiments of the disclosure employ rAAV9 to deliver polynucleotides to nerve and glial cells. In some embodiments, the glial cell is a microglial cell, an oligodendrocyte or an astrocyte. In some embodiments, the rAAV9 is used to deliver a polynucleotide to a Schwann cell.

Uses include, for example, treatment of lower motor neuron diseases such as SMA and ALS as well as Pompe disease, lysosomal storage disorders, Glioblastoma multiforme and Parkinson's disease. Lysosomal storage disorders include, but are not limited to, Activator Deficiency/GM2 Gangliosidosis, Alpha-mannosidosis, Aspartylglucosaminuria, Cholesteryl ester storage disease, Chronic Hexosaminidase A Deficiency, Cystinosis, Danon disease, Fabry disease, Farber disease, Fucosidosis, Galactosialidosis, Gaucher Disease (Type I, Type II, Type III), GM1 gangliosidosis (Infantile, Late infantile/Juvenile, Adult/Chronic), I-Cell disease/Mucolipidosis II, Infantile Free Sialic Acid Storage Disease/ISSD, Juvenile Hexosaminidase A Deficiency, Krabbe disease (Infantile Onset, Late Onset), Metachromatic Leukodystrophy, Mucopolysaccharidoses disorders (Pseudo-Hurler polydystrophy/Mucolipidosis IIIA, MPSI Hurler Syndrome, MPSI Scheie Syndrome, MPS I Hurler-Scheie Syndrome, MPS II Hunter syndrome, Sanfilippo syndrome Type A/MPS III A, Sanfilippo syndrome Type B/MPS III B, Sanfilippo syndrome Type C/MPS III C, Sanfilippo syndrome Type D/MPS III D, Morquio Type A/MPS WA, Morquio Type B/MPS IVB, MPS IX Hyaluronidase Deficiency, MPS VI Maroteaux-Lamy, MPS VII Sly Syndrome, Mucolipidosis I/Sialidosis, Mucolipidosis IIIC, Mucolipidosis type IV), Multiple sulfatase deficiency, Niemann-Pick Disease (Type A, Type B, Type C), Neuronal Ceroid Lipofuscinoses (CLN6 disease (Atypical Late Infantile, Late Onset variant, Early Juvenile), Batten-Spielmeyer-Vogt/Juvenile NCL/CLN3 disease, Finnish Variant Late Infantile CLN5, Jansky-Bielschowsky disease/Late infantile CLN2/TPP1 Disease, Kufs/Adult-onset NCL/CLN4 disease, Northern Epilepsy/variant late infantile CLN8, Santavuori-Haltia/Infantile CLN1/PPT disease, Beta-mannosidosis, Pompe disease/Glycogen storage disease type II, Pycnodysostosis, Sandhoff Disease/Adult Onset/GM2 Gangliosidosis, Sandhoff Disease/GM2 gangliosidosis-Infantile, Sandhoff Disease/GM2 gangliosidosis-Juvenile, Schindler disease, Salla disease/Sialic Acid Storage Disease, Tay-Sachs/GM2 gangliosidosis, Wolman disease.

In further embodiments, use of the methods and materials is indicated for treatment of nervous system disease such as Rett Syndrome, Alzheimer's disease, Parkinson's disease, Huntington's disease, or for treatment of nervous system injury including spinal cord and brain trauma/injury, stroke, and brain cancers. In one embodiment, use of the methods and materials is indicated for treatment of spinal muscular atrophy (SMA).

There are four types of SMA, which are conventionally classified by age of onset and highest motor function achieved. All forms of SMA are autosomal recessive inheritance and caused by mutations of the survival motor neuron 1 (SMN1) gene. Humans also carry a second nearly identical copy of the SMN gene called SMN2. Lefebvre et al. "Identification and characterization of a spinal muscular atrophy-determining gene." *Cell,* 80(1):155-65. Monani et al. "Spinal muscular atrophy: a deficiency in a ubiquitous protein; a motor-neuron specific disease." *Neuron,* 48(6): 885-896. Both the SMN1 and SMN2 genes express SMN protein, however SMN2 contains a translationally silent mutation in exon 7, which results in inefficient inclusion of exon 7 in SMN2 transcripts. Thus, SMN2 produces both full-length SMN protein and a truncated version of SMN lacking exon 7, with the truncated version as the predominant form. As a result, the amount of functional full-length protein produced by SMN2 is much less (by 70-90%) than that produced by SMN1. Lorson et al. "A single nucleotide in the SMN gene regulates splicing and is responsible for spinal muscular atrophy." PNAS, 96(11) 6307-6311. Monani et al, "A single nucleotide difference that alters splicing patterns distinguishes the SMA gene SMN1 from the copy gene SMN2." *Hum Mol Genet* 8(7):1177-1183. Although SMN2 cannot completely compensate for the loss of the SMN1 gene, patients with milder forms of SMA generally have higher SMN2 copy numbers. Lefebvre et al., "Correlation between severity and SMN protein level in spinal muscular atrophy." *Nat Genet* 16(3):265-269. Park et al., "Spinal muscular atrophy: new and emerging insights from model mice." *Curr Neurol Neurosci Rep* 10(2):108-117. A caveat is that SMN2 copy number is not the sole phenotypic modifier. In particular, the c.859G>C variant in exon 7 of the SMN2 gene has been reported as a positive disease modifier. Patient with this particular mutation have less severe disease phenotypes. Prior et al., "A positive modified of spinal muscular atrophy in the SMN2 gene." *Am J Hum Genet* 85(3):408-413.

Type I SMA (also called infantile onset or Werdnig-Hoffmann disease) is when SMA symptoms are present at birth or by the age of 6 months. In this type, babies typically have low muscle tone (hypotonia), a weak cry and breathing distress. They often have difficulty swallowing and sucking, and do not reach the developmental milestone of being able to sit up unassisted. They often show one or more of the SMA symptoms selected from hypotonia, delay in motor skills, poor head control, round shoulder posture and hypermobility of joints. Typically, these babies have two copies of the SMN2 gene, one on each chromosome 5. Over half of all new SMA cases are SMA type I.

Type II or intermediate SMA is when SMA has its onset between the ages of 7 and 18 months and before the child can stand or walk independently. Children with type 2 SMA generally have at least three SMN2 genes. Late-onset SMA (also known as types III and IV SMA, mild SMA, adult-onset SMA and Kugelberg-Welander disease) results in variable levels of weakness. Type III SMA has its onset after 18 months, and children can stand and walk independently, although they may require aid. Type IV SMA has its onset in adulthood, and people are able to walk during their adult years. People with types III or IV SMA generally have between four and eight SMN2 genes, from which a fair amount of full-length SMN protein can be produced.

In one embodiment, the term "treatment" comprises the step of administering intravenously, or via the intrathecal route, an effective dose, or effective multiple doses, of a composition comprising a rAAV as disclosed herein to an animal (including a human being) in need thereof. If the dose is administered prior to development of a disorder/disease, the administration is prophylactic. If the dose is administered after the development of a disorder/disease, the administration is therapeutic. In embodiments, an effective dose is a dose that alleviates (either eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. Examples of disease states contemplated for treatment are set out herein.

In one embodiment, the compositions comprising rAAV of the disclosure are administered intravenously to a patient in need thereof having an SMA type I. In another embodiment, the compositions comprising rAAV of the disclosure are administered intrathecally to a patient in need thereof having SMA types II, III, or IV.

A method of treating type I SMA in a patient in need thereof, by administering the AAV9 viral vector via an intrathecal or intravenous route is disclosed herein. In some embodiments, the patient is 0-9 months of age. In some other embodiments, the patient is 0-6 months of age. In some embodiments where the viral vector is used for treating type I SMA in a patient, the weight of the patient is determined. In some embodiments, the patient has a body weight of less than 8.5 kg. In some embodiments, the patient has a body weight of more than 2.6 kg. In some embodiments, the patient has a body weight of 2.6-8.5 kg.

In some embodiments, the patient has mutations, e.g., a null mutation, in one copy of the SMN1 gene (encompassing any mutation that renders the encoded SMN1 nonfunctional). In some embodiments, the patient has mutations, e.g., a null mutation, in two copies of the SMN1 gene. In some embodiments, the patient has mutations, e.g., a null mutation, in all copies of the SMN1 gene. In some embodiments, the patient has a deletion in one copy of the SMN1 gene. In some embodiments, the patient has a deletion in two copies of the SMN1 gene. In some embodiments, the patient has biallelic SMN1 mutations, that is, either a deletion or substitution of SMN1 in both alleles of the chromosome. In some embodiments, the patient has at least one functional copy of the SMN2 gene. In some embodiments, the patient has at least two functional copies of the SMN2 gene. In some embodiments, the patient has at least two functional copies of the SMN2 gene. In some embodiments, the patient has at least three functional copies of the SMN2 gene. In some embodiments, the patient has at least four functional copies of the SMN2 gene. In some embodiments, the patient has at least five functional copies of the SMN2 gene. In some embodiments, the patient does not have a c.859G>C substitution in exon 7 of at least one copy of the SMN2 gene. In some embodiments, the genetic sequence of the SMN1 or SMN2 gene may be determined by full genome sequencing.

In other embodiments, the genetic sequence and copy number of the SMN1 or SMN2 gene may be determined by high-throughput sequencing. In some embodiments, the genetic sequence and copy number of the SMN1 or SMN2 gene may be determined by microarray analysis. In some embodiments, the genetic sequence and copy number of the SMN1 or SMN2 gene may be determined by Sanger sequencing. In some embodiments, the copy number of the SMN1 or SMN2 gene may be determined by fluorescence in-situ hybridization (FISH).

In some embodiments, the patient shows one or more SMA symptoms. SMA symptoms can include hypotonia, delay in motor skills, poor head control, round shoulder posture and hypermobility of joints. In some embodiments, poor head control is determined by placing the patient in a ring sit position with assistance given at the shoulders (front and back). Head control is assessed by the patient's ability to hold the head upright. In some embodiments, spontaneous movement is observed when the patient is in a supine position and motor skills is assessed by the patient's ability to lift their elbows, knees, hands and feet off the surface. In some embodiments, the patient's grip strength is measured by placing a finger in the patient's palm and lifting the patient until their shoulder comes off the surface. Hypotonia and grip strength is measured by how soon/long the patient maintains grasp. In some embodiments, head control is assessed by placing the patient's head in a maximum available rotation and measuring the patient's ability to turn head back towards midline. In some embodiments, shoulder posture may be assessed by sitting patient down with head and trunk support, and observing if patient flexes elbows or shoulder to reach for a stimulus that is placed at shoulder level at arms length. In some embodiments, shoulder posture may also be assessed by placing patient in a side-lying position, and observing if patient flexes elbows or shoulder to reach for a stimulus that is placed at shoulder level at arms length. In some embodiments, motor skills are assessed by observing if the patients flex their hips or knees when their foot is stroked, tickled or pinched. In some embodiments, shoulder flexion, elbow flexion, hip adduction, neck flexion, head extension, neck extension, and/or spinal incurvation may be assessed by known clinical measures, e.g., CHOP INTEND. Other SMA symptoms may be evaluated according to known clinical measures, e.g., CHOP INTEND.

In some embodiments, patients are treated after they show symptoms of type I SMA (e.g., one or more symptoms), as determined using one of the tests described herein. In some embodiments, patients are treated before they show symptoms of type I SMA. In some embodiments, patients are diagnosed with type I SMA based on genetic testing, before they are symptomatic.

Combination therapies are also contemplated herein. Combination as used herein includes either simultaneous treatment or sequential treatments. Combinations of methods can include the addition of certain standard medical treatments (e.g., riluzole in ALS), as are combinations with novel therapies. For example, other therapies for SMA include antisense oligonucleotides (ASOs) that alter bind to pre-mRNA and alter their splicing patterns. Singh. et al., "A multi-exon-skipping detection assay reveals surprising diversity of splice isoforms of spinal muscular atrophy genes." Plos One, 7(11):e49595. In one embodiment, nusinersen (U.S. Pat. Nos. 8,361,977 and 8,980,853, incorporated herein by reference) may be used. Nusinersen is an approved ASO that target intron 6, exon 7 or intron 7 of SMN2 pre-mRNA, modulating the splicing of SMN2 to more efficiently produce full-length SMN protein. In some embodiments, the method of treatment comprising the AAV9 viral vector is administered in combination with a muscle enhancer. In some embodiments, the method of treatment comprising the AAV9 viral vector is administered in combination with a neuroprotector. In some embodiments, the method of treatment comprising the AAV9 viral vector is administered in combination with an antisense oligonucleotide-based drug targeting SMN. In some embodiments, the method of treatment comprising the AAV9 viral vector is administered in combination with nusinersen. In some embodiments, the method of treatment comprising the AAV9 viral vector is administered in combination with a myostatin-inhibiting drug. In some embodiments, the method of treatment comprising the AAV9 viral vector is administered in combination with stamulumab.

While delivery to an individual in need thereof after birth is contemplated, intrauteral delivery to a fetus is also contemplated.

Methods of treating type I SMA patients using the pharmaceutical compositions comprising the viral vector are contemplated. In some embodiments, the viral vector is formulated at a concentration of about $1\text{-}8\times10^{13}$ AAV9 viral vector genomes/mL (vg/mL). In some embodiments, the viral vector is formulated at a concentration of about $1.7\text{-}2.3\times10^{13}$ vg/mL. In some embodiments, the viral vector is formulated at a concentration of about $1.9\text{-}2.1\times10^{13}$ vg/mL. In some embodiments, the viral vector is formulated at a concentration of about $2.0\times10^{13}$ vg/mL.

In some embodiments where the viral vector is used for treating type I SMA in a patient, the AAV viral vector (e.g. AAV SMN) is administered to the patient at a dose of about $1.0\text{-}2.5\times10^{14}$ vg/kg. In some embodiments where the viral vector is used for treating type I SMA in a patient, the AAV viral vector is administered to the patient at a dose of about $1.1\times10^{14}$ vg/kg. In some embodiments where the viral vector is used for treating type I SMA in a patient, the AAV viral vector is infused into the patient over about 45-70 min. In some embodiments where the viral vector is used for treating type I SMA in a patient, the AAV viral vector is infused into the patient over about 60 min. In some embodiments where the viral vector is used for treating type I SMA in a patient, the AAV viral vector is infused into the patient using an infusion pump, a peristaltic pump or any other equipment known in the art. In some embodiments where the viral vector is used for treating type I SMA in a patient, the AAV viral vector is infused into the patient using a syringe pump.

Titers of rAAV viral vector to be administered will vary depending, for example, on the particular rAAV, the mode of administration, the treatment goal, the individual, and the cell type(s) being targeted, and may be determined by methods standard in the art. Titers of rAAV may range from about $1\times10^6$, about $1\times10^7$, about $1\times10^8$, about $1\times10^9$, about $1\times10^{10}$, about $1\times10^{11}$, about $1\times10^{12}$, about $1\times10^{13}$, about $1\times10^{14}$, or more DNase resistant particles (DRP) per ml. Dosages may also be expressed in units of vector genomes (vg). The genomic titer can be determined using ddPCR as described in this application, in Lock et al., or any other methods known in the art.

Dosages may also vary based on the timing of the administration to a human. These dosages of rAAV may range from about $1\times10^{11}$ vg/kg, about $1\times10^{12}$ vg/kg, about $1\times10^{13}$ vg/kg, about $1\times10^{14}$ vg/kg, about $1\times10^{15}$ vg/kg, about $1\times10^{16}$ vg/kg, or more vector genomes per kilogram body weight in an adult. For a neonate, the dosages of rAAV may range from about $1\times10^{11}$ vg/kg, about $1\times10^{12}$ vg/kg, about $3\times10^{12}$ vg/kg, about $1\times10^{13}$ vg/kg, about $3\times10^{13}$ vg/kg, about $1\times10^{14}$ vg/kg, about $3\times10^{14}$ vg/kg, about $1\times10^{15}$ vg/kg, about $3\times10^{15}$ vg/kg, about $1\times10^{16}$ vg/kg, about $3\times10^{16}$ vg/kg, or more vector genomes per kilogram body weight.

Dosages may also vary based on the timing of the administration to a human. These dosages of rAAV may range from about $1\times10^{11}$ vg/kg/week, about $1\times10^{12}$ vg/kg/week, about $1\times10^{13}$ vg/kg/week, about $1\times10^{14}$ vg/kg/week, about $1\times10^{15}$ vg/kg/week, about $1\times10^{16}$ vg/kg/week, or more vector genomes per kilogram body weight in an adult. For a neonate, the dosages of rAAV may range from about $1\times10^{11}$ vg/kg/week, about $1\times10^{12}$ vg/kg/week, about $3\times10^{12}$ vg/kg/week, about $1\times10^{13}$ vg/kg/week, about $3\times10^{13}$ vg/kg/week, about $1\times10^{14}$ vg/kg/week, about $3\times10^{14}$ vg/kg/week, about $1\times10^{15}$ vg/kg/week, about $3\times10^{15}$ vg/kg/week, about $1\times10^{16}$ vg/kg/week, about $3\times10^{16}$ vg/kg/week, or more vector genomes per kilogram body weight per week. Dosages of rAAV $1\times10^{11}$ vg/1.5 kg/week, about $1\times10^{12}$ vg/1.5 kg/week, about $1\times10^{13}$ vg/1.5 kg/week, about $1\times10^{14}$ vg/1.5 kg/week, about $1\times10^{15}$ vg/1.5 kg/week, about $1\times10^{16}$ vg/1.5 kg/week, or more vector genomes per kilogram body weight in an adult. For a neonate, the dosages of rAAV may range from about $1\times10^{11}$ vg/1.5 kg/week, about $1\times10^{12}$ vg/1.5 kg/week, about $3\times10^{12}$ vg/kg/week, about $1\times10^{13}$ vg/1.5 kg/week, about $3\times10^{13}$ vg/1.5 kg/week, about $1\times10^{14}$ vg/1.5 kg/week, about $3\times10^{14}$ vg/1.5 kg/week, about $1\times10^{15}$ vg/1.5 kg/week, about $3\times10^{15}$ vg/1.5 kg/week, about $1\times10^{16}$ vg/1.5 kg/week, about $3\times10^{16}$ vg/1.5 kg/week, or more vector genomes per 1.5 kilogram body weight per week.

In an embodiment, the dose is about $1.1\times10^{14}$ vector genomes per kg (vg/kg) of patient body weight. In an embodiment, a 5 kg patient would receive a total dose of between $0.5\times10^{14}$ to $5.0\times10^{1}$ vector genomes. In an embodiment, the viral vector is administered in a Tris-buffered Saline. In an embodiment, the viral vector is administered in about 5-20 mL/kg, about 10-20 mL/kg, or about 5.5-6.5 mL/kg of Tris-buffered Saline.

The dose can be determined in a number of standard ways. PCR with primers specific to the viral vector can provide relative measurements, but qPCR may be used for smaller samples and absolute measurements. ddPCR is a method for performing digital PCR that is based on water-oil emulsion droplet technology. Baker et al., "Digital PCR hits its stride." *Nature Methods,* 9(6):541-544. Sykes et al., "Quantitation of targets for PCR by use of limiting dilution." *Biotechniques,* 13(3)444-449. A sample is fractionated into tens of thousands of droplets, and PCR amplification of the template molecules occurs in each individual droplet. One does not need to make a standard curve or have primers with high amplification efficiency, hence ddPCR does not typically use as much sample as traditional PCR-based techniques. Examples of commercially available ddPCR machines include, but are not limited to, the BioRad QX100 ddPCR and the RainDance Raindrop Digital PCR. In one embodiment, the dose is determined using PCR. In another embodiment, the dose is determined using qPCR. In another embodiment, the dose is determined using digital droplet PCR (ddPCR). In some embodiments, the PCR-based methods detect and quantify encapsidated AAV9 viral genome using specifically designed primers and probes targeting the SMN gene. In other embodiments, the PCR-based methods detect and quantify encapsidated AAV9 viral genome using specifically designed primers and probes targeting the chicken beta-actin promoter. In other embodiments, the PCR-based methods detect and quantify encapsidated AAV9 viral genome using specifically designed primers and probes targeting the CMV enhancer. In other embodiments, the PCR-based methods detect and quantify encapsidated AAV9 viral genome using specifically designed primers and probes targeting the ITR sequences. In other embodiments, the PCR-based methods detect and quantify encapsidated AAV9 viral genome using specifically designed primers and probes targeting the bovine growth hormone polyadenylation signal.

In one aspect, the dose is administered according to the following table, using $2.0 \times 10^{13}$ vg/ml as the target concentration of the drug product.

TABLE 2

Dosing

| Patient Weight Range (kg) | Dose Volume[a] (mL) |
|---|---|
| 2.6-3.0 | 16.5 |
| 3.1-3.5 | 19.3 |
| 3.6-4.0 | 22.0 |
| 4.1-4.5 | 24.8 |
| 4.6-5.0 | 27.5 |
| 5.1-5.5 | 30.3 |
| 5.6-6.0 | 33.0 |
| 6.1-6.5 | 35.8 |
| 6.6-7.0 | 38.5 |
| 7.1-7.5 | 41.3 |
| 7.6-8.0 | 44.0 |
| 8.1-8.5 | 46.8 |

[a]NOTE:
Dose Volume is calculated using the upper limit of the Patient Weight Range.

In some embodiments pharmaceutical composition comprising the AAV viral vector is infused into the patient over about 20-70 minutes, for example over about 45-70 minutes. In some embodiments, the pharmaceutical composition comprising the AAV viral vector is infused into the patient over about 60 min. In some embodiments, the pharmaceutical composition comprising the AAV viral vector is infused into the patient using an infusion pump, a peristaltic pump or any other equipment known in the art. In some embodiments, the pharmaceutical composition comprising the AAV viral vector is infused into the patient using a syringe pump.

The pre-screening of patients amenable to treatment is also contemplated, as well as the administration of treatment to patients identified according to criteria disclosed herein. AAVs may give rise to both a cellular and humoral immune response. As a result, a fraction of potential patients for AAV-based gene therapy harbors pre-existing antibodies against AAV. Jeune et al., "Pre-existing anti-Adeno-Associated Virus antibodies as a challenge in AAV gene therapy." *Hum Gene Ther Methods*, 24(2):59-67. Boutin et al., "Prevalence of serum IgG and neutralizing factors against adeno-associated virus (AAV) types 1, 2, 5, 6, 8, and 9 in the healthy population: implications for gene therapy using AAV vectors." *Hum Gene Ther*, 21:704-712. Because even very low levels of antibodies can prevent successful transduction, antecedent anti-AAV antibodies pose a serious obstacle to the universal application of AAV gene therapy. In some embodiments, the levels of anti-AAV9 antibody titers in a patient is determined prior to administration of the AAV viral vector. In some embodiments, the levels of anti-AAV9 antibody titers in a patient is determined by an ELISA binding immunoassay. In some embodiments, the patient has anti-AAV9 antibody titers at or below 1:100 as determined by an ELISA binding immunoassay prior to administration of treatment. In some embodiments, the patient has anti-AAV9 antibody titers at or below 1:50 as determined by an ELISA binding immunoassay prior to administration of treatment. In some embodiments, the patient has anti-AAV9 antibody titers above 1:100 as determined by an ELISA binding immunoassay after treatment and is monitored for 1-8 weeks or until titers decrease to below 1:100. In some embodiments, the patient has anti-AAV9 antibody titers above 1:100 as determined by an ELISA binding immunoassay after treatment and is monitored for 1-8 weeks or until titers decrease to below 1:50.

One approach to overcome high anti-AAV antibody titer is the use of immunosuppressant drugs. Monoclonal anti-CD20 antibody rituximab in combination with cyclosporine A has been shown to be effective in bringing down anti-AAV titers. Mingozzi et al., "Pharmacological modulation of humoral immunity in a nonhuman primate model of AAV gene transfer for hemophilia B." *Mol Ther*, 20:1410-1416. Another approach is the use of plasmapheresis to deplete neutralizing antibodies prior to vector administration. Monteilhet et al., "A 10 patient case report on the impact of plasmapheresis upon neutralizing factors against adeno-associated virus (AAV) types 1, 2, 6, and 8." *Mol Ther*, 19(11):2084-2091. During plasmapheresis, blood is withdrawn from a patient and the plasma and blood cells are separated by either centrifugation or hollow fiber filtration. The blood cells are then returned to the patient together with either treated plasma or replacement fluids, such as a 4.5% human albumin in saline. A common use of therapeutic apheresis is the removal of undesired immunoglobulins but in this case, plasmapheresis represents an attractive approach to deplete anti-AAV antibodies. In some embodiments, the patient has anti-AAV9 antibody titers above 1:100 as determined by an ELISA binding immunoassay prior to or after treatment and is treated with plasmapheresis. In some embodiments, the patient has anti-AAV9 antibody titers above 1:50 as determined by an ELISA binding immunoassay prior to or after treatment and is treated with plasmapheresis.

Pre-existing maternal antibodies to AAV9 may be transferred to an infant patient through breast milk or placental transfer in utero. In some embodiments, the patient has anti-AAV9 antibody titers above 1:100 as determined by an ELISA binding immunoassay prior to or after treatment and is switched to formula feeding. In some embodiments, the patient has anti-AAV9 antibody titers above 1:50 as determined by an ELISA binding immunoassay prior to or after treatment and is switched to formula feeding.

Prior to and after administration of treatment, the condition of the patient may be monitored. Some patients who have received AAV-based treatments have experienced thrombocytopenia, which is a condition characterized by low platelet count. Thrombocytopenia can be detected by a full blood count using a diluted sample of blood on a hemocytometer. Thrombocytopenia can also be detected by viewing a slide prepared with the patient's blood (a thin blood film or peripheral smear) under the microscope. Normal human platelet counts range from 150,000 cells/ml to about 450,000 cells/ml.

In some embodiments, the patient has platelet counts above about 67,000 cells/ml prior to administration or above about 100,000 cells/ml, or above about 150,000 cells/ml. In some embodiments, the patient has platelet counts below about 150,000 cells/ml prior to administration or below about 100,000 cells/ml, or below about 67,000 cells/ml, and is monitored for 1-8 weeks or until platelet counts increase to above about 67,000 cells/ml, or above about 100,000 cells/ml, or above about 150,000 cells/ml. In some embodiments where platelet counts are below about 67,000 cells/ml after administration of the viral vector, the patient may be treated with platelet transfusion. In some embodiments, the patient does not have thrombocytopenia prior to administration of the viral vector. In some embodiments, the patient has thrombocytopenia after administration of the viral vector and is monitored for about 1-8 weeks or until the patient does not have thrombocytopenia. In some embodiments, the patient has thrombocytopenia after administration of the viral vector and is treated with a platelet transfusion.

Monitoring the condition of patients may also involve standard blood tests that measure levels of platelets, serum protein electrophoresis, serum gamma-glutamyl transferase (GGT), aspartate transaminase (AST) and alanine aminotransferase (ALT), total bilirubin, glucose, creatine kinase (CK), creatinine, blood urea nitrogen (BUN), electrolytes, alkaline phosphatase and amylase. Troponin I levels are a general measure for heart health, and elevated levels reflect heart damage or heart-related conditions. In some embodiments, troponin-I levels are monitored after administration of the viral vector. In some embodiments, patients may have troponin-I levels less than about 0.3, 0.2, 0.15, or 0.1 µg/ml before administration of the viral vector. In some embodiments, patients may have troponin-I levels less than about 0.176 µg/ml before administration of the viral vector. In some embodiments, patients may have troponin-I levels above about 0.176 µg/ml after administration of the viral vector. In some embodiments, patients receive cardiac monitoring after administration of the viral vector until troponin-I levels are less than about 0.176 µg/ml.

Aspartate transaminase (AST) and alanine aminotransferase (ALT) and total bilirubin are a general measure of hepatic function, while creatinine tracks renal function. Elevated levels of AST, ALT or total bilirubin may indicate hepatic malfunction. In some embodiments, the patient has normal hepatic function prior to administration of the viral vector. In some embodiments, the patient has hepatic transaminase levels less than about 8-40 U/L prior to administration of the viral vector. In some embodiments, the patient has AST or ALT levels less than about 8-40 U/L prior to administration of the viral vector. In some embodiments, the patient has bilirubin levels less than 3.0 mg/dL prior to administration of the viral vector. In some embodiments, patients have creatinine levels less than 1.8 mg/dL prior to administration of the viral vector. In some embodiments, patients have hemoglobin (Hgb) levels between 8-18 g/dL prior to administration of the viral vector. In some embodiments, the patient has white blood cell (WBC) counts less than 20000 per mm$^3$ prior to administration of the viral vector.

The efficacy of the treatment method may be determined using a variety of tests for motor skills before and after treatment. In particular, the Children's Hospital of Philadelphia Infant Test of Neuromuscular Disorders (CHOP INTEND) was developed to evaluate the motor skills of patients with type I SMA. Glanzman et al., "The Children's Hospital of Philadelphia Infant Test of Neuromuscular Disorders (CHOP INTEND): Test development and reliability." *Neuromuscular Disorders,* 20(3):155-161. The CHOP INTEND test was developed following the evaluation of 26 infants with Type I SMA, mean age 11.5 months (1.4-37.9 months) with the Test of Infant Motor Performance (TIMP) and The Children's Hospital of Philadelphia Test of Strength in SMA (CHOP TOSS), a newly devised motor assessment for SMA. Testing of treating efficacy is not limited to the CHOP INTEND test, but may also include other motor skills tests known in the art, including but not limited to TIMP, CHOP TOSS, the Peabody Development Motor Scales, the Brazelton Neonatal Behavior Assessment test, Motor Milestone Development Survey, Ability Captured Through Interactive Video Evaluation (ACTIVE), the Bayley Scale of Infant Development and measurements of compound motor action potentials (CMAP).

In some embodiments, baseline testing before treatment is performed using the CHOP INTEND scale. In one embodiment, the efficacy of treatment is determined using the CHOP INTEND scale during follow up visits. In some embodiments, the CHOP INTEND includes measures of head control, righting reactions, trunk movements in supported sitting, supine and prone positions. In some embodiments, the CHOP INTEND includes measures of antigravity movements in assisted rolling, ventral suspension and supported standing.

In many gene therapy studies involving AAV vectors, an antigen specific T-cell response to the AAV vector has been observed, and may be expected between 2-4 weeks following gene transfer. One possible consequence to such antigen specific T-cell response is clearance of the transduced cells and loss of transgene expression. In an attempt to dampen the host immune response to the AAV based therapy, patients may be given immune suppressants. In some embodiments, patients may be given glucocorticoids before administration of viral vector. In some embodiments, patients may be given a corticosteroid before administration of viral vector. In some embodiments, patients may be given an oral steroid before administration of viral vector. Examples of oral steroids include but are not limited to prednisone, prednisolone, methylprednisolone, triamcinolone, bethamethasone, dexamethasone and hydrocortisone. In some embodiments, the oral steroid is or comprises prednisolone. In some embodiments, the patient is started on prophylactic steroid at least 24 hours prior to administering the viral vector. In some embodiments, the patient is given oral steroid for at least 30 days after administering the viral vector. In some embodiments, the oral steroid is administered once daily. In some embodiments, the oral steroid is administered twice daily. In some embodiments, the oral steroid is given at a dose of about 0.1-10 mg/kg, e.g, about 1 mg/kg. In some embodiments, the oral steroid is given at a dose of about 0.1-10 mg/kg/day, e.g., about 1 mg/kg/day. In some embodiments, the levels of AST and ALT are monitored after administration of the viral vector. In such embodiments, the oral steroid treatment is administered when AST and ALT levels exceed twice the upper limit of normal, e.g., as determined by clinical standards and methods known in the art, or about 120 IU/L. In some embodiments, the oral steroid treatment is administered for more than 30 days as long as AST and ALT levels exceed twice the upper limit of normal, e.g., as determined by clinical standards and methods known in the art, or exceed about 120 IU/L. During sustained treatment with corticosteroids, the adrenal glands naturally decrease production of cortisol. If corticosteroid treatment is stopped abruptly, the body may experience cortisol deficiency. In some embodiments where oral steroid is given to a patient for at least 30 days, the steroid dose is slowly tapered on a schedule. In some embodiments, the oral steroid dose is tapered when AST and ALT levels fall below twice the upper limit of normal, e.g., as determined by clinical standards and methods known in the art, or about 120 IU/L. In some embodiments, tapering comprises stepped decrements to 0.5 mg/kg/day for 2 weeks followed by 0.25 mg/kg/day for 2 more weeks. In some other embodiments, tapering of the oral steroid occurs at the discretion of the doctor.

Kit

The disclosure herein also provides a kit for treating SMA in a patient in need thereof, wherein the kit comprises one or more doses of a pharmaceutical composition comprising an effective amount or dose of a viral vector comprising an SMN polynucleotide disclosed herein and depending on the type of SMA (as further disclosed herein) the kit further comprises a contrast agent (—e.g., omnipaque 180), and instructions on how to use the pharmaceutical preparation or composition and the contrast agent.

In some embodiments, the kit contains vials of a viral vector pharmaceutical composition. In some embodiments, the viral vector pharmaceutical composition is at a concentration of about $1.7$-$2.3\times10^{13}$ vg/mL. In some embodiments, the viral vector pharmaceutical composition is at a concentration of about $1.9$-$2.1\times10^{13}$ vg/mL. In some embodiments, the viral vector pharmaceutical composition is at a concentration of about $2.0\times10^{13}$ vg/mL. In some embodiments, the vials contain about 5.9 mL of a viral vector pharmaceutical composition. In some embodiments, the vials contain about 8.7 mL of a viral vector pharmaceutical composition. In some embodiments, the kit contains no 5.9 mL vial, at least one 5.9 mL vial, at least two 5.9 mL vials or at least three 5.9 mL vials. In some embodiments, the kit contains no 8.7 mL vial, at least one 8.7 mL vial, at least two 8.7 mL vials, at least three 8.7 mL vials, at least four 8.7 mL vials, at least five 8.7 mL vials, at least six 8.7 mL vials.

In some embodiments where the kit is used for treating type I SMA in a patient, the weight of the patient is determined. In some embodiments where the kit is used for treating type I SMA in a patient, the weight of the patient is at least about 2.6 kg. In some embodiments where the kit is used for treating type I SMA in a patient, the weight of the patient is no more than about 8.5 kg. In some embodiments where the kit is used for treating type I SMA in a patient, the weight of the patient is about 2.6-8.5 kg. In some embodiments where the kit is used for treating type I SMA in a patient, the AAV viral vector from the vials in the kit is administered to the patient. In some embodiments where the kit is used for treating type I SMA in a patient, the AAV viral vector from the vials in the kit is administered to the patient at a dose of about $1.0$-$2.5\times10''$ vg/kg. In some embodiments where the kit is used for treating type I SMA in a patient, the AAV viral vector from the vials in the kit is administered to the patient at a dose of about $1.1\times10''$ vg/kg. In some embodiments where the kit is used for treating type I SMA in a patient, the AAV viral vector from the vials in the kit is infused into the patient over about 45-70 min. In some embodiments where the kit is used for treating type I SMA in a patient, the AAV viral vector from the vials in the kit is infused into the patient over about 60 min. In some embodiments where the kit is used for treating type I SMA in a patient, the AAV viral vector from the vials in the kit is infused into the patient using an infusion pump, a peristaltic pump or any other equipment known in the art. In some embodiments where the kit is used for treating type I SMA in a patient, the AAV viral vector from the vials in the kit is infused into the patient using a syringe pump.

In one embodiment, the vector is administered intravenously or intrathecally. In one embodiment, the vector is administered intravenously. In one embodiment, the vector is administered intravenously together with omnipaque 180. In another embodiment, the vector is administered intrathecally together with omnipaque 180.

In another aspect, methods of transducing target cells of a patient (including, but not limited to, nerve or glial cells) with rAAV are contemplated herein.

Transduction of cells of a patient with rAAV disclosed herein can results in sustained expression of polypeptide or RNA encoded by the rAAV. The present disclosure thus provides methods of administering/delivering rAAV (e.g., encoding SMN protein) to an animal or a human patient. These methods include transducing nerve and/or glial cells with one or more rAAV. Transduction may be carried out with gene cassettes comprising tissue specific control elements. For example, promoters that allow expression specifically within neurons or specifically within astrocytes. Examples include neuron specific enolase and glial fibrillary acidic protein promoters. Inducible promoters under the control of an ingested drug may also be developed.

In some aspects, it is contemplated that the transduction of cells is increased when a vector of the disclosure is used in combination with a contrast agent as described herein relative to the transduction of a vector of the disclosure when not used in combination with a contrast agent. In various embodiments, the transduction of cells is increased by at least about 1%, or at least about 5%, at least about 10%, at least about 20%, at least about 30%, at least about 40%, at least about 50%, at least about 60%, at least about 70%, at least about 80%, at least about 90%, at least about 100%, at least about 120%, at least about 150%, at least about 180%, at least about 200%, at least about 250%, at least about 300%, at least about 350%, at least about 400%, at least about 450%, at least about 500% or more when a vector of the disclosure is used in combination with a contrast agent as described herein, relative to the transduction of a vector of the disclosure when not used in combination with a contrast agent. In further embodiments, the transduction of cells is increased by about 10% to about 50%, or by about 10% to about 100%, or by about 5% to about 10%, or by about 5% to about 50%, or by about 1% to about 500%, or by about 10% to about 200%, or by about 10% to about 300%, or by about 10% to about 400%, or by about 100% to about 500%, or by about 150% to about 300%, or by about 200% to about 500% when a vector of the disclosure is used in combination with a contrast agent as described herein, relative to the transduction of a vector of the disclosure when not used in combination with a contrast agent.

The disclosure also provides aspects wherein intrathecal administration of a vector of the disclosure and a contrast agent to the central nervous system of a patient in need thereof results in an increase in survival of the patient relative to survival of the patient when a vector of the disclosure is administered in the absence of the contrast agent. In various embodiments, the vector of the disclosure and a contrast agent are separately administered intrathecally to the central nervous system of a patient in need thereof. In other embodiments, the vector and contrast agent are co-formulated and administered intrathecally to the central nervous system or a patient in need thereof. In other embodiments, the vector and contrast agent are provided in the same package for administering intrathecally to the central nervous system or a patient in need thereof. In various embodiments, administration of a vector of the disclosure and a contrast agent to the central nervous system of a patient in need thereof results in an increase of survival of the patient of at least about 1%, at least about 5%, at least about 10%, at least about 20%, at least about 30%, at least about 40%, at least about 50%, at least about 60%, at least about 70%, at least about 80%, at least about 90%, at least about 100%, at least about 150%, at least about 200% or more relative to survival of the patient when a vector of the disclosure is administered in the absence of the contrast agent.

In some aspects, it is contemplated that the transduction of cells is further increased when a vector of the disclosure is used in combination with a contrast agent and when the patient is put in the Trendelenberg position (head down position). In some embodiments, for example, the patients is tilted in the head down position at about 1 degree to about 30 degrees, about 15 to about 30 degrees, about 30 to about 60 degrees, about 60 to about 90 degrees, or about 90 up to about 180 degrees) during or after intrathecal vector infusion. In various embodiments, the transduction of cells is increased by at least about 1%, or at least about 5%, at least about 10%, at least about 20%, at least about 30%, at least about 40%, at least about 50%, at least about 60%, at least about 70%, at least about 80%, at least about 90%, at least about 100%, at least about 120%, at least about 150%, at least about 180%, at least about 200%, at least about 250%, at least about 300%, at least about 350%, at least about 400%, at least about 450%, at least about 500% or more when a vector of the disclosure is used in combination with a contrast agent and Trendelenberg position as described herein, relative to the transduction of a vector of the disclosure when not used in combination with a contrast agent and Trendelenberg position. In further embodiments, the transduction of cells is increased by about 10% to about 50%, or by about 10% to about 100%, or by about 5% to about 10%, or by about 5% to about 50%, or by about 1% to about 500%, or by about 10% to about 200%, or by about 10% to about 300%, or by about 10% to about 400%, or by about 100% to about 500%, or by about 150% to about 300%, or by about 200% to about 500% when a vector of the disclosure is used in combination with a contrast agent and Trendelenberg position as described herein, relative to the transduction of a vector of the disclosure when not used in combination with a contrast agent and Trendelenberg position.

The disclosure also provides aspects wherein intrathecal administration of a vector of the disclosure and a contrast agent to the central nervous system of a patient in need thereof put in the Trendelenberg position results in a further increase in survival of the patient relative to survival of the patient when a vector of the disclosure is administered in the absence of the contrast agent and the Trendelenberg position. In various embodiments, administration of a vector of the disclosure and a contrast agent to the central nervous system of a patient in need thereof put in the Trendelberg position results in an increase of survival of the patient of at least about 1%, at least about 5%, at least about 10%, at least about 20%, at least about 30%, at least about 40%, at least about 50%, at least about 60%, at least about 70%, at least about 80%, at least about 90%, at least about 100%, at least about 150%, at least about 200% or more relative to survival of the patient when a vector of the disclosure is administered in the absence of the contrast agent and the Trendelenberg position.

As used in this disclosure and the appended claims, the singular forms "a", "an", and "the" include plural referents unless the context clearly dictates otherwise. Optional or optionally means that the subsequently described event or circumstance can or cannot occur, and that the description includes instances where the event or circumstance occurs and instances where it does not. For example, the phrase optionally the composition can comprise a combination means that the composition may comprise a combination of different molecules or may not include a combination such that the description includes both the combination and the absence of the combination (i.e., individual members of the combination). Ranges may be expressed herein as from about one particular value, and/or to about another particular value. When such a range is expressed, another aspect includes from the one particular value and/or to the other particular value. Similarly, when values are expressed as approximations, by use of the antecedent about, it will be understood that the particular value forms another aspect. It will be further understood that the endpoints of each of the ranges are significant both in relation to the other endpoint, and independently of the other endpoint.

The present disclosure is further illustrated by the following examples that should not be construed as limiting. The contents of all references, patents, and published patent applications cited throughout this application, as well as the Figures, are incorporated herein by reference in their entirety for all purposes.

EXAMPLES

The following examples are to be considered illustrative and not limiting on the scope of the disclosure described above.

Example 1—Generation of Pre-GMP Master Cell Bank

Methods

Thaw: A single cell vial ($1\times10^6$ cells) was thawed in a 37° C. water bath for about 1 minute and contents diluted in 5 mL of pre-warmed complete growth media. The cells were transferred into a T-25 $cm^2$ flask and grown in a 37° C. incubator for 4 days, with a replacement of culture media with pre-warmed complete growth media every day.

Figure 2:
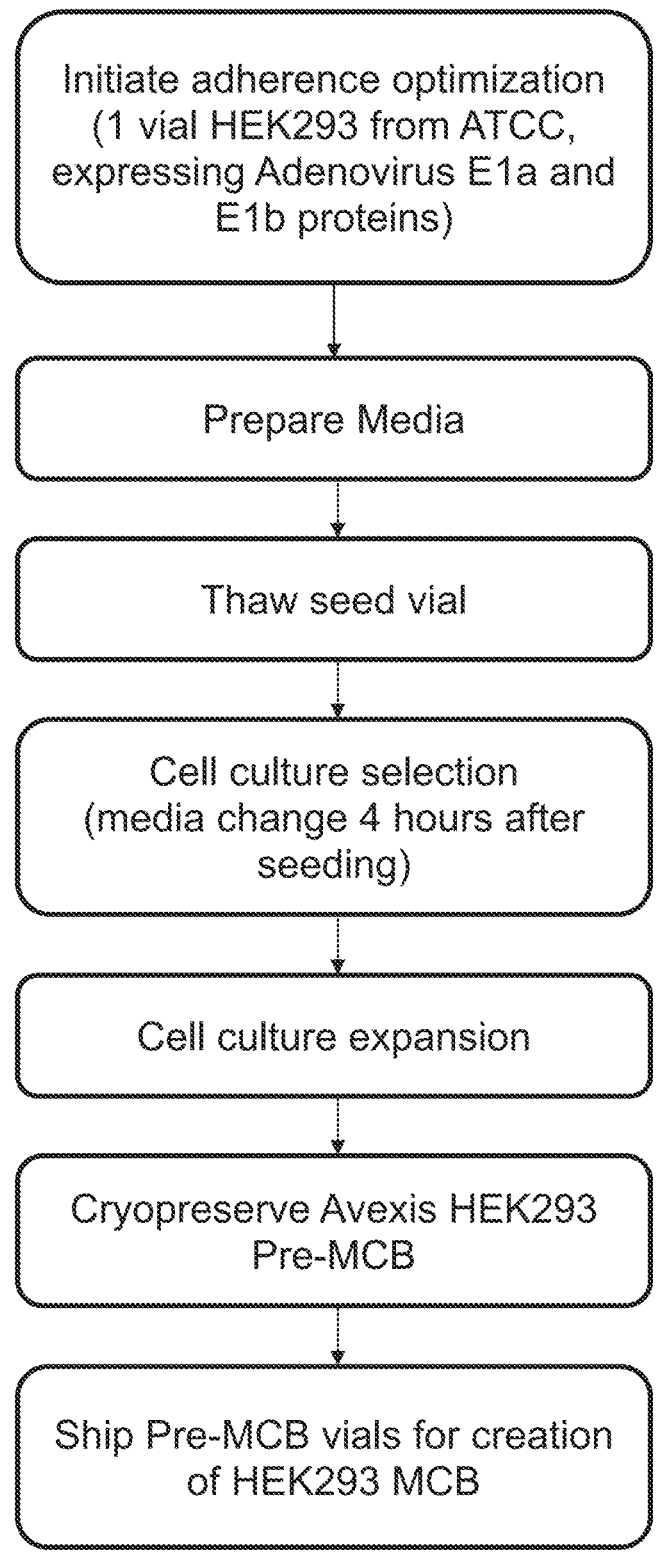
FIG. 2 shows a process flow chart for the selection of HEK293 cells for exceptional adherence and pre-master cell bank (MCB) banking.

Selection for Increased Adherence: The cells were cultured using the following technique to select for strongly adherent cells. Once the cells reached 95% confluency in the 25 $cm^2$ flask, the cells were subcultured. Cells were washed with 5 mL of PBS then dissociated with 0.5-1 mL of HyQTase for ~2 minutes at room temperature. Dissociation was stopped by adding 5 mL complete growth media and repeatedly pipetted to dissociate cell clumps. Cell suspension was then centrifuged for 4 minutes at 200×g. Supernatant was discarded and cell pellet was resuspended in 10 mL of complete growth media. Cells were transferred to a 75 $cm^2$ flask. after 4 hours of incubation in the 37° C. incubator, weakly adherent cells were washed away by aspirating cell culture media to remove weakly adherent and non-adherent cells. Culture media was replaced with 10 mL pre-warmed complete growth media. This process reduced cell mass by up to 35% of cell number, by visual inspection. The cells were incubated for an additional 2 days before being subcultured again. This selection process, consisting of the media change 4-hour post-seeding, was performed three times prior to expansion of the selected cell population (FIG. 2 and FIG. 3). In the final selection step, cells were seeded into 2×175 $cm^2$ flasks, with a final volume of 25 mL. It was noted that there was reduction in cell loss after the last 4-hour post-seeding media change.

Cell Expansion: Cells were subsequently expanded once the cells were confluent in the 2×175 $cm^2$ flasks. Cells were washed with 15 mL PBS then dissociated with 3 mL HyQTase and incubation for ~2 minutes at room temperature. Dissociation was stopped by adding 10 mL of complete growth media. Cell suspension was then centrifuged to produce 2 cell pellets once the supernatant was aspirated. Each pellet was resuspended in 8 mL of complete growth media and 2 mL of this concentrated cell suspension was added to 8×175 $cm^2$ flasks. The flasks were prepared by adding 20 mL of complete growth media, resulting in a total of 22 mL cell suspension and a splitting ratio of 1:4. The next expansion step used the same procedure with the following variations: 4×175 $cm^2$ flasks were expanded at a splitting ratio of 1:2 and 4×175 cm² flasks were expanded at a splitting ratio of 1:3. This resulted in a total of 20×175 cm² flasks.

Harvest: Cells were harvested from 20×175 cm² flasks. Cells were washed with 15 mL of PBS then dissociated with 3 mL HyQTase as previously described. Cell dissociation was stopped by adding 10 mL of complete growth media and collected into 50 mL tubes with cell suspension from 4×175 cm² flasks added to 1×50 mL tube. This resulted in 5×50 mL tubes with 40 mL of cell suspension in each. Tubes were centrifuged to create cell pellets, supernatants were aspirated, and cell were resuspended with 10 mL of complete growth media resulting in 50 mL of cell suspension.

The volume was split into 2×50 mL tubes, with a total of 25 mL of cell suspension in each tube. The samples diluted 1:2 were used to calculate viable cell counts per tube cells using a haemocytometer and Toludine (trypan) Blue. Tube 1 sample had a viable cell count of $1.99 \times 10^6$ cells/mL yielding a cell concentration of $3.98 \times 10^6$ cells/mL and Tube 2 sample had a viable cell count of $2.4 \times 10^6$ cells/mL (total $1 \times 10^8$ cells) yielding a cell concentration of $4.8 \times 10^6$ cells/mL (total $1.2 \times 10^8$ cells). Thus, a total of $2.2 \times 10^8$ cells were harvested. Both tubes were centrifuged again (6 minutes, 200×g) and pellets were resuspended in 10 mL (Tube 1) and 12 mL (Tube 2) of freezing medium, respectively, to adjust the cell concentration to $1 \times 10^7$ cells/mL. The two cell suspensions were pooled and 1 mL aliquots (each containing $1 \times 10^7$ cells) were filled in 22 sterile cryovials (Table 3).

TABLE 3

Calculation of total harvested cells

| | Cell Concentration for a 1:2 sample | Cell Concentration for Harvest | Total cells for Harvest |
|---|---|---|---|
| Tube 1 | $1.99 \times 10^6$ cells/mL | $3.98 \times 10^6$ cells/mL | $1 \times 10^8$ cells |
| Tube 2 | $2.4 \times 10^6$ cells/mL | $4.8 \times 10^6$ cells/mL | $1.2 \times 10^8$ cells |
| Total | — | — | $2.2 \times 10^8$ cells |

Filled vials were then transferred to a freezing chamber with fresh isopropanol overnight in a −80° C. freezer for controlled rate freezing. The frozen vials were then transferred to vapor phase liquid nitrogen in a liquid nitrogen tank. Ten vials were transferred on dry ice to be banked in a GMP facility.

HEK293 cells from ATCC were thawed and successfully adapted for increased adherence in 3 passages prior to expansion and successful banking of a seed bank. The seed bank was tested for growth and presence of adventitious agents (mycoplasma, fungi and bacteria). Testing showed that the seed bank is suitable for Master Cell Banking in a GMP facility.

Example 2—Upstream Process

Figure 1B:
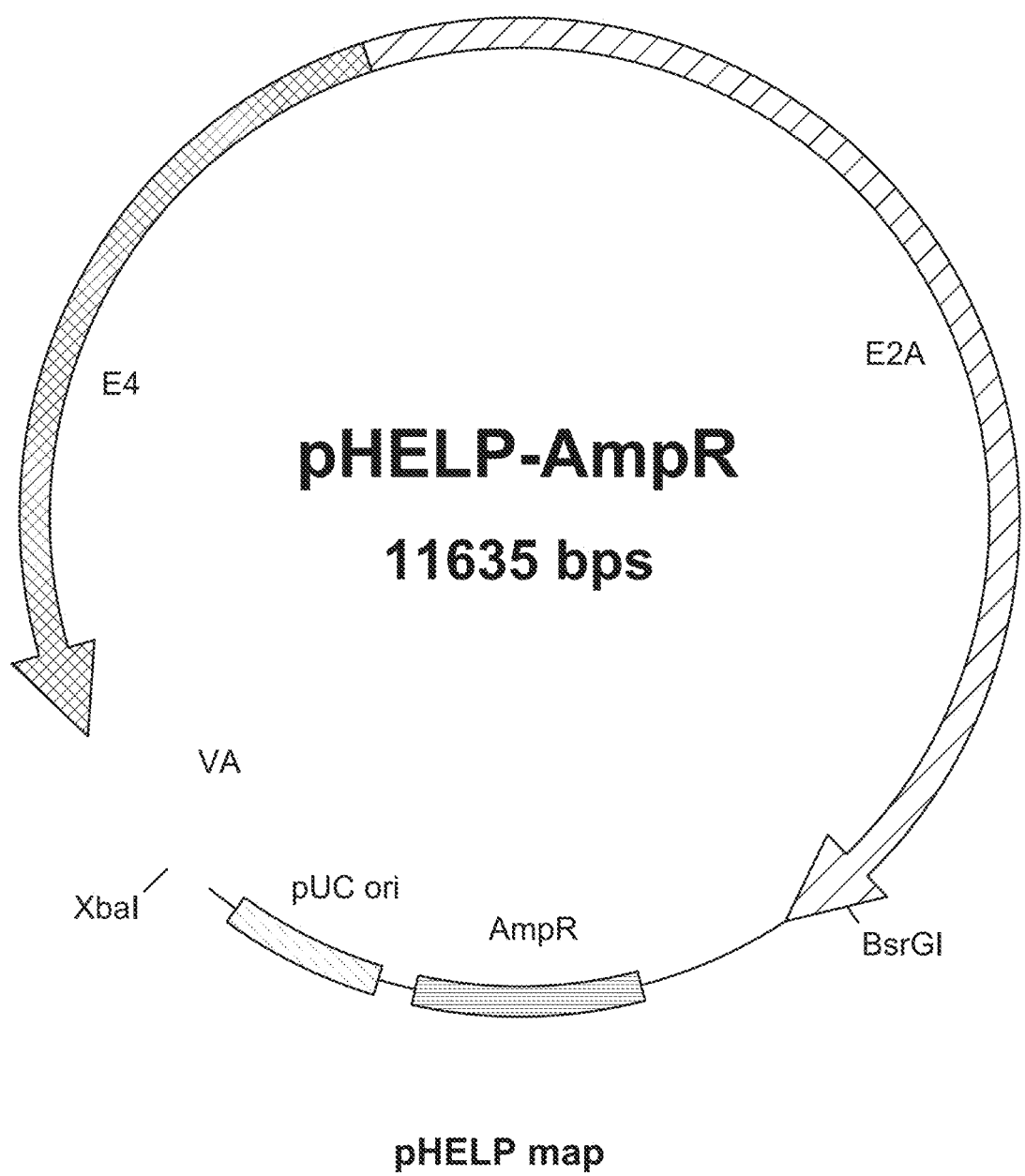
Figure 1C:
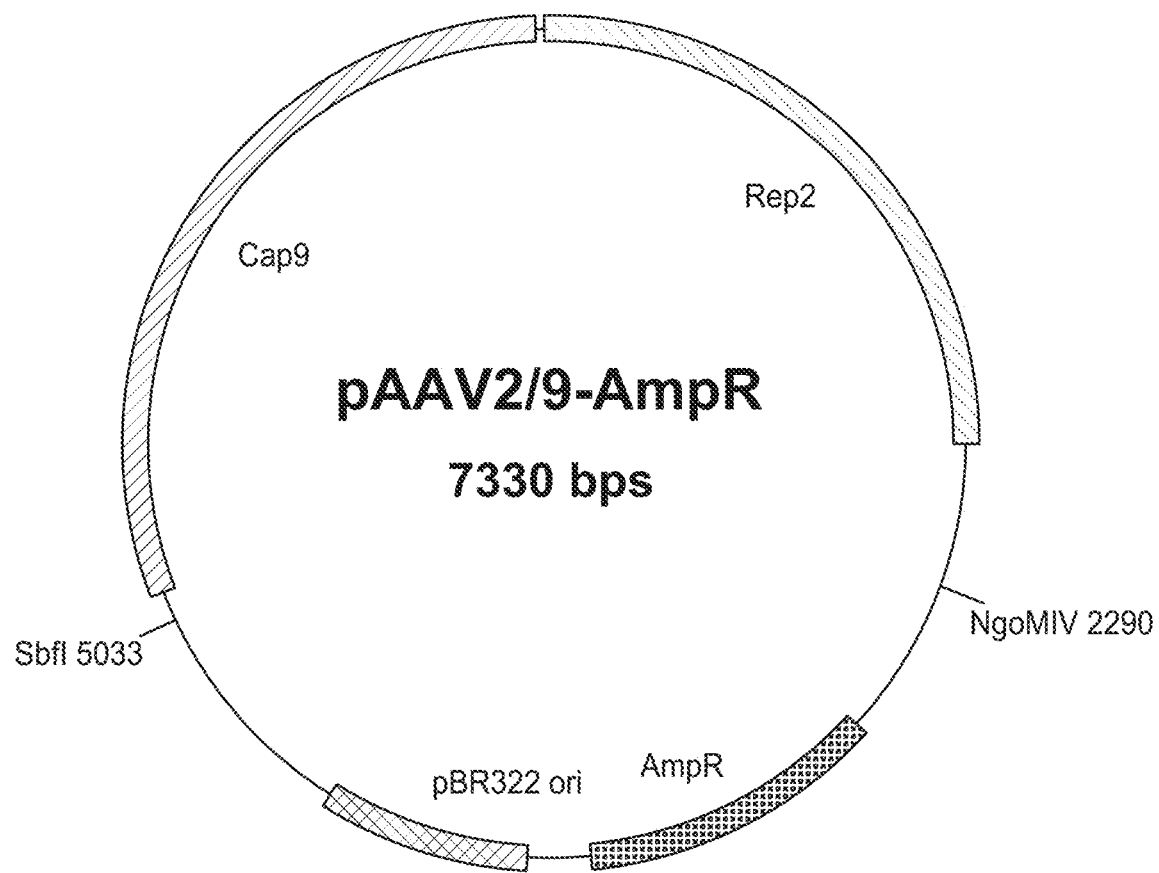
Figure 4:
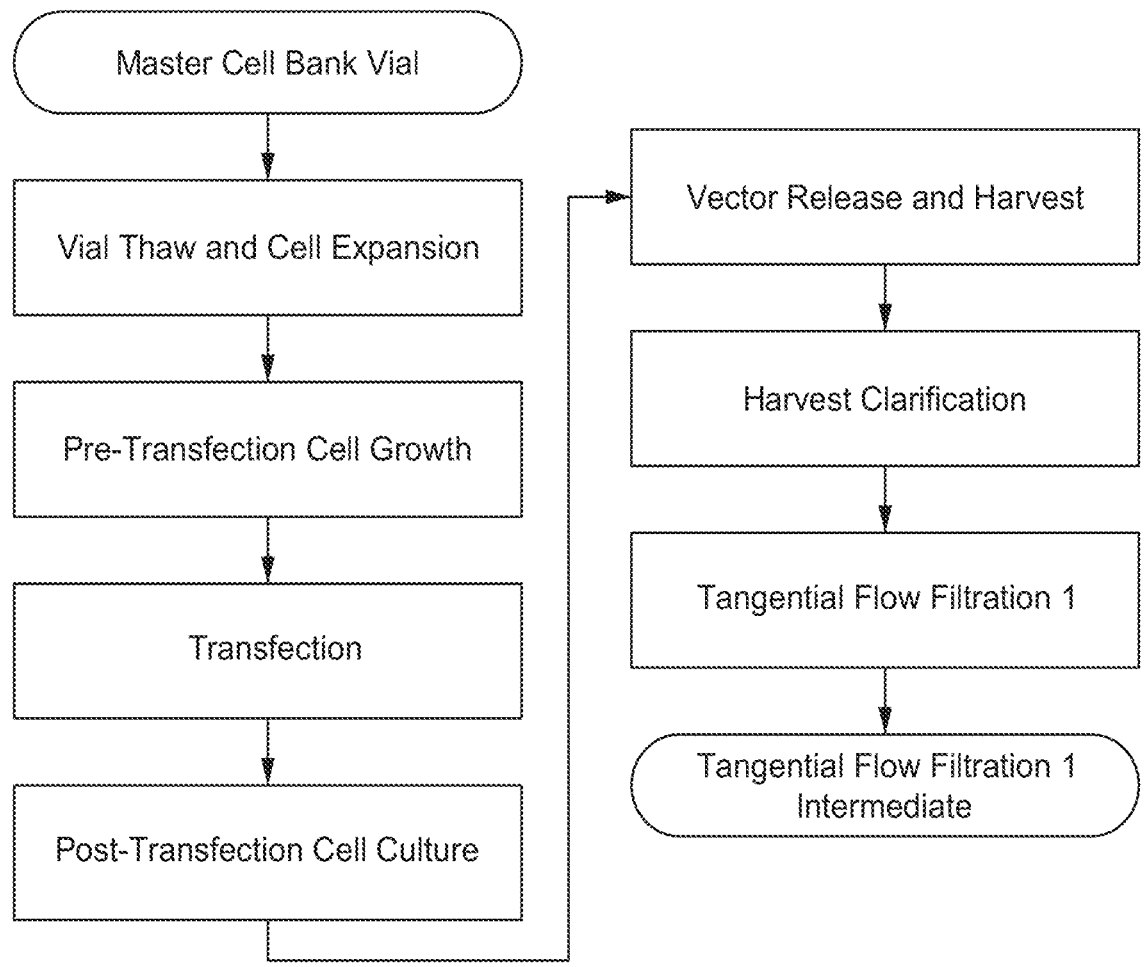
FIG. 4 describe the drug substance upstream process flow diagram.

An upstream process (see, e.g., FIG. 4) was used to produce an intermediate derived from a working cell bank, wherein the upstream process comprises the steps of (a) culturing adherent cells, (b) transfecting the cultured cells with three plasmids as shown in FIGS. 1A-1C (e.g., comprising AAV SMN described herein) to enable production of the AAV viral vector, (c) lysing the adherent cells to isolate the AAV viral vector, (d) purifying the viral particles via filtration to remove any intact cells or cellular debris, and (e) subjecting the purified product of (d) to tangential flow filtration, and (f) freezing the resultant intermediate preparation of purified viral particles. In alternate embodiments, the AAV prepared with the upstream process disclosed herein encodes an shRNA targeting SOD1 or an MECP2 as disclosed herein.

(a) Culturing Adherent Cells

HEK293 cells were thawed and expanded through seven passages in disposable flasks with the use of $CO_2$ incubators. The thawed cells were washed with Cell Expansion Growth Media, centrifuged and resuspended with fresh Cell Expansion Growth Media. The resuspended cells were seeded into a flask containing Cell Expansion Growth Media and incubated.

When cells were confluent, they were washed with DPBS and removed from the flasks with TrypLE Select enzyme solution. Cell Expansion Growth Media was added to neutralize the enyme solution, and the suspended cells were split and reseeded into new flasks containing Cell Expansion Growth Media. This expansion process was repeated for 7 times. In the last iteration, the suspended cells were not reseeded in flasks, but the cell slurry was instead inoculated in a bioreactor for further expansion.

An iCELLis 500/200 m² or an iCELLis 500/333 m² adherent cell bioreactor was prepared for inoculation in advance of inoculation. Preparation activities included unpacking of the disposable bioreactor, physical inspection, leak testing, tubing assembly attachment, and probe equilibration. Cell Expansion Growth Media was charged to equilibrate the bioreactor. Once the pH (pH 6.9 to 7.5), temperature (35° C. to 39° C.), and dissolved oxygen (40-125%) were verified to be within the defined ranges, the bioreactor was seeded at a target seeding density of 4800-7000 cells/cm² (for 200 m² reactor) or 5000-12000 cells/cm² (for 333 m² reactor). The cell slurry from the previous step was added to media in a recirculation media bag and circulated through the bioreactor.

(b) Transfecting Adherent Cells

On days 4, 5 or 6 from time of bioreactor inoculation, adherent HEK293 cells were transfected with a triple DNA plasmid PEI co-precipitation. The 3 plasmids utilized for this transfection are pSMN, pAAV2/9, and pHELP. The DMEM growth medium used for cell expansion is removed from the bioreactor and replaced with Transfection Media. The scAAV9.CB.SMN vector is produced using triple DNA plasmid transfection into Adherent Human Embryonic Kidney (HEK293) cells using a polyethylenimine ("PEI") co-precipitation in a large-scale adherent cell bioreactor. The vector plasmid pSMN contains the cDNA for the human survival motor neuron protein (SMN). The 3 plasmids utilized for this transfection are pSMN (222 mg), pAAV2/9 (333 mg), and pHELP (444 mg). The plasmids may be transfected at a ratio of 1:1:1 mole. The transfection medium was allowed to equilibrate in the bioreactor until the bioreactor temperature is >30° C. prior to the addition of the PEI-Plasmid co-precipitation. The PEI-Plasmid co-precipitation process involves the addition of the plasmids to Transfection Media and 0.2μ filtration into a reaction bag. The PEI was added to transfection medium and then to the reaction bag. The PEI-plasmid ratio is about 1:1 by weight. The PEI—Plasmid reaction was manually mixed to form a homogeneous suspension and the reaction occurs over a 15-30 minute period. At the end of the reaction time, the PEI-Plasmid co-precipitation was transferred from the reaction bag to the bioreactor. The PEI-Plasmid co-precipitation was allowed to mix in the bioreactor for 1-2 hours (alternative durations are described in Example 7) prior to restarting agitation. The Transfection Media was recirculated in the bioreactor for 18-24 hours before the next media change.

On bioreactor day 6, 18-24 hours post transfection, the bioreactor was drained and the Transfection Media recirculation media bag was replaced with Post-Transfection Media. The bioreactor was re-filled with Post-Transfection Media with recirculation in the bioreactor. On day 7, 18-24 hours post the media change on day 6, the Post-Transfection Media in the recirculation bag was replaced with a fresh bag of Post-Transfection Media. The bioreactor was not drained during this step. Recirculation of the media continues until harvest usually at day 9.

(c) Lysing the Transfected Adherent Cells

After 9 days in the bioreactor, the final pre-harvest samples were taken from the reactor and the total cell lysis process was initiated. Benzonase was added to the bioreactor to a final concentration of 100 U/mL. The Benzonase was allowed to mix in the reactor, and the Lysis Buffer was added to the reactor. The Lysis Buffer was mixed in the reactor at 15-25° C. for 2 hours before the contents of the bioreactor were transferred to the harvest bag. A Salt Sucrose Solution (SSS) which quenches the Benzonase reaction was added to the harvest bag and mixed for 15 minutes. The bioreactor was then rinsed with the Bioreactor Rinse Buffer for 15 minutes, and the rinse was then collected in the harvest collection bag, along with the quenched cell lysis solution. Once the rinse had been added to the collection bag, the contents were mixed for 15 minutes and the bulk harvest samples taken.

(d) Preparing the Viral Particles by Filtration and Tangential Flow Filtration

The mixed bulk harvest was filtered through a POD depth filter into a collection bag. Once all bulk harvest had been filtered, the depth filter was chased with TFF1 Buffer. The depth filter pool was mixed and sampled. The depth filter pool was then filtered through a 0.45 µm filter to further clarify the bulk harvest material. The 0.45 µm filter was then chased with TFF1Buffer.

For the TFF1 step, 5.0 m² of 300 kDa MW cut off regenerated cellulose membrane cassettes were flushed, sanitized with NaOH solution and equilibrated with TFF1 buffer. The concentration phase of this operation was designed to reduce the volume of the clarified harvest by approximately 10×. Once the target retentate volume was reached, diafiltration operation are started. The retentate was diafiltered with 6 diavolumes of TFF1 buffer. Alternatively, the retentate may be diafiltered with more than 6 diavolumes of TFF1 buffer, e.g., 10 divolumes, 12 diavolumes, or 15 diavolumes. Once 6 diavolumes of permeate total flow were achieved, the retentate was concentrated again and harvested into a collection bag. Two successive rinses of the membrane were executed to maximize the product recovery from the TFF system to produce an intermediate drug substance.

(e) Freezing Intermediate

The TFF1 intermediate was aliquoted into 1 or 2 liter sterile PETG bottles in a LFH hood and then frozen on dry ice or in a freezer and transferred to −60° C. storage.

TABLE 4

Buffers used in Upstream Process

| Name | Formulation | Process Step(s) Used |
|---|---|---|
| Cell Expansion Growth Media | DMEM with 10% FBS, 4.5 g/l glucose, 4 mM L-glutamine | Cell expansion, iCELLis Bioreactor pre-transfection |
| Transfection Media | DMEM with no FBS, no calcium, no L-glutamine and 4.5 g/L glucose | iCELLis Bioreactor transfection |
| Post Transfection Media | OptiMEM with 2.3 g/L glucose, 4 mM L-glutamine, and no FBS | iCELLis Bioreactor post transfection |
| Lysis Buffer | 500 mM HEPES, 10% Tween 20, 20 mM $MgCl_2$, pH 8.0 | iCELLis Bioreactor cell lysis |
| Salt Sucrose Solution (SSS) | 3700 mM NaCl, 10% Sucrose | Clarification |
| Bioreactor Rinse Buffer | 20 mM Tris, 1 mM $MgCl_2$, 500 mM NaCl, 1% Tween 20, 1% Sucrose | iCELLis bioreactor harvest |
| TFF1 Buffer | 20 mM Tris, 1 mM $MgCl_2$, 500 mM NaCl, 1% Sucrose | Clarification, TFF1 |
| TFF1 Sanitization Buffer | 0.5M NaOH | TFF1 membrane sanitization |

Example 3—Downstream Process

Figure 5:
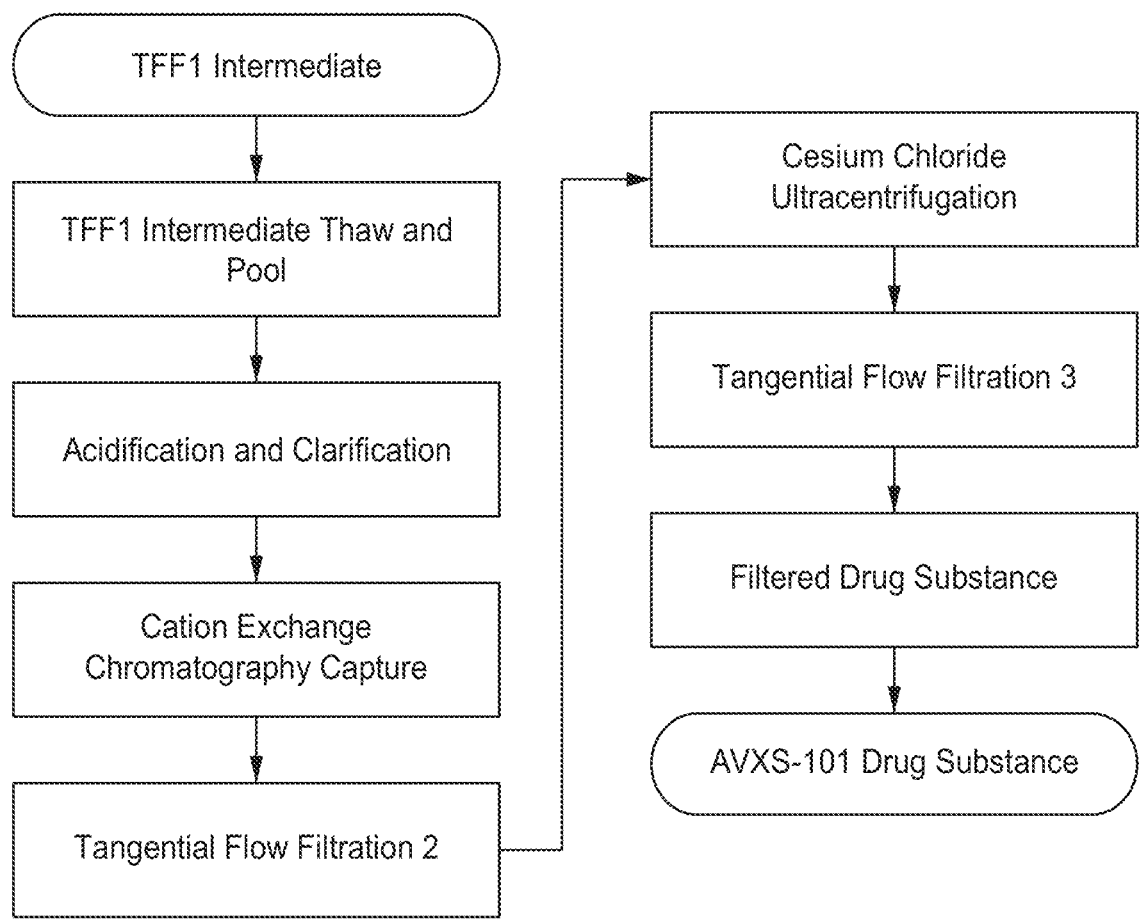
FIG. 5 describes the drug substance downstream process flow diagram.

A downstream process (see, e.g., FIG. 5) was used to process the TFF1 intermediate to a filtered drug substance. In some embodiments, the downstream process disclosed herein may be used to process an intermediate comprising an AAV SMN, an AAV MECP2, or an AAV encoding shRNA targeting SOD1 as described herein. The downstream process steps include: (a) acidifying and clarifying the intermediate (using filtration), (b) purifying using cation exchange chromatography, (c) filtering with tangential flow filtration ("TFF2"), (d) ultracentrifuging using CsCl buffer to separate filled and empty viral capsids, (e) collecting the AAV viral vectors, and (d) filtering the collected AAV viral vectors with a second tangential flow filtration ("TFF3") step.

(a) Acidification and Clarification

The TFF1 intermediate material from the upstream process (thawed to room temperature if previously frozen) was pumped into a bag with a mixer. The pooled TFF 1 Intermediate was mixed, and a sample was taken to determine the titer. The pooled TFF1 Intermediate was immediately processed by the adding 11-14% of Tween 20. Tween 20 was used to promote flocculation of the bulk of host cell proteins and DNA under acidic pH conditions. The mixture was allowed to incubate for a 12-20 hours. The pH was then lowered by the addition of Acidification Buffer (1M glycine) to pH 3.3-3.7. The precipitate formed after the pH was lowered was then removed by filtering the solution through a 1.1 m² Clarisolve and a 2.2 m² Millistak+C0HC depth filters and 0.45 µm polishing filters. This process resulted in the Acidified and Clarified TFF Intermediate.

(b) Purification with Cation Exchange Chromatography

The cation exchange (CEX) chromatography step was used to separate the viral capsids from proteins, DNA, and other process impurities, e.g., host cell lipids, TWEEN 20. This step utilized a CIMmultus S03-8000 Advanced Composite Column (Sulfonyl) (0.2 µm pores) chromatography column (8.0 L) operated using an automated process chromatography system. Buffers and solutions are described in the following table:

TABLE 5

Buffers and solutions for one CEX cycle

| Solution name | Composition | Purpose | Volume (L) for one 8 L CEX Cycle |
|---|---|---|---|
| WFI | WFI | Column flushes | 200 L |
| CEX A-Buffer | 50 mM glycine, 500 mM NaCl, 1.0% sucrose, 0.20% Poloxamer 188, pH 3.5 ± 0.1 at 20° C. | Equilibration, wash, elution | 256 L |
| CEX B-Buffer | 50 mM glycine, 2.0M NaCl, 1.0% sucrose, 0.20% Poloxamer 188, pH 3.5 ± 0.1 at 20° C. | Column equilibration and elution | 40 L |
| Monolith Cleaning Solution | 1M NaOH, 2M NaCl | Column Sanitization, CIP | 96 L |
| 1M ammonium acetate | 1M ammonium acetate | Restore column pH | 40 L |
| pH 9.0 Neutralization buffer | 1.0M Tris pH 9.1 ± 0.1 at 20° C. | pH adjustment of CEX product | 0.5 L |
| Storage solution | 20% Ethanol in WFI | Column storage | 40 L |

The Acidified and Clarified TFF Intermediate (i.e., CEX Load) was loaded onto a cleaned and equilibrated CEX column. The conditions were such that the viral vectors bind to the monolithic column. The unbound material was washed from the column with CEX A Buffer. The product was eluted from the resin with a gradient of CEX B Buffer in CEX A Buffer. Collection of Fraction 1 was initiated at the start of the elution gradient for 10 column volumes (CV)ea defined volume of 2.3-2.7 CV. The chromatography column was discarded after each batch (i.e., the chromatography column was not re-used). The CEX product eluate (Fraction 2) was then neutralized using Neutralization Buffer to a pH of 7.7-8.3.

(c) Filtering with Tangential Flow Filtration (TFF2)

The TFF step concentrated the viral vector, removed protein impurities, and exchanged the buffer to an appropriate buffer for the CsCl ultracentrifugation step. The Neutralized CEX Eluate was processed using a TFF system fitted with 0.3 m² of 300 kDa MWCO regenerated cellulose membrane.

The volume of the Neutralized CEX Eluate was reduced to a target retentate volume. Once the target retentate volume was reached, diafiltration was started in discontinuous TFF mode (batch mode). The retentate was diluted 2-fold with TFF2 NaCl Diafiltration Buffer, and the retentate is concentrated to its initial volume. This was repeated until diafiltration with TFF2 NaCl Diafiltration Buffer was complete. The retentate was then diluted 2-fold with TFF2 CsCl Diafiltration Buffer and the retentate was concentrated to its initial volume. This was repeated until diafiltration with TFF2 NaCl Diafiltration Buffer was complete.

The retentate was further concentrated to a final mass based on the physical titer of the Neutralized CEX Eluate, the system hold-up volume, system flush volume, and retentate density to achieve the desired target vector concentration and recovered into a collection bag. One flush cycle of the system with TFF2 CsCl Diafiltration Buffer was followed by product blowdown to maximize the product recovery from the TFF system. A sample of the TFF2 Retentate, which contains the retentate and flush) was taken for physical titer measurement. The TFF2 membrane cassettes were discarded after each batch (i.e., TFF membranes were not reused).

TABLE 6

Buffers for TFF2

| Solution Name | Composition |
|---|---|
| TFF2 NaCl Diafiltration Buffer | 20 mM Tris, 2 mM MgCl₂, 150 mM NaCl, 0.2% Poloxamer 188, 1% Sucrose , pH 8.1 ± 0.1 at 20° C. |
| TFF2 CsCl Diafiltration Buffer | 20 mM Tris, 2 mM MgCl₂, 3M CsCl, 0.2% Poloxamer 188, pH 8.1 ± 0.1 at 20° C. |

(d) CsCl Ultracentrifugation

The purpose of the ultracentrifugation step was to remove empty capsids from full capsids by utilizing cesium chloride gradient ultracentrifugation. The TFF2 Retentate was added to ultracentrifugation tubes and the tubes were sealed. The tubes were placed in an ultracentrifuge, like an automated Optima XPN 100 Ultra Centrifuge system or equivalent system equipped with Type 50.2 Ti rotor or equivalent rotor. The filled tubes were centrifuged at 45,000 rpm for 22 hours at 20° C.

(e) Collecting AAV Viral Vectors

After completion of centrifugation step, tubes were removed from the ultracentrifuge and placed in a biosafety cabinet. Product containing tubes were mounted on ring stands above a waste container. A lamp was positioned directly under the tube to visualize the empty capsids band (Band A, highest band), the full capsid doublet bands (Band B and Band C, upper and lower bands of the doublet), and lowest band below the doublet (Band D). The tubes were punctured with a needle attached to a syringe to vent the tubes, and bands B, C, and D were removed by a needle. The collected material was transferred to a collection bag. The collected ultracentrifuged pool (UC Pool) was diluted with TFF2 Buffer to reach a consistent starting CsCl concentration in the TFF2 Load material. The diluted UC Pool is processed in the TFF3 step. The buffer for the CsCl ultracentrifugation step is listed in the table below:

TABLE 7

Buffer for CsCl Ultracentrifugation

| Solution Name | Composition |
| --- | --- |
| TFF2 CsCl Diafiltration Buffer | 20 mM Tris, 2 mM MgCl2, 3M CsCl, 0.2% Poloxamer 188, pH 8.1 ± 0.10 |

(f) Filtering with Tangential Flow Filtration (TFF3)

The TFF3 step removed CsCl and concentrated the full vector using Final Formulation Buffer. A tangential flow filtration system was utilized in conjunction with 50 cm$^2$ of 300 kDa MWCO regenerated cellulose membranes. The viral vector was retained by the membranes.

The volume of the Diluted UC Pool was reduced to a target retentate volume. Once the target volume was reached, continuous diafiltration at a constant retentate volume was started. The retentate was diafiltered with TFF3 Buffer. A sample of the diafiltered retentate was taken for physical titer measurement. The retentate was further concentrated by targeting a permeate weight, which was calculated by 1) the volume of retentate in the TFF system at the end of diafiltration, 2) the Diluted UC Pool physical titer, 3) a target drug substance (DS) concentration, 4) the combined volume of system flushes and filter flushes, and 5) the density of the TFF3 Buffer. The TFF3 membrane cassettes were discarded after each batch (i.e., cassettes are not reused).

TABLE 8

Buffers for TFF3

| Solution Name | Composition |
| --- | --- |
| TFF3 Buffer option 1 | 20 mM Tris, 1 mM MgCl$_2$, 200 mM NaCl, 0.001% Poloxamer 188, pH 8.0 ± 0.1 at 20° C. |
| TFF3 Buffer option 2 | 20 mM Tris, 1 mM MgCl$_2$, 200 mM NaCl, 0.005% Poloxamer 188, pH 8.0 ± 0.1 at 20° C. |

Two successive 20 mL rinses of the TFF membranes with the TFF3 Buffer were performed to recover the vector from the TFF system. The rinses were recovered through a 0.2 mm Pall Supor® EKV Sterilizing-Grade Filter (Mini Kleenpak). A filter rinse was performed with TFF3 Buffer to recover any vector remaining in the filter and to adjust the final volume of the Filtered TFF3 Pool (i.e., Drug Substance DS). The DS was aliquoted into 125 or 250 mL PETG bottles and frozen at <~−60° C.

Example 4—Formulating and Filling

The Drug Product (DP) was a single-dose, preservative-free, sterile, clear to slightly opaque, and colorless to faint white, intravenous infusion of non-replicating, self-complementary AAV9 vector at a target concentration of 2.0×10$^{13}$ vg/ml. The DP comprised 20 mM Tris, 1 mM MgCl$_2$, 200 mM NaCl, 0.005% w/v Poloxamer 188. The pH range of the solution was 7.7 to 8.3.

TABLE 9

Drug Product Unit Operation - Buffer Composition

| Solution Name | Composition |
| --- | --- |
| Drug Product (DP) Formulation Buffer option 1 | 20 mM Tris, 1 mM MgCl$_2$, 200 mM NaCl, 0.001% Poloxamer 188, pH 8.0 ± 0.1 |
| Drug Product (DP) Formulation Buffer option 2 | 20 mM Tris, 1 mM MgCl$_2$, 200 mM NaCl, 0.005% Poloxamer 188, pH 8.0 ± 0.1 |

The DP was filled into sterile, ready to use, 10 ml Crystal Zenith (CZ) vials, stoppered with sterile, ready to use, chrlorobutyl elastomeric stoppers, and sealed with sterile, 20 mm flip-off aluminum seals. The vials were filled with a nominal fill volume of either 5.5 mL or 8.3 mL. The target overfill was 0.4 mL, and the vials were filled to 5.9±0.1 mL or 8.7±0.1 mL.

Example 5—Potency Assay

The relative potency of the drug product was measured using a quantitative, in vivo assay. The assay used an established mouse model of SMA disease. Breeding pairs of the SMAΔ7 mouse strain (Jackson Laboratories, #005025) are phenotypically normal but ~25% of their offspring are homozygous for the targeted SMN gene mutation and display the SMA-like phenotype. By Day 5 they show signs of muscle weakness and in the following week, develop an abnormal gait and a tendency to fall over. Jackson Laboratories reports the mean survival for animals with the SMA-like phenotype as ~15±2 days. Pilot studies demonstrated a median survival time for untreated animals with SMA-like phenotype of 16.3 days (geometric mean; n=3 studies; 10 mice per study).

Biologically active drug product administered by intravenous (IV) infusion yields an increase in survival time that is a function of dose (vg/kg). Drug product potency was measured relative to the reference material (prior batch of vector). The titer of drug product and the reference material (vector genomes/mL; vg/mL) was determined by Droplet Digital polymerase chain reaction (ddPCR). Vector was diluted in saline to achieve each of three specified dose levels that will be administered to mice with the SMA-like phenotype.

An assay's results are considered to be acceptable if the assay passes suitability. Assay suitability consists of the following:
1. Acceptance limit for the Negative Control sample (15±2 days, Median Survival)
2. Acceptance limit for the Positive Control sample (>40 days, Median Survival)
3. Acceptance limits on the reference standard Median Survival dose-response curve A prior batch of vector (hereinafter, Prior Batch) was used in this study to determine the linear correlation between median survival (days) of SMAΔ7 mouse when dosed with drug product (hereinafter, Sample Batch) at five different dose levels including the 0 (zero) dose using 0.9% saline solution (untreated group).

The relative potency of drug product Sample Batch was established by comparing the linear regression curve of the Prior Batch reference standard to that of the drug product Sample Batch linear regression curve. This was accomplished by using the ratio of the y-intercept and slope of each linear regression line (i.e., Reference Standard and Test Article). The percent Relative Potency calculation is delineated in equation (1) below:

$$\% \text{ RP} = [(y\text{-Intercept/slope of Test Article}) \div (y\text{-Intercept/slope of Reference Standard})] \times 100 \quad (1)$$

The Prior Batch used in the Phase-1 clinical trial was used as the Reference Standard batch and was assigned a potency of 100%.

The Δ7 mouse model was used to demonstrate efficacy of SMA therapeutics, including drug product. TFF3 Buffer Solution (vehicle)-treated control animals provide a reliable baseline control from which product potency can be measured as an increase in median survival. Development work with drug product identified three (3) doses (excluding the vehicle treated dose) determined by Genomic Titer using Droplet Digital PCR (ddPCR) which affect survival in the mouse model with a linear correlation when administered dose (vg/kg) is log-transformed and plotted against the Median Survival (in days) of the treated SMAΔ7 neonatal mouse. See standard titers (vg/mL) in Table 11 for the low, mid, and high titer standards. In addition, the TFF Buffer (vehicle) solution is used for both the zero (0) calibration curve point as well as a Negative Control. A dose demonstrating 40 day survival (greater than the dose that demonstrates doubling of the median survival) was also included as a Positive Control.

TABLE 11

| Target Doses | | |
| --- | --- | --- |
| Dose (vg/kg) | Median Survival (days) | Standards and Controls |
| TEF Buffer Solution (Vehicle) | 15 ± 2 | Negative Control (untreated) |
| $1.10 \times 10^{14}$ | ≥40 days Median Survival | Positive Control |
| $1.00 \times 10^{12}$ | 16 ± 2 | Standard-1 |
| $1.2 \times 10^{13}$ | 22 ± 3 | Standard-2 |
| $7.5 \times 10^{13}$ | 31 ± 3 | Standard-3 |

Dose Solution Preparations (refer to Table 12 for the dilution scheme example.

Negative Control—The TFF3 Buffer Solution (Drug Product final formulation buffer) is used as the Negative Control Positive Control—The Test Article lot is prepared at a $1.10 \times 10^{14}$ vg/kg using TFF3 Buffer Solution. See Table12 for the dilution scheme example.

Reference Standard Solutions—The Reference Standard lot is prepared in three concentrations delineated in Table 11 using the TFF3 Buffer Solution.

TABLE 12

| Reference Standard and Test Article Dilution Scheme (Example) | | | | | |
| --- | --- | --- | --- | --- | --- |
| Dose (vg/kg) | Reference Standard/Test Article ddPCR Titer (vg/mL) | Conversion to vg/μL | Reference Standard/Test Article volume to use (μL) | Saline Solution (μL) | Total Dose Volume (μL) |
| $1.2 \times 10^{13}$ | $5.0 \times 10^{13}$ | $5.0 \times 10^{10}$ | 2.6 | 47.4 | 50.0 |

Test Article Preparation—The test article was diluted using the TFF3 Buffer Solution. Dilutions were calculated to generate the test doses (vg/kg) delineated in Table 11 per mouse in a total final volume of 50 μl. Dilutions were made for 12 mice at the time with one extra volume as a Positive Control targeted to increase minimum lifespan of treated mice to ≥40 days of Median Survival (days).

Acceptance Limits on Control Samples

Negative Control (untreated mice)—The assay acceptance limit for the Negative Control group was that the SMAΔ7 mice meet the median survival of 15±2 days. In addition, any mouse expiring in ≤10 days will be excluded from the analysis.

Positive Control (group treated at the target clinical dose)—The assay acceptance limit for the Positive Control group was that at a minimum lifespan of treated mice to be to ≥40 days Median Survival. In addition, any mouse expiring in ≤10 days will be excluded from the analysis.

Acceptance Limits on the Reference Standard Dose Response Curve

Assay suitability criteria will be determined for the reference standard Linear dose response curve plotting Median Survival (days) against the administered dose (vg/mL).

Y-Intercept/Slope Ratio—A linear regression curve of the Median Survival (days) versus the administered Dose (vg/kg) for the Reference Standard and the Test Article is determined. The ratio of y-Intercept to the slope for each linear regression is calculated.

Reporting Results

Qualitative Reporting of Relative Potency Results—The Assay Suitability criteria is evaluated for each assay prior to determination of a single point Median Survival (days) read at ≥40 days for the Positive Control material. If the Median Survival of the Positive Control group is ≥40 days, the Test Article may be dispositioned if the below criteria is met.

Quantitative Reporting of Relative Potency Results—The Assay Suitability criteria is evaluated for each assay prior to quantitative determination of Relative Potency for the Test Article. Relative potency for the Test Article may be reported once the Positive control reaches ≥40 days and the Median Survival of 31±3 days for the mouse group representing the upper standard dose of $7.5 \times 10^{13}$ vg/kg is reached. The Percent Relative Potency (% RP) for a Test Article will be calculated using the y-intercept and slope of the linear regression of the Median Survival (days) dose-response as follows:

$$\% \text{ RP} = 100\% \ast [(\text{Test Article y-intercept/slope}) \div (\text{Reference Standard y-intercept/slope})]$$

Example 6: Surfactant Inactivation Study

To separate the influence of low pH and tween, a sample of drug substance TFF1 Intermediate that has a pH of 7.6 and 4-8% Tween-20 was used for the surfactant inactivation study. The Tween-20 concentration in TFF1 Intermediate is about 2.5-fold lower than in the full process when Tween-20 is added to TFF1 Intermediate prior to acidification. This lower Tween-20 concentration was considered a worst-case condition for surfactant driven inactivation in the drug substance process. The test article for the virus inactivation step by surfactant treatment was the TFF-1 Intermediate containing 4-8% Tween-20. To evaluate the capacity for virus inactivation by the surfactant treatment step, XMuLV and PRV were each used to spike the test article with virus in duplicate experiments. Virus was quantitated using a plaque-forming infectivity assay.

The TFF1 manufacturing step generates a surfactant concentration range of 4-8% Tween-20. The TFF1 Intermediate was pooled, and 12% more Tween-20 was added to the TFF1 Intermediate at an operating temperature of 16-20° C. with mixing for a duration of 12-20 hours. The viral clearance process was performed at a concentration of 4-8% Tween-20 and at a controlled temperature of 16.0° C.±0.1° C. The duration of the inactivation process was 120 minutes versus the typical process time of 16 hours.

For the inactivation process, the inactivation load was prepared by measuring the volume of the test article, equilibrating to the target temperature, and then spiking with virus. Samples of the spiked inactivation load were removed at six (6) time points to demonstrate the kinetics of inactivation over time: <1 minute, 15 minutes, 30 minutes, 60 minutes, 90 minutes, and 120 minutes. After collection, each sample was diluted in growth medium to cease virus inactivation, and was assayed for virus. To increase assay sensitivity at 90 minutes and 120 minutes, large volumes of these time point samples were also assayed for virus. Due to the presence of Tween-20 in the test article for this step, the titer of the inactivation load was calculated from the titer of the spiking virus and the volume of virus spiked.

Figure 6:
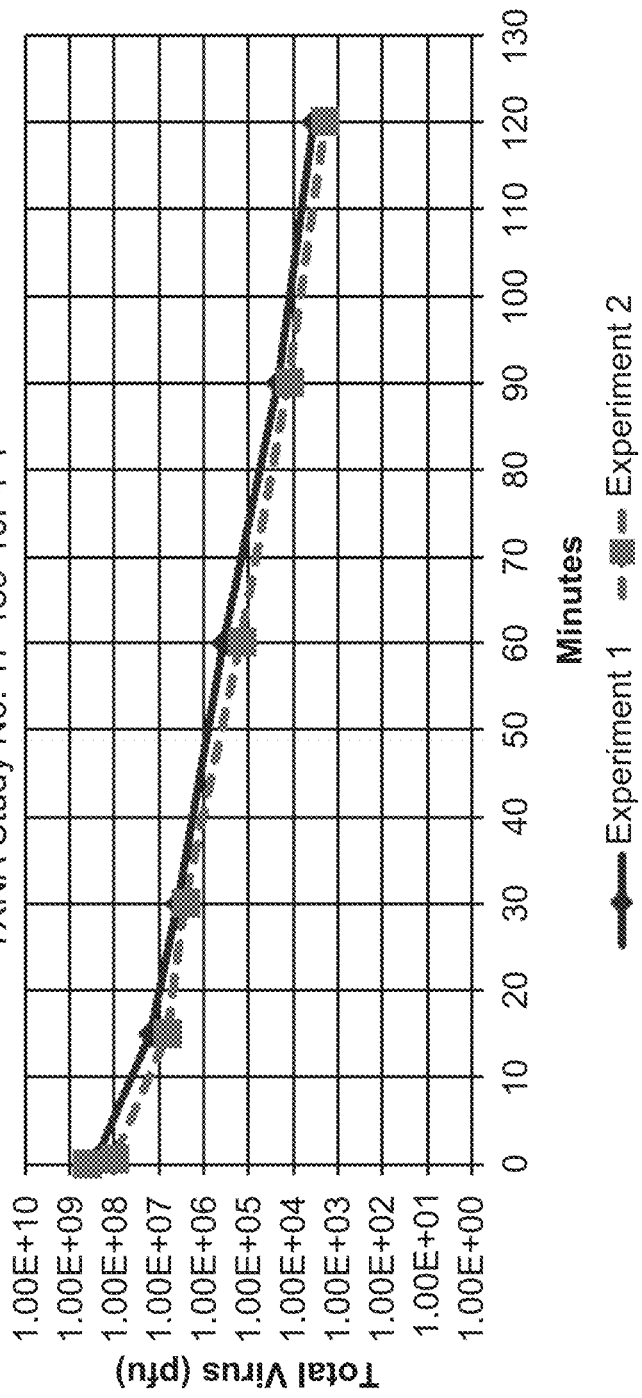
FIG. 6 shows the inactivation of XMuLV by Tween 20 added at up to 120 min.
Figure 7:
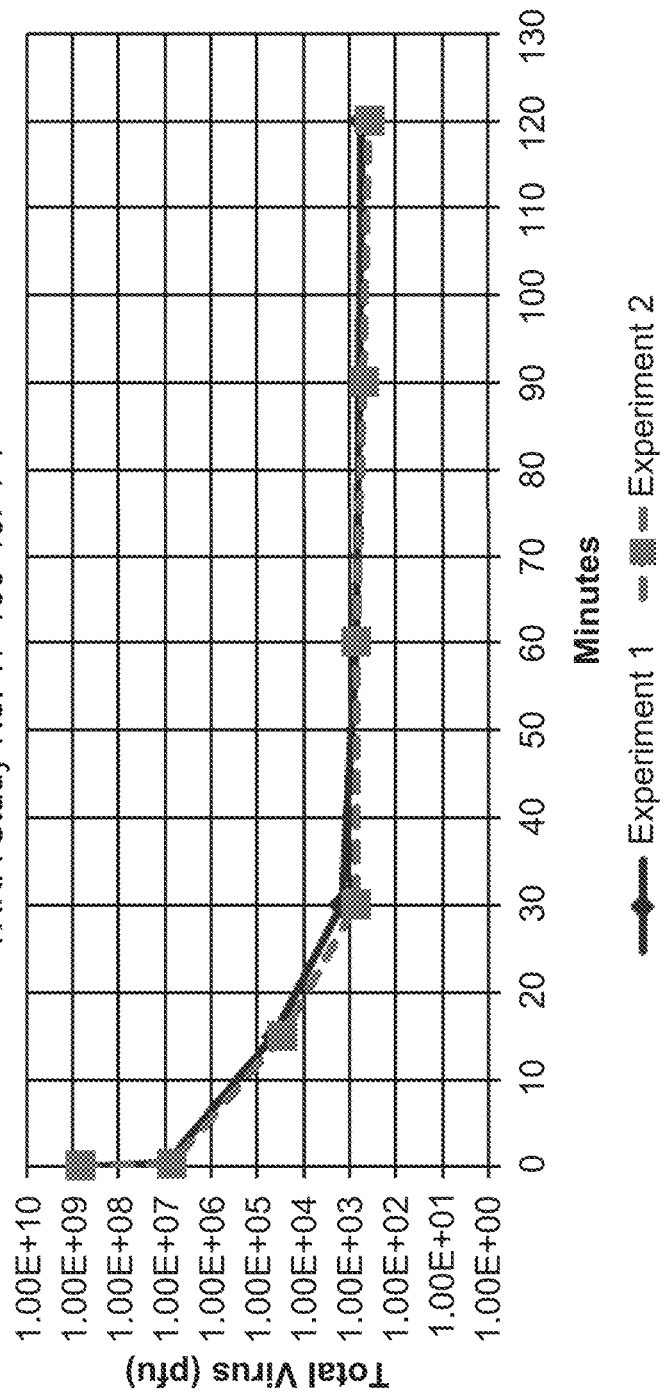
FIG. 7 shows the inactivation of PRV by Tween 20 added at up to 120 min.

The effectiveness of virus inactivation by surfactant treatment (Tween-20) was shown to be effective as evidenced by LRV values greater than 4 log 10 for both viruses at the 90-minute time point. The kinetics of inactivation by surfactant treatment are illustrated in FIG. 6 and FIG. 7 as graphs of the rate of virus inactivation over the course of 120 minutes during the Tween-20 surfactant treatment.

Example 7: Effect of Higher Seeding Density, Transfecting and Harvesting Earlier and DNA/PEI Mix Times on the Production of Drug Substance The effect of higher seeding density, transfecting and harvesting one day early and DNA/PEI mix times on the production of DS was evaluated. Each condition was evaluated in duplicate in a 1.6 $m^2$ bioreactor.

Materials and Methods

Cell Scale Up

Figure 8:
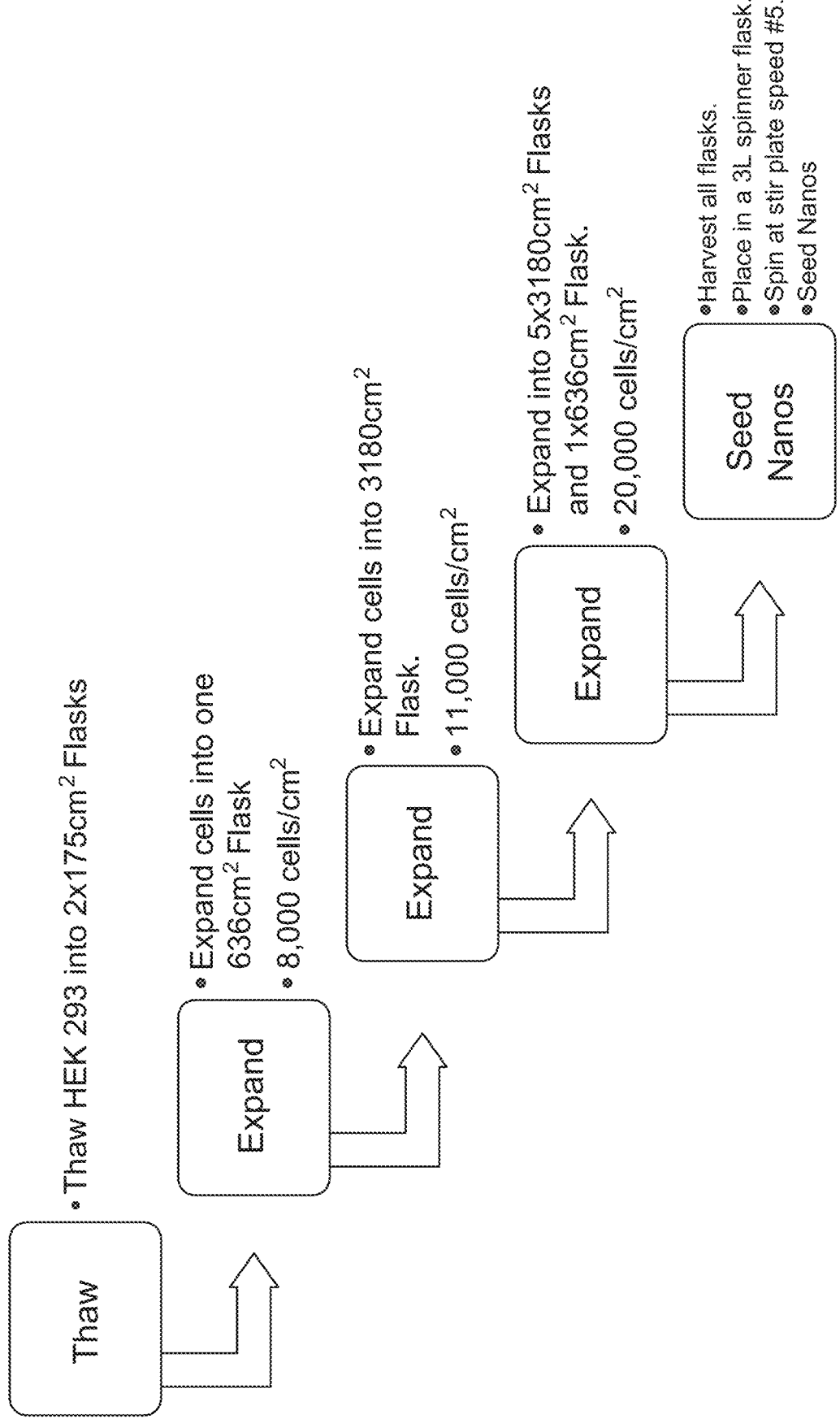
FIG. 8 describes the HEK 293 cell expansion process flow during cell seeding density experiments.
Figure 9A:
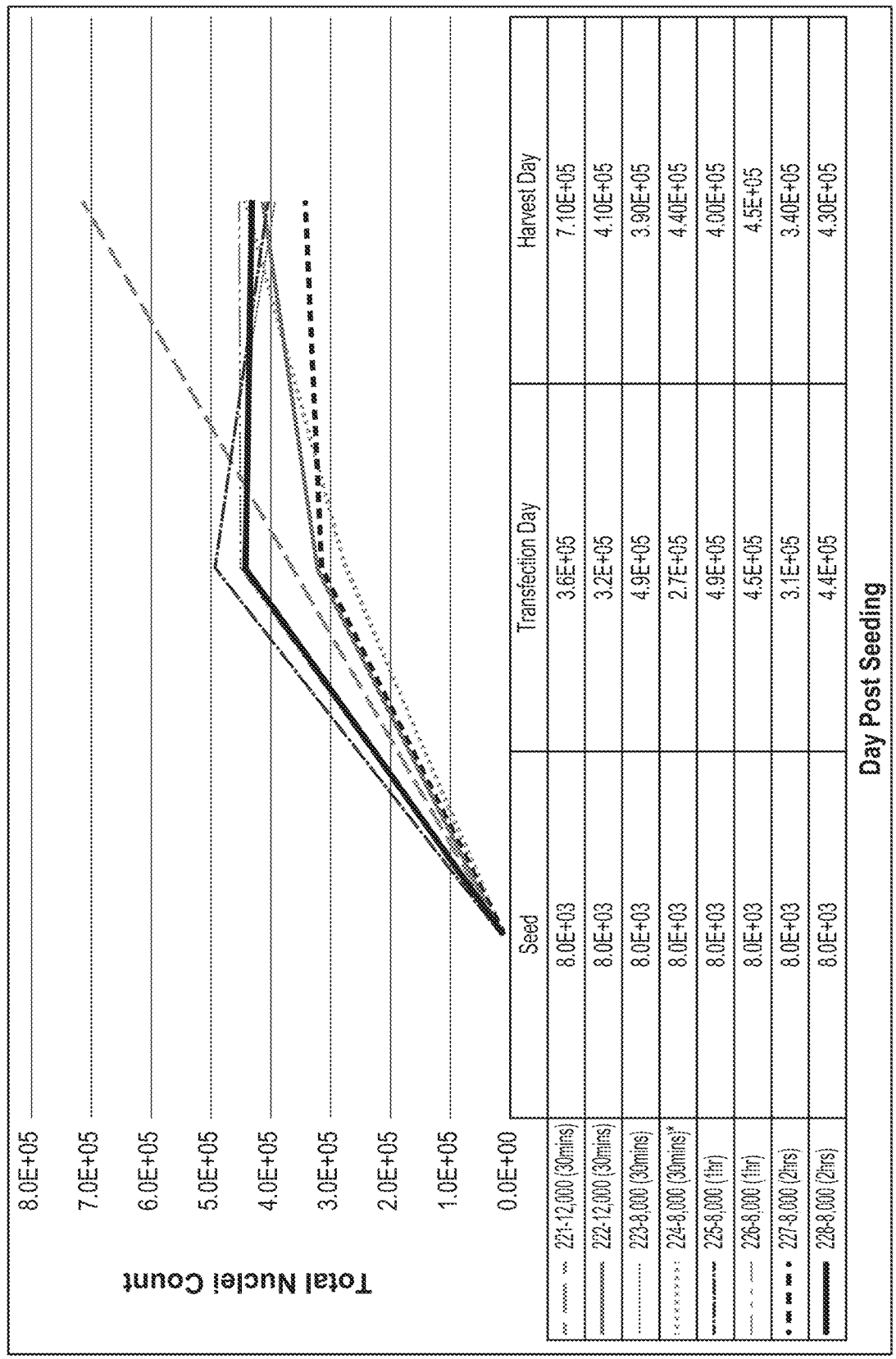
FIGS. 9A-E show growth and metabolite profiles. HEK 293 cells were seeded in duplicate at 12,000 and 8,000 cells/cm$^2$ in bioreactors (pH 7.23, 37.0° C., 55% dissolved oxygen (DO)). Cells were transfected with DNA plasmids/PEI at four days (12,000 cells/cm$^2$) and five days (8,000 cells/cm$^2$) post-seeding. Bioreactors were harvested eight days (12,000 cells/cm$^2$) and nine days (8,000 cells/cm$^2$) post-seeding. pH and metabolite readings were read daily on Nova BioFlex.
Figure 9B:
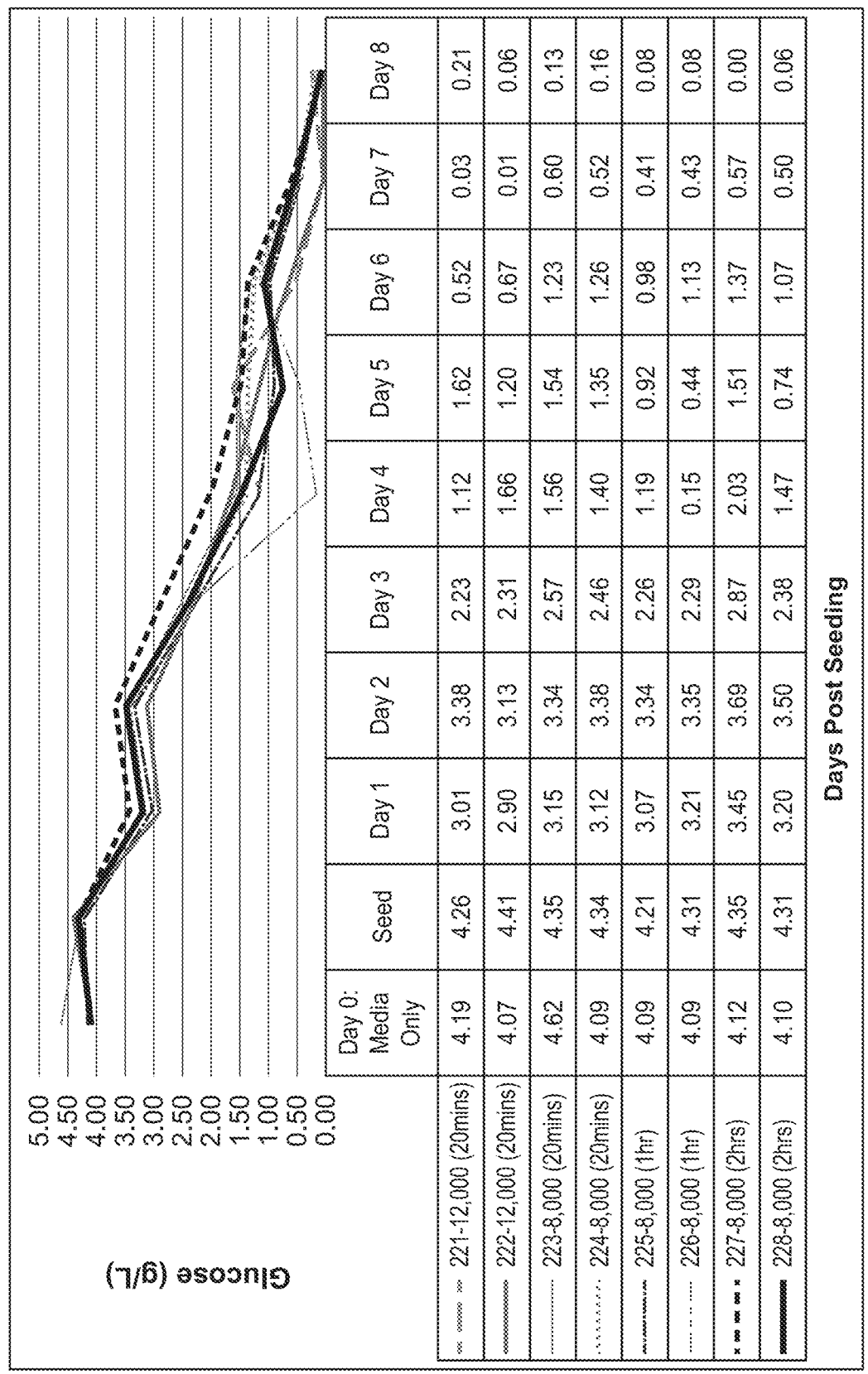
Figure 9C:
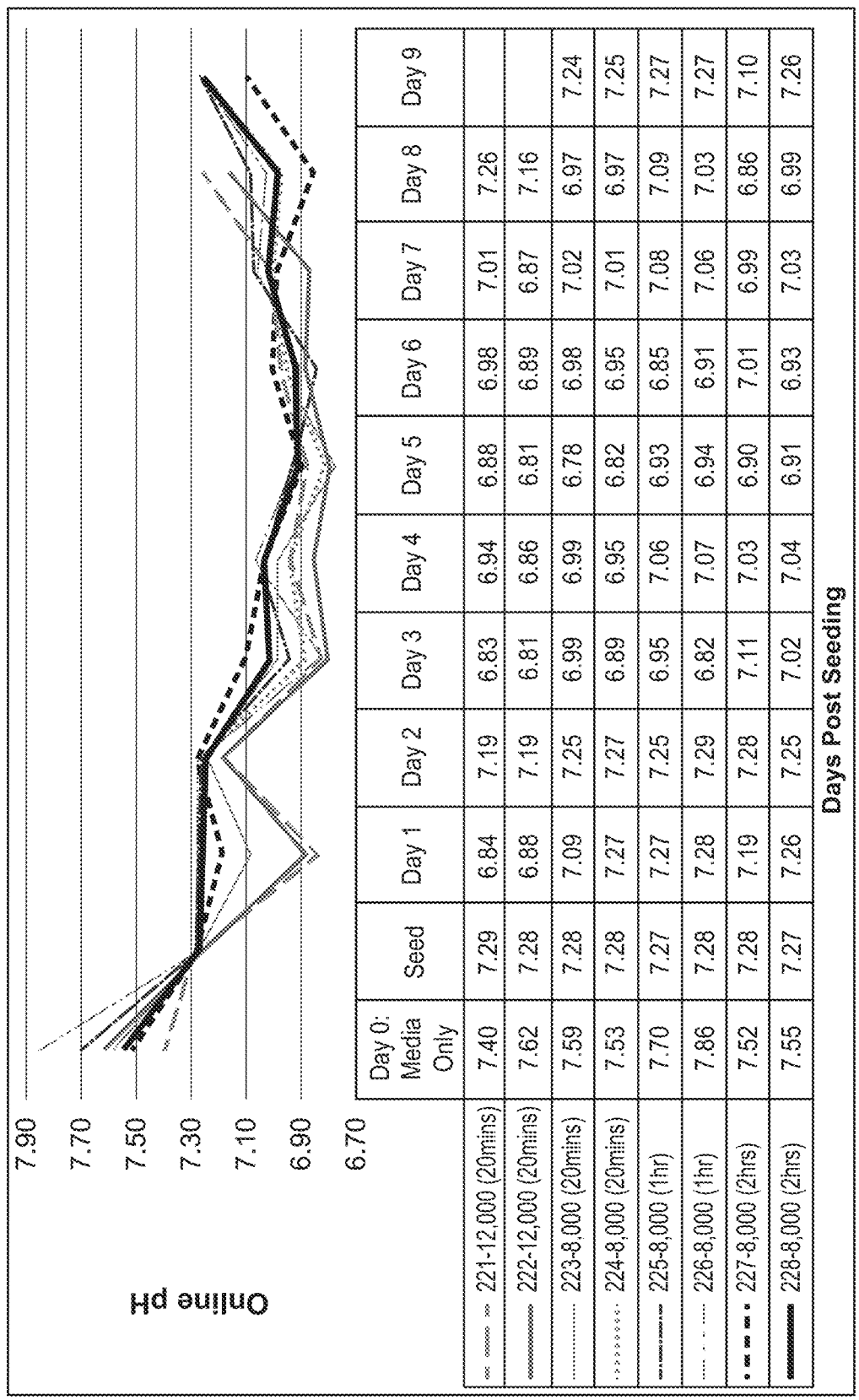
Figure 9D:
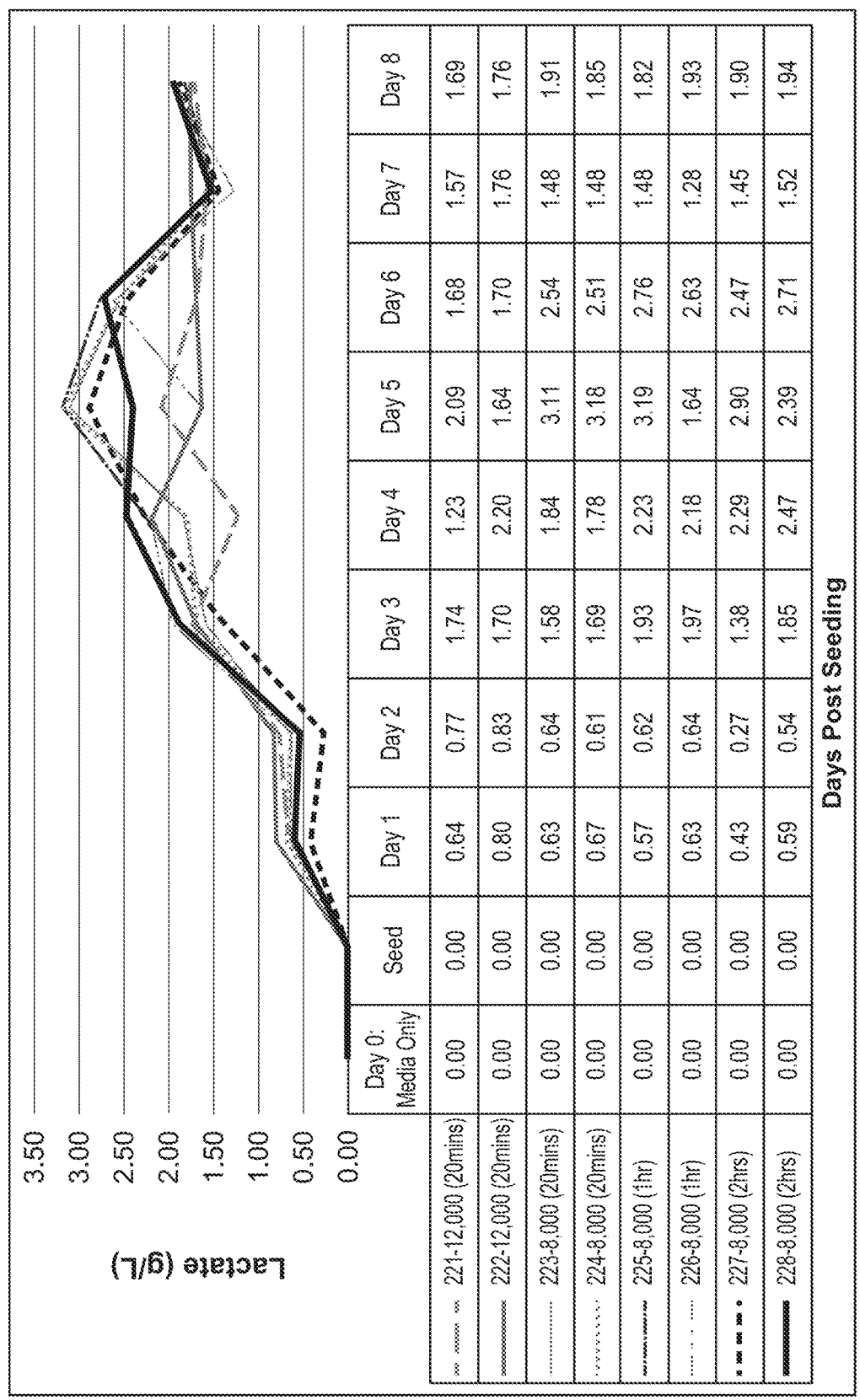
Figure 9E:
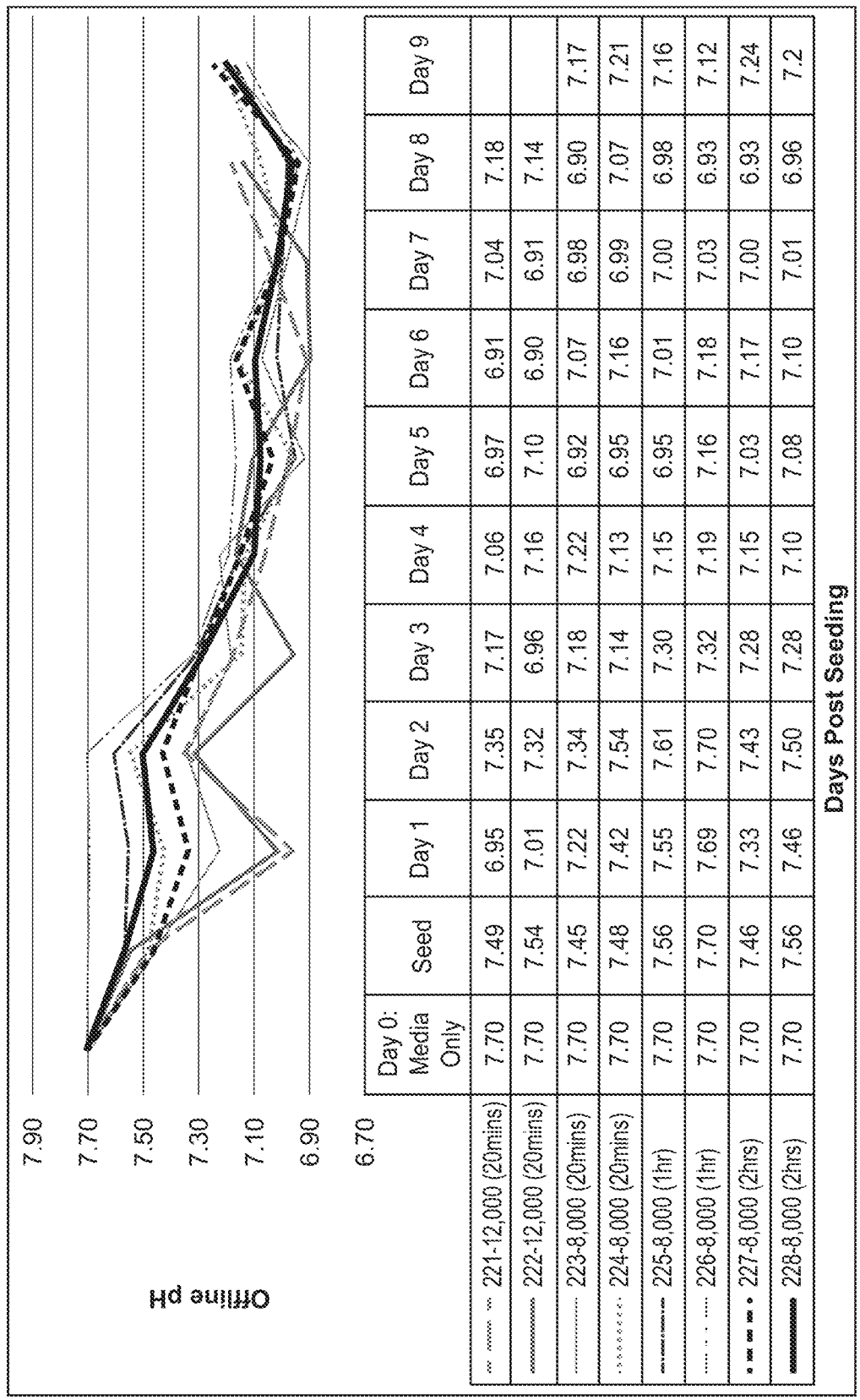

HEK 293 cells were thawed and resuspended in DMEM supplemented with 10% FBS. Cells were centrifuged at 209×g, 5 min, in room temperature, then supernatant was removed and fresh DMEM+10% FBS was added. Cells were counted for viable cell density and viability and were seeded in 2×T175 $cm^2$ flasks and incubated at 37.0° C., 5% $CO_2$ for three days until cultures reached ~90% confluency. For each cell passage, spent media was removed, flasks were washed with PBS (—$CaCl_2$, —$MgCl_2$) at 0.08 $mL/cm^2$, and then flasks treated with TrypLE Select (0.04 $mL/cm^2$) and incubated at 37.0° C., 5% $CO_2$ for 2-3 mins. Trypsin was quenched with DMEM+10% FBS (0.04 $mL/cm^2$). Cells were expanded and seeded per the diagram in FIG. 8.

Cell Inoculation and Monitoring

Bioreactors were inoculated in duplicate with HEK 293 cells at a target density of 8,000 cells/$cm^2$ and 12,000 cells/$cm^2$ in growth media (high glucose DMEM+10% Australian Origin FBS+1:100 Penicillin Streptomycin (Pen Strep) with agitation. Process parameters were set to pH 7.23, 37.0° C., 55% dissolved oxygen (DO) and linear speed of 2 cm/s. 24 hours' post seeding, recirculation with DMEM growth media (0.188 $mL/cm^2$) was turned on to a recirculation speed (12.5 mL/min). Daily samples taken for offline pH, metabolites, and nutrients were read using a Nova BioFlex. On day four (12,000 cells/$cm^2$), day five (8,000 cells/$cm^2$) and day nine post seeding, three fibers were removed and lysed with 1:1:1 v/v PBS, A100 and B100 solution (ChemoMetec) and counted (NucleoCounter NC-200) for total nuclei to monitor culture growth.

Transfection

Day four (12,000 cells/$cm^2$) and day five (8,000 cells/$cm^2$) post cell inoculation, recirculation was stopped, and cells in each bioreactor were transfected with plasmid DNA and Polyethylenimine (PEI). DNA and PEI were mixed in a 1:1 mg/mg ratio. Plasmid DNAs were transfected in a 1:1.5:2 mass ratio with pSMN plasmid, pAAV2/9 plasmid and pHELP plasmid were added to DMEM -/- media; high glucose, —$CaCl_2$, —L-glutamine and 0.2 µM filtered and mixed by inversion. PEI was added to DMEM -/-media and mixed by inversion. PEI was then added to DNA, mixed by inversion and incubated at room temperature for 20 minutes for the 8,000 cells/$cm^2$ (control) and 12,000 cells/$cm^2$. DNA/PEI was incubated for 1 hr and 2 hr for the other two 8,000 cells/$cm^2$ conditions. This DNA/PEI complex mixture was used to transfect two bioreactors for each of the four conditions. DNA/PEI complex was added to each bioreactor and incubated at process parameters for two hours. Two hours post transfection recirculation loop was turned back on.

Post Transfection Media Exchange 24 hours post transfection, all media in bioreactors and recirculation loops were removed and replaced with OptiMEM+1:100 Pen Strep (0.132 $mL/cm^2$) and recirculated for 24 hours at process parameters. 48 hours post transfection all media removed from recirculation only and replaced with OptiMEM+1:100 Pen Strep (12 mL/min) and recirculated at process parameters.

Harvest

Day eight (12,000 cells/$cm^2$) and day nine (8,000 cells/$cm^2$) post cell inoculation, Benzonase (100 U/mL) was added, chased with Lysis Buffer (50 mM HEPES, 1% Tween 20), and incubated for two hours at process parameters. Bioreactors were drained and Sucrose Salt Solution (500 mM NaCl, 1% w/v Sucrose) was added, and these were mixed by inversion. The bioreactors were washed with bioreactor rinse buffer (500 mM NaCl, 1% w/v Sucrose, 20 mM Tris Base, 1% v/v Tween 20, 1 mM $MgCl_2.6H_2O$) for about 15 mins at process parameters. The bioreactors were drained and bioreactor rinse buffer was pooled with crude bulk harvest, mixed by inversion and sampled for ddPCR assay.

Depth Filtration and Tangential Flow Filtration

On day eight (12,000 cells/$cm^2$) and day nine (control 8,000 cells/$cm^2$), post cell inoculation bioreactors were harvested, sampled and crude lysate was pooled for each condition (n=2 bioreactors). Pooled lysate was then clarified through Millistak COHC Pod, 270 $cm^2$ filter and Millipak 40, 0.45 µm, Durapore, 200 $cm^2$ polish filter (EMD Millipore). Samples were taken post COHC+0.45 and frozen at ~80.0° C. Clarified lysate was then concentrated via tangential flow a Pellicon® 2 Ultrafiltration Module PLCMK C 0.1 $m^2$ filter (EMD Millipore). At least 6 diavolumes was used to diafiltrate the final product. Post TFF1 filtration samples were obtained and frozen at −80.0° C. All samples were submitted for AAV2/9 titer and host cell protein.

Plasmids were used to produce DS in bioreactors. Data represent each condition in duplicate, corresponding bioreactor number and condition shown in Table 14.

TABLE 14

Bioreactor numbers and corresponding conditions

| Bioreactor Number | Seeding Density cells/cm$^2$ | Transfection Day | PEI/DNA Incubation Time (mins) | Harvest Day |
|---|---|---|---|---|
| 221, 222 | 12,000 | 4 | 20 | 8 |
| 223, 224* | 8,000 | 5 | 20 | 9 |
| 225, 226 | 8,000 | 5 | 60 | 9 |
| 227, 228 | 8,000 | 5 | 120 | 9 |

Cell Growth: Cells were counted on the day of seeding (Day 0), and nuclei were counted at day 4 (12,000 cells/cm$^2$), day 5 (8,000 cells/cm$^2$) and day 9 post-seeding. Data indicates that cells in all reactors grew exponentially between day 0 and day 5. After transfection, day 9 nuclei count suggest that bioreactors 221 increased 2.0-fold in total nuclei from day 5 to day 9. All other reactors (222 through 228) did not exhibit significant growth between day 5 and day 9. The increase in growth in bioreactor 221 may be an artifact based on uneven distribution of cells on individual fibers used for total nuclei counts. It is possible that cells in all bioreactors grew similarly based on metabolite data shown in FIGS. 9A-E.

pH, Nutrients and Metabolites: Glucose consumption trended the same in all bioreactor cultures, suggesting that despite the increase in bioreactor 221 growth curve, cells consumed glucose at similar rates. pH for bioreactors seeded at 12,000 cells/cm$^2$ averaged 7.06 and 8,000 cells/cm$^2$ averaged 7.18 for first three days. pH declined slightly with increased nutrient metabolism, and increased by day 9 concurrent with rise in ammonium ion levels. Lactate increased until day 5 (bioreactors 221, 223, 224, 225, 227) and day 6 (bioreactors 222, 226, 228) then leveled off toward the end of production, suggesting utilization of lactate as an energy source at this stage.

Production Titers

Figure 10:
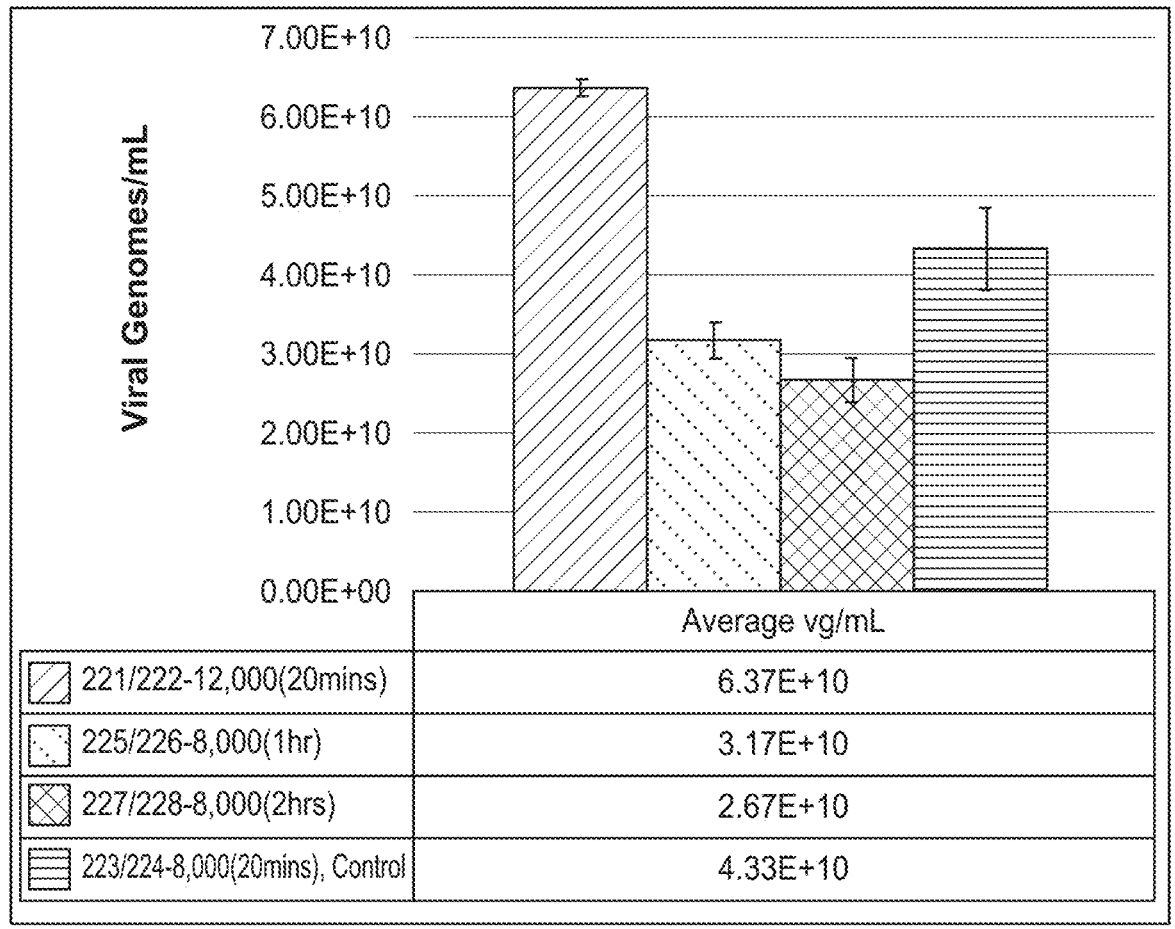
FIG. 10 shows viral genome production as a function of cell seeding density (8000 or 12000 cells/cm$^2$) and four different lengths of transfection time (20 min, 1 hr or 2 hours).

Viral genomes from harvest material were measured by digital droplet (ddPCR). Titers were about 1.5-fold higher in bioreactors seeded at 12,000 cells/cm$^2$ with an average titer measure of 6.37E+10 vg/mL (n=2) vs control bioreactors seeded at 8,000 cells/cm$^2$ with an average titer measure of 4.33E+10 vg/mL (n=2). Titer data suggests that seeding at a higher density, transfecting and harvesting one day early supports higher DS production yields. Titer yield for DNA/PEI incubated for one-hour exhibited a 1.4-fold decrease in average titer measured (3.17E 10vg/mL n=2) and for two-hour incubation average titer measured was 1.6-fold decrease (2.67E10vg/mL n=2) compared to the control in which DNA/PEI incubated for 20 mins (4.33E10vg/mL n=2). Data suggests that longer incubation time leads to decrease titer. This may be due to DNA and PEI forming large complexes that are unable to efficiently transfect HEK293 cells. Virus production per mL and surface area values are given in FIG. 10, as compared to production in a known process as a positive control.

Figure 11:
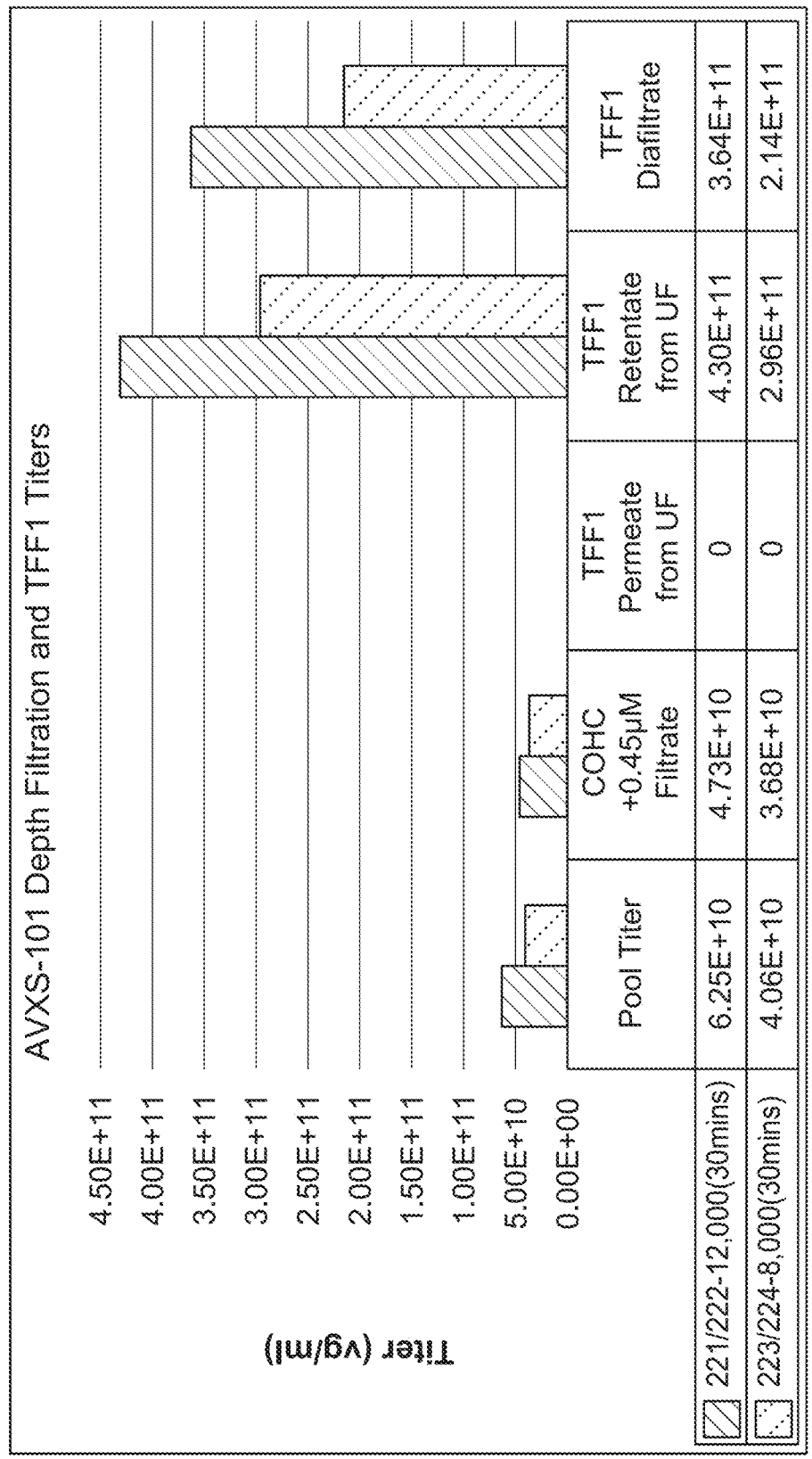
FIG. 11 shows viral titers from intermediates sampled at different filtration steps throughout the manufacturing process.

The viral titer measured at each step of the clarification and concentration steps are shown in FIG. 11. The residual host cell protein at each step during the TFF1 step is shown in FIGS. 12A-B.

Example 8: Effect of Seeding Density on Production of Drug Substance

The effect of seeding density on production of DS was evaluated. Four seeding densities were evaluated and each seeding density were in duplicate in a bioreactor.

Cell Scale Up

Figure 13:
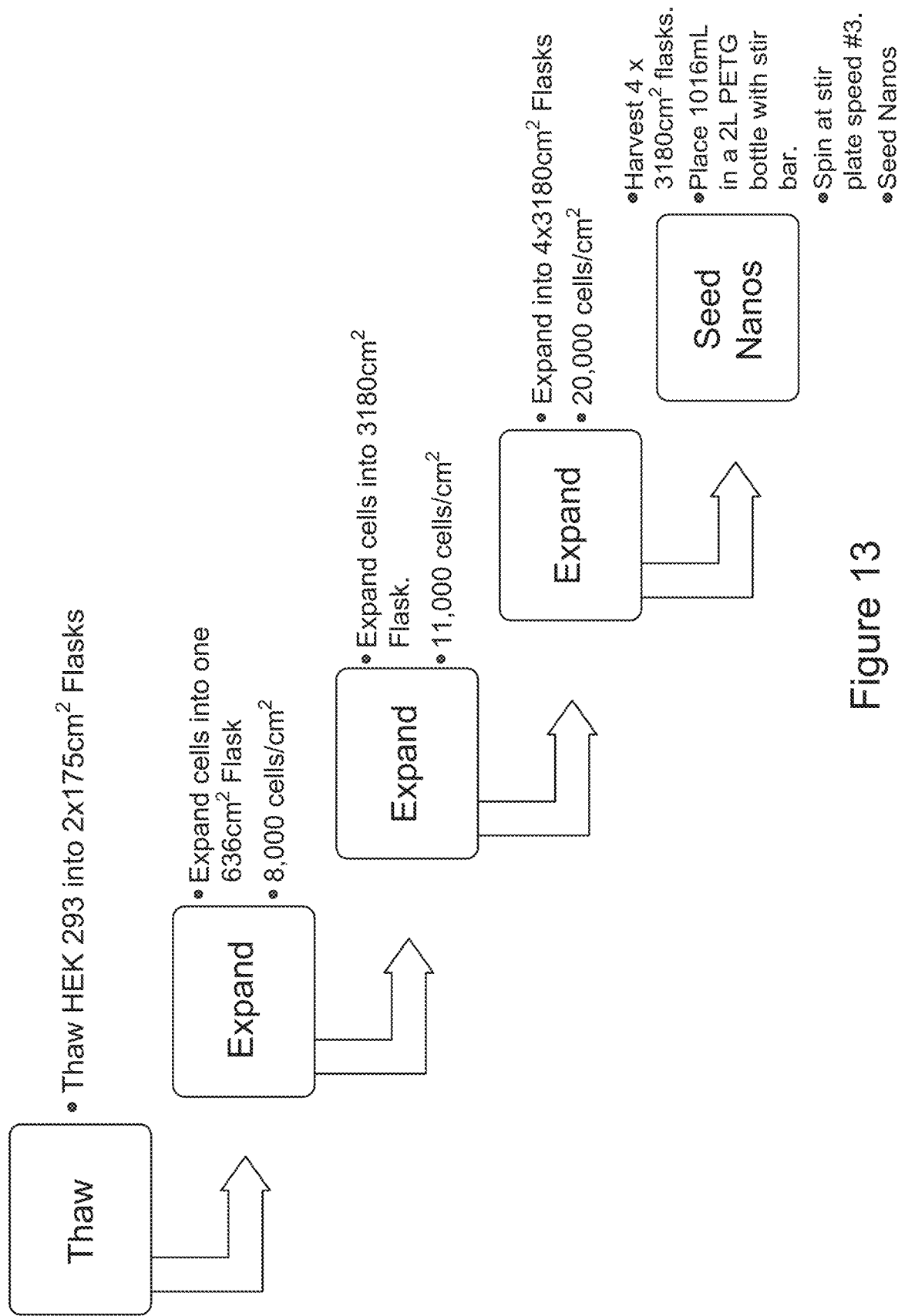
FIG. 13 describes the HEK 293 cell expansion process flow during cell seeding density experiments.

HEK 293 cells were thawed and resuspended in DMEM supplemented with 10% FBS. Cells were centrifuged at 209×g, 5 min, in room temperature, then supernatant was removed and fresh DMEM+10% FBS was added. Cells were counted for viable cell density and viability and were seeded in 2×T175 cm$^2$ flasks and incubated at 37.0° C., 5% CO$_2$ for four days until cultures reached ~90% confluency. For each cell passage, spent media was removed, flasks were washed with PBS (—CaCl$_2$, —MgCl$_2$) at 0.08 mL/cm$^2$, and then flasks treated with TrypLE Select (0.04 mL/cm$^2$) and incubated at 37.0° C., 5% CO$_2$ for 2-3 mins. Trypsin was quenched with DMEM+10% FBS (0.04 mL/cm$^2$). Cells were expanded and seeded per the diagram in FIG. 13.

Cell Inoculation and Monitoring

Bioreactors were inoculated with HEK 293 cells at four target densities, each in duplicate: 8,000 cells/cm$^2$, 9,350 cells/cm$^2$, 10,700 cells/cm$^2$ and 12,050 cells/cm$^2$ in 700 ml growth media (high glucose DMEM+10% Australian Origin FBS+1:100 Pen Strep) with agitation. Process parameters were set to pH 7.23, 37.0° C., 55% dissolved oxygen (DO) and linear speed of 2 cm/s. 24 hours post seeding, recirculation with DMEM growth media (total volume now 0.188 mL/cm2) was turned on to a recirculation speed (12.5 mL/min). Daily samples were taken for offline pH, metabolites, and nutrients were read using a Nova BioProfile 400. On day five and day nine post seeding, three fibers were removed and lysed with 1:1:1 v/v PBS, A100 and B100 solution (ChemoMetec) and counted (NucleoCounter NC-200) for total nuclei to monitor culture growth.

Transfection

Day five post cell inoculation, recirculation was stopped, and the media inside each bioreactor chamber (not recirculation bottle) was replaced with 600 ml DMEM −/−medium (high glucose, —CaCl2, —Lglutamine). Each reactor was transfected with plasmid DNA and Polyethylenimine (PEI-pro) in a 1:1 mass ratio. Plasmid DNAs were mixed in a 1:1.5:2 mass ratio (pSMN—3.56 mg, pAAV2/9—5.34 mg, and pHELP—7.1 mg), added to 300 mL DMEM −/−media, 0.2 µM filtered and mixed by inversion. PEI (16 mL) was added to 300 mL DMEM −/−media and mixed by inversion. The PEI and DNA mixtures were combined, mixed by inversion and incubated at room temperature for 20 minutes. Each 600 ml PEI/DNA complex mixture was used to transfect two Bioreactors, repeated for each corresponding seeding density. PEI/DNA complex was added to each bioreactor and incubated at process parameters for two hours. The recirculation loop was turned back on two hours post transfection (12.5 mL/min).

Post Transfection Media Exchange 24 hours post transfection, all media in bioreactors and recirculation loops was removed and replaced with OptiMEM (0.132 mL/cm$^2$) and recirculated (12.5 mL/min) for 24 hours at process parameters. 48 hours post transfection media in the recirculation bottle was exchanged with fresh OptiMEM and recirculated at process parameters (12 mL/min).

Harvest

Day nine post cell inoculation, Benzonase (100 U/mL) was added, chased with Lysis Buffer (50 mM HEPES, 1% Tween 20), and incubated for two hours at process parameters. Bioreactors were drained and Sucrose Salt Solution (500 mM NaCl, 1% w/v Sucrose) added, mixed by inversion. Bioreactor washed with bioreactor rinse buffer (500 mM NaCl, 1% w/v Sucrose, 20 mM Tris Base, 1% v/v Tween 20, 1 mM $MgCl_2.6H2O$) for 15 mins at process parameters. Bioreactors drained and bioreactor rinse buffer pooled with crude bulk harvest, mixed by inversion and sampled for ddPCR assay.

Plasmids were used to produce Drug Substance in Bioreactors. Reactors were seeded at varying densities, and transfected and harvested on the same schedule (day 5, day 9 post seeding, respectively). Data represent duplicates of each seeding density, as shown in Table 15 below:

TABLE 15

| Starting Seeding Density | Bioreactor Number |
|---|---|
| 8,000 cells/$cm^2$ | 221, 222 |
| 9,350 cells/$cm^2$ | 223, 224 |
| 10,700 cells/$cm^2$ | 225, 226 |
| 12,050 cells/$cm^2$ | 227, 228 |

Figure 14A:
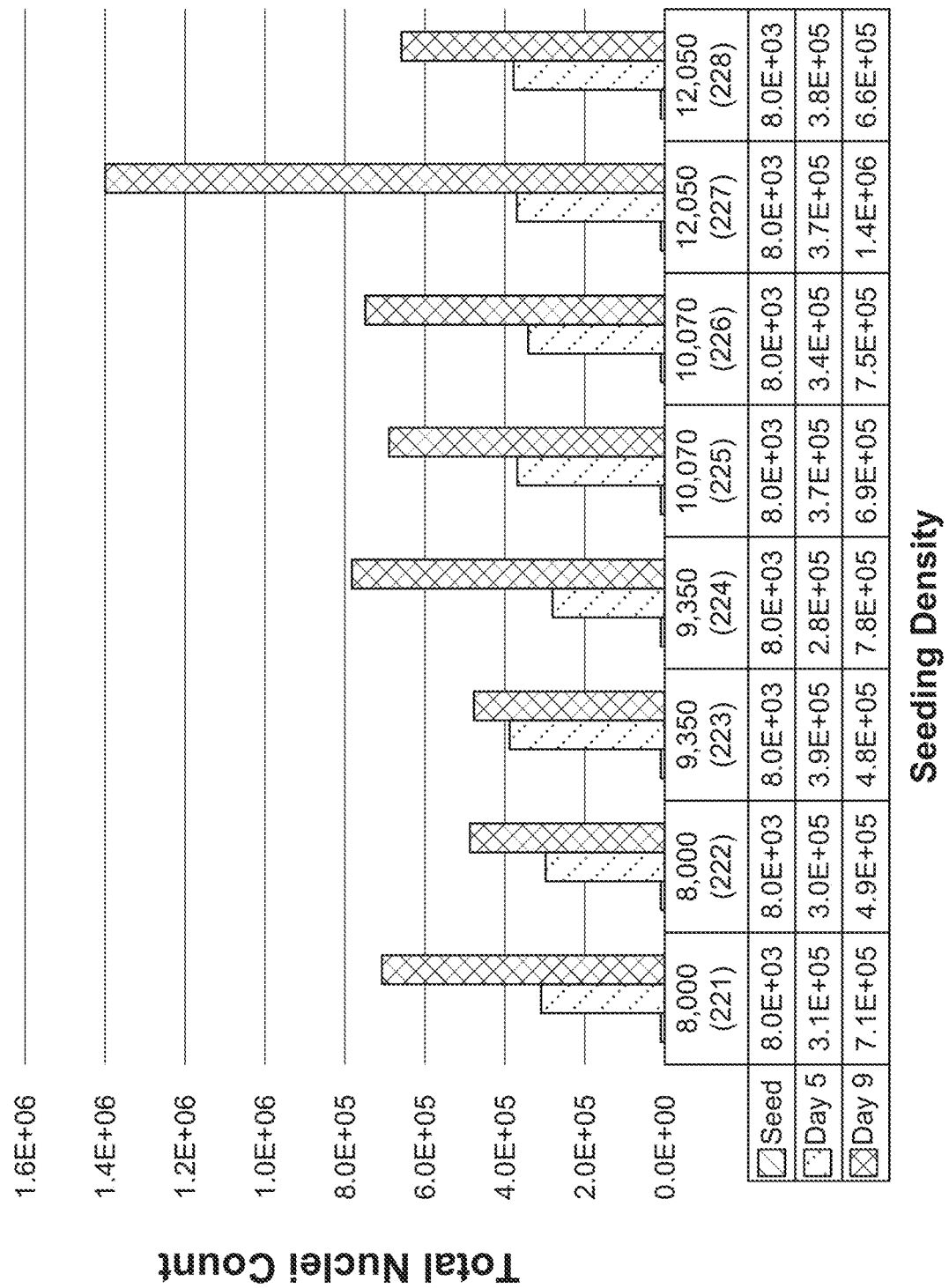
FIGS. 14 A-E show that HEK 293 cells were seeded in duplicate at 8,000 cells/cm$^2$, 9,350 cells/cm$^2$, 10,700 cells/cm$^2$, 12,050 cells/cm$^2$ in bioreactors (pH 7.23, 37.0° C., 55% DO). Cells were transfected with DNA plasmids/PEI (1:1 m/m) five days post-seeding. pH and metabolite analysis were performed using NOVA BioProfile 400.
Figure 14B:
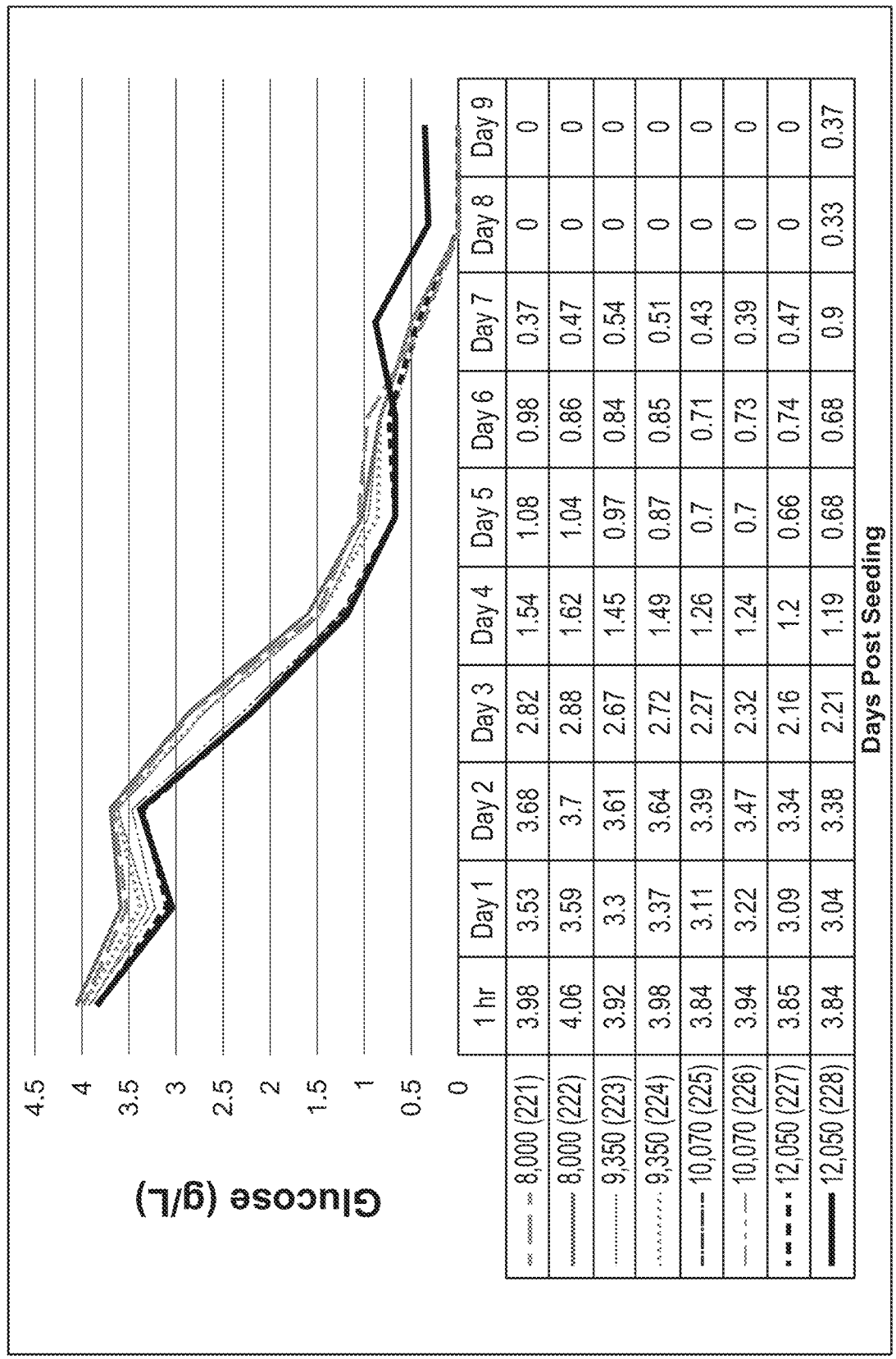
Figure 14C:
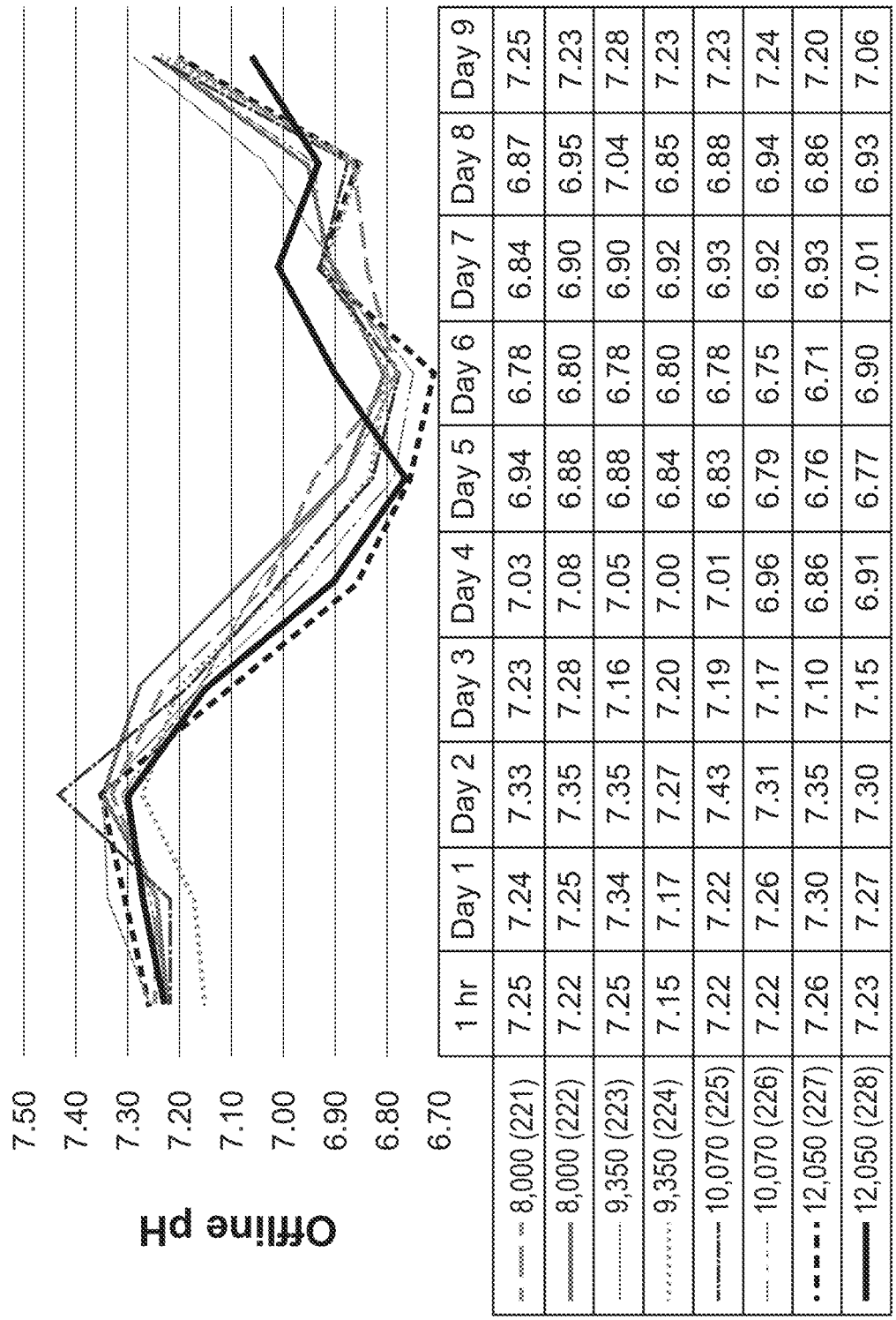
Figure 14D:
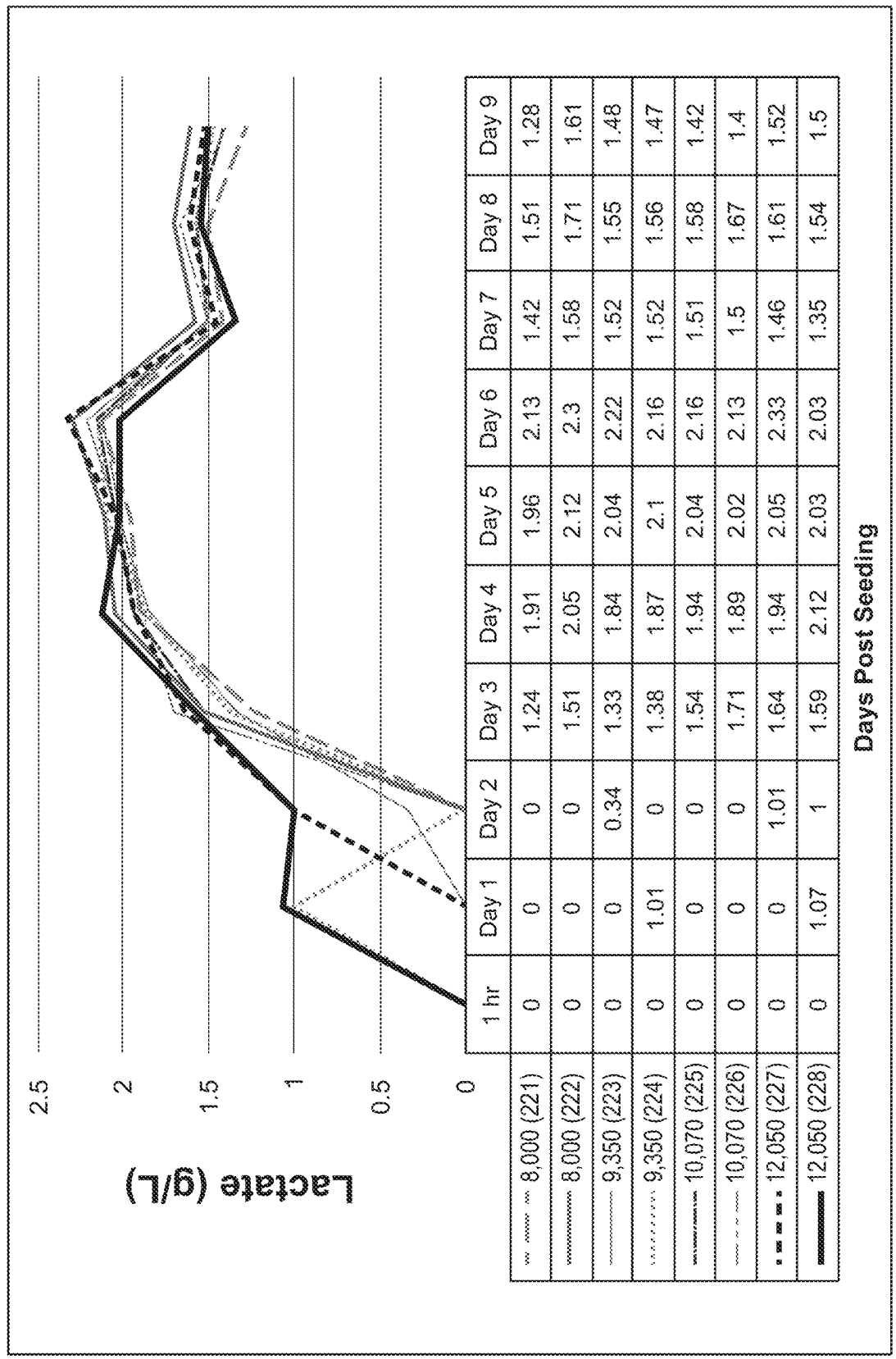
Figure 14E:
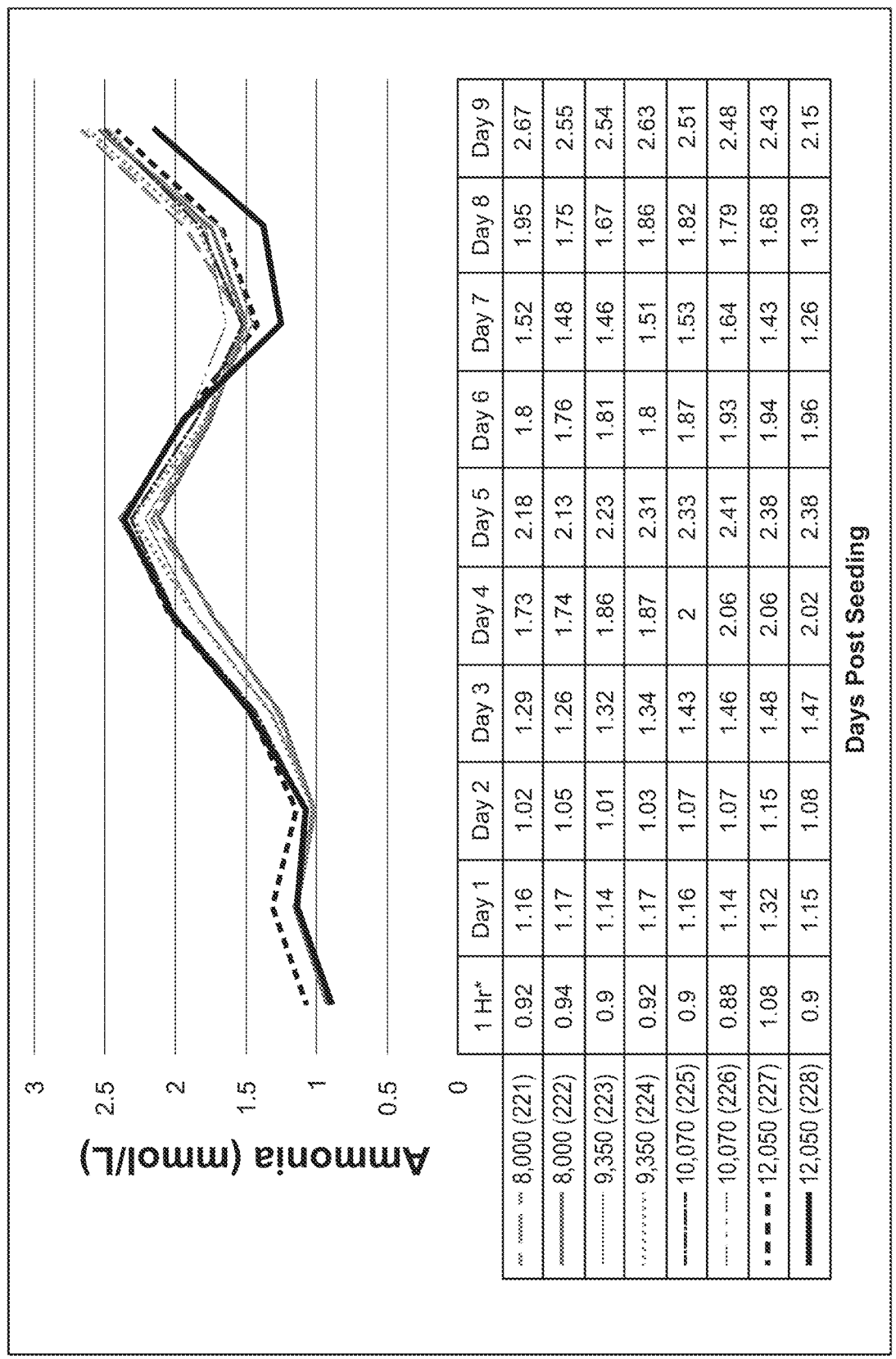

Cell Growth: Cells were counted on the day of seeding (Day 0), and nuclei were counted at day 5 and 9 post-seeding. Data indicate that cells in all reactors grew exponentially between day 0 and day 5. Despite differences in starting seeding densities, nuclei counts do not indicate major differences in cell numbers between groups at day 5. After transfection, day 9 nuclei count suggest that five of the reactors (221, 224, 225, 226, 228) doubled in total nuclei from day 5 to day 9. Two reactors (222, 223) increased 1.4-fold in total nuclei, as shown in FIG. 14A. Reactor 227 increased 3.8-fold in total nuclei from day 5 to day 9. This difference may be an artifact based on uneven distribution of cells between individual fibers used for counts. It is possible that cells in all reactors grew similarly based on metabolite data shown in FIGS. 14B-E.

pH, Nutrients and Metabolites: Glucose consumption (FIG. 14B) trended the same in all bioreactor cultures, suggesting that despite the differences in starting seeding densities, cultures consumed glucose at similar rates. Offline pH (FIG. 14C) remained consistent (pH 7.25) for first three days in all cultures, declined with increased nutrient metabolism, and increased post day 8 concurrent with rise in ammonium ion levels (FIG. 14E). Lactate (FIG. 14D) increased until day 6 and then leveled off toward the end of production, suggesting utilization of lactate as an energy source at this stage. No significant difference in metabolite profiles were observed between reactors seeded at different starting densities. This could be because the difference in starting seeding densities is minimal, <1.2-fold difference.

Production Titers

Figure 15A:
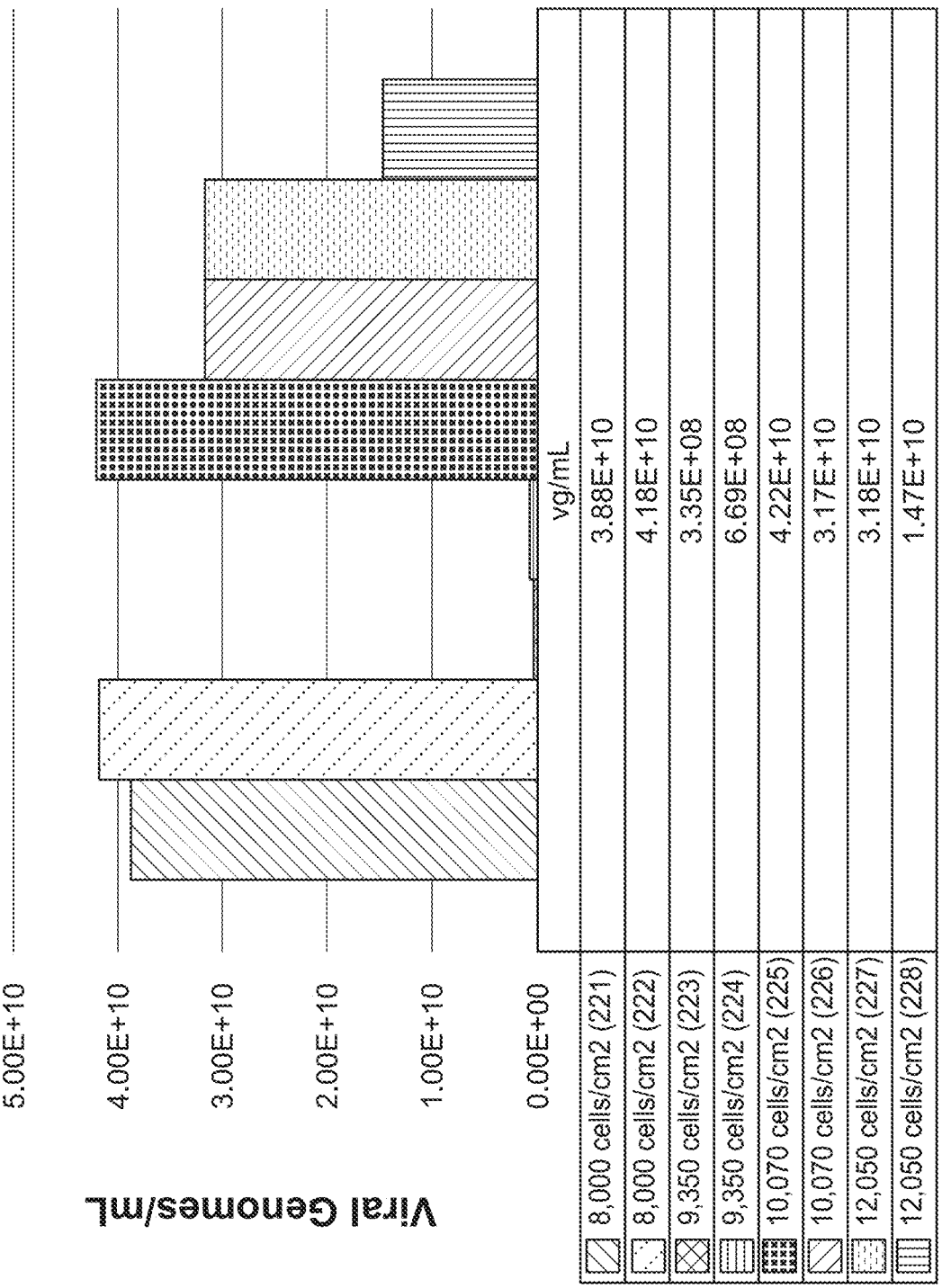
FIGS. 15 A-B show drug substance production from four starting seeding densities in bioreactors. Comparison of virus titer and vector genome harvested per unit surface area.

Viral genomes from harvest material were measured by digital droplet (ddPCR). Titers were comparable between starting seeding densities of 8,000 cells/$cm^2$ and 10,070 cells/$cm^2$, averaging 3.99E+10±2.1E+09 vg/mL (n=2) and 3.70E+10±7.4E+09 vg/mL (n=2), respectively. For an unidentifiable reason, reactors seeded at 9,350 cells/cm2 exhibited an average titer measure of 5.02E+08 vg/mL (n=2), approximately 2 logs lower than average titers of reactors seeded at flanking densities. This difference is likely a result of an unidentified operational error during transfection or harvest rather than lack of productivity at this seeding density. Replicate reactors seeded at 12,050 cells/$cm^2$ demonstrated a twofold difference between each other, with one reactor in range observed for lower seeding densities, 3.2E+10 vg/ml, while the second produced a titer of only 1.4E+10 vg/ml. Virus production per mL and surface area values are given in FIG. 15A.

Figure 15B:
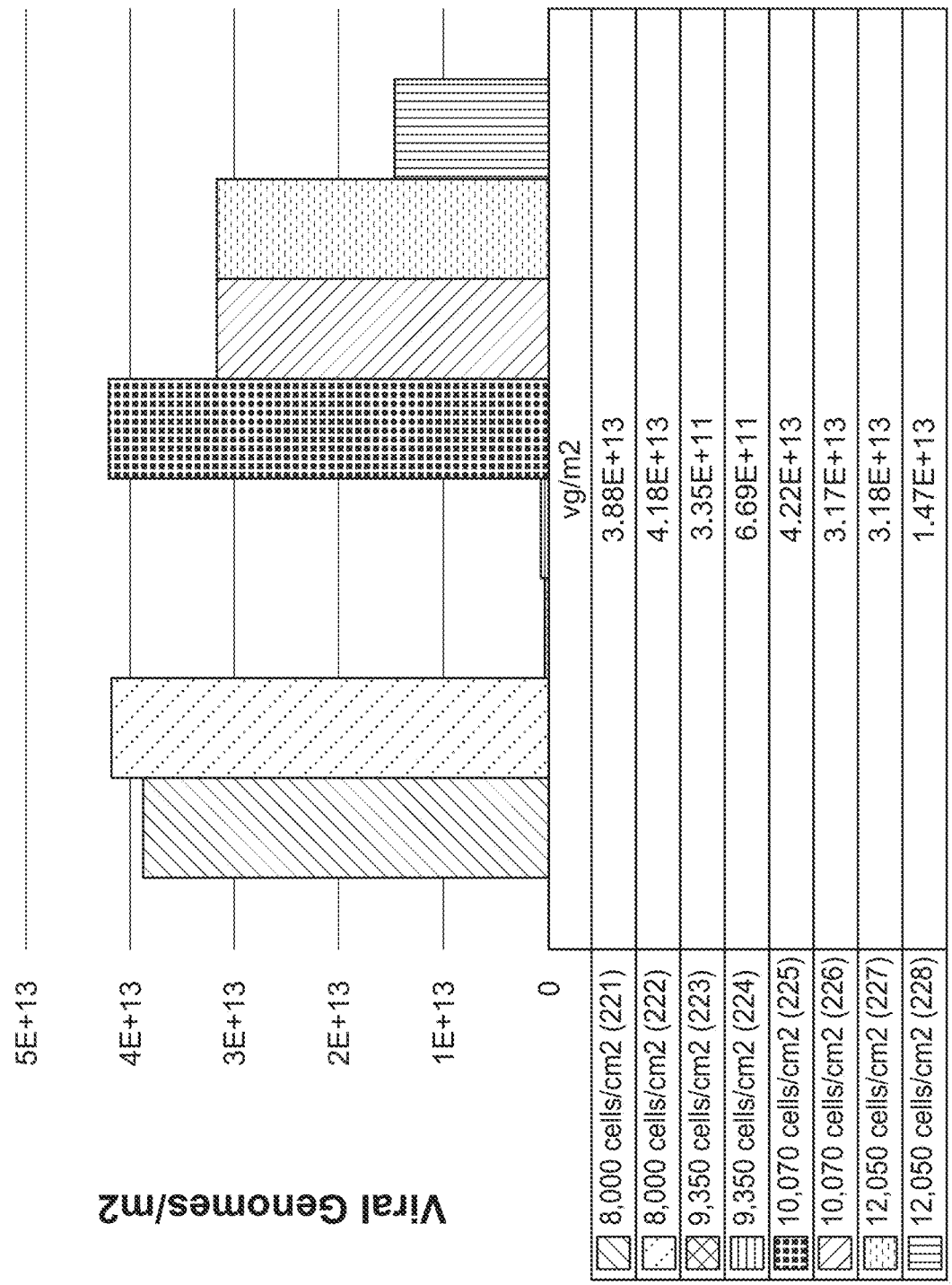

Seeding density and production of DS were evaluated, as shown in FIG. 15B. HEK 293 cells seeded in the range of 8E+03 to 10E+03 cells/$cm^2$ showed consistent growth profiles, pH, glucose consumption, lactate and ammonia generation. Additionally, comparable titers were produced suggesting slightly higher seeding density does not negatively impact production. In contrast, reactors seeded at the higher density of $12 \times 10^3$ cells/$cm^2$ exhibited more variability between duplicates, including lower average titer compared to other conditions, suggesting the approached used in this experiment may not be optimal for production. These results support seeding cells at a density ranging between $8 \times 10^3$ and $1 \times 10^4$ cells/$cm^2$ for bioreactor experiments.

Example 9: Comparability Assessment

Figure 16:
FIG. 16 shows Phase 1 (Process A) and Phase 3 Trial (Process B) Manufacturing Processes.

The comparability between AVXS-101 drug product used in Phase 1 clinical studies (Process A) and drug product used in pivotal clinical studies (Process B) was assessed as the primary objective with a secondary objective to assess manufacturing consistency using Process B by comparing drug product Lots 600156 and 600307. FIG. 16 represents the Phase 1 (Process A) and Phase 3 trial (Process B) manufacturing processes flows and the differences between them.

The comparability assessment was performed using Phase 1 clinical drug product Lot NCHAAV9SMN0613 manufactured at Nationwide Children's Hospital (NCH) and drug product Lot 600156 manufactured at AveXis.

Product

The following lots of material were evaluated, as summarized in Table 16. The assessment included a direct comparison of resulting quality attributes from the Phase 1 clinical drug product Lot NCHAAV9SMN0613 using Process A and AVXS-101 drug product Lot 600156 using Process B. In addition, the release testing results of Lot 600156 with Lot 600307 were evaluated holistically for scale-up process reproducibility and consistency.

TABLE 16

AVXS-101 Drug Product to be Evaluated for Comparability Between Process A (Phase 1) and Process B (Phase 3) and Manufacturing Consistency for Process B

| Use | Lot Number | MFG Date | MFG Date | Storage Condition |
|---|---|---|---|---|
| Phase 1 Study | NCHAAV9SMN0613 | 10 Dec. 2013 | Process A | ≤−60° C. |
| Phase 3 Study | AVXS-101 Lot 600156 | 7 Nov. 2017 | Process B | ≤−60° C. |
| | AVXS-101 Lot 600307 | 4 Dec. 2017 | Process B | ≤−60° C. |

Manufacturing Process Overview

FIG. 17A-B provides a summary of the comparability results.

Comparability and Manufacturing Consistency Assessment

Process A and Process B materials for assessed to be comparable and the Process B materials were assessed to be consistent. Process B materials were also determined to have additional benefits, e.g., for industrial scale production.

Test Methods pH pH analysis was performed on Lot NCHAAV9SMN0613 (Process A), Lot 600156 (Process B) and Lot 600307 (Process B). The results from both processes ranged from 7.9-8.0. This demonstrated that the pH of the Process A and Process B materials were comparable and that the Process B materials are consistent.

Appearance

Appearance by visual inspection was performed on Lot NCHAAV9SMN0613 (Process A), Lot 600156 (Process B) and Lot 600307 (Process B). The apparent differences in appearance results between Process A and Process B were due to different vector concentrations (genomic titer). Lot NCH AAV9SMN0613 had a lower vector concentration than the Process B lots. As a result, Lot NCH AAV9SMN0613 was more dilute leading to a more clear and colorless solution while the colorless to white and slightly opaque observations for Process B lots results from approximately 4 times concentration of viral particles in solution per mL.

Considering the concentration difference, the appearance of the Process A and Process B materials were assessed to be comparable and the Process B materials were assessed to be consistent.

Osmolality

Osmolality by freezing point depression was performed on Lot NCHAAV9SMN0613 (Process A), Lot 600156 (Process B) and Lot 600307 (Process B). The results from both processes ranged from 410-415 mOSm/kg. This demonstrated that the osmolality of the Process A and Process B materials were comparable and that the Process B materials were consistent.

Sub-visible Particles

Sub-visible particles by light obscuration was performed on Lot NCHAAV9SMN0613 (Process A), Lot 600156 (Process B) and Lot 600307 (Process B). The results from both processes were well below the recommended limits in the USP monograph for injectable drug products. This demonstrated that the sub-visible particle counts for the Process A and Process B materials were comparable and that the Process B materials were consistent.

Genomic Titer

Genomic titer by ddPCR was performed on Lot NCHAAV9SMN0613 (Process A), Lot 600156 (Process B) and Lot 600307 (Process B). Genomic titer for AVXS-101 lots was expected to fluctuate based on target concentrations in manufacturing. Genomic titer produced by Process B ($3.7 \times 10^{13}$ vg/mL and $4.0 \times 10^{13}$ vg/ml) was at least 3 fold higher than that from Process A ($1.1 \times 10^{13}$ vg/mL), hence Process B was a better method for large-scale manufacture of AVXS-101.

Infectious Titer

Infectious titer by $TCID_{50}$ was performed on Lot NCHAAV9SMN0613 (Process A), Lot 600156 (Process B) and Lot 600307 (Process B). Process B ($1.3 \times 10^{10}$ IU/mL and $6.7 \times 10^{9}$ IU/ml) produced on average 66% higher infectious titer than Process A ($5.9 \times 10^{10}$ IU/mL), which may be advantageous, e.g., for large-scale manufacture of rAAV, e.g., AVXS-101.

Total Protein

Total Protein by micro BCA was performed on Lot NCHAAV9SMN0613 (Process A), Lot 600156 (Process B) and Lot 600307 (Process B). Normalized to $1.0 \times 10^{13}$ vg/mL, the results from both processes ranged from 167-179 µg/mL. The normalized total protein values demonstrated that the Process A and Process B materials were comparable and that the Process B materials were consistent.

Identity by Western Blot

Identity by Western Blot was performed on Lot NCHAAV9SMN0613 (Process A), Lot 600156 (Process B) and Lot 600307 (Process B). The blot profile and apparent molecular weight values for the main bands (VP1, VP2, and VP3) were assessed to be comparable for the Process A and Process B materials and it was also assessed that the Process B materials were consistent.

% Empty Capsid by AUC

% Empty Capsid by AUC was performed on Lot NCHAAV9SMN0613 (Process A), Lot 600156 (Process B) and Lot 600307 (Process B). The result for Lot NCHAAV9SMN0613 (Process A) was 7%. The results for Lots 600156 and 600307 (Process B) were 2% and 4% respectively. Process B (2% and 4%) produced about two-fold less empty capsids as measured by AUC than Process A (7%). Hence, Process B was able to produce an improved composition comprising a lower concentration of empty capsids.

Identity and Purity by SDS-PAGE

Identity and Purity by SDS-PAGE was performed on Lot NCHAAV9SMN0613 (Process A), Lot 600156 (Process B) and Lot 600307 (Process B). The % Total Purity from both processes were ≥98% and the banding patterns as well as the apparent molecular weight for each of the three capsid proteins were highly consistent. These results demonstrated that the Process A and Process B materials were comparable and that the Process B materials were consistent.

Residual Host Cell Protein

Residual Host Cell Protein by ELISA was performed on Lot NCHAAV9SMN0613 (Process A), Lot 600156 (Process B) and Lot 600307 (Process B). The results for all lots tested were <LOQ (8 ng/mL) for the assay. These results demonstrated that the Process A and Process B materials were comparable and that the Process B materials were consistent.

Residual Bovine Serum Albumin (BSA)

Residual BSA was performed on Lot NCHAAV9SMN0613 (Process A), Lot 600156 (Process B) and Lot 600307 (Process B). The results for all lots tested were <LOQ (0.50 ng/mL) for the assay. These results demonstrate that the Process A and Process B materials are comparable and that the Process B materials are consistent.

Residual Benzonase

Residual Benzonase by ELISA was performed on Lot NCHAAV9SMN0613 (Process A), Lot 600156 (Process B) and Lot 600307 (Process B). The results for all lots tested were <LOQ (0.20 ng/mL) for the assay. These results demonstrate that the Process A and Process B materials are comparable and that the Process B materials are consistent.

Residual Host Cell DNA

Residual Host Cell DNA by qPCR was performed on Lot NCHAAV9SMN0613 (Process A), Lot 600156 (Process B) and Lot 600307 (Process B). Normalized to $1.0 \times 10^{13}$ vg/mL, the result for Process A was $3.7 \times 10^{5}$ pg/mL while the results for Process B were $0.76 \times 10^{5}$ pg/mL and $0.68 \times 10^{5}$ pg/mL, respectively. Hence, Process B produced viral vectors with significantly lower residual hcDNA, which may be advantageous, e.g., for large-scale manufacture of rAAV, e.g., AVXS-101.

Statistical Analysis

Statistical analysis was performed on the quantitative quality attributes. Comparisons were performed pair-wise between the Process A Lot (NCHAAV9SMN0613) and each Process B Lot (600156 and 600307) as listed below. These results are shown in FIGS. 18 and 19.

These studies show that Process B is a superior method of producing viral vectors. Process B consistently produced a larger quantity of viral vectors (as measured by genomic titer and infectious titer) with few impurities (lower residual hcDNA) with fewer empty capsids.

Next Generation Sequencing

Next Generation Sequencing (NGS) was also performed to establish the identity of (determine and/or confirm the genomic sequence) and assess if sequence variants (sub-populations) existed for the AVXS-101 drug product Phase 3 material from Process B. Alignment of the sequence dataset against the Sponsor provided reference sequence (pscSMN) revealed complete (100%) breadth and sufficient depth of coverage across the full length of the genome to enable variant detection. A total of four minor variant positions were noted, however these appear to represent sequencing errors within difficult to sequence regions (e.g., the inverted terminal repeats (ITRs) of AAVs which are notoriously difficult to sequence owing to their high GC content and palindromic sequences), rather than true variants. Refer to Table 17 for the sequencing results.

residual hcDNA. All results were consistent relative to the Test Limit for each quality attribute.

Furthermore, to establish manufacturing consistency using Process B, pair-wise comparison was performed using Lots 600156 and 600307. The result from this initial pair-wise comparison between Process B Lot 600156 and 600307 exhibit consistency in manufacturing. All results were also consistent relative to the Test Limit for each quality attribute.

Based on the results evaluation, the resulting quality attributes from the Phase 1 clinical drug product Lot NCHAAV9SMN0613 using Process A and AVXS-101 drug product Lot 600156 using Process B demonstrated that Process B yields higher amounts of viral vector and improved purity, which may be advantageous, e.g., for large-scale manufacture of rAAV. Additionally, the two lots of material generated from Process B (Lots 600156 and 600307) were found to be reproducible further exhibiting manufacturing consistency.

Example 10: Analytical Ultracentrifugation (AUC) Analysis

The material from Phase-1 (Process A, Lot NCHAAV9SMN0613) and Phase-3 (Process B, Lots 600156 and 600307) were analyzed using the AUC method. The AUC Profiles (analyzed in duplicate) for the

TABLE 17

| DNA Sequencing Results of AVXS-101 Phase 3 Lot 600156 from Process B | | | | | | | | | |
|---|---|---|---|---|---|---|---|---|---|
| Total # of Reads Used for Mapping | Reference Sequence | Reference Length (Bases) | Total # of Mapped Reads | % of Population Mapped | Average Depth of Coverage | Consensus Length Generated by Mapping | % Reference Coverage | % Similarity to Reference | Total # of Unmapped or Low Quality Positions |
| 44,705,268 | AVXS-101 | 5,991 | 48,854,239 | 98.1 | 1,606,995.7 | 5,991 | 100 | 100 | 0 |

Phase 1 Lot NCHAAV9SMN0613 Stability Profile

Lot NCHAAV9SMN0613 was stored for 12 months at ≤−60° C. At each time point, the lot was analyzed. No unfavorable trends are noted. FIG. 20 shows the stability results to date.

A comparability study was completed for AVXS-101 used in Phase 1 clinical studies. The assessment was performed using Phase 1 clinical drug product Lot NCHAAV9SMN0613 manufactured at Nationwide Children's and AVXS-101 drug product Lot 600156 manufactured at AveXis. In addition, manufacturing consistency was evaluated using Process B Lots 600156 and 600307. For both the comparability assessment (Process A vs Process B) and manufacturing consistency (Process B Lots 600156 vs 600307), the study evaluated the identity, quality, purity, of AVXS-101 clinical trial material using the newly improved process and analytical methods to enable a robust assessment of comparability and manufacturing consistency.

Figure 21:
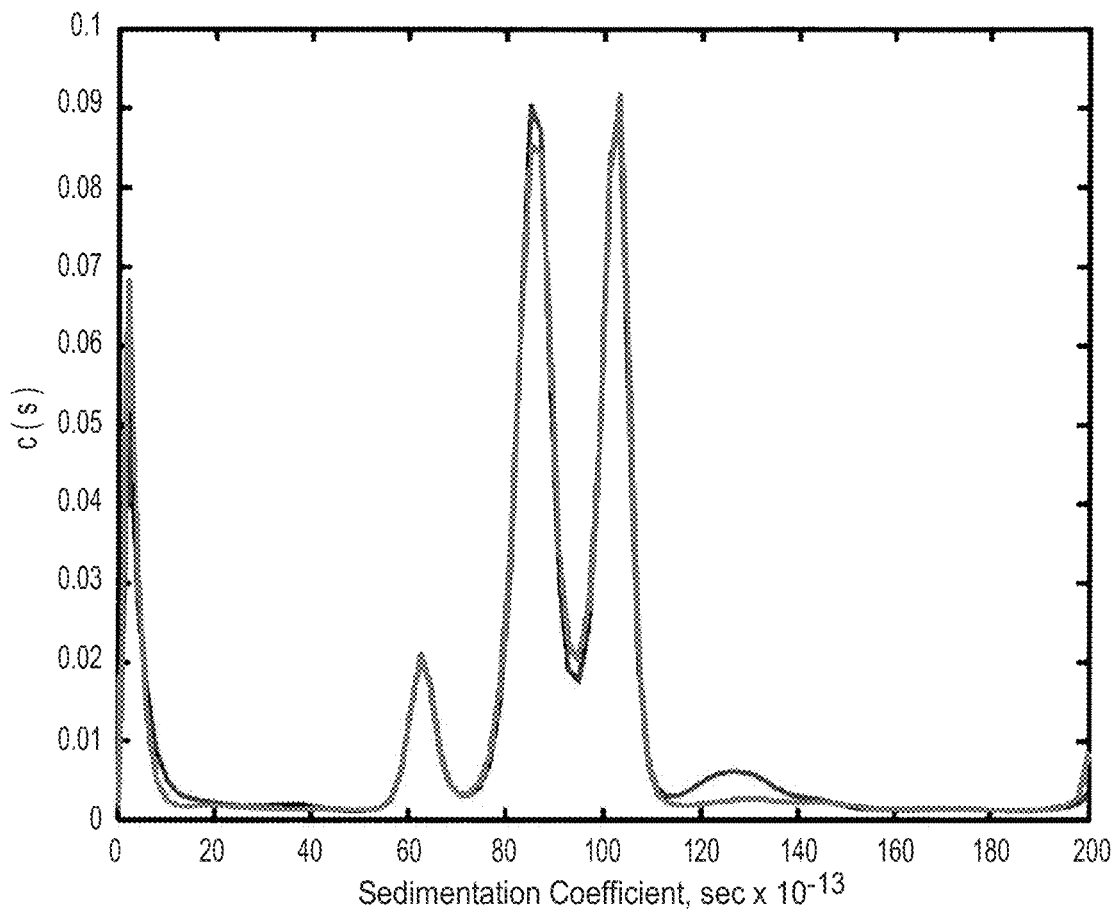
FIG. 21 shows sedimentation coefficients (sec×$10^{-13}$) for the Phase-1 material (NCHAAV9SMN0613) showing empty capsids (7%) with sedimentation coefficient of approximately 60×$10^{-13}$ sec, and the full capsids with sedimentation coefficient range of approximately 80-150×$10^{-13}$ sec.
Figure 22:
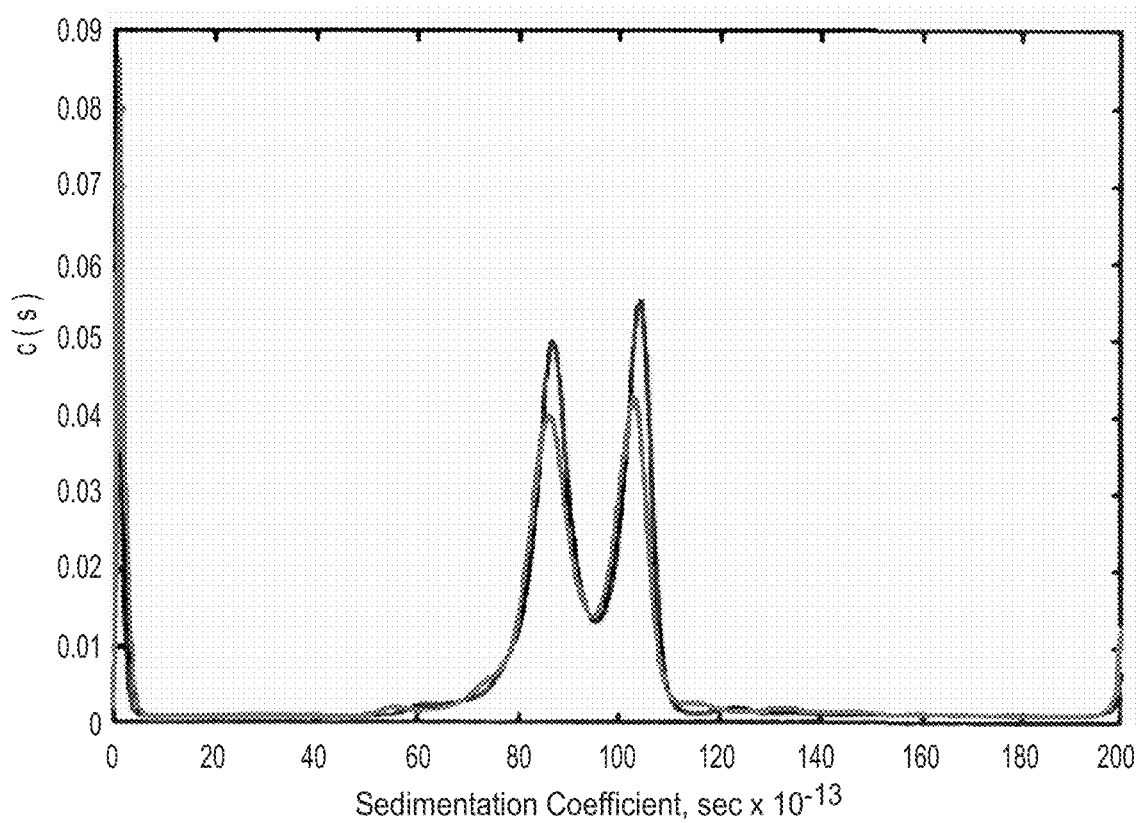
FIG. 22 shows sedimentation coefficients (sec×$10^{-13}$) for the Phase-3 material (600156) showing empty capsids (2%) with sedimentation coefficient of approximately 60×$10^{-13}$ sec, and the full capsids with sedimentation coefficient range of approximately 80-150×$10^{-13}$ sec.
Figure 23:
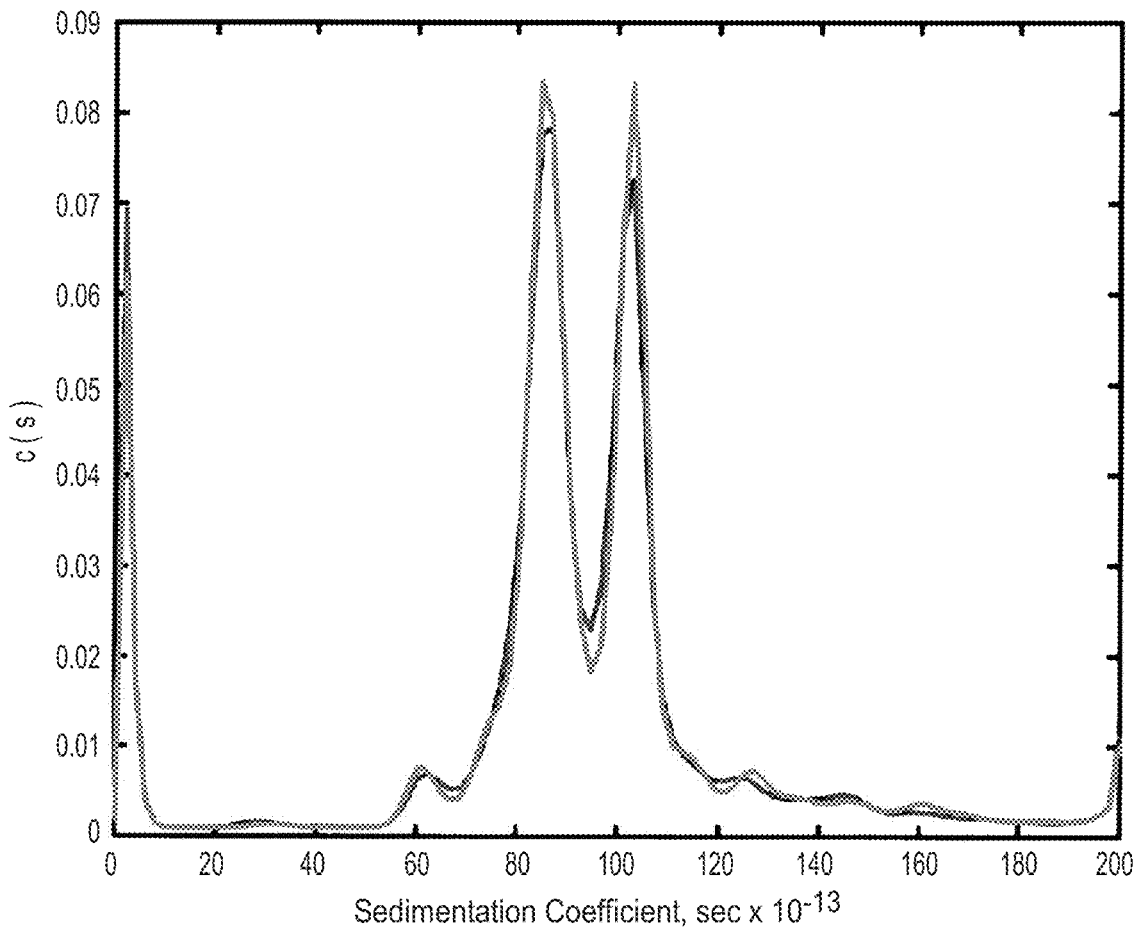
FIG. 23 shows sedimentation coefficients (sec×$10^{-13}$) for the Phase-3 material (600307) showing empty capsids (4%) with sedimentation coefficient of approximately 60×$10^{-13}$ sec, and the full capsids with sedimentation coefficient range of approximately 80-150×$10^{-13}$ sec.

Statistical analysis was performed on the quantitative quality attributes. Comparisons were performed pair-wise between the Process A Lot NCHAAV9SMN0613 and Process B Lot 600156. Process B was a better method that produced higher amounts of viral vectors at a higher purity than Process A. For example, as compared to Process A, viral vectors produced by Process B had a higher infectious titer, 8% higher genomic tier, 92% fewer subvisible particles more than 10 μm size, 50% fewer subvisible particles more than 25 μm size, 100% fewer empty capsids and 11% less NCHAAV9SMN0613, 600156, and 600307 are shown in FIG. 21, FIG. 22, and FIG. 23, respectively.

The AUC analysis of each material exhibits similar sedimentation coefficients for the empty and the full capsids with the Phase-1 material (Process A, Lot NCHAAV9SMN0613) showing elevated empty capsid content (7%) when compared to the Phase-3 material (Process B, Lots 600156 and 600307) with empty capsid contents of 2% and 4% respectively. This is due to the ability of the CsCl gradient ultracentrifugation manufacturing step in Process B to more effectively separate the empty capsids from the full capsids with compared with the iodixanol gradient ultracentrifugation manufacturing step employed by Process A.

AVXS-101 production lots using the clinical and commercial presentation consistently exhibit three visible bands of capsids when subjected to the CsCl gradient purification process using ultracentrifugation, both in the Phase-1 clinical trial material produced at Nationwide Children's Hospital (NCHAAV9SMN0613) and in each subsequent production lots by AveXis. Based on the AUC profiles for the Phase 1 clinical drug product Lot NCHAAV9SMN0613 using Process A and AVXS-101 drug product Lot 600156 using Process B, these materials are considered to be comparable. Additionally, the AUC profiles for two lots of material generated from Process B (Lots 600156 and 600307) were assessed to be consistent.

Example 11—Upstream Process

An upstream process was used to produce intermediate derived from a working cell bank, wherein the upstream process comprises the steps of (a) culturing cells, (b) transfecting the cultured cells with three plasmids as shown in FIG. 1, (c) harvesting the expanded viral particles from the cells after a culture period, (d) purifying the viral particles via filtration to remove any intact cells or cellular debris, (e) subjecting the eluent from step (d) to tangential flow filtration, and (f) freezing the resultant intermediate preparation of purified viral particles.

Pre-transfection, cells were expanded for in suitable culture media, in flasks or a suitable bioreactor, or both. One culture media is DMEM with 10% FBS, 4.5 g/L glucose, 4 mM L-glutamine. In one embodiment, the adherent cells are grown in flasks initially and then transferred into an iCELLis bioreactor for further adherent cell expansion within the bioreactor.

After cell expansion, adherent HEK293 cells were transfected with a triple DNA plasmid PEI co-precipitation. The 3 plasmids utilized for this transfection are; pSMN, pAAV2/9, and pHELP. The DMEM growth medium used for cell expansion is replaced with a modified DMEM transfection media. The DMEM transfection media contained no FBS, no calcium, no L-glutamine and 4.5 g/L glucose. The scAAV9.CB.SMN vector was produced using triple DNA plasmid transfection into adherent HEK293 cells using a PEI co-precipitation in a large scale adherent cell bioreactor. The vector plasmid pSMN contains the cDNA for the human SMN. The 3 plasmids utilized for this transfection are; pSMN (222 mg), pAAV2/9 (333 mg), and pHELP (444 mg). The transfection medium was allowed to equilibrate in the bioreactor until the bioreactor temperature is >30° C. prior to the addition of the PEI-Plasmid co-precipitation. The PEI-Plasmid co-precipitation process involved the addition of the plasmids to the transfection media and 0.2μ filtration into a reaction bag. The PEI was added to transfection medium and then to the reaction bag. The PEI—Plasmid reaction was manually mixed to form a homogeneous suspension and the reaction occurs over a 15-30 minute period.

At the end of the reaction time, the PEI-Plasmid co-precipitation was added to the bioreactor. The PEI-Plasmid co-precipitation was allowed to mix in the bioreactor for 1-2 hours prior to restarting the recirculation. The DMEM growth media was recirculated in the bioreactor for 18-24 hours before the next media change.

The rAAV SMN genome (nucleotides 980-3336 of SEQ ID NO: 1) has in sequence an AAV2 ITR, the chickenβ-actin promoter with a cytomegalovirus enhancer, an SV40 intron, the SMN coding DNA set out in (GenBank Accession Number NM_000344.2), a polyadenylation signal sequence from bovine growth hormone and another AAV2 ITR. Conservative nucleotide substitutions of SMN DNA are also contemplated (e.g., a guanine to adenine change at position 625 of GenBank Accession Number NM_000344.2). The genome lacks AAV rep and cap DNA, that is, there is no AAV rep or cap DNA between the ITRs of the genome. SMN polypeptides contemplated include, but are not limited to, the human SMN1 polypeptide set out in NCBI protein database number NP_000335.1. The rAAV9 SMN vector is described in Foust et al., Nature Biotechnology 28(3): 271-274 (2010), wherein the sequence of the vector genome insert is shown as nucleotides 980-3336 of SEQ ID NO: 1).

On bioreactor day 6, 18-24 hours post transfection, the bioreactor was drained and the DMEM recirculation media bag was replaced with 200 liters of fresh OptiMEM post transfection media. The bioreactor was re-filled with 64 liters and recirculation in the bioreactor re-started.

On day 7, 18-24 hours post the media change on day 6, the OptiMEM post transfection media in the recirculation bag (~135 liters) was replaced with a fresh bag of OptiMEM media. The bioreactor was not drained during this step. Recirculation of the media continued until harvest at day 9.

After 9 days in the bioreactor, the final pre-harvest samples were taken from the reactor and the cell lysis process was initiated. Benzonase was added to the bioreactor to a final concentration of 100 U/mL. After the Benzonase was allowed to mix in the reactor, 7.1 liters of lysis solution was added to the reactor. The lysis solution was mixed in the reactor for 2 hours prior to the first harvest step. At the end of the 2 hour lysis, the contents of the bioreactor were transferred to the harvest bag. 8.9 liters of salt sucrose solution (SSS) was added to the harvest bag and mixed for 15 minutes. The SSS solution quenched the Benzonase in the harvest media. The bioreactor was then rinsed with the bioreactor rinse buffer. For the bioreactor rinse, 64 liters of bioreactor rinse buffer was added to the bioreactor and mixed for 15 minutes. The rinse was then transferred to the common harvest collection bag. Once the rinse had been added to the collection bag, the contents were mixed for 15 minutes and the bulk harvest samples taken.

The mixed bulk harvest was filtered through the depth filter into a collection bag. Once all bulk harvest had been filtered, the depth filter was chased with 50 liters of TFF1 diafiltration buffer. The depth filter pool was mixed and sampled. The depth filter pool was then filtered through a 0.45 μm filter to further clarify the bulk harvest material. The 0.45 μm filter is then chased with 6 liters of TFF1 buffer.

For the TFF1 step, 5.0 m$^2$ of 300 kDaMW cut off regenerated cellulose membrane cassettes were flushed, sanitized with NaOH solution and equilibrated with TFF1 buffer. The concentration phase of this operation was designed to reduce the volume of the clarified harvest approximately 10×. Once the target retentate volume was reached, diafiltration operation are started. The retentate was diafiltered with 6 diavolumes of TFF1 buffer. Once 6 diavolumes of permeate total flow were achieved, the retentate was concentrated again and harvested into a collection bag. Two successive rinses of the membrane were executed to maximize the product recovery from the TFF system to produce an intermediate drug substance. The TFF1 intermediate was aliquoted into 1 or 2 liter sterile PETG bottles in a LFH hood and then frozen on dry ice or in a freezer and transferred to ~60° C. storage.

TABLE 18

Buffers used in Upstream Process

| Name | Formulation | Process Step(s) Used |
| --- | --- | --- |
| Cell Expansion Growth Media | DMEM with 10% FBS, 4.5 g/l glucose, 4 mM L-glutamine | Cell expansion, iCELLis Bioreactor pre-transfection |
| Transfection | DMEM with no FBS, no calcium, | iCELLis Bioreactor transfection |

TABLE 18-continued

Buffers used in Upstream Process

| Name | Formulation | Process Step(s) Used |
|---|---|---|
| Media | no L-glutamine and 4.5 g/L glucose | |
| Post Transfection Media | OptiMEM with 2.3 g/L glucose, 4 mM L-glutamine, and no FBS | iCELLis Bioreactor post transfection |
| Lysis Buffer | 500 mM HEPES, 10% Tween 20, 20 mM $MgCl_2$, pH 8.0 | iCELLis Bioreactor cell lysis |
| Salt Sucrose Solution (SSS) | 3700 mM NaCl, 10% Sucrose | Clarification |
| Bioreactor Rinse Buffer | 20 mM Tris, 1 mM $MgCl_2$, 500 mM NaCl, 1% Tween 20, 1% Sucrose | iCELLis bioreactor harvest |
| TFF1 Buffer | 20 mM Tris, 1 mM $MgCl_2$, 500 mM NaCl, 1% Sucrose | Clarification, TFF1 |
| TFF1 Sanitization Buffer | 0.5M NaOH | TFF1 membrane sanitization |

Example 12—Downstream Process

A downstream process was used to process the intermediate to a filtered drug substance. The downstream process steps included an acidification and clarification step (using filtration), followed by cation exchange chromatography, tangential flow filtration ("TFF2"), CsCl ultracentrifugation and a further tangential flow filtration step ("TFF3") to produce a filtered drug substance where the purified AAV particles are suspended in a pharmaceutically acceptable carrier. Specifically, the downstream process contained the following manufacturing steps subsequent to production of the TFF1 intermediate: thaw and pool TFF1 intermediate, acidification and clarification, cation exchange chromatography (CEX), tangential flow filtration (TFF2), CsCl ultracentrifugation for Full/Empty Capsid Separation, tangential flow filtration (TFF3) for Concentration/Buffer Exchange, TFF 3 pool material filtration to generate drug substance, dilution and filtration of drug substance to produce drug product, storage of the drug product and filling of drug product into vials.

The TFF1 intermediate material was thawed and gently mixed. Tween 20 was used to promote flocculation of the bulk of host cell proteins and DNA under acidic pH. The pH of the TFF1 intermediate pool containing 15% Tween 20 was lowered for CEX chromatography (pH 3.5). The precipitate formed after the pH was lowered, was then removed by filtering the solution through a depth and 0.45 µm filters.

Tween 20 (36% Tween 20 solution in 20 mM Tris, 1 mM $MgCl_2$, 500 mM NaCl, 1% Sucrose m/v, pH 8.1) was slowly added to the TFF1 Intermediate solution over 4 hours to achieve a final concentration of 20% Tween 20. After overnight incubation at Room Temperature (RT) the pH of the Tween 20 containing TFF1 Intermediate was lowered by adding approximately 4 g of 1M glycine pH 2.5 per kg of TFF1 intermediate/Tween spike pool to achieve a target pH of 3.5 ±0.1. Once the pH was within the acceptable range, the solution was passed through the Clarisolve POD depth filter in line with a 0.45 µm Opticap XL10 Duraporе filter or 0.8/0.45µ PES filter followed by a flush of the filters two times the hold-up volume of the POD filter plus one hold-up volume of the polishing filter with CEX Buffer A.

The cation exchange (CEX) capture chromatography step was used to separate the viral capsids from protein, DNA and other process impurities. This step utilized a CIMmultus S03-8000 Advanced Composite Column (Sulfonyl) (Pores 2 µm) chromatography column (8.0 L) operated using an automated process chromatography system. Buffers and solutions are described in the following table:

TABLE 19

Buffers and solutions for one CEX cycle

| Solution name | Composition | Purpose | Volume (L) for one 8 L CEX Cycle |
|---|---|---|---|
| WFI | WFI | Column flushes | 200 L |
| CEX A-Buffer | 50 mM glycine, 500 mM NaCl, 1.0% sucrose, 0.20% Poloxamer 188, pH 3.5 ± 0.1 at 20° C. | Equilibration, wash, elution | 256 L |
| CEX B-Buffer | 50 mM glycine, 2.0M NaCl, 1.0% sucrose, 0.20% Poloxamer 188, pH 3.5 ± 0.1 at 20° C. | Column equilibration and elution | 40 L |
| Monolith Cleaning Solution | 1M NaOH, 2M NaCl | Column Sanitization, CIP | 96 L |
| 1M ammonium acetate | 1M ammonium acetate | Restore column pH | 40 L |

TABLE 19-continued

Buffers and solutions for one CEX cycle

| Solution name | Composition | Purpose | Volume (L) for one 8 L CEX Cycle |
|---|---|---|---|
| pH 9.0 Neutralization buffer | 1.0M Tris pH 9.1 ± 0.1 at 20° C. | pH adjustment of CEX product | 0.5 L |
| Storage solution | 20% Ethanol in WFI | Column storage | 40 L |

The CEX column load was determined by the protein content of the clarified, acidified, TFF1 intermediate. The protein load for the CEX column was set at 70% of the maximum column capacity.

The elution peak was collected manually starting at a sharp rise in OD280. The OD280 rose when the conductivity was between 80-85 mS/cm. The approximate volume of CEX eluate (product) was ~20 liters or 2.5 CVs (column volumes). The CEX eluate was collected in two fractions. The first fraction started at the sharp rise in OD280 and was collected for 1.5 CVs. The second fraction started immediately after the first fraction and was collected for 1.0 CV. The two fractions were neutralized to pH 8.0±0.30 using pH 9.0 Neutralization Buffer.

The TFF2 step concentrated, removed protein impurities, and exchanged the buffer to an appropriate buffer for the CsCl ultracentrifugation step. A tangential flow filtration system was utilized in conjunction with 0.4 m² (two CEX cycles) or 0.2 m² (one CEX cycle) 300 k MWCO regenerated cellulose membranes.

The concentration phase of this operation reduced the volume of the CEX eluates. Once the target retentate volume was reached, diafiltration was started in discontinuous TFF mode (batch mode). The retentate was diluted 2× and diafiltered with 8 diavolumes of TFF2 NaCl diafiltration buffer and after that with 8 diavolumes of TFF2 CsCl diafiltration buffer in discontinuous TFF mode. Once CsCl diafiltration was complete, the retentate was concentrated to a prescribed volume that was dependent on the system hold-up volume. Two successive rinses of the membrane were executed to maximize the product recovery from the TFF2 system.

The retentate feed rate was set at 5 L/m²/min (500 mL/min per 0.1 m² cassette) with a 20% conversion rate to permeate (a permeate flow rate of 100 ml per 500 mL of retentate feed rate). The permeate flow rate was controlled by a clamp on the permeate tubing to maintain a permeate flow rate of 20% of retentate feed flow rate.

TABLE 20

Buffers for TFF2

| Solution Name | Composition |
|---|---|
| TFF2 NaCl Diafiltration Buffer | 20 mM Tris, 2 mM MgCl2, 150 mM NaCl, 0.2% Poloxamer 188, 1% Sucrose , pH 8.1 ± 0.1 at 20° C. |
| TFF2 CsCl Diafiltration Buffer | 20 mM Tris, 2 mM MgCl2, 3M CsCl, 0.2% Poloxamer 188, pH 8.1 ± 0.1 at 20° C. |

Ultracentrifugation may be used to remove empty capsids from full capsids by utilizing cesium chloride gradient ultracentrifugation. An automated Optima XPN 100 Ultra Centrifuge system or equivalent system equipped with Type 50.2 Ti rotor or equivalent rotor was used for CsCl ultracentrifugation step. TFF2 purified filtered material was slowly added in ultracentrifuge tubes along the inside of the tube wall without introducing bubbles into the solution. The filled tubes were sealed with handheld heat sealer and centrifuged at 302,000 g (50,000 rpm in 50.2 Ti rotor) for 17 hours at 20° C. After completion of centrifugation step, tubes were removed from the Ultra Centrifuge and placed in a biosafety cabinet. Product containing tubes were mounted on ring stands above a waste container. A Lamp was positioned directory under the tube and the empty capsids band (Band A is the highest band), the full capsid doublet bands (Bands B and C upper and lower bands of the doublet), and lowest band below the doublet was marked on the tubes. The bands B, C, and D were removed by an 18 G needle attached to 30 mL syringe inserted just below band D to middle of tube. The collected material was transferred to a sterile 1 L PETG bottle. Material from all centrifuge tubes was pooled into a sterile 1 L PETG bottle to produce the Ultracentrifuge (UC) Pool. The Buffer for the CsCl ultracentrifugation step is listed in the table below:

TABLE 21

Buffer for CsCl Ultracentrifugation

| Solution Name | Composition |
|---|---|
| TFF2 CsCl Diafiltration Buffer | 20 mM Tris, 2 mM MgCl2, 3M CsCl, 0.2% Poloxamer 188, pH 8.1 ± 0.10 |

The TFF3 step removed CsCl and concentrated the full vector using Final Formulation Buffer. A tangential flow filtration system was utilized in conjunction with two 50 cm² 300k MWCO regenerated cellulose membranes. The concentration phase of TFF3 operation was designed to reduce the concentration of residual CsCl and volume of the UC Pool. Once the target retentate volume was reached, diafiltration was started. The retentate was diafiltered with 10 diavolumes of TFF3 Buffer. Once diafiltration was complete, the concentrated retentate was transferred to a secondary conical tube through a 0.2 µm Pall Supor® EKV Sterilizing-Grade Filter (Mini Kleenpak) Filter.

A successive rinse of the membrane was executed to recover vector from the TFF3 system. TFF3 Buffer was added to the primary conical tube that previously held the TFF3 retentate. This material was recirculated through the cellulose membranes. After recirculation, the flush was transferred to the secondary conical tube through the 0.2 µm Pall Supor® EKV Sterilizing-Grade Filter (Mini Kleenpak) Filter. The TFF3 concentrate and partial pool was mixed to achieve a final vector concentration of ≥4.5×10$^{13}$ vg/mL of Drug Substance (pooled TFF3 retentate+two rinses).

A successive rinse of the membrane was executed to maximize the product recovery from the TFF3 system. TFF3 Buffer was added to the primary conical tube that previously held the TFF3 retentate and initial flush material. This material was recirculated through the cellulose membranes.

The secondary flush is transferred to a secondary conical tube through the 0.2 μm Pall Supor® EKV Sterilizing-Grade Filter (Mini Kleenpak) Filter until the determined weight was achieved in the secondary conical tube. The final concentrated solution is referred to as Drug Substance (DS).

TABLE 22

Buffers for TFF3

| Solution Name | Composition |
|---|---|
| TFF3 Buffer | 20 mM Tris, 1 mM $MgCl_2$, 200 mM NaCl, 0.001% Poloxamer 188, pH 8.0 ± 0.1 at 20° C. |

The DS was filtered with a Pall Supor® EKV Sterilizing-Grade Filter (Mini Kleenpak) into a sterile 1 L glass bottle using a sterilized single use assembly. Before filtration of the TFF3 pool, the filter was flushed by passing TFF3 Buffer through the filter using a peristaltic pump and discarding to a waste flush bag. The Drug Substance (DS) was then filtered through the flushed filter using a peristaltic pump and collected in the 1 L sterile glass bottle. Based on the targeted concentration of DS at $5 \times 10^{13}$ vg/mL, TFF3 Buffer was added to the secondary conical tube which held the DS and passed through the filter to prepare dilute drug product ("DP") to a target concentration of $3.5 \times 10^{13}$ vg/mL.

The TFF3 Buffer used in the filter flush and DS dilution to prepare the DP is comprised of the following formulation.

TABLE 23

Drug Product Unit Operation - Buffer Composition

| Solution Name | Composition |
|---|---|
| TFF3 Buffer | 20 mM Tris, 1 mM $MgCl_2$, 200 mM NaCl, 0.001% Poloxamer 188, pH 8.0 ± 0.1 |

The DP was filled into 5 mL sterile, ready to use, Crystal Zenith (CZ) vials, stoppered with sterile, ready to use, stoppers, and sealed with sterile, ready to use, seals.

Example 13—Potency Assay

The relative potency of the drug product was measured using a quantitative, in vivo assay. The assay used an established mouse model of SMA disease. Breeding pairs of the SMAΔ7 mouse strain (Jackson Laboratories, #005025) are phenotypically normal but ~25% of their offspring are homozygous for the targeted SMN gene mutation and display the SMA-like phenotype. By Day 5 they show signs of muscle weakness and in the following week, develop an abnormal gait and a tendency to fall over. Jackson Laboratories reports the mean survival for animals with the SMA-like phenotype as ~15±2 days. Pilot studies demonstrated a median survival time for untreated animals with SMA-like phenotype of 16.3 days (geometric mean; n=3 studies; 10 mice per study).

Biologically active drug product administered by intravenous (IV) infusion yields an increase in survival time that is a function of dose (vg/kg). Drug product potency was measured relative to the reference material (prior batch of vector). The titer of drug product and the reference material (vector genomes/mL; vg/mL) was determined by Droplet Digital polymerase chain reaction (ddPCR). Vector was diluted in saline to achieve each of three specified dose levels that will be administered to mice with the SMA-like phenotype.

An assay's results are considered to be acceptable if the assay passes suitability. Assay suitability consists of the following:

4. Acceptance limit for the Negative Control sample (15±2 days, Median Survival)
5. Acceptance limit for the Positive Control sample (>40 days, Median Survival)
6. Acceptance limits on the reference standard Median Survival dose-response curve A prior batch of vector (hereinafter, Prior Batch) was used in this study to determine the linear correlation between median survival (days) of SMAΔ7 mouse when dosed with drug product at five different dose levels including the 0 (zero) dose using 0.9% saline solution (untreated group).

The Δ7 mouse model was used to demonstrate efficacy of SMA therapeutics, including drug product. Untreated or saline-treated control animals provide a reliable baseline control from which product potency can be measured as an increase in median survival. Development work with drug product identified three (3) doses (excluding the vehicle treated dose) determined by Genomic Titer using Droplet Digital PCR (ddPCR) which affect survival in the mouse model with a linear correlation when administered dose (vg/kg) is log-transformed and plotted against the Median Survival (in days) of the treated SMAΔ7 neonatal mouse. See standard titers (vg/mL) in Table 26 for the low, mid, and high titer standards. In addition, the TFF Buffer (vehicle) solution is used for both the zero (0) calibration curve point as well as a Negative Control. A dose demonstrating ≥40 day survival (greater than the dose that demonstrates doubling of the median survival) was also included as a Positive Control.

TABLE 25

| Target Doses | | |
|---|---|---|
| Dose (vg/kg) | Median Survival (days) | Standards and Controls |
| Saline | 15 ± 2 | Negative Control (untreated) |
| $1.50 \times 10^{14}$ | ≥40 days Median Survival | Positive Control |
| 0 (saline) | 15 ± 2 | Standard-1 |
| $1.2 \times 10^{13}$ | 22 ± 3 | Standard-2 |
| $7.5 \times 10^{13}$ | 31 ± 3 | Standard-3 |

Dose Solution Preparations (refer to Table 26 for the dilution scheme example.

Negative Control—The 0.9% saline Solution is used as the Negative Control

Positive Control—The Test Article lot is prepared at a $1.5 \times 10^{14}$ vg/kg using saline.

Reference Standard Solutions—The Reference Standard lot is prepared in three concentrations delineated in Table 25 using the saline Solution.

TABLE 26

Reference Standard and Test Article Dilution Scheme (Example)

| Dose (vg/kg) | Reference Standard/Test Article ddPCR Titer (vg/mL) | Conversion to vg/μL | Reference Standard/Test Article volume to use (μL) | Saline Solution (μL) | Total Dose Volume (μL) |
|---|---|---|---|---|---|
| $1.2 \times 10^{13}$ | $5.0 \times 10^{13}$ | $5.0 \times 10^{10}$ | 2.6 | 47.4 | 50.0 |

Test Article Preparation—The test article was diluted using the saline Solution. Dilutions were calculated to generate the test doses (vg/kg) delineated in Table 26 per mouse in a total final volume of 50 μl. Dilutions were made for 10 mice at the time with one extra volume as a Positive Control targeted to increase minimum lifespan of treated mice to ≥40 days of Median Survival (days).

Acceptance limits on control samples

Negative Control (untreated mice)—The assay acceptance limit for the Negative Control group was that the SMAΔ7 mice meet the median survival of 15±2 days. In addition, any mouse expiring in ≤10 days will be excluded from the analysis. If more than 7 mice are used in a group, a maximum of 2 mice may be excluded for expiring at <=10 days.

Positive Control (group treated at the target clinical dose)—The assay acceptance limit for the Positive Control group was that at a minimum lifespan of treated mice to be to ≥40 days Median Survival. In addition, any mouse expiring in ≤10 days will be excluded from the analysis. If more than 7 mice are used in a group, a maximum of 2 mice may be excluded for expiring at <=10 days.

Acceptance Limits on the Reference Standard Dose Response Curve

Assay suitability criteria will be determined for the reference standard Linear dose response curve plotting Median Survival (days) against the administered dose (vg/mL).

Y-Intercept/Slope Ratio—A linear regression curve of the Median Survival (days) versus the administered Dose (vg/kg) for the Reference Standard and the Test Article is determined. The ratio of y-Intercept to the slope for each linear regression is calculated.

Reporting Results

Qualitative Reporting of Relative Potency Results—The Assay Suitability criteria is evaluated for each assay prior to determination of a single point Median Survival (days) read at ≥40 days for the Positive Control material. If the Median Survival of the Positive Control group is ≥40 days, the Test Article may be dispositioned if the below criteria is met.

Quantitative Reporting of Relative Potency Results—The Assay Suitability criteria is evaluated for each assay prior to quantitative determination of Relative Potency for the Test Article. Relative potency for the Test Article may be reported once the Positive control reaches ≥40 days and the Median Survival of 31±3 days for the mouse group representing the upper standard dose of $7.5 \times 10^{13}$ vg/kg is reached. The Percent Relative Potency (% RP) for a Test Article will be calculated using the y-intercept and slope of the linear regression of the Median Survival (days) dose-response as follows:

% RP=100%*[(Test Article y-intercept/slope)÷(Reference Standard y-intercept/slope)]

Example 14—Single-Dose Gene-Replacement Therapy for Spinal Muscular Atrophy: A Dose Study Spinal muscular atrophy (SMA) is a severe childhood monogenic disease resulting from loss or dysfunction of the gene encoding survival motor neuron 1 (SMN1). The incidence of this disease is approximately 1 in 10,000 live births, with a carrier frequency of 1 in 54. SMA is characterized by the degeneration and loss of lower motor neurons, which leads to muscle atrophy. The disease is divided into four subtypes (1 through 4) on the basis of the age at onset and milestone achievement. SMA type 1 (SMA1) is the most severe form and most common genetic cause of death among infants. There are two forms of SMN; SMN1 is the primary gene responsible for functional production of SMN protein. SMN2 preferentially excludes exon 7 during splicing and, as a result, produces only a small fraction of functional SMN protein as compared with SMN1. Therefore, the SMN2 copy number modifies the disease phenotype, and the presence of two copies of SMN2 is associated with SMA1. Infants with SMN1 biallelic deletions and two copies of SMN2 have a 97% risk of SMA1.

Recent studies of the natural history of SMA1 (historical cohort) showed that the median age at symptom onset among infants with the disease was 1.2 months (range, 0 to 4 months), and the disease was characterized by hypotonia, severe weakness from early infancy, and failure to sit without support. In infants with SMA1 who have two copies of SMN2, the median age at death or the need for noninvasive ventilation for at least 16 hours per day for at least 14 consecutive days (considered equivalent to permanent ventilation) was 10.5 months. In one cohort of affected children, only 25% survived without permanent ventilatory support at 13.6 months, and 8% survived without this support by 20 months. Another prospective, multicenter historical study sponsored by the National Institutes of Health (NeuroNEXT) involving patients with two copies of SMN2 showed a median survival free of tracheostomy of 8 months (95% confidence interval, 6 to 17). All patients with SMA1 have a precipitous decline in respiratory and swallowing functions after birth and ultimately require mechanical nutritional support (through a nasogastric or gastrostomy tube) to maintain adequate nutrition and reduce the respiratory risks associated with aspiration. For patients with SMA1 in whom the onset of symptoms occurs by 3 months of age, most patients require feeding support by 12 months of age.

Patients with SMA1 also do not achieve major milestones in motor function and have a decline in function, as measured on the CHOP INTEND (Children's Hospital of Philadelphia Infant Test of Neuromuscular Disorders) scale, which ranges from 0 to 64, with higher scores indicating better motor function, a tool that is sensitive to minor changes in motor function, such as antigravity movements of limbs. In a historical analysis of 34 patients with SMA1, all but 1 of the patients did not reach a score of at least 40 after 6 months of age. In the NeuroNEXT cohort, CHOP INTEND scores decreased by a mean of 10.7 points from 6 months to 12 months of age.

Therapeutic strategies to increase levels of SMN protein in motor neurons have focused on enhancing the effectiveness of SMN2. One approach has been central nervous system delivery of nusinersen (Ions Pharmaceuticals/Biogen), an antisense oligonucleotide that was developed to inhibit exon 7 splicing in SMN2. This drug has been shown to improve weakness in the murine model of severe SMA and to increase the median life span of affected mice from 16 days to 25 days. In December 2016, nusinersen was approved by the Food and Drug Administration for the treatment of SMA. This drug is administered by means of repeated intrathecal injections after four loading doses within the first 2 months of life.

A potential alternative treatment for SMA1 is gene therapy, given as a one-time intravenous administration that delivers a copy of SMN in a self-complementary adeno-associated viral serotype 9 (scAAV9). (The coding region of this recombinant virus forms an intramolecular double-stranded DNA [or self-complementary] template.) This approach has induced SMN expression in motor neurons and peripheral tissues, which has countered the effects of SMA in a murine model and extended the average survival in this model from 15 days to 28.5 days with a low dose ($6.7 \times 10^{13}$ vg per kilogram of body weight) and to more than 250 days with higher doses of the vector ($2.0 \times 10^{14}$ and $3.3 \times 10^{14}$ vg per kilogram).

In addition to crossing the blood-brain barrier and targeting central nervous system neurons at all regions of the spinal cord, the systemic administration of AAV9-mediated gene therapy may be advantageous, given that SMN protein is ubiquitously expressed and SMA1 affects multiple systems (e.g., autonomic and enteric nervous systems, cardiovascular system, and pancreas), along with many cell types (e.g., heart, pancreas, and skeletal muscle). The self-complementary feature of the vector combined with a hybrid cytomegalovirus enhancer-chicken betaactin promoter enables rapid and sustained expression of SMN. In April 2014, we initiated a study of gene-replacement therapy involving infants with SMA1 who received a one-time dose of scAAV9 with delivery of the human survival motor neuron gene (hSMN), under control of the chicken beta-actin promoter (scAAV9.CB.hSMN) (AVXS-101).

Methods

Patient and Study Procedures: For the purposes of the study, all the patients had a genetically confirmed diagnosis of SMA1, homozygous SMN1 exon 7 deletions, and two copies of SMN2. Patients with the c.859G→C disease modifier in exon 7 of SMN2 were excluded. Patients who were selected had showed onset of disease from birth up to 6 months of age, characterized by hypotonia as determined by clinical evaluation accompanied by a delay in motor skills, poor head control, round shoulder posture and hypermobility of joints. Patients with active viral infections (including HIV or serology positive for hepatitis B or C) or concomitant illness that created unnecessary risks for gene transfer were excluded from the study. Patients that needed invasive ventilatory support (tracheotomy with positive pressure) or pulse oximetry <95% saturation at screening visit were also excluded.

Patients were enrolled in two cohorts, according to the dose of gene therapy that was administered. Patients in cohort 1 received a low dose ($6.7 \times 10^{13}$ vg per kilogram) and were enrolled over the course of five months; those in cohort 2 received a high dose ($2.0 \times 10^{14}$ vg per kilogram) and were enrolled over the course of one year. At day 30 post dosing, the IFN-γ ELISpot assay on Patient 1 in cohort 1 detected a T-cell response, and showed a sudden spike in spot forming cells (SFCs) per $10^6$ peripheral blood mononuclear cells (PBMCs) that was >50 directed against the AAV9 capsid (normal, <50 SFCs per $10^6$ PBMCs). Prednisolone was started at 2 mg/kg and was maintained for 35 days until T-cell response and serum transaminases were reduced. As a result, the experimental protocol was amended, and Patients 2 through 15 received oral prednisolone at a dose of 1 mg per kilogram per day for approximately 30 days, starting 24 hours before the administration of gene vector. Treatment was continued with prednisolone maintained until AST and ALT enzymes fell below the level of 120 IU/L and T-cell response fell below 100 SFCs per $10^6$ PBMCs, at which point the prednisolone would be tapered off based on clinical judgment.

The vector was delivered in normal saline (approximately 10 to 20 ml per kilogram) that was infused intravenously during a period of approximately 60 minutes. At the time of enrollment, some patients required enteral feeding by means of a gastrostomy or nasogastric tube, the choice of which was based on the preference of the parents or the primary physician. Once enrolled in the study, all the patients who required nutritional support underwent placement of a gastrostomy tube, and the tubes were not removed during the study.

Outcomes: The primary outcome was the determination of safety on the basis of any treatment-related adverse events of grade 3 or higher. The secondary outcome was the time until death or the need for permanent ventilatory assistance. The latter was defined as at least 16 hours of respiratory assistance per day continuously for at least 14 days in the absence of an acute, reversible illness or a perioperative state. Exploratory outcomes included motor-milestone achievements (particularly, sitting unassisted) and CHOP INTEND scores.

The maintenance of scores of more than 40 points has been considered to be clinically meaningful in SMA in the application of the CHOP INTEND scale. Sitting unassisted was evaluated and classified according to the following criteria: sitting unassisted for at least 5 seconds, according to item 22 of the Bayley Scales of Infant and Toddler Development gross motor subtest ("sitting unassisted"); sitting unassisted for at least 10 seconds, according to the World Health Organization (WHO) criteria ("sitting unassisted per WHO criteria"); and sitting unassisted for at least 30 seconds, according to item 26 of the Bayley Scales mentioned above ("independent functional sitting"). Major motor milestones were confirmed by means of an examination of video recordings of the patients by an independent reviewer by Ability Captured Through Interactive Video Evaluation-mini (ACTIVE-mini). Compound muscle action potentials (CMAP) were recorded from surface electrodes at baseline and every 6 months after infusion. Pathological status of muscles was quantified by Electrical Impedance Myography (EIM).

Statistical Analysis: Safety analyses were performed in all the patients, who were also included in the primary analysis of survival (as defined above and in the protocol) and in analyses of changes on the CHOP INTEND scale from baseline to 1 month and 3 months. Such changes from baseline to each study visit were analyzed with the use of a mixed-effects model for repeated measurements. The mixed model included the fixed effects of cohort and visit and a covariate of baseline score. Milestone achievements and nutritional and ventilatory support were analyzed in cohort 2. Statistical analyses were performed with the use of SAS software, version 9.4. All comparisons with historical cohorts were solely descriptive.

Results

Patients: Of the 16 patients who were screened, 1 was excluded because of persistently elevated anti-AAV9 antibody titers (>1:50). Of the 15 patients who were included in the study, 3 were enrolled in the low-dose cohort 1 and 12 were enrolled in the high-dose cohort 2. The mean age of patients at the time of treatment was 6.3 months (range, 5.9 to 7.2) in cohort 1 and 3.4 months (range, 0.9 to 7.9) in cohort 2 (Table 28).

TABLE 28

Demographic and Clinical Characteristics of the 15 Patients

| Characteristic | Cohort 1 (N = 3) | Cohort 2 (N = 12) |
|---|---|---|
| Mean age (range) - mo | 6.3 (5.9-7.2) | 3.4 (0.9-7.9) |
| Mean weight (range) - kg | 6.6 (6.0-7.1) | 5.7 (3.6-8.4) |
| Sex - no. (%) | | |
| Male | 1 (33) | 5 (42) |
| Female | 2 (67) | 7 (58) |
| Race - no. (%) | | |
| White | 3 (100) | 5 (42) |
| Other | 0 | 1 (8) |
| Mean age at symptom onset (range) - mo | 1.7 (1.0-3.0) | 1.4 (0-3.0) |
| Mean age at genetic diagnosis (range) - days | 33 (4-85) | 60 (0-136) |
| Mean score on CHOP INTEND scale (range) | 16 (2-27) | 28 (12-50) |
| Patients with clinical support - no. (%) | | |
| Nutritional | 3 (100) | 5 (42) |
| Ventilatory | 3 (100) | 2 (17) |

Survival and Permanent Ventilation: As of the end of the study, all the patients had reached an age of at least 20 months and did not require permanent mechanical ventilation; the median age at their last pulmonary assessment was 30.8 months in cohort 1 and 25.7 months in cohort 2. In contrast, only 8% of the patients in a historical cohort did not require permanent mechanical ventilation. At 29 months of age, one patient in cohort 1 required permanent ventilation because of hypersalivation. After salivary gland ligation, the requirement for the use of noninvasive ventilation was reduced by 25% to 15 hours per day.

Motor Function Assessments: All the patients in cohorts 1 and 2 had increased scores from baseline on the CHOP INTEND scale and maintained these changes during the study.

Patients in cohort 2 had mean increases of 9.8 points at 1 month and 15.4 points at 3 months ($P<0.001$ for both comparisons); 11 patients attained and sustained scores of more than 40 points. At the study cutoff on Aug. 7, 2017, patients in cohort 1 had a mean increase of 7.7 points from a mean baseline of 16.3 points, and those in cohort 2 had a mean increase of 24.6 points from a mean baseline of 28.2 points.

Motor Milestones in Cohort 2: A total of 11 of 12 patients in cohort 2 were able to sit unassisted for at least 5 seconds, 10 for at least 10 seconds, and 9 for at least 30 seconds (Table 31). A total of 11 achieved head control, 9 could roll over, and 2 were able to crawl, pull to stand, stand independently, and walk independently. Eleven patients attained the ability to speak. No patients in the historical cohorts had achieved any of these motor milestones and rarely had achieved the ability to speak.

TABLE 29

Event-free Survival and Motor and Other Milestones among the 12 Patients of Cohort 2.

| Variable | Age at Study Entry mo | Event-free Survival | Brings Hand to Mouth | Controls Head | Rolls Over | Sits with Assistance | Sits Unassisted ≥5 sec | ≥10 sec | ≥30 sec | Speaks | Swallows | No NIV Use | No Nutritional Support |
|---|---|---|---|---|---|---|---|---|---|---|---|---|---|
| Patient no. | | | | | | | | | | | | | |
| 4 | 5.6 | 31.1 | + | + | + | + | + | | | + | + | | |
| 5 | 4.2 | 28.5 | + | + | + | + | + | + | + | + | + | + | + |
| 6 | 1.9 | 26.1 | + | + | + | + | + | + | + | + | + | + | + |
| 7 | 3.6 | 28.1 | + | + | + | + | + | + | | + | + | + | |
| 8 | 7.9 | 32.4 | + | | | | | | | | | | |
| 9 | 4.9 | 28.9 | + | + | | + | + | + | + | + | + | + | + |
| 10 | 0.9 | 25.3 | + | + | + | + | + | + | + | + | + | + | + |
| 11 | 2.3 | 23.8 | + | + | + | + | + | + | + | + | + | | |
| 12 | 2.6 | 23.9 | + | + | + | + | + | + | + | + | + | + | + |
| 13 | 0.9 | 22.1 | + | + | | + | + | + | + | + | + | | |
| 14 | 4.1 | 22.0 | + | + | + | + | + | + | + | + | + | + | + |
| 15 | 2.1 | 20.6 | + | + | | + | + | + | + | + | + | | |

TABLE 29-continued

Event-free Survival and Motor and Other Milestones among the 12 Patients of Cohort 2.

| Variable | Age at Study Entry mo | Event-free Survival | Motor Milestones | | | | | | | Other Achievements | | | |
|---|---|---|---|---|---|---|---|---|---|---|---|---|---|
| | | | Brings Hand to Mouth | Controls Head | Rolls Over | Sits with Assistance | Sits Unassisted ≥5 sec | ≥10 sec | ≥30 sec | Speaks | Swallows | No NIV Use | No Nutritional Support |
| | | | | | Patients with outcome (%) | | | | | | | | |
| This Study | | 100 | 100 | 92 | 75 | 92 | 92 | 83 | 75 | 92 | 92 | 58 | 50 |
| Naturel History Studies | | 8 by 20 mo | NA | 0 | 0 | 0 | 0 | 0 | 0 | NA | NA | NA | 8 by 20 mo |

Pulmonary and Nutritional Status in Cohort 2: Among the 12 patients in cohort 2, 10 did not require noninvasive ventilation at baseline as compared with 7 who were independent of ventilatory assistance at the last follow-up visit (Table 29). At baseline, 7 patients did not require enteral feeding, including 1 who later required placement of a gastrostomy tube after gene-replacement therapy, possibly in association with scoliosis surgery. Of the 5 patients who had received enteral feeding before gene-replacement therapy, at the last follow-up, 11 of the 12 patients had achieved or retained the ability to swallow independently and 4 were able to feed orally.

Safety: As of the end of the study, a total of 56 serious adverse events were observed in 13 patients in the two cohorts. Of these events, investigators determined that 2 events were treatment-related grade 4 events on the basis of laboratory values, according to Common Terminology Criteria for Adverse Events (Table 30). Patient 1 in cohort 1 had elevations in serum aminotransferase levels (31 times the upper limit of the normal range for alanine aminotransferase (ALT) and 14 times the upper limit for aspartate aminotransferase (AST)) without other liver-function abnormalities (i.e., total and indirect bilirubin and alkaline phosphatase) and without clinical manifestations. As described above, these elevations were attenuated by prednisolone treatment, which was subsequently administered in the remaining patients. One patient in cohort 2 required additional prednisolone to attenuate elevated serum ALT and AST levels (35 times the upper limit of the normal range for ALT and 37 times for AST). Of the 241 nonserious adverse events, 3 were deemed to be treatment related and consisted of asymptomatic elevations in serum aminotransferase levels in 2 patients (ALT and AST, both less than 10 times the upper limit of the normal range), which were resolved without additional prednisolone treatment (Table 0. There were no other abnormalities on liver-function testing. Of the 15 patients, 14 had respiratory illnesses, which in children with SMA1 frequently result in death or the need for tracheostomy.

TABLE 30

Adverse Events.

| | Cohort 1 (N = 3) | | Cohort 2 (N = 12) | | All Patients (N = 15) | |
|---|---|---|---|---|---|---|
| Event | Events no. | Patients no. (%) | Events no. | Patients no. (%) | Events no. | Patients no. (%) |
| Any adverse event | 44 | 3 (100) | 253 | 12 (100) | 297 | 15 (100) |
| Any serious adverse event | 7 | 3 (100) | 49 | 10 (83) | 56 | 13 (87) |
| Adverse event associated with treatment | 1 | 1 (33) | 4 | 3 (25) | 5 | 4 (27) |
| Common adverse event | | | | | | |
| Upper respiratory tract infection | 3 | 1 (33) | 26 | 10 (83) | 29 | 11 (73) |
| Vomitting | 0 | 0 | 11 | 8 (67) | 11 | 8 (53) |
| Constipation | 4 | 4 (33) | 9 | 7 (58) | 10 | 8 (53) |
| Pyrexia | 1 | 1 (33) | 10 | 6 (50) | 11 | 7 (47) |
| Nasal congestion | 0 | 0 | 8 | 6 (50) | 8 | 6 (40) |
| Gastroesophageal reflux | 1 | 1 (33) | 6 | 5 (42) | 7 | 6 (40) |
| Enterovirus infection | 1 | 1 (33) | 7 | 4 (33) | 8 | 5 (33) |
| Pneumonia | 0 | 0 | 11 | 5 (42) | 9 | 5 (33) |
| Rhinovirus infection | 1 | 1 (33) | 10 | 4 (33) | 11 | 5 (33) |

TABLE 30-continued

Adverse Events.

| Event | Cohort 1 (N = 3) | | Cohort 2 (N = 12) | | All Patients (N = 15 | |
|---|---|---|---|---|---|---|
| | Events no. | Patients no. (%) | Events no. | Patients no. (%) | Events no. | Patients no. (%) |
| Cough | 0 | 0 | 9 | 5 (42) | 9 | 5 (33) |
| Otitis media | 6 | 2 (67) | 3 | 2 (17) | 9 | 4 (27) |
| Elevated aminotransferase level | 1 | 1 (33) | 3 | 3 (25) | 4 | 4 (27) |
| Respiratory failure | 1 | 1 (33) | 5 | 3 (25) | 6 | 4 (27) |
| Parainfluenza virus infection | 1 | 1 (33) | 4 | 3 (25) | 5 | 4 (27) |
| Rash | 0 | 0 | 5 | 4 (33) | 5 | 4 (27) |
| Atelectasis | 0 | 0 | 4 | 4 (33) | 4 | 4 (27) |
| Viral gastroenteritis | 0 | 0 | 4 | 4 (33) | 4 | 4 (27) |
| Rhinorrhea | 0 | 0 | 4 | 3 (25) | 4 | 3 (20) |
| Bronchiolitis | 0 | 0 | 3 | 3 (25) | 3 | 3 (20) |
| Diarrhea | 0 | 0 | 3 | 3 (25) | 3 | 3 (20) |
| Ear Infection | 1 | 1 (33) | 2 | 2 (17) | 3 | 3 (20) |
| Injury from fall | 0 | 0 | 3 | 3 (25) | 3 | 3 (20) |
| Human rhinovirus | 0 | 0 | 3 | 3 (25) | 3 | 3 (20) |
| Streptococcal pharyngitis | 1 | 1 (33) | 2 | 2 (17) | 3 | 3 (20) |
| Respiratory syncytial virus | | | | | | |
| Pneumonia | 1 | 1 (33) | 2 | 2 (17) | 3 | 3 (20) |
| Bronchiolitis | 1 | 1 (33) | 2 | 2 (17) | 3 | 3 (20) |
| Viral upper respiratory tract infection | 0 | 0 | 3 | 3 (25) | 3 | 3 (20) |

A single intravenous infusion of adeno-associated viral vector containing DNA coding for SMN in patients with SMA1 resulted in longer survival than in historical cohorts with this disease. All 15 patients surpassed the previously reported median age of survival without permanent ventilation of 10.5 months for patients with SMA1 with two SMN2 copies. All the patients also surpassed the benchmark of 20 months, at which time only 8% of the patients with this disease typically survive without permanent ventilation.4 Of the 12 patients in cohort 2, all but 1 achieved motor-function milestones that have not been reported in historical cohorts. The attained motor function was clinically meaningful, as reflected by feeding (hand to mouth), sitting, and talking. The majority of the patients who did not require supportive care at enrollment were free of nutritional support (6 of 7 patients) and ventilatory support (7 of 10 patients) at the last follow-up visit. In the two cohorts, the patients had increases in the score on the CHOP INTEND scale from baseline. Within the first month in cohort 2, the mean increase was 9.8 points, in contrast to a decline of a mean of more than 10 points between 6 and 12 months of age in the historical cohort in the NeuroNEXT study.

Preclinical studies of SMN gene-replacement therapy in the SMNΔ7 mouse model showed improvements in survival and motor function with early treatment, presumably at a time when motor neurons are still intact. The clinical findings in our study of early treatment reflected the direction of those in the preclinical studies. Two patients were able to crawl, stand, and walk without support after early treatment. Both of these patients had a family history of SMA, which probably contributed to the early diagnosis. Although all the patients in the two cohorts in our study have continued to have improvements in motor function, the preclinical and clinical data suggest a benefit for early treatment and newborn screening for SMA.

Serious adverse events caused by AAV gene replacement therapy were limited to elevated serum aminotransferase levels without other liver enzyme abnormalities approximately 3 weeks after treatment in two patients; two other patients had elevations that did not reach the cutoff for the definition of serious adverse events (i.e., >10 times the normal range). Elevations in liver enzymes were attenuated by prednisolone treatment. One patient did not pass screening owing to the presence of anti-AAV9 antibody, which is consistent with population studies that suggest a low rate of anti-AAV9 seropositivity among children and young adults and increasing rates of anti-AAV9 seropositivity among persons older than 40 years of age. However, the presence of antibodies to the virus may be a limitation of AAV gene-replacement therapy.

This study used a single-group design with a historical cohort as a control, which is one of a limited number of options when the natural history of a disease is well characterized and lethal. In order to enroll a homogeneous sample that was similar to those in published historical studies, we restricted enrollment to include only symptomatic patients with SMA1 who had biallelic SMN1 mutations and two SMN2 copies and did not enroll patients with the c.859 G→C genetic modifier in exon 7 of SMN2, since this genetic modifier predicts a milder phenotype of the disease. However, this gene replacement therapy need not be limited to symptomatic patients, or patients with a specific genomic subtype.

In conclusion, a one-time intravenous infusion of a high dose of adeno-associated viral vector containing DNA coding for SMN in patients with SMA1 resulted in extended survival, improved motor function, and increased scores on the CHOP INTEND scale to levels that had not previously been observed in this disease. Such improvements resulted in a lower percentage of patients who needed supportive care than those in historical studies. In follow-ups of up to 2 years, no waning of effect or clinical regression in motor function had been reported. Several patients had transient and asymptomatic elevations in aminotransferase levels. Further studies are necessary to assess the long-term safety and durability of gene-replacement therapy in patients with SMA1.

Example 15—Pharmacokinetics of scAAV9.CB.hSMN

Conventional clinical pharmacokinetic studies are not applicable to gene replacement therapy products. However, scAAV9.CB.hSMN vector shedding studies, which assess the amount of vector eliminated from the body through fluids and waste, are a measure that may be used in lieu of conventional pharmacokinetic studies for gene replacement therapies.

Vector shedding after infusion with scAAV9.CB.hSMN was investigated at multiple time points during the clinical study. Samples of saliva, urine and stool were collected weekly through day 30 and then monthly through Month 12 and every 3 months thereafter. Samples from 5 patients were used for scAAV9.CB.hSMN vector shedding analysis by droplet digital polymerase chain reaction through the Month 18 visit. All 5 patients analyzed for scAAV9.CB.hSMN vector shedding were dosed with the therapeutic dose of $1.1 \times 10^{14}$ vg/kg.

scAAV9.CB.hSMN was detectable in shed samples post-infusion. scAAV9.CB.hSMN concentrations in urine and saliva were 0.1% to 0.01% of initial concentration in the body at day 1 post-infusion, after which concentrations fell below the limit of quantitation. In stool, levels 10% to 30% of the initial concentration in the body were detectable at day 1 post-infusion. One patient showed a peak concentration in stool at day 14 post-infusion of 280% of initial concentration in body. In contrast, 3 patients for whom data were available showed a concentration of <1% of initial concentration in the body at day 14 post-infusion, with concentrations declining approximately 4 logs (10,000-fold) over 30 days post-infusion. Overall, scAAV9.CB.hSMN was primarily cleared from the body in stool and by day 60 post-infusion was below the limit of quantitation in stool.

Example 16—Non-clinical Toxicology Tests

Animal Pharmacology: Following infusion of scAAV9.CB.hSMN vector in a delta 7 SMA mouse model of disease (SMN Δ7 mice), body weight increased, righting behavior improved, survival was significantly extended in a dose-dependent manner and SMA-related cardiac deficits returned toward normal compared to untreated SMN Δ7 mice.

Animal Toxicology: Following intravenous infusion in the mouse, vector and transgene were widely distributed with the highest expression generally observed in heart and liver, and substantial expression in the brain and spinal cord. In pivotal Good Laboratory Practice (GLP) compliant 3-month mouse toxicology studies, the main target organs of toxicity were the heart and liver. scAAV9.CB.hSMN vector-related findings in the ventricles of the heart were comprised of dose-related inflammation, edema and fibrosis, and in the atrium, inflammation and thrombosis. Liver findings were comprised on hepatocellular hypertrophy, Kupffer cell activation, and scattered hepatocellular necrosis. A No Adverse Effect Level (NoAEL) was not identified for scAAV9.CB.hSMN vector-related heart and liver findings in the mouse, and the Maximum Tolerated Dose was defined as $1.5 \times 10^{14}$ vg/kg, providing a safety margin of approximately 1.4-fold relative to the recommended therapeutic dose of $1.1 \times 10^{14}$ vg/kg. The translatability of the observed findings in mice to primates is not known at this time.

Example 17—Spinal Muscular Atrophy in Pediatric Patients

This trial was a Phase 1 study evaluating safety and efficacy of scAAV9.CB.hSMN vector in SMA Type 1 patients genetically tested to confirm bi-allelic SMN1 deletions, 2 copies of survival motor neuron 2 (SMN2), negative findings for the c.859G→C modification in exon 7 and with the onset of clinical symptoms before 6 months of age. scAAV9.CB.hSMN vector was delivered intravenously during a single-dose infusion in patients 0.9 to 7.9 months of age. Two cohorts were dosed: Cohort 1 (n=3) received the low dose used in this study and Cohort 2 (n=12) received the high dose (therapeutic dose: $1.1 \times 10^{14}$ vg/kg) used in this study. The reported study outcomes reflect Cohort 2 and includes follow-up of all patients out to 24 months following scAAV9.CB.hSMN vector infusion.

Mortality and Event-Free Survival

Survival and time-to-event analyses support the efficacy of scAAV9.CB.hSMN vector. In Cohort 2, all 12 patients (100%) were over 24 months of age and event-free, as opposed to only 8% of patients in a natural history study. This indicates a significant and clinically meaningful increase in overall survival for patients infused with scAAV9.CB.hSMN vector when compared to untreated patients. At 2 years following infusion, no patient deaths were reported.

Development Motor Milestones

Development motor milestones were examined; assessments for all 15 patients were video-recorded to allow confirmation of the achievement of developmental motor milestones. Patients in Cohort 2 consistently achieved and maintained key developmental motor milestones. At 24 months of follow-up post-dose, 11 patients (91.7%) were able to hold their head erect for ≥3 seconds and sit without support for ≥5 seconds, 10 patients (83.3%) were able to sit without support for ≥10 seconds, 9 patients (75.0%) were able to sit without support for ≥30 seconds and 2 patients each (16.7%) were able to stand alone, walk with assistance and walk alone. Cohort 2 patients who are currently enrolled in an ongoing observational long-term follow-up of this study have maintained their developmental motor milestones, with some achieving additional motor milestones.

TABLE 31

Patients Who Developed Significant Motor Function Milestones Based on Independent Central Review at 24 Months of Follow-up Post-Dose (Full Analysis Set)

| | scAAV9.CB.hSMN vector Cohort 2 (N = 12) n (%) |
|---|---|
| Rolling (back to side from both sides) | 9 (75.0) |
| Hold head erect ≥3 seconds, unsupported | 11 (91.7) |
| Sits with support, non-independent sitting | 11 (91.7) |

TABLE 31-continued

Patients Who Developed Significant Motor Function Milestones
Based on Independent Central Review at 24 Months of
Follow-up Post-Dose (Full Analysis Set)

| | scAAV9.CB.hSMN vector Cohort 2 (N = 12) n (%) |
|---|---|
| Sits without support ≥5 seconds | 11 (91.7) |
| Sits without support ≥10 seconds | 10 (83.3) |
| Sits without support ≥30 seconds | 9 (75.0) |
| Stands with assistance | 2 (16.7) |
| Stands alone | 2 (16.7) |
| Walks with assistance | 2 (16.7) |
| Walks alone | 2 (16.7) |

Pulmonary

Of the 10 patients in Cohort 2 that were not using non-invasive ventilation (NIV) at baseline, 7 were free of daily NIV use at 24 months of follow-up. Nearly all patients experienced common childhood respiratory illnesses that, in children with SMA Type 1, typically result in tracheostomy or death. All patients survived respiratory hospitalizations without tracheostomy or the need for permanent ventilation.

Nutritional

Nutritional gains were also observed. In Cohort 2, seven patients did not receive enteral feeding prior to gene replacement therapy. One (1) of these 7 patients had nutritional support to assist wound healing following a difficult recovery from scoliosis surgery but was also feeding orally. Four (4) of the 5 patients in Cohort 2 who received enteral feeding prior to gene replacement therapy were able to feed orally at end of study; thus, a total of 11 of the 12 patients in Cohort 2 were able to feed orally, 6 exclusively.

Motor Function (CHOP-INTEND)

Patients receiving the therapeutic dose achieved statistically significant motor function improvements by Month 1 and Month 3; Children's Hospital of Philadelphia Infant Test of Neuromuscular Disorders (CHOP-INTEND) mean increases from baseline were 9.8 points (n=12, P<0.001) and 15.4 points (n=12, P<0.001), respectively.

Motor function improvements were sustained over time in patients infused with scAAV9.CB.hSMN vector. Eleven of twelve (91.7%) Cohort 2 patients achieved a ≥50 CHOP-INTEND score at 24 months. Early intervention and dose appear to positively affect the response. In general clinical practice, untreated SMA Type 1 children 6 months of age or older do not surpass a score of 40 points on the CHOP-INTEND. Furthermore, an average decline of 10.7 points between the ages of 6 and 12 months were reported amongst untreated infants followed as part of a prospective natural history.

Example 18—Measurement of Residual Host Cell DNA in AAV9 Viral Vectors using qPCR Method This method was used for quantification of residual hc DNA in AAV drug substance, e.g., AVXS-101, and in-process samples by qPCR. Up to six samples were tested per plate. A qPCR assay was performed using a TaqMan probe. The TaqMan probe has a fluorogenic reporter dye bound to the 5'-end and a non-fluorescent quencher bound to the 3'-end. While the probe is intact, the proximity of the quencher to the reporter dye greatly reduces the fluorescence emitted by the reporter dye. Cleavage of the probe separates the reporter dye and quencher, increasing the reporter fluorescence.

Flanking forward and reverse primers, designed to bind to a repetitive sequence within the human genome, were added to the reaction mixture and annealed to the target sequence present in the sample and standards. The TaqMan fluorogenic probe annealed between primer sites. Successive cycles of template denaturation, primer annealing and product extension amplified the target sequence. During the extension step of the amplification cycle, the exonuclease activity of Taq DNA polymerase released the reporter dye from the probe, freeing the dye from the quencher, resulting in a fluorescence emission proportional to the amount of template.

The fluorescence of each well of a 96-well plate was measured by a qPCR instrument. Through additional PCR cycles, increasing amounts of the target sequence were made, and the result is that more reporter dye was released from the probe and higher fluorescence in each successive PCR cycle. The number of amplification cycles required for the fluorescent signal to reach a pre-determined threshold value is measured. This cycle is referred to as the threshold cycle or CT value. The greater the starting concentration of DNA in the sample or standard well, the fewer the number of PCR cycles required to reach the threshold fluorescence level, and the lower the CT value. The standard curve is determined by plotting log 10(DNA concentration) versus the CT value measured for each standard point. The CT value is used to determine the amount of DNA present in the sample by using the individual CT value for the sample and solving for the DNA value.

Samples were first prepared using a Wako DNA Extractor Kit (Wako, 295-50201). Briefly, the samples for testing were mixed well and diluted 1000-fold. The diluted samples were split into four tubes (500 µL each) and 50 µL of water was added to two of the tubes (unspiked replicates) while 50 µL of 30,000 pg/mL DNA standard was added to the other two tubes (spiked control). Protein solubilization was performed by adding 20 µL of Sodium N-Lauroyl Sarcosinate solution to each tube, vortexing for 5 seconds then centrifuging briefly. NaI solution containing glycogen and Pellet Paint (Novagen, 70748) was prepared such that they were in a ratio of 2000:5:4 of NaI:Glycogen:Pellet Paint. 500 µL of the NaI mixture was added to each tube and incubated at 53° C.±1° C. for 15 minutes. The tubes were removed from heat, mixed with 900 µL of isopropanol and incubated at room temperature for 15 minutes. The tubes were then centrifuged at 10,000 g for 15 min at 18° C. and the supernatant decanted. The remaining pellet was washed with 800 µL of Wash Solution A, spun and repelleted two times. Finally, the pellet was washed with 1500 µL of chilled Isopropanol Wash Solution containing glycogen, spun and repelleted. The final pelleted was resuspended in 500 µL nuclease-free water.

The qPCR was performed using a resDNA SEQ Human Quantitative Kit (Applied Biosystems, A26366). A Reaction Mix was prepared by combining 2× Environmental Master Mix, 10× Human DNA Assay Mix and Negative control as instructed in the kit. 20 µL Reaction Mix was mixed with 10 µL of prepared sample and added to each well on the PCR plate. Each sample was plated in triplicate. The plate was sealed with optical adhesive film. During thermocycling, a melt was first performed at 95° C. for 10 min, and then the samples were cycled between 95° C. for 15 sec and 60° C. for 1 min for 40 cycles.

A standard curve was generated by plotting the CT value vs. quantity of DNA in log([pg/mL]). The data was fit to a straight line given by the following equation:

$$CT\ value = m \times \log 10(x) + b$$

where x=concentration of standard in pg/mL, m is the slope and b is the y-intercept. The concentration of host cell DNA was back-calculated from the CT value of the well using the above equation, then corrected by the dilution factor.

Results

The residual host cell DNA measured by qPCR was $3.7 \times 10^5$ pg/mL for prior batch of vector, $0.76 \times 10^5$ pg/mL for AVXS-101 Lot 600156, $0.68 \times 10^5$ pg/mL for AVXS1-101 Lot 600307 and $1.3 \times 10^5$ pg/mL for AVXS-201 DS.

Example 19—Measurement of Residual Host Cell Protein (HCP) in AAV9 Viral Vectors by ELISA Method The host cell protein (HCP) concentration in AVXS-101 samples was measured using a commercial enzyme-linked immunosorbent assay (ELISA) kit. THe Cygnus Technologies Human Embryonic Kidney 293 HCP ELISA Kit is a solid phase two-site enzyme immunoassay. It is based on a direct sandwich technique in which two polyclonal antibodies are directed against separate antigenic determinants of HCP. During incubation, the HCP in the sample bound with anti-HCP antibodies bound to a microplate well and with peroxidase-conjugated anti-HCP antibodies in solution.

After the incubation period, the wells were washed to remove any unbound enzyme-conjugated antibody. A 3,3', 5,5'-tetramethylbenzidine (TMB) substrate solution was then added to the wells. The bound peroxidase conjugate catalyzed a color change reaction in the substrate. The reaction was stopped by the addition of acid, which gave a colorimetric endpoint that could be read spectrophotmetrically at 450 nm. The amount of hydrolyzed substrate was directly proportional to the concentration of HCP present.

The samples to be tested were diluted to meet the range of the method, from 4 ng/mL to 200 ng/mL. Each sample was then diluted 2-fold in SDB (110 μL samples and 110 μL SDB) and mixed. Spiked controls were also made to check for consistency. In the spiked controls, 110 μL of each sample was mixed with 27.5 μL of 200 ng/mL HCP standard and 82.5 μL of SDB. Finally, 50 μL of each standard, control or test sample was added to a well on the 96-well plate and mixed with 100 μL of anti-HEK 293-HRP conjugate. All conditions were plated in triplicates. The plate was sealed with a sealing tape and shaken at 400-600 rpm for 2 hours at room temperature. After the incubation, the solutions in the wells were removed by flicking the plate upside down and blotting with an absorbent towel. The wells were washed with a wash bottle, blotted quickly and tapped without letting the wash solution soak in the wells. The wash was repeated 4 times and allowed to rest upside down for about 20 sec to drain after the last wash. Finally, 100 μL of TMB Substrate was added to each well of the plate and incubated for 20-30 min at room temperature with no agitation. The reaction was stopped by adding 100 μL of Stop Solution to each well. The plate was loaded onto a plate reader within 45 min of adding the Stop Solution and the plate was read at 450 nm and 650 nm.

The mean absorbance of the standards were plotted against the theoretical HCP concentration of the standards in a semi-logarithmic graph to generate a four-parameter logistic (4PL) fit curve based on the following equation:

$$Y = [(A-D)/(1+(X/C)^B)] + D$$

where A is the bottom asymptote, B is the Hill-slope, C is the concentration corresponding to the midpoint absorbance values between the two asymptotes (ng/mL), D is the top asymptote, X is the sample concentration (ng/mL) and Y is the absorbance. The standard curve was then used to determine the HCP concentration in the spiked sample control and the unspiked test samples using SoftMax Pro Software. The test was only accepted if the $r^2$ of the standard curve was ≥0.98, the mean corrected absorbance of the 200 ng/mL standard was ≥1.0 OD, the mean corrected absorbance of the 0 ng/mL standard was ≤0.2 OD, and the coefficient of variation of the corrected absorbance over 3 well replicates was ≤15%. The HCP final concentration for each sample was calculated using the equation:

HCP Concentration$_{sample}$(ng/mL)=Diluation factor× Mean measured HCP concentration (ng/mL).

Results

The residual host cell protein measured by ELISA was below the limit of quantification (8 ng/mL) for prior batch of vector, AVXS-101 Lot 600156, AVXS1-101 Lot 600307 and AVXS-201 DS.

Example 20—Measurement of Residual Benzonase in AAV9 Viral Vectors by ELISA

Method

The residual benzonase concentration in the AAV product, e.g., AVXS-101, was measured using a commercial enzyme-linked immunosorbent assay (ELISA) kit. The Merck Benzonase Endonuclease ELISA Kit II is a solid phase two-site enzyme immunoassay. It is based on a direct sandwich technique in which two polyclonal antibodies are directed against separate antigenic determinants of Benzonase. During incubation, the Benzonase in the sample bound with anti-Benzonase antibodies bound to a microplate well and with peroxidase-conjugated anti-Benzonase antibodies in solution.

After the incubation period, the wells were washed to remove any unbound enzyme-conjugated antibody. A 3,3', 5,5'-tetramethylbenzidine (TMB) substrate solution was then added to the wells. The bound peroxidase conjugate catalyzed a color change reaction in the substrate. The reaction was stopped by the addition of acid, which gave a colorimetric endpoint that could be read spectrophotometrically at 450 nm. The amount of hydrolyzed substrate is directly proportional to the concentration of Benzonase present.

Briefly, samples were diluted 2-fold by combining 175 μL of sample with 175 μL of PBST. In parallel, a benzonase spiked sample control was also prepared by combining 175 μL of sample with 35 μL of 10 ng/mL Benzonase standard and 140 μL of PBST. Pre-coated ELISA strips from the kit were mounted in a strip support and 100 μL of each test mix was loaded per well. For blanks, 100 μL of PBST was loaded instead of sample. Each condition was loaded in triplicate. The plate was sealed and incubated at room temperature for 2 hours ±5 minutes with agitation on a plate shaker (450 rpm). After incubation, the contents were discarded and the plate was washed by adding ~350 μL if PBST using an immunowasher and incubated for 1 minute, then inverted and tapped onto an absorbent towel. A total of 3 washes were performed before 100 μL of diluted HRP-Conjugated Antibody was added to each well. The plate was sealed and incubated at room temperature for 1 hour±5 minutes with agitation on a plate shaker (450 rpm). After incubation, the contents were discarded and the plate was washed by adding ~350 μL of PBST using an immunowasher and incubated for 1 minute, then inverted and tapped onto an absorbent towel. A total of 3 washes were performed before 100 μL of TMB substrate was added to each well. The plate was sealed and the contents incubated for 15-40 minutes at room temperature without agitation in the dark. The reaction was stopped by adding 100 μL of 0.2N H$_2$SO$_4$ Stop Solution to each well. The absorbance of the plate was measured using a spectrophotometer at 450 nm within 45 minutes of the addition of the Stop Solution.

The mean absorbance of the standards was plotted against the theoretical Benzonase concentration of the standards in a semi-logarithmic graph to generate a four-parameter logistic (4 PL) fit curve based on the following equation:

$$Y=[A-D)/(1+(X/C)\hat{}B)]+D$$

where A is the bottom asymptote, B is the Hill-slope, C is the concentration corresponding to the midpoint absorbance values between the two asymptotes (ng/mL), D is the top asymptote, X is the sample concentration (ng/mL) and Y is the absorbance. The standard curve was then used to determine the HCP concentration in the spiked sample control and the unspiked test samples using SoftMax Pro Software. The test was only accepted if the $r^2$ of the standard curve was ≥0.98, the mean corrected absorbance of the 2.5 ng/mL standard was ≥1.0 OD, the mean corrected absorbance of the 0.10 ng/mL standard was greater than the mean OD of the PBST blank, and the coefficient of variation of the corrected absorbance over 3 well replicates was ≤15%. The HCP final concentration for each sample was calculated using the equation:

Benzonase Concentration$_{sample}$(ng/mL)=Dilution factor×Mean measured Benzonase concentration (ng/mL).

Results

The residual benzonase concentration measured by ELISA was below the limit of quantification (0.2 ng/mL) for prior batch of vector, AVXS-101 Lot 600156, AVXS1-101 Lot 600307 and AVXS-201 DS.

Example 21—Measurement of Protein Concentration in AAV9 Viral Vectors by Micro BCA Assay Method The amount of proteins in in-process, drug substance and drug product samples, e.g., of AVXS-101, were measured by micro BCA plate assay, using a 2 mg/mL Bovine Serum Albumin (Thermo Fisher Scientific, 23209) reference protein standard and a Micro BCA Protein Assay Kit (Thermo Fisher Scientific, 23235). The assay is based on a detergent-compatible bicinchoninic acid (BCA) formulation for colorimetric detection and quantitation of total protein. The BCA detects $Cu^{1+}$ which is formed when $Cu^{2+}$ is reduced by protein in an alkaline environment. A purple-colored reaction product is formed by the chelation of two molecules of BCA with one cuprous ion ($Cu^{1+}$), which exhibits a strong absorbance at 562 nm that is linear with increasing protein concentrations.

Briefly, standards were prepared by performing serial dilutions of 2 mg/mL BSA in Diluent (20-fold dilution of the Formulation Buffer, 200 mM NaCl, 20 mM Tris, 1 mM MgCl2, 0.001% w/v Pluronic F-68, pH 8.0). The test samples of AVXS-101 were also diluted 20-fold in water and serial dilutions made in Diluent. The target concentration is about 7.5 μg/mL. The Working Reagent (WR) was prepared by mixing 25 parts Micro BCA Reagent A, 24 parts Reagent B and 1 part of Reagent C from the kit. 150 μL of each standard and test sample was loaded in triplicate into a 96-well plate, and mixed with 150 μL of WR. The plate was sealed and shaken at 300 rpm on a plate shaker for 30 seconds. The plate was then incubated without shaking at 37° C.±2° C. for 2 hours. After incubation, the plate was centrifuge at 1000 rpm for 2 minutes to collect the condensation, and the plate was cooled for 15-60 min after incubation. The plate was read in a plate reader at 562 nm and the data was analyzed with SoftMax Pro.

The mean absorbance of the standards vs. the theoretical protein concentration of the standards was plotted in a semi-logarithmic plot and a quadratic fit was generated. The quadratic fit is based on the equation:

$$Y=A+Bx+Cx^2$$

where A, B, C are curve fit parameters, x is the sample concentration in μg/mL and Y is the absorbance in OD. The test was only accepted if the $r^2$ of the standard curve was ≥0.98, the mean absorbance of the blank was less than that of the lowest standard (1 μg/mL), and the coefficient of variation of the absorbance over 3 well replicates of each standard was ≤10%.

The standard curve was then used to determine the protein concentration in the test samples. The final protein concentration was calculated using the equation:

Total Protein Concentration (μg/mL)=Dilution Factor×Mean measured protein concentration (μg/mL).

Results

The total protein concentration measured by Micro BCA was 167 μg/mL per $1.0×10^{13}$ vg/mL for prior batch of vector, 179 μg/mL per $1.0×10^{13}$ vg/mL for AVXS-101 Lot 600156, 176 μg/mL per $1.0×10^{13}$ vg/mL for AVXS1-101 Lot 600307, 182 μg/mL per $1.0×10^{13}$ vg/mL for AVXS-201 DP and 418 μg/mL per $1.0×10^{13}$ vg/mL for AVXS-301 DP.

Example 22—Purity and Release Specifications of AVXS-101, AVXS-201 and AVXS-301

AVXS-101 Drug Substance and AVXS-101 Drug Product from Examples 1 to 4 were tested for purity. Table 32 and 33 shows the specification and release criteria for these products.

TABLE 32

| Release specification for AVXS-101 Drug Substance | | |
|---|---|---|
| Process-Related Impurity | Origin | Acceptance Criteria |
| Host Cell Protein (HCP) | Cell Substrate | ≤4 ng per 1.0E13 vg |
| Host cell DNA | Cell Substrate | ≤1.15E5 pg per 1.0E13 vg |
| Bovine Serum Albumin (BSA) | Cell Culture | ≤0.22 ng per 1.0E13 vg |
| Plasmid DNA (pDNA) | Cell Culture | ≤6.8E5 pg per 1.0E13 vg |
| Polyethyleimine (PEI) | Cell Culture | Not tested at Release |
| Benzonase | Downstream Processing | ≤0.09 ng per 1.0E13 vg |
| Tween 20 | Downstream Processing | Not tested at Release |
| Poloxamer 188 | Downstream Processing | 20-80 ppm |

TABLE 32-continued

Release specification for AVXS-101 Drug Substance

| Process-Related Impurity | Origin | Acceptance Criteria |
|---|---|---|
| Cesium (Cs) | Downstream Processing | ≤30 µg/g (ppm) |
| Ethanol | Downstream Processing | Not tested at Release |

TABLE 33

Release specifications for AVXS-101 Drug Product

| Category | Attribute | Acceptance Criterion |
|---|---|---|
| General | Appearance per USP <631> and USP <855> | Clear to slightly opaque, colorless to faint white solution, free of visible particulates |
|  | pH per USP <791> | 7.7-8.3 |
|  | Psmolality per USP <785> | 390-430 mOsm/kg |
|  | Sub-visible particles per USP <787> | ≤600 particles ≥25 µm per container ≤6000 particles ≥10 µm per container |
| Quantity | Genomic Titer by ddPCR | 1.7E13-2.3E13 vg/mL |
|  | Infectious Titer by TaqMan $TCID_{50}$ | 3.9E8-8.4E10 IU per 1.0E13 vg |
|  | Total Protein by Micro BCA | 100-300 µg per 1.0E13 vg |
|  | Pluronic F-68 Content by HPLC-ELSD | 20-80 ppm |
| Potency | In vivo Functionality Test by Δ7SMA Mouse Model | Median Survival representing the 7.5E13 vg/kg dose is ≥24 days |
|  | In vitro Relative Potency by Cell-based Assay | 70-130% |
| Identity | Vector Genome Identity by ddPCR | Confirms |
|  | Identity (Protein) by SDS-PAGE | Main Bands of VP1, VP2, VP3 co-migrate with the AVXS-101 Reference Standard |
|  | Identity (Protein) by Western Blot | Positive for AAV capsid protein |
| Purity | % Capsid Distribution by SV-AUC | % Empty ≥5% <br> % Peak 1 + Peak 2 ≥91.9% <br> % Full (Peak 1) 37.4-70.3% <br> % Full (Peak 2) 24.9-60.1% <br> % Total Other Peaks ≤5% |
|  | % Total Purity by SDS-PAGE | % Total Purity (VP1, VP2, VP3) ≥95.0% |
|  | % Total Impurities by SDS-PAGE | % Total Impurities ≤5% <br> No single un-named related impurity >2.0% <br> Named related impurities: Report value (%) to 0.1% (down to LOQ) <br> Imp 1A (~71-73 kDa) <br> Imp 1 (~61-67 kDa) <br> Imp 2 (~56-64 kDa) <br> Imp 3 (~48-58 kDa) <br> Imp 4 (~33-38 kDa) <br> Imp 5 (~30-34 kDa) |
| Safety | Endotoxin per USP <85> | ≤0.75 EU/mL |
|  | Sterility per USP <71> | No growth |
|  | Container Closure Integrity per USP <1207> Vacuum Decay | Pass |

AVXS-201 and AVXS-301 can be manufactured and purified using the same process as described for AVXS-101, e.g., as described in Examples 1-4. The specification and release criteria for batches of each product produced in bioreactors are shown in Table 34-36.

TABLE 34

AVXS-201 Drug Substance Lot 283-0218-005

| Test Description | Result |
|---|---|
| Bioburden | <1 CFU/mL |
| pH | 7.8 |
| Appearance by Visual Inspection | Clear, colorless solution |
| Osmolality by Freezing Point Depression | 411 mOsm/kg |
| Genomic Titer by ddPCR | $4.0 \times 10^{13}$ vg/mL |
| Vector Genome Identity by ddPCR | Confirms |

TABLE 34-continued

AVXS-201 Drug Substance Lot 283-0218-005

| Test Description | Result |
| --- | --- |
| Vector Identity by SDS-PAGE | Main Bands of VP1, VP2, VP3 co-migrate with AVXS-201 control |
| Purity by SDS-PAGE | 98% |
| % Empty Capsid by AUC | TBD |
| Total Impurities by SDS-PAGE | Total % Impurities: 2% |
| | % Impurities with MW: |
| | 53.2 kDa, <1.0% |
| | 36.9 kDa, <1.0% |
| | 29.9 kDa, <1.0% |
| Residual BSA by ELISA | <LOQ (<0.50 ng/mL) |
| Residual Plasmid DNA by qPCR | $1.2 \times 10^6$ pg/mL per $1.0 \times 10^{13}$ vg/mL |
| Residual Host Cell DNA by qPCR | $1.3 \times 10^5$ pg/mL per $1.0 \times 10^{13}$ vg/mL |
| Residual Benzonase by ELISA | <LOQ (<0.20 ng/mL) |
| Host Cell Protein by ELISA | <LOQ (<8 ng/mL) |

TABLE 35

AVXS-201 Drug Product Lot 283-0218-006

| Test Description | Result |
| --- | --- |
| Sterility | No Growth |
| Endotoxin | 0.02 EU/mL per $1.0 \times 10^{13}$ vg/mL |
| Replication Competent AAV | TBD |
| pH | 7.8 |
| Appearance by Visual Inspection | Clear, colorless solution with no visible particles |
| Osmolality by Freezing Point Depression | 409 mOsm/kg |
| Sub-visible Particles by Light Obscuration | 0 particles greater than or equal to 25 µm per container |
| | 0 particles greater than or equal to 10 µm per container |
| Genomic Titer by ddPCR | $3.6 \times 10^{13}$ vg/mL |
| Infectious Titer by $TCID_{50}$ | $8.26 \times 10^{10}$ TCID50/mL |
| Total Protein by Micro BCA | 182 µg/mL per $1.0 \times 10^{13}$ vg/mL |
| Pluronic by HPLC-ELSD | 46 ppm |
| Vector Genome Identity by ddPCR | Confirms |
| Identity by Western Blot | Positive for AAV Capsid Protein |
| | Main Band MW |
| | VP1: 79.0 kDa |
| | VP2: 65.0 kDa |
| | VP3: 57.7 kDa |
| Identity by SDS-PAGE | Main Bands of VP1, VP2, VP3 co-migrate with AVXS-201 control |
| % Empty Capsid by AUC | 2% |
| % Total Purity by SDS-PAGE | 98% |
| % Total Impurities by SDS-PAGE | Total % Impurities: 2% |
| | % Impurities with MW: |
| | 52.5 kDa, <1.0% |
| | 36.4 kDa, <1.0% |
| | 29.1 kDa, <1.0% |
| Cesium by ICP-MS | 28 µg/g (ppm) |

TABLE 36

Purity of a test batch of AVXS-301 Drug Product

| Test Description | Result |
| --- | --- |
| Sterility | No Growth |
| Endotoxin | 0.09 EU/mL |
| Replication Competent AAV | Negative |
| pH | 8.0 |
| Appearance by Visual Inspection | Clear and colorless solution |
| Osmolality by Freezing Point Depression | 408 mOsm/kg |
| Sub-visible Particles by Light Obscuration | 0 particles greater than or equal to 25 µm per container |
| | 0 particles greater than or equal to 10 µm per container |

TABLE 36-continued

Purity of a test batch of AVXS-301 Drug Product

| Test Description | Result |
| --- | --- |
| Genomic Titer by ddPCR | $2.5 \times 10^{13}$ vg/mL |
| Infectious Titer by $TCID_{50}$ | $5.62 \times 10^{10}$ $TCID_{50}$/mL |
| Total Protein by Micro BCA | 418 µg/mL |
| Pluronic by HPLC-ELSD | 53.2 ppm |
| Vector Genome Identity by ddPCR | Confirms |
| Identity (Protein) by Western Blot | Positive for AAV Capsid Protein |
| Identity (Protein) by SDS-PAGE | Main Bands of VP1, VP2, VP3 co-migrate with AVXS-301 control |
| % Empty Capsid by AUC | 3% |
| % Total Purity by SDS-PAGE | 98% |
| % Total Impurities by SDS-PAGE | Total Impurities: 2% Impurities with MW: Imp 1 (~61-67 kDa): 2% |
| Cesium by ICP-MS | Below LOQ (<20 µg/g (ppm)) |

The high purity achieved for AVXS-201 and AVXS-301 shows that the methods of producing and purifying AAV viral vectors as described in this application shows broad applicability across AAV viral vectors with different payloads.

Having described embodiments with reference to the accompanying drawings, it is to be understood that the disclosure is not limited to the precise embodiments, and that various changes and modifications may be effected therein by those skilled in the art without departing from the scope or spirit of the disclosure and embodiments as defined in the appended claims.

List of Exemplary Embodiments

1. A pharmaceutical composition comprising:
   (a) between $1-8 \times 10^{13}$ vector genomes/ml of parvovirus engineered with a transgene;
   (b) less than 5.0% empty capsids;
   (c) less than 40 ng/ml residual host cell protein per $1 \times 10^{13}$ vg/ml;
   (d) less than $1.2 \times 10^6$ pg/ml residual host cell DNA per $1 \times 10^{13}$ vg/ml; and,
   (e) at least 80% of the $1-8 \times 10^{13}$ vector genomes/ml are functional.

2. The composition of embodiment 1, wherein the amount of residual plasmid DNA comprises less than $1.7 \times 10^6$ pg per $1 \times 10^{13}$ vg.

3. The composition of embodiment 1, wherein the amount of vector genomes/ml of parvovirus comprises $1.8-2.2 \times 10^{13}$ vector genomes/ml.

4. A method for the purification of AAV particles from a mammalian host cell culture to form a frozen intermediate drug substance comprising the steps of:
   (a) culturing cells that have been transfected with a recombinant AAV virion;
   (b) harvesting the expanded viral particles from the cells after a culture period;
   (c) purifying the viral particles via filtration to remove any intact cells or cellular debris;
   (d) subjecting the eluent from step (c) to tangential flow filtration; and,
   (e) freezing the resultant intermediate preparation of purified viral particles.

5. The method of embodiment 4, wherein an endonuclease is used during the harvesting step.

6. The method of embodiment 5, wherein the endonuclease is benzonase.

7. The method of embodiment 4, wherein the purifying step uses depth filtration followed by filtration through a filter that removes large molecule contaminants and cell debris.

8. The method of embodiment 4, wherein the tangential flow filtration step uses cellulose membranes.

9. A method for the purification of a sample of AAV particles from a mammalian host cell culture to form a drug product comprising the steps of:
   (a) an acidification and clarification step;
   (b) a cation exchange chromatography step;
   (c) a tangential flow filtration step;
   (d) a CsCl ultracentrifugation step to remove empty capsids; and,
   (e) a tangential flow filtration step.

10. The method of embodiment 9, wherein the acidification and clarification step comprises adjusting the sample to pH 3.5 and host cell proteins and DNA are removed via flocculation with a detergent.

11. The method of embodiment 9, wherein the cation exchange column comprises a sulfonyl resin.

12. The method of embodiment 9, wherein the tangential flow filtration step (c) uses cellulose membranes with a molecular weight cutoff of 300 kDa MW and reduces the eluate volume of the cation exchange step by at least six-fold.

13. The method of embodiment 9, wherein the CsCl ultracentrifugation step removes at least 80% of the empty capsids in the sample uses depth filtration followed by filtration through a 0.45 micron filter.

14. The method of embodiment 9, wherein the tangential flow filtration step (e) uses cellulose membranes with a molecular weight cutoff of 300 kDa MW.

15. A method of treating a neurological disease in a patient in need thereof comprising intravenous or intrathecal delivery of the pharmaceutical composition of any one of embodiments 1-3, wherein the parvovirus comprises a self-complementary AAV9 genome, and wherein the engineered transgene comprises an SMN polynucleotide and wherein the disease is SMA.

16. A method of treating a neurological disease in a patient in need thereof comprising intrathecal delivery of the pharmaceutical composition of any one of embodiments 1-3 with a contrast agent, wherein the parvovirus comprises a self-complementary AAV9 genome, and wherein the engineered transgene comprises an SMN polynucleotide, wherein the disease is SMA, and wherein the contrast agent is omnipaque 180.

17. The method of any one of embodiments 15-16, wherein the SMA is type II, type III or type IV SMA.

18. A method of treating a type II, III, or IV SMA in a patient in need thereof comprising intrathecal delivery of the pharmaceutical composition of any one of embodiments 1-3 with a contrast agent, wherein the parvovirus comprises a self-complementary AAV9 genome, wherein the engineered transgene comprises an SMN polynucleotide, and wherein the contrast agent is omnipaque 180.

19. A method treating type I SMA in a patient in need thereof comprising intravenous delivery of the pharmaceutical composition of any one of embodiments 1-3 wherein the parvovirus comprises a self-complementary AAV9 genome, and wherein the engineered transgene comprises an SMN polynucleotide.

20. The method of embodiment 19, wherein the patient is 0-9 months old.

21. The method of embodiment 20, wherein the patient is 0-6 months old.

22. The method of embodiment 19, wherein the pediatric patient is up to about 8 kg in weight.

The invention claimed is:
1. A method of manufacturing an AAV viral vector, comprising:
   a. acidifying and clarifying a cell lysate from cells expressing the AAV viral vector;
   b. purifying the product of (a) using cation exchange chromatography (CEX);
   c. filtering the product of (b) using a first tangential flow filtration (TFF) step;
   d. ultracentrifuging the product of (c) in a cesium chloride (CsCl) buffer; and
   e. collecting the AAV viral vector from the product of (d); wherein a composition comprising the AAV viral vector from (d) comprises less than $2 \times 10^5$ pg/mL residual host cell DNA per $1 \times 10^{13}$ vg/mL.

2. The method of claim 1, wherein the AAV is AAV9.

3. The method of claim 1, wherein the AAV is self-complementary (scAAV).

4. The method of claim 1, wherein the cells are HEK293 cells.

5. The method of claim 1, comprising, prior to step (a):
i. culturing cells;
ii. transfecting the cells with plasmid(s) to enable production of the AAV viral vector; and
iii. lysing the cells to produce the cell lysate.

6. The method of claim 5, wherein step (i) comprises seeding the cells in a large-scale bioreactor that can provide continuous circulation of cell culture media.

7. The method of claim 6, wherein the seeding density is about 8,000-12,000 cells/cm$^2$.

8. The method of claim 5, wherein the transfecting step (ii) comprises contacting the cells with an adenovirus helper plasmid and a plasmid encoding AAV rep and cap genes.

9. The method of claim 8, wherein the AAV rep gene is rep2 and the AAV cap gene is cap9.

10. The method claim 5, wherein the transfecting step (ii) comprises contacting the cells with a plasmid comprising a polynucleotide encoding a survival motor neuron (SMN) protein, a polynucleotide encoding MeCP2 or a polynucleotide encoding a SOD1 shRNA.

11. The method of claim 10, wherein the plasmid comprising the polynucleotide encoding SMN1 protein comprises a modified AAV2 ITR, a chicken beta-actin (CB) promoter, a cytomegalovirus (CMV) immediate/early enhancer, a modified SV40 late 16s intron, a Bovine growth hormone (BGH) polyadenylation signal, and an AAV2 ITR.

12. The method of claim 10, wherein the polynucleotide encoding SMN encodes the SMN protein of SEQ ID NO: 2.

13. The method of claim 5, wherein the transfecting step comprises contacting the cells with the transfection agent polyethylenimine (PEI).

14. The method claim 5, wherein the transfecting step comprises contacting the cells with a transfection medium that does not contain serum, calcium, or glutamine.

15. The method of claim 1, wherein the AAV viral vector comprises SEQ ID NO: 1.

16. The method claim 5, wherein the lysing step comprises a lysis buffer supplemented with benzonase and Tween.

17. The method of claim 1, further comprising freezing the cell lysate prior to the acidification step of (a).

18. The method of claim 1 comprising the step of:
(f) filtering the product of (e) through a second TFF step.

19. The method of claim 1, wherein the acidification step comprises acidifying the cell lysate to a pH of about 3.0-4.0.

20. The method of claim 1, wherein the ultracentrifugation is performed between 40,000-50,000 rpm.

21. The method of claim 1, wherein the CsCl buffer comprises about 3 M ClsCl, Tris, MgCl2, and Poloxamer 188, and is between about pH 7.5 and 8.5.

22. The method of claim 1, wherein the cell lysate is incubated with Tween prior to the acidification step.

23. The method of claim 1, wherein the clarification step comprises filtering the cell lysate through a depth filter.

24. The method of claim 1, wherein the CEX comprises a sulfonyl resin.

25. The method of claim 1, wherein at least one TFF step comprises using cellulose membranes with a molecular weight cutoff of about 300 kDa MW.

26. The method of claim 1, wherein the number of empty viral capsid is less than 7%, less than 5%, less than 3% or less than 1% of the total viral capsids after collecting the AAV viral vectors from the ultracentrifuged cell lysate.

27. The method of claim 18, wherein the AAV viral vectors collected after the second TFF step are stored in a solution comprising Tris, MgCl2, NaCl, and Poloxamer 188, and the pH is between about pH 7.5 and 8.5.

28. The method of claim 18, wherein the AAV viral vectors collected after the second TFF step contain less than about 30 µg/g or less than about 20 µg/g of CsCl.

29. The method of claim 18, wherein the concentration of AAV viral vectors collected after the second TFF step is greater than or equal to about $3\times10^{13}$ vector genomes (vg)/ml.

30. The method of claim 1, wherein the produced yield of AAV is more than $5\times10^{15}$ vg, or more than $8\times10^{15}$ vg or more than $1\times10^{16}$ vg per manufacturing batch.

31. The method of claim 1, wherein the AAV vector comprises a polynucleotide encoding a survival motor neuron (SMN) protein, a polynucleotide encoding MeCP2 or a polynucleotide encoding a SOD1 shRNA.

32. A pharmaceutical composition comprising an AAV9 viral vector manufactured according to the method of claim 1.

33. The pharmaceutical composition claim 32, comprising at least one of the following:
a. less than about 0.09 ng of benzonase per $1.0\times10^{13}$ vg,
b. less than about 30 µg/g (ppm) of cesium,
c. about 20-80 ppm of Poloxamer 188,
d. less than about 0.22 ng of BSA per $1.0\times10^{13}$ vg,
e. less than about $6.8\times10^5$ pg of residual plasmid DNA per $1.0\times10^{13}$ vg,
f. less than about $1.1\times10^5$ pg of residual hcDNA per $1.0\times10^{13}$ vg,
g. less than about 4 ng of rHCP per $1.0\times10^{13}$ vg,
h. about pH 7.7-8.3,
i. about 390-430 mOsm/kg,
j. less than about 600 particles that are ≥25 µm in size per container,
k. less than about 6000 particles that are >10 µm in size per container,
l. about $1.7\times10^{13}$-$2.3\times10^{13}$ vg/mL genomic titer,
m. infectious titer of about $3.9\times10^8$-$8.4\times10^{10}$ IU per $1.0\times10^{13}$ vg,
n. total protein of about 100-300 ug per $1.0\times10^{13}$ vg,
o. relative potency of about 70-130%, or
p. less than about 5% empty capsid.

34. A pharmaceutical composition comprising:
a. between 1-$8\times10^{13}$ AAV9 viral vector genomes/mL (vg/mL);
b. less than about 7% empty viral capsids;
c. less than about 100 ng/ml host cell protein per $1\times10^{13}$ vg/mL;
d. less than about $5\times10^6$ pg/mL residual host cell DNA per $1\times10^{13}$ vg/mL;
and wherein at least about 80% of the 1-$8\times10^{13}$ AAV9 viral vector genomes/mL are functional.

35. The composition of claim 34, wherein the AAV9 viral vector comprises a polynucleotide encoding a survival motor neuron (SMN) protein, a polynucleotide encoding MeCP2 or a polynucleotide encoding a SOD1 shRNA.

36. The composition of claim 34, wherein the AAV9 viral vector comprises a modified AAV2 ITR, a chicken beta-actin (CB) promoter, a cytomegalovirus (CMV) immediate/early enhancer, a modified SV40 late 16s intron, a bovine growth hormone (BGH) polyadenylation signal, and an unmodified AAV2 ITR.

37. The composition of claim 35, wherein the polynucleotide encodes the SMN protein of SEQ ID NO: 2.

38. The composition of claim 34, wherein the AAV9 viral vector comprises SEQ ID NO: 1.

39. The composition of claim 34, comprising between 1.7-2.3×10$^{13}$ AAV9 vg/mL.

40. The composition of claim 34, wherein the composition is an aqueous pharmaceutical formulation.

41. The composition of claim 40, wherein the aqueous pharmaceutical formulation comprises a Tris buffer, MgCl2, NaCl, and Poloxamer 188.

42. The composition of claim 40, wherein the aqueous pharmaceutical formulation does not comprise a preservative.

43. The composition of claim 41, wherein:
(i) the Tris buffer concentration is about 10-30 nM;
(ii) the pH of the formulation is about 7.7 to about 8.3;
(iii) the MgCl2 concentration is about 0.5-1.5 mM;
(iv) the NaCl concentration is about 100-300 mM;
(v) the formulation comprises about 0.005% w/v Poloxamer 188; or
(vi) the aqueous pharmaceutical formulation has an osmolality of 390-430 mOsm/kg.

44. A method of treating type I spinal muscular atrophy (SMA) in a patient in need thereof, comprising administering the composition of claim 35 to the patient, wherein the patient:
a. is nine months old or younger;
b. has a body weight of at least about 2.6 kg;
c. has bi-allelic SMN1 null mutations or deletions; and
d. has at least one functional copy of SMN2.

45. The method of claim 44, wherein the viral vector is administered at a dose of about 1-2.5×10$^{14}$ vg/kg.

46. The method of claim 44, wherein the patient has a body weight of no more than about 8.5 kg.

47. The method of claim 44, wherein the patient does not have a c.859G>C substitution in exon 7 of at least one copy of the SMN2 gene.

48. The method of claim 44, wherein the composition is administered to the patient before the age of 6 months, or before the onset of one or more SMA symptoms selected from hypotonia, delay in motor skills, poor head control, round shoulder posture and hypermobility of joints.

49. The method of claim 44, wherein the viral vector is administered in about 5-20 mL/kg, about 10-20 mL/kg, or about 5.5-6.5 mL/kg of Tris-buffered saline.

50. The method of claim 44, wherein efficacy is determined using the CHOP-INTEND scale.

51. The method of claim 44, comprising administering a dose volume selected from the group consisting of a dose of 16.5 mL for a patient weighing 2.6-3.0 kg, a dose of 19.3 mL for a patient weighing 3.1-3.5 kg, a dose of 22.0 mL for a patient weighing 3.6 to 4.0 kg, a dose of 24.8 mL for a patient weighing 4.1-4.5 kg, a dose of 27.5 mL for a patient weighing 4.6-5.0 kg, a dose of 30.3 mL for a patient weighing 5.1-5.5 kg, a dose of 33.0 mL for a patient weighing 5.6-6.0 kg, a dose of 35.8 mL for a patient weighing 6.1-6.5 kg, a dose of 38.5 mL for a patient weighing 6.6-7.0 kg, a dose of 41.3 mL for a patient weighing 7.1-7.5 kg, a dose of 44.0 mL for a patient weighing 7.6-8.0 kg, and a dose of 46.8 mL for a patient weighing 8.1-8.5 kg.

52. The method of claim 44, wherein the composition is administered by intravenous or intrathecal infusion to a patient in need thereof.

53. The method of claim 52, wherein the viral vector is infused over about 45-75 minutes.

54. A kit comprising vials containing about 5.5 mL or about 8.3 mL of an AAV9 viral vector comprising a polynucleotide encoding a survival motor neuron (SMN) protein, and formulated at a concentration of about 2.0×10$^{13}$ vg/mL in 20 mM Tris, 1 mM MgCl2, 200 mM NaCl, 0.005% w/v Poloxamer 188 at pH 7.7-8.3.

* * * * *